US012502429B2

(12) United States Patent
Ardeleanu et al.

(10) Patent No.: US 12,502,429 B2
(45) Date of Patent: Dec. 23, 2025

(54) METHODS FOR TREATING ATOPIC DERMATITIS BY ADMINISTERING AN IL-4R ANTAGONIST

(71) Applicants: REGENERON PHARMACEUTICALS, INC., Tarrytown, NY (US); Sanofi Biotechnology, Paris (FR)

(72) Inventors: Marius Ardeleanu, White Plains, NY (US); Neil Graham, Croton-on-Hudson, NY (US); Jennifer Davidson Hamilton, Ridgefield, CT (US); Stephane C. Kirkesseli, Paris (FR); Sudeep Kundu, New York, NY (US); Jeffrey Ming, Bridgewater, NJ (US); Allen Radin, New York, NY (US); Ross E. Rocklin, Basking Ridge, NJ (US); Steven Paul Weinstein, Hartsdale, NY (US)

(73) Assignees: Regeneron Pharmaceuticals, Inc., Tarrytown, NY (US); Sanofi Biotechnology, Paris (FR)

( * ) Notice: Subject to any disclaimer, the term of this patent is extended or adjusted under 35 U.S.C. 154(b) by 433 days.

(21) Appl. No.: 17/951,987

(22) Filed: Sep. 23, 2022

(65) Prior Publication Data

US 2023/0058395 A1 Feb. 23, 2023

Related U.S. Application Data

(63) Continuation of application No. 15/610,267, filed on May 31, 2017, now abandoned, which is a continuation of application No. 14/017,333, filed on Sep. 4, 2013, now abandoned.

(60) Provisional application No. 61/816,191, filed on Apr. 26, 2013, provisional application No. 61/782,420, filed on Mar. 14, 2013, provisional application No. 61/770,091, filed on Feb. 27, 2013, provisional application No. 61/768,229, filed on Feb. 22, 2013, provisional application No. 61/764,624, filed on Feb. 14, 2013, provisional application No. 61/748,588, filed on Jan. 3, 2013, provisional application No. 61/738,715, filed on Dec. 18, 2012, provisional application No. 61/697,972, filed on Sep. 7, 2012.

(30) Foreign Application Priority Data

Jul. 10, 2013 (FR) ...................................... 1356759

(51) Int. Cl.

| | |
|---|---|
| ***A61K 39/395*** | (2006.01) |
| ***A61K 31/573*** | (2006.01) |
| ***A61K 31/58*** | (2006.01) |
| ***A61K 45/06*** | (2006.01) |
| ***C07K 16/28*** | (2006.01) |
| ***G01N 33/53*** | (2006.01) |
| *A61K 39/00* | (2006.01) |

(52) U.S. Cl.

CPC ........ *A61K 39/3955* (2013.01); *A61K 31/573* (2013.01); *A61K 31/58* (2013.01); *A61K 45/06* (2013.01); *C07K 16/2866* (2013.01); *G01N 33/53* (2013.01); *A61K 2039/54* (2013.01); *C07K 2317/21* (2013.01); *G01N 2800/202* (2013.01)

(58) Field of Classification Search

CPC .................................................. A61K 39/3955

See application file for complete search history.

(56) References Cited

U.S. PATENT DOCUMENTS

| | | | |
|---|---|---|---|
| 5,599,905 | A | 2/1997 | Mosley |
| 5,714,146 | A | 2/1998 | Lewis |
| 5,717,072 | A | 2/1998 | Mosley |
| 5,856,296 | A | 1/1999 | Mosley |
| 5,985,280 | A | 11/1999 | Ritter |
| 6,156,877 | A | 12/2000 | Ritter |
| 6,391,581 | B1 | 5/2002 | Mosley |
| 6,548,655 | B1 | 4/2003 | Mosley |
| 6,716,587 | B2 | 4/2004 | Mosley |
| 7,141,653 | B2 | 11/2006 | Greenfeder |
| 7,186,809 | B2 | 3/2007 | Pluenneke |
| 7,317,090 | B2 | 1/2008 | Mosley |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Blauvelt, Andrew et al., "No Increased Risk of Overall Infection in Adults with Moderate-to-Severe Atopic Dermatitis Treated for up to 4 Years with Dupilumab", Advances in Therapy, vol. 40, No. 1, Nov. 1, 2022, pp. 367-380.

(Continued)

*Primary Examiner* — Prema M Mertz

(74) *Attorney, Agent, or Firm* — Schwabe, Williamson & Wyatt PC; Lisa Dornbach Flanagan

(57) ABSTRACT

The present invention provides methods for treating atopic dermatitis (AD). Also provided are methods for improving one or more AD-associated parameter(s), and methods for decreasing the level of at least one AD-associated biomarker in a subject in need thereof. The methods of the present invention comprise administering to a subject in need thereof a pharmaceutical composition comprising an interleukin-4 receptor (IL-4R) antagonist such as an anti-IL-4R antibody.

42 Claims, 60 Drawing Sheets

Specification includes a Sequence Listing.

(56) References Cited

U.S. PATENT DOCUMENTS

| | | | | |
|---|---|---|---|---|
| 7,422,742 | B2 | 9/2008 | Greenfeder | |
| 7,531,169 | B2 | 5/2009 | Singh | |
| 7,605,237 | B2 | 10/2009 | Stevens | |
| 7,608,693 | B2 | 10/2009 | Martin | |
| 7,794,717 | B2 | 9/2010 | Stevens | |
| 8,030,003 | B2 | 10/2011 | Rothenberg | |
| 8,075,887 | B2 | 12/2011 | Martin | |
| 8,075,897 | B2 | 12/2011 | Spertini | |
| 8,092,802 | B2 | 1/2012 | Stevens | |
| 8,092,804 | B2 | 1/2012 | Eriksson | |
| 8,252,284 | B2 | 8/2012 | Singh | |
| 8,324,192 | B2 | 12/2012 | Dohil | |
| 8,337,839 | B2 | 12/2012 | Martin | |
| 8,338,135 | B2 | 12/2012 | Stevens | |
| 8,497,528 | B2 | 7/2013 | Lee | |
| 8,604,171 | B2 | 12/2013 | Singh | |
| 8,637,239 | B2 | 1/2014 | Furuta | |
| 8,735,095 | B2 | 5/2014 | Martin et al. | |
| 8,945,559 | B2 | 2/2015 | Dix | |
| 9,238,692 | B2 | 1/2016 | Dix | |
| 9,290,574 | B2 | 3/2016 | Kostic | |
| 9,415,015 | B2 | 8/2016 | Jacobi et al. | |
| 9,574,004 | B2 | 2/2017 | Ardeleanu | |
| 10,059,771 | B2 | 8/2018 | Mannent | |
| 10,066,017 | B2 | 9/2018 | Mannent | |
| 10,137,193 | B2 | 11/2018 | Pirozzi | |
| 10,370,449 | B2 | 8/2019 | Graham | |
| 10,392,439 | B2 | 8/2019 | Stahl | |
| 10,435,473 | B2 | 10/2019 | Dix | |
| 10,485,844 | B2 | 11/2019 | Radin | |
| 10,669,341 | B2 | 6/2020 | Stahl | |
| 10,676,530 | B2 | 6/2020 | Stahl | |
| 10,730,948 | B2 | 8/2020 | Kostic | |
| 11,034,768 | B2 | 6/2021 | Amin | |
| 11,053,309 | B2 | 7/2021 | Radin | |
| 11,167,004 | B2 * | 11/2021 | Radin | A61K 38/02 |
| 11,292,847 | B2 | 4/2022 | Bansal | |
| 2003/0103938 | A1 | 6/2003 | Jinquan | |
| 2003/0113387 | A1 | 6/2003 | Tsuchida | |
| 2003/0124121 | A1 | 7/2003 | Pluenneke | |
| 2005/0031609 | A1 | 2/2005 | Hultsch | |
| 2005/0074462 | A1 | 4/2005 | Holmgren | |
| 2005/0118176 | A1 | 6/2005 | Mosley | |
| 2005/0255532 | A1 | 11/2005 | Ruben | |
| 2005/0282181 | A1 | 12/2005 | Yan | |
| 2006/0013811 | A1 | 1/2006 | Dina | |
| 2007/0041976 | A1 | 2/2007 | Pluenneke | |
| 2007/0274996 | A1 | 11/2007 | Carter | |
| 2008/0054606 | A1 | 3/2008 | Mitsuo et al. | |
| 2008/0160035 | A1 | 7/2008 | Stevens et al. | |
| 2009/0074793 | A1 | 3/2009 | Martin | |
| 2009/0098142 | A1 | 4/2009 | Kasaian | |
| 2009/0264392 | A1 | 10/2009 | Warndahl | |
| 2010/0021476 | A1 | 1/2010 | Stevens et al. | |
| 2010/0047254 | A1 | 2/2010 | Martin | |
| 2010/0291107 | A1 | 11/2010 | Stevens et al. | |
| 2011/0195500 | A1 | 8/2011 | Rothenberg | |
| 2012/0004205 | A1 | 1/2012 | Rothenberg | |
| 2012/0052072 | A1 | 3/2012 | Martin | |
| 2012/0097565 | A1 | 4/2012 | Dix | |
| 2012/0135010 | A1 | 5/2012 | Stevens et al. | |
| 2012/0164080 | A1 | 6/2012 | Hill | |
| 2012/0207815 | A1 | 8/2012 | Benhamou | |
| 2013/0052190 | A1 | 2/2013 | Collins | |
| 2013/0078675 | A1 | 3/2013 | Martin | |
| 2013/0324435 | A1 | 12/2013 | Rothenberg | |
| 2014/0072583 | A1 | 3/2014 | Ardeleanu | |
| 2014/0187523 | A1 | 7/2014 | Dohil | |
| 2014/0271681 | A1 | 9/2014 | Martin | |
| 2014/0356372 | A1 | 12/2014 | Stahl | |
| 2015/0017176 | A1 | 1/2015 | Kostic | |
| 2015/0185228 | A1 | 7/2015 | Reisacher | |
| 2015/0246973 | A1 | 9/2015 | Graham | |
| 2016/0152718 | A1 | 6/2016 | Kostic | |
| 2016/0185866 | A1 | 6/2016 | Mannent | |
| 2017/0333557 | A1 | 11/2017 | Ardeleanu | |
| 2018/0078603 | A1 | 3/2018 | Radin | |
| 2018/0094069 | A1 | 4/2018 | Stahl | |
| 2018/0094070 | A1 | 4/2018 | Stahl | |
| 2018/0179288 | A1 | 6/2018 | Martin et al. | |
| 2019/0040126 | A1 | 2/2019 | Radin | |
| 2019/0169299 | A1 | 6/2019 | Amin | |
| 2019/0183973 | A1 | 6/2019 | Hamilton | |
| 2019/0345253 | A1 | 11/2019 | Bansal | |
| 2019/0367622 | A1 | 12/2019 | Graham | |
| 2020/0246416 | A1 | 8/2020 | Radin | |
| 2020/0299393 | A1 | 9/2020 | Stahl | |
| 2020/0332014 | A1 | 10/2020 | Kostic | |
| 2020/0345843 | A1 | 11/2020 | Asrat | |
| 2021/0038715 | A1 | 2/2021 | Hamilton | |
| 2021/0040222 | A1 | 2/2021 | Bansal | |
| 2021/0163611 | A1 | 6/2021 | Martin | |
| 2021/0220470 | A1 | 7/2021 | Bryce et al. | |
| 2021/0363237 | A1 | 11/2021 | Radin | |
| 2021/0363264 | A1 | 11/2021 | Hamilton | |
| 2022/0110999 | A1 | 4/2022 | Radin | |
| 2022/0220211 | A1 | 7/2022 | Orengo | |
| 2022/0298250 | A1 | 9/2022 | Bansal | |
| 2023/0102151 | A1 | 3/2023 | Bansal et al. | |
| 2023/0167171 | A1 | 6/2023 | Bansal | |
| 2023/0220089 | A1 | 7/2023 | Geba | |
| 2023/0357416 | A1 | 11/2023 | Graham | |
| 2024/0141051 | A1 | 5/2024 | Bansal | |

FOREIGN PATENT DOCUMENTS

| | | | |
|---|---|---|---|
| EP | 1113818 | B1 | 5/2006 |
| EP | 2022507 | A1 | 2/2009 |
| EP | 1527100 | | 7/2009 |
| EP | 3889181 | A1 | 10/2021 |
| EP | 3110848 | B1 | 2/2024 |
| EP | 3515465 | | 2/2024 |
| JP | 05-246874 | | 9/1993 |
| JP | 2006-131623 | | 5/2006 |
| JP | 2016521713 | | 7/2016 |
| JP | 2018-611322 | | 4/2018 |
| RU | 2162711 | | 2/2001 |
| RU | 2283665 | C2 | 9/2006 |
| RU | 2453303 | C1 | 6/2012 |
| RU | 2552929 | C1 | 6/2015 |
| RU | 2758092 | C1 | 10/2021 |
| WO | 1992/19259 | | 11/1992 |
| WO | 1994/14975 | | 7/1994 |
| WO | 2001/092340 | | 12/2001 |
| WO | 2003/048083 | | 6/2003 |
| WO | 2005/047331 | | 5/2005 |
| WO | 2005/085284 | | 9/2005 |
| WO | 2006/003407 | | 1/2006 |
| WO | 2006/072564 | | 7/2006 |
| WO | 2006/083390 | | 8/2006 |
| WO | 2008/054606 | | 5/2008 |
| WO | 2008/116149 | | 9/2008 |
| WO | 2009/124954 | | 10/2009 |
| WO | 2010/053751 | | 5/2010 |
| WO | 2010/065557 | | 6/2010 |
| WO | 2010/120524 | | 10/2010 |
| WO | 2011/026966 | | 3/2011 |
| WO | 2012/047954 | | 4/2012 |
| WO | 2012/094643 | | 7/2012 |
| WO | 2012/177945 | | 12/2012 |
| WO | 2013/051928 | | 4/2013 |
| WO | 2013/088109 | | 6/2013 |
| WO | 2013/116287 | | 8/2013 |
| WO | 2013/155010 | | 10/2013 |
| WO | 2014/031610 | | 2/2014 |
| WO | 2014/039461 | | 3/2014 |
| WO | 2014/059178 | | 4/2014 |
| WO | 2014/122144 | | 8/2014 |
| WO | 2014/197470 | | 12/2014 |
| WO | 2014/205365 | | 12/2014 |
| WO | 2015/006571 | | 1/2015 |
| WO | 2015/127229 | | 8/2015 |
| WO | 2016/077675 | | 5/2016 |
| WO | 2017/143270 | | 8/2017 |

(56) References Cited

FOREIGN PATENT DOCUMENTS

| | | |
|---|---|---|
| WO | 2018/035393 | 2/2018 |
| WO | 2018/045130 | 3/2018 |
| WO | 2018/057776 | 3/2018 |
| WO | 2018/151836 | 8/2018 |
| WO | 2018/201051 | 11/2018 |
| WO | 2019/089473 | 5/2019 |
| WO | 2021/195530 | 9/2021 |
| WO | 2022/076289 A | 4/2022 |

OTHER PUBLICATIONS

Van Assche, Gert, et al., "Management of loss of response to anti-TNF drugs: Change the dose or change the drug?", Journal of Crohn's and Colitis, vol. 2, No. 4, Dec. 1, 2008, pp. 348-351.

Silverberg et al., "Atopic Dermatitis: Update on Pathogenesis and Comorbidities", Curr Derm Rep (2012) 1:168-178.

Wikipedia, "Mycosis fungoides", retrieved from: https://en.wikipedia.org/w/index.php?title=Mycosis_fungoides&oldid=1156079659, obtained on May 31, 2023, 9 pages.

Callewaert, Chris et al., "IL-4Ra Blockade by Dupilumab Decreases Staphlyococcus aureus Colonization and Increases Microbial Diversity in Atopic Dermatitis", Journal of Investigative Dermatology (2020) 140, 191-202.

Prokofieva, L.V. et al., "A course of lectures on general pharmacology: a teaching aid", Ulyanovsk: UIGU, 2017, p. 155, p. 15, paragraph 7, with English translation of specified paragraph, 156 pgs. total.

Russian Office Action in Application 2020140639 mailed Jan. 12, 2023, with English translation, 9 pages.

Oosterhaven, Jart et al., "Dupilumab Treatment of Very Severe Refractory Atopic Hand Eczema", JAMA Dermatology, vol. 154, No. 8, Aug. 1, 2018, p. 969-70.

Anonymous, ClinicalTrials.gov Record History; ver. 3: Sep. 3, 2021, pp. 1-12, retrieved on Feb. 2, 2024 from https://clinicaltrials.gov/study/NCT03861455?tab=history&a=3, entitled "Efficacy and Safety of Dupilumab Chronic Hands Eczema Refractory to Highly Potent Topical Corticosteroids (Dupeczemain)", last updated Aug. 23, 2023.

Silverberg, Jonathan et al., "Dupilumab provides clinical benefits to patients with atopic dermatitis who do not achieve clear or almost clear skin according to the Investigator's Global Assessment: a pooled analysis of data from two phase III trials", British Journal of Dermatology, John Wiley, UDS, vol. 181, No. 1, Apr. 11, 2019, pp. 80-87.

Cole, Patrick et al., "Dupilumab. Anti-IL-4Ralpha monoclonal antibody, treatment of atopic dermatitis, treatment of asthma", Drugs of the Future, vol. 40, No. 1, Jan. 1, 2015, pp. 7-13.

Brancaccio, R. et al., "0606: Dupilumab efficacy in different atopic dermatitis phenotypes", Allergy, vol. 75, No. S109, Aug. 1, 2020, p. 442, retrieved from the internet: https://onlinelibrary.wiley/com/doi/10.1111/all.14508.

Tokura et al., "Extrinsic and intrinsic types of atopic dermatitis", Journal of Dermatological Science, Elsevier, vol. 58, No. 1, Apr. 1, 2010, pp. 1-7.

Nettis et al., "Efficacy of dupilumab in atopic comorbidities associated with moderate-to-severe adult atopic dermatitis", Allergy, Wiley-Blackwell Publishing Ltd., UK, vol. 75, No. 10, May 18, 2020, pp. 2653-2661.

Ichiyama, Susumu et al., Letters to the Editor: "Severe atopic dermatitis effectively treated with dupilumab changed from interleukin-5 inhibitors for concomitant severe bronchial asthma", Journal of Dermatology, vol. 48, No. 2, Nov. 8, 2020, pp. e76-e77.

D'Adamio et al., "A life with atopic dermatitis: the patient's point of view after the new hope with dupilumab", Clinical and Experimental Dermatology, Blackwell Scientific Publications, GB, vol. 45, No. 6, May 30, 2020, pp. 809-810.

Boguniewicz, Mark et al., 27406 Abstract: "Dupilumab improves signs and symptoms of severe atopic dermatitis in children aged 6-11 years with or without comorbid asthma", Journal of the American Academy of Dermatology, Mosby, Inc., vol. 85, No. 3, Aug. 7, 2021, 1 page.

Agache, Ioana et al., "EAACI Biologicals Guidelines-dupilumab for children and adults with moderate-to-severe atopic dermatitis", Allergy, Wiley-Blackwell, UK, vol. 76, No. 4, Dec. 27, 2020, pp. 988-1009.

Regeneron: "Dupixent: Highlights of Prescribing Information", Mar. 1, 2019, retrieved from the internet on Aug. 1, 2019 at: https://dlegnxy4jx1q3f.cloudfront.net/Regeneron/Dupixent_FPI.pdf, 13 pages total.

Paller, Amy et al., "The atopic march and atopic multimorbidity: Many trajectories, many pathways", Journal of Allergy and Clinical Immunology, vol. 143, No. 1, Nov. 17, 2018, pp. 46-55.

Czarnowicki, Tali et al., "Novel concepts of prevention and treatment of atopic dermatitis through barrier and immune manipulations with implications for the atopic march", Journal of Allergy and Clinical Immunology, vol. 39, No. 6, Jun. 2, 2017, pp. 1723-1734.

Czarnowicki, Tali et al., "Circulating CLA+ T cells in atopic dermatitis and their possible role as peripheral biomarkers", Allergy, vol. 72, No. 3, Dec. 15, 2016, pp. 366-372.

Clinical Trials.gov Identifier NCT03054428, "Efficacy and Safety of Dupilumab in Participants ≥12 to <18 Years of Age, With Moderate-to-severe Atopic Dermatitis", ClinicalTrials.gov ID NCT03054428, located online on Mar. 4, 2024 at: URL: https://clinicaltrials.gov/study/NCT03054428?term=nct03054428&limit=10&rank=1, 16 pgs.

Akademik, Medical Encyclopedia, "Treatment", located online on Mar. 4, 2024 at: https://dic.academic.ru/dic.nsf/enc_medicine/16487/%D0%9B%D0%B5%D1%87%D0%B5%D0%BD%D0%B8%D0%B5, 8 pages.

Eichenfield, Lawrence et al., "Guidelines of Care for the Management of Atopic Dermatitis: Part 1: Diagnosis and Assessment of Atopic Dermatitis", Feb. 2014, J. Am. Acad. Dermatol. 70:338-51.

Boguniewicz, Mark et al., "Recent insights into atopic dermatitis and implications for management of infectious complications", Journal of Allergy and Clinical Immunology, Jan. 2010, 125(1):4-13.

Applicant's submission filed during examination proceedings on Aug. 8, 2019 (Re: EP Patent App. 15710650.1-1116 from Dr. David Power), 4 pages.

Brandt and Sivaprasad, "Th2 Cytokines and Atopic Dermatitis", J Clin Cell Immunol Aug. 10, 2011;2(3):110 (13 pages).

Lebwohl et al., "Pathways to Managing Atopic Dermatitis—Consensus from the Experts", J Clin Aesthet Dermatol. Jul. 2013;6(7 Suppl):S2-S18.

Biedermann, "Dissecting the Role of Infections in Atopic Dermatitis", Acta Derm Venereol 2006; 86(2):99-109. Published: May 2, 2006.

Leung, "New Insights into Atopic Dermatitis: Role of Skin Barrier and Immune Dysregulation", Allergol Int. Jun. 2013;62(2):151-161.

Abstracts of "6th International Investigative Dermatology Meeting" May 8-11, 2013 in Edinburgh, Scotland, United Kingdom, J Invest Dermatol. 2013 TM13 May;133 Suppl 1: S1-311.

Bieber et al., "Dupilumab Monotherapy in Adults with Moderate-to-Severe Atopic Dermatitis: A 12-Week, Randomized, Double-Blind, Placebo-Controlled Study", J Allergy Clin Immunol. Feb. 2014;133(2 Suppl):AB404. Available online: Jan. 23, 2014; https://www.sciencedirect.com/science/article/abs/pii/S0091674913029886.

Printout of the website of ScienceDirect showing that D13 (Bieber abstract AB404) was available online as of Jan. 23, 2014 (3 pages).

Correspondence (email) with the Editors of the Journal of Allergy and Clinical Immunology about publication date of D13 (Bieber abstract AB404), 4 pgs.

Bosshardt et al., "Necrotizing soft-tissue infections", In: "Surgical Treatment—Evidence-Based and Problem-Oriented", edited by RG Holzheimer and JA Mannick, W. Zuckschwerdt Verlag Munchen, 2001, p. 655-660.

U.S. Centers for Disease Control and Prevention (CDC)—excerpt on Ringworm and Fungal Nail Infections (Apr. 4, 2024), 3 pgs.

MSD Manual—Professional Version, excerpt on Cellulitis (Jun. 2023), 9 pages.

(56) References Cited

OTHER PUBLICATIONS

Akdis et al.; 2006; J. Allergy Clin. Immunol; vol. 118; pp. 152-169; "Diagnosis and treatment of atopic dermatitis in children and adults", European Academy of Allergology and Clinical Immunology/ American Academy of Allergy, Asthma and Immunology/Practall Consensus Report; doi: 10.1016/j.jaci.2006.03.045 (18 pgs).
Bieber; 2008; N. Engl. J. Med.; vol. 358; pp. 1483-1494; Review Article, "Mechanisms of Disease: Atopic Dermatitis".
Bieber; 2010; Ann. Dermatol.; vol. 22, No. 2; pp. 125-137; "Atopic Dermatitis"; doi: 10.5021/ad.2010.22.2.125.
Ong et al.; 2010; Immunol. Clin. N. Am.; vol. 30; pp. 309-321; "The Infectious Aspects of Atopic Dermatitis"; doi:10.1016/j.jac.2010.05.001.
Boguniewicz et al.; 2011; Immunological Reviews; vol. 242; pp. 233-246; "Atopic dermatitis: a disease of altered skin barrier and immune dysregulation".
Boguniewicz et al., "Atopic dermatitis", Clin. Pearls, J Allergy Clin Immunol 2006;118:40-3, Jun. 5, 2006.
Wollenberg et al., "Viral infections in atopic dermatitis: pathogenic aspects and clinical management", J Allergy Clin Immunol 2003; 112: 667-74. Oct. 2003.
Howell et al., "Mechanism of HBD-3 deficiency in atopic dermatitis", Clin Immunol 2006; 121: 332-8. Oct. 2, 2006.
Remitz et al., "Letters to the Editor", J Allergy Clin Immunol. Jan. 2001;107(1):196-7.
Gilles Paintaud, Pharmacocinetique des anticorps Monoclonaux, Medecine/Sciences 2009;25:1057-62.
Gibaldi, Biopharmaceutics and clinical pharmacokinetics, Fourth Edition, 1991, p. 12-13 re: dosing.
Chapter 19, "Dosage Regimens" of Aulton's Pharmaceuticals: The Science of Dosage Form Design, 2nd Edition 2001, 16 pages.
Panaccione and Ghosh, "Optimal use of biologics in the management of Crohn's disease", Therapeutic Advances in Gastroenterology 2010, 3(3), 179-189.
Mould and Green, "Pharmacokinetics and Pharmacodynamics of Monoclonal Antibodies", Concepts and Lessons for Drug Development, 2010, Biodrugs 24(1), 23-39.
Eisenstein, "Something new under the skin", Nature Biotechnology, Feb. 2011, 29(2), 107-109.
Tauber et al., "*Staphylococcus aureus* density on lesional and nonlesional skin is strongly associated with disease severity in atopic dermatitis", J Allergy Clin Immunol 2016; 137:1272-1274. Nov. 11, 2015.
Infection v. Colonization. Multi Drug-Resistant Organisms Management in Long Term Care Facilities Workshop Louisiana Office of Public Health Healthcare-Associated Infections Program, https://ldh.la.gov/assets/oph/Center-PHCH/Center-CH/infectiousepi/HAI/MDRO2017/handouts/ColonizationvInfection.pdf, 2017, 7 pages.
CDR Clinical Review Report for Dupixent (Appendix 4), Cadth Common Drug Review, 117-127, Jun. 2020, 11 pages.
Nilsson EJ, Henning CG, Magnusson J., "Topical corticosteroids and *Staphylococcus aureus*in atopic dermatitis", J Am Acad Dermatol. Jul. 1992;27(1):29-34.
He et al., "Mild atopic dermatitis lacks systemic inflammation and shows reduced nonlesional skin abnormalities", J Allergy Clin Immunol. Apr. 2021;147(4):1369-1380.
Ogonowska et al., "Colonization with *Staphylococcus aureus* in Atopic Dermatitis Patients: Attempts to Reveal the Unknown", Front Microbial. Jan. 11, 2021 ;11: 567090. Jan. 2021.
Spergel, J. and Paller, A., "Atopic dermatitis and the atopic march", Journal of Allergy and Clinical Immunology, vol. 112, Issue 6, Supplement, 2003, pp. S118-S127.
EMA, Annex I, Summary of product characteristics for dupilumab, Sep. 2, 2022, 7 pages.
Chong AC, Visitsunthorn K, Ong PY, "Genetic/Environmental Contributions and Immune Dysregulation in Children with Atopic Dermatitis", J Asthma Allergy. Nov. 23, 2022; 15:1681-1700.
U.S. Appl. No. 61/946,237, certified copy, 96 pages. (referred to as "P1" in 76 opposition proceedings).
U.S. Appl. No. 61/952,245, 100 pages. (referred to as "P2" in 76 opposition proceedings).
U.S. Appl. No. 61/986,371, 103 pages. (referred to as "P3" in 76 opposition proceedings).
EP 140306476.4, filed Sep. 24, 2014, 95 pages. (referred to as "P4" in 76 opposition proceedings).
U.S. Appl. No. 62/100,128, 109 pages. (referred to as "P5" in 76 opposition proceedings).
Pages 159 to 162 of Rispens and Vidarsson, Antibody Fc: Linking Adaptive and Innate Immunity, Chapter 9, "Human IgG Subclasses", pp. 159 to 162, 2013; and evidence of its publication date, 8 pgs.
Regeneron Pharmaceuticals, Inc., SEC Form 8-K dated Mar. 4, 2024, including Exhibit 99.1: Bieber T. et al. Dupilumab Monotherapy in Adults with Moderate-to-Severe Atopic Dermatitis: A 12-Week, Randomized, Double-Blind, Placebo Controlled Study ("Bieber et al."), 23 pages.
Furue, M. et al., "Correlation between serum thymus and activation-regulated chemokine levels and stratum corneum barrier function in healthy individuals and patients with mild atopic dermatitis", J Dermatol Sci. Apr. 2012;66(1 ):60-3. doi: 10.1016/j.jdermsci.2012.01.011, Epub Feb. 16, 2012, PMID: 22391243, 4 pgs.
Guttman-Yassky E. et al., "Contrasting pathogenesis of atopic dermatitis and psoriasis-part II: immune cell subsets and therapeutic concepts", J Allergy Clin Immunol. Jun. 2011;127(6):1420-32. doi: 10.1016/j.jaci.2011.01.054, Epub Mar. 21, 2011, PMID: 21419481, 9 pages.
Ong P.Y. et al., "Endogenous antimicrobial peptides and skin infections in atopic dermatitis", N Engl J Med., Oct. 10, 2002;347(15):1151-60. doi: 10.1056/NEJMoa021481, PMID: 12374875.
Thaci et al., "Safety and Efficacy of Dupilumab Versus Placebo for Moderate-to-Severe Atopic Dermatitis in Patients Using Topical Corticosteroids (TCS): Greater Efficacy Observed with Concomitant Therapy Compared to TCS Alone", Abstract 664, J Allergy Clin Immunol, Feb. 2014, AB192 Abstracts, 1 page.
Marques et al., "Nanotechnology-based topical delivery of natural products for the management of atopic dermatitis", Pharmaceutics, 2023, 15: 1-37.
Karamova et al., "Assessment of the severity of atopic dermatitis—SCORAD and EASI", Vestnik Dermatologii I Venerologii, 2022; 98(3):53-60; English translation precedes the Russian language article.
Forooghian, Farzin et al., "Tachyphylaxis Following Intravitreal Bevacizumab for Exudative Age-Related Macular Degeneration", Retina, Jun. 2009, 29(6): 723-731, retrieved from: https://www.ncbi.nlm.nih.gov/pmc/articles/PMC2770842/pdf/nihms-139616.pdf.
Gasperini, Julie et al., "Bevacizumab and ranibizumab tachyphylaxis in the treatment of choroidal neovascularisation", British Journal of Opthalmology, vol. 96, No. 1, Jul. 26, 2011, pp. 14-20.
Jorge, E. et al., "Dupilumab for off-label treatment of moderate to severe childhood atopic dermatitis", Sep. 2018, Cutis, 102(3); 201-204.
Werfel et al., 2012; Textbook "Allergy" by Drs. Stephen Holgate, Martin, Church, David Broide, and Fernando Martinez, chapter 13 on "Atopic dermatitis and allergic contact dermatitis", Elsevier Ltd.; ISBN 978-0-7234-3658-4; https://doi.ora/10.1016/C2009-0-46113-0, 24 pgs.
WHO Drug Information, vol. 26, No. 4, 2012, Proposed INN, List 108, published on Dec. 9, 2012 (see also: https://www.who.int/publications/m/item/innpl-108), 73 pgs.
Beck et al (Supplementary Appendix), 42 pages.
Beck et al (Protocol), 420 pages.
Cohen et al., "Pharmacokinetics of Subcutaneous Dupilumab Injection With an Autoinjector Device or Prefilled Syringe", Clin Pharmacol Drug Dev., 2022;11 (5):675-681.
Thaci et al., (w/Supplementary Appendix), 34 pgs.
Bai et al., "A Guide to Rational Dosing of Monoclonal Antibodies", Clin Pharmacokinet, 2012; 51 (2): 119-135. Oct. 18, 2012.
U.S. Appl. No. 62/397,988, certified copy, 57 pages.
U.S. Appl. No. 62/442,083, certified copy, 72 pgs.
U.S. Appl. No. 62/443,819, certified copy, 76 pgs.
U.S. Appl. No. 62/445,774, certified copy, 80 pgs.

(56) References Cited

OTHER PUBLICATIONS

U.S. Appl. No. 62/519,896, certified copy, 86 pgs.
NCT02755649, Aug. 2016, National Library of Medicine, clinicaltrials.gov, 13 pages.
Werfel et al., Jan. 2016, Dtsch. Dermatol. Ges., 14(1):92-106; "S2k guideline on diagnosis and treatment of atopic dermatitis—short version"; 14 pages, https://doi: 10.1111 /ddq.12871. ("Werfel 2").
Ring et al., 2012, J. Eur. Acad. Derm. Vener., vol. 26, pp. 1176-1193, "Guidelines for treatment of atopic eczema (atopic dermatitis) Part II"; https://doi:10.1111/j.1468-3083.2012.04636.x. ("Ring (1)".
Ring, Mar. 2016, Textbook "Atopic Dermatitis—Eczema", Springer International Publishing Switzerland, ISBN 978-3-319-22242-4; https://doi.org/10.1007/978-3-319-22243-01, 241 pgs. ("Ring (2)").
Eichenfield et al., 2014, J. Am. Acad. Dermatol., vol. 71, No. 1, pp. 116-132; "Guidelines of care for the management of atopic dermatitis Section 2. Management and treatment of 2 atopic dermatitis with topical therapies"; http://dx.doi.org/10.1016/j.jaas.2014.03.023. ("Eichenfield 2").
Sidbury et al, 2014, J. Am. Acad. Dermatol., vol. 71, No. 2, pp. 327-349; "Guidelines of care for the management of atopic dermatitis Section 3. Management and treatment with phototherapy and systemic agents"; http://dx.doi.org/10.1016/j.jaas.2014.03.030. ("Sidbury").
Supplementary Appendix to D2, pdf dated Oct. 3, 2016, 84 pages.
Simpson et al., (Trial Protocol), PDF updated May 26, 2017, 620 pgs.
Supplementary Appendix to Blauvelt 2017, the Lancet, 46 pages.
Clinical study record for NCT01639040, Version 6, Sep. 27, 2013.
Clinical study record for NCT02277743 "Solo 1", Version 17, Aug. 16, 2016, 8 pages.
Clinical study record for NCT02277769 "Solo 2", Version 15, Feb. 26, 2016.
Regeneron Press Release: "Regeneron and Sanofi announce positive dupilumab topline results from two Phase 3 trials in inadequately controlled moderate-to-severe atopic dermatitis patients", Apr. 1, 2016, 4 pages.
Clinical study record for NCT02260986 "Chronos", Version 17, Sep. 2, 2016.
Regeneron Press Release: "Regeneron and Sanofi announce that dupilumab used with topical corticosteroids (TCS) was superior to treatment with TCS alone in long-term Phase 3 trial in inadequately controlled moderate-to-severe atopic dermatitis patients", Jun. 6, 2016, 4 pgs.
Bieber and Straeter, "Off-label prescriptions for atopic dermatitis in Europe", Allergy, 2015, vol. 70, 6-11.
Leshem et al., "What the Eczema Area and Severity Index score tells US about the severity of atopic dermatitis and interpretability study", British Journal of Dermatology, vol. 172, 1353-1357, 2015.
McGregor et al., "Dupilumab for the treatment of atopic dermatitis: A clinical trial review", Expert Opin. Biol. Ther., vol. 15(11), 1657-1660, 2015.
Tsianakas and Luger, "The anti-IL-4 receptor alpha antibody dupilumab: facing a new era in treating atopic dermatitis", Expert Opin. Bio. Ther., vol. 15(11), 1661-1664, 2015.
Dupixent FDA Approval call with investors, Mar. 28, 2017, 15 pgs.
Press release: "Sanofi and Regeneron Announce Positive Study Results for Dupixent (dupilumab) in Patients with Moderate-to-Severe Atopic Dermatitis", https://www.sanofi.com/en/mediaroom/press_releases/2017/2017-09-16-06-15-00-1123825, dated Sep. 16, 2017, 5 pages.
EMA, Annex I Summary of Product Characteristics for Dupilumab, 7 pages.
Oct. 2016—IR call—Dupilumab https://www.slideshare.net/slideshow/201610-ir-calldupilumab/66670161, 35 pgs.
Periman et al., "A Review of the Mechanism of Action of Cyclosporine A: The Role of Cyclosporine A in Dry Eye Disease and Recent Formulation Developments", Clinical Ophthalmology, 2020:14 4187-4200.
Hanifin et al., "The eczema area and severity index (EASI): assessment of reliability in atopic dermatitis", Exp Dermatol 2001: 10: 11-18.
Schram et al., "EASI, (objective) SCORAD and POEM for atopic eczema: responsiveness and minimal clinically important difference", Allergy, 67, 99-106.
De Bruin-Weller et al., Allergy 2017, vol. 72, No. Suppl. 103, pp. 46-47.
De Bruin-Weller et al., Allergy 2017, vol. 72, No. Suppl. 103, pp. 47-48.
NCT01949311; "Open-label Study of Dupilumab in Patients With Atopic Dermatitis", version 4: Jul. 12, 2016.
Patentee's submission dated Dec. 2, 2020. (letter from JA Kemp to EPO), 7 pages.
Patentee's submission dated Aug. 24, 2022. (letter from JA Kemp to EPO), 4 pages.
Official confirmation that D3 ("IR Thematic Call on Dupilumab") was published on Oct. 3, 2016 (in German).
English translation of D3a email ("IR Thematic Call on Dupilumab").
Abstracts of the Australasian College of Dermatologists, 49th Annual Scientific Meeting, first published: Apr. 20, 2016, 83 pages.
Regeneron Pharmaceuticals Inc., Annual report on Form 10-K for the fiscal year 2015; Filing date: Feb. 11, 2016, 197 pgs.
Screenshot showing that D6 was archived on Wayback Machine on Apr. 9, 2016.
Guidance for Applicants wishing to apply for a Promising Innovative Medicines designation, publ. Dec. 18, 2014, Gov.UK, 20 pgs.
A Study to Assess the Efficacy and Safety of Dupilumab in Participants . . . version 3, first published: Aug. 24, 2016.
Official confirmation from ClinicalTrials.gov that D11 was published no later than Apr. 26, 2016.
Heavy and light chain amino acid sequences of dupilumab, published on Apr. 22, 2015.
UK Summary of Product Characteristics for Dupixent.
Khattri et al., Journal of Allergy and Clinical Immunology, 2014, vol. 133, issue 6, pp. 1626-1634, 9 pgs., published Apr. 28, 2014.
EP 17306081.5 filed Aug. 18, 2017, 77 pages.
WHO Child Growth Standards, Centers for Disease Control and Prevention (Year: 2009).
Kircik, Leon et al., "Transepidermal water loss (TEWL) and corneometry with hydrogel vehicle in the treatment of atopic dermatitis: a randomized, investigator-blind pilot study", J Drugs Dermatol., 2012, vol. 11(2):180-184 (abstract).
Kamal, Mohamed et al., "The Posology of Dupilumab in Pediatric Patients with Atopic Dermatitis", Clinical Pharmacology and Therapeutics, vol. 110, No. 5, Nov. 2021, pp. 1318-1328.
Simpson, Eric et al., "Efficacy and Safety of Dupilumab in Adolescents With Uncontrolled Moderate to Severe Atopic Dermatitis: A Phase 3 Randomized Clinical Trial", JAMA Dermatol. 2020; 156(1):44-56.
Oosterhaven, Jart et al., "Effect of dupilumab on hand eczema in patients with atopic dermatitis: An observational study", Journal of Dermatology 2019; 46: 680-685.
Voorberg, Angelique et al., "The long-term effect of dupilumab on chronic hand eczema in patients with moderate to severe atopic dermatitis—52 week results from the Dutch BioDay Registry", Contact Dermatitis, 2022; 87: 185-191.
Voorberg, Angelique et al., "Efficacy and safety of dupilumab in patients with severe chronic hand eczema with inadequate response or intolerance to alitretinoin: a randomized, double-blind, placebo-controlled phase IIb proof-of-concept study", British Journal of Dermatology, 2023; 189: 400-409.
Zirwas, Matthew, "Dupilumab for hand eczema", Research Letters, J Am Acad Dermatol, 2018, vol. 79, No. 1, pp. 167-169.
Waldman, Reid et al., "Dupilumab for the treatment of dyshidrotic eczema in 15 consecutive patients", Research Letters, J Am Acad Dermatol, 2021, vol. 82, vol. 5, pp. 1251-1252.
Weston, Gillian et al., "Dupilumab in the Treatment of Dyshidrosis: A Report of Two Cases", Journal of Drugs in Dermatology, Mar. 2018, vol. 17, Issue 3, pp. 355-356.
Sela-Culang et al., "The structural basis of antibody-antigen recognition", Frontiers in. Immunology, vol. 4: Article 302, Oct. 2013, 13 pages.

(56) References Cited

OTHER PUBLICATIONS

Dotti, Gianpietro et al., "Design and Development of Therapies using Chimeric Antigen Receptor-Expressing T cells", Immunol Rev 257(1):107-126, Jan. 2014.
Frankel, Hillary et al., "Comparative Effectiveness of Topical Calcineurin Inhibitors in Adult Patients with Atopic Dermatitis", American Journal of Clinical Dermatology, vol. 14, No. 2, Apr. 1, 2012, pp. 113-123.
Treister, Alison et al., "Long-term off-label dupilumab in pediatric atopic dermatitis: A case series", Pediatric Dermatology 2019; 36(1):85-88.
Regeneron, "Positive Phase 3 Trial of Dupixent(R)( Dupilumab) in Adolescents With Inadequately Controlled Moderate-To-Severe Atopic Dermatitis", [online], 2018, <URL: https://investor.regeneron.com/news-releases/news-release-details/positive-phase-3-trial-dupixentr-dupilumab-adolescents/> searched on Jul. 20, 2024, 6 pages.
De Bruin-Weller, M. et al., "Dupilumab with concomitant topical corticosteroid treatment in adults with atopic dermatitis with an inadequate response or intolerance to ciclosporin A or when this treatment is medically inadvisable: a placebo-controlled, randomized phase III clinical trial (Liberty AD Cafe)", British Journal of Dermatology (2018) 178, pp. 1083-1101.
Abonia et al. (Apr. 2013) Journal of Allergy Clin Immunol "High prevalence of eosinophilic esophagitis in patients with inherited connective tissue disorders", vol. 132, No. 2, pp. 378-386.
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.
Aceves et al. (Feb. 29, 2009) Immunol Allergy Clin N Am 29:197-211 "Relationships Between Eosinophilic Inflammation, Tissue Remodeling, and Fibrosis in Eosinophilic Esophagitis".
Akinlade, B. et al: "Conjunctivitis in dupilumab clinical trials", British Journal of Dermatology, (Mar. 9, 2019), pp. 1-15.
Akiyama, et al., A Study on Indoor Allergens Measured in Home Environments of Adult-Asthmatic Patients, Housing Research Foundation, Research Annual Report, 1997, No. 24, Study No. 9620, 1-10, English Synopsis Only.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (Aug. 10, 2011) Gastroenterology, vol. 141, No. 5, pp. 1593-1604, "An Antibody Against IL-5 Reduces Numbers of Esophageal Intraepithelial Eosinophils in Children with Eosinophilic Esophagitis".
Assa'ad, Amal, What is new in the Treatment of Eosinophilic Eosophagitis? Clinical and Translational Allergy 2011 (Suppl 1):S69, doi: 10.1186/2045-7022-1-S 1-S69.
Ayars, Andrew G. et al., "Pharmacologic Therapies in Pulmonology and Allergy", 2016 Med Clin N Am 100(4): 851-868.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balint and Larrick, (Dec. 27, 1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (Nov. 3, 2008) The Journal of Clinical Investigation 118(11):3546-3556 "The cytokine network in asthma and chronic obstructive pulmonary disease".
Barthelemy, Pierre et al., "Comprehensive analysis of the factors contributing to the stability and solubility of autonomous human VH domains", Journal of Biological Chemistry, 2008, 283:3639-3654.
Bateman et al. (2004) Am. J. Respir. Crit. Care Med. 170:836-844 "Can guideline-defined asthma control be achieved?", The Gaining Optimal Asthma Control Study.
Beck et al. (Jul. 10, 2014) New England Journal of Medicine 371(2): 130-139 "Dupilumab treatment in adults with moderate-to-severe atopic dermatitis".
Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.
Bergmann, M.M. et al., "Evaluation of Food Allergy in Patients with Atopic Dermatitis", J Allergy Clin Immunol, 1, pp. 22-28, Jan. 1, 2013.
Beyer et al. (Apr. 2, 2002) Journal of Allergy Clin Immunol 109(4):707-713 "Human milk-specific mucosal lymphocytes of the gastrointestinal tract display a TH2 cytokine profile".
Bhardwaj and Ghaffari (Sep. 2012) Annals of Allergy, Asthma & Immunol 109 (3):155-159 "Biomarkers for eosinophilic esophagitis: a review".
Bieber, T., et al., "Atopic dermatitis: a candidate for disease-modifying strategy," Allergy 67 (2012) 969-975.
Blanchard and Rothenberg, (Feb. 2009) Immunol Allergy Clin N Am 29 (1):141-148 "Chemotactic Factors Associated with Eosinophilic Gastrointestinal Diseases".
Blanchard et al. (Jan. 1, 2011) J Allergy Clin Immunol 127(1):208-217 "A striking local esophageal cytokine expression profile in eosinophilic esophagitis".
Blanchard et al. (Dec. 2, 2007) Journal of Allergy Clin Immunol 120(6); 1292-1300, "IL-13 involvement in eosinophilic esophagitis: Transcriptome analysis and reversibility with glucocorticoids".
Blanchard et al. (Feb. 2006) The Journal of Clinical Investigation 116(2): 536-47, "Eotaxin-3 and a uniquely conserved gene-expression profile in eosinophilic esophagitis".
Blanchard et al. (Apr. 2010) The Journal of Immunology "Coordinate Interaction between IL-13 and Epithelial Differentiation Cluster Genes in Eosinophilic Esophagitis" vol. 184, No. 7, pp. 4033-4041.
Blanchard et al. (Aug. 24, 2005) Clin Exp Allergy 35 (8):1096-1103 "Inhibition of human interleukin-13-induced respiratory and oesophageal inflammation by anti-human-interleukin-13 antibody (CAT-354)".
Blankestijn, Mark et al., "Could Duratumumab be used to treat severe allergy?", Journal of Allergy and Clinical Immunology, vol. 139, No. 5, Jan. 19, 2017, p. 1677-1678.e3.
Blauvelt, Andrew, et al., "Long-term management of moderate-to-severe atopic dermatitis with dupilumab and concomitant topical corticosteroids (Liberty AD Chronos): a 1-year, randomised, double-blinded, placebo-controlled, phase 3 trial," www.thelancet.com, published online May 4, 2016, http://dx.doi.org/10.1016/S0140-6736(17)31191-1, 65 pgs.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
BSACI News Report confirming BSACI conference date of Jul. 8-10, 2013, 2 pages.
Buddenkotte, J. et al., "Pathophysiology and therapy of pruritis in allergic and atopic diseases", Allergy 65 (2010), 805-821.

(56) References Cited

OTHER PUBLICATIONS

Burmeister-Getz et al. (2009) J. Clin. Pharmacol. 49:1025-1036, "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology 6(4); 740-50, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carr, Warner, "Topical Calcineurin Inhibitors for Atopic Dermatitis: Review and Treatment Recommendations", Pediatric Drugs, 2013, vol. 15, pp. 303-310.
Carter, Paul J., (May 2006) The Journal of Immunology 6:(5);343-357 "Potent Antibody Therapeutics by Design".
Casset et al. (2003) Biochemical and Biophysical Research Communication 307:198-205 "A peptide mimetic of an anti-CD4 monoclonal antibody by rational design".
Celakovska, J. et al., "Sensitization to aeroallergens in atopic dermatitis patients: association with concomitant allergic diseases", JEADV 2015; 29, 1500-1505.
Choi, Yoonjoo et al., "Predicting antibody complementarity determining region structures without classification", Molecular Biosystems, 2011, 7:3327-334.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Chan, L.S. et al., "Expression of Interleukin-4 in the epidermis of transgenic mice results in pruritic inflammatory skin disease: an experimental animal model to study atopic dermatitis", J. Invest. Dermatol., Oct. 1, 2001, 117(4): 977-983.
Chehade and Sampson (Feb. 2009) Immunol Allergy Clin N Am 29:149-158 "The Role of Lymphocytes in Eosinophilic Gastrointestinal Disorders".
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, 10 pages, Available from: https://clinicaltrials.gov/ct2/show/NCT01312961.
Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients with Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov Identifier: NCT02407756; Last Update posted Aug. 22, 2016, A Study to Determine the Safety and Tolerability of Dupilumab (REGN668/SAR231893) in Patients Aged >6 to <18 Years with Atopic Dermatitis (Eczema), 11 pages.
Collins, Margaret H et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.
Corren et al., "A Randomized, Controlled, Phase 2 Study of AMG 317, an IL-4R Antagonist, in Patients with Asthma", (2010) American Journal of Respiratory and Critical Care Medicine 181(8):788-796.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
Cortes, J.R., et al., Proton pump inhibitors inhibit IL-4 and IL-13 signaling stat6 activation, European Journal of Immunology, (Sep. 2009) vol. 39, p. 5204, Supp.
Darsow, Ulf et al., "Pruritus and Atopic Dermatitis", Clinic Rev Allerg Immunol (2011) 41:237-244.
Database EMBase [Online], Elsevier Science Publishers, Amsterdam, NL; (May 1, 2019), Cork M. J: "605 Efficacy and safety of dupilumab in adolescent patients with moderate-to-severe atopic dermatitis", XP002793331, Database accession No. EMB-002001809007 abstract.
Database EMBase [Online], Elsevier Science Publishers, Amsterdam, NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract.
Davies et al. (1996) Immunotechnol. 2(3):169-179 "Affinity improvement of single antibody VH domains: residues in all three hypervariable regions affect antigen binding".
Davis (Aug. 2004) Seminars in Immunology 16(4):239-243 "The evolutionary and structural 'logic' of antigen receptor diversity".
De Genst, Erwin et al., "Antibody repertoire development in camelids", Developmental and Comparative Immunology, 30 (2006); 187-198.
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the Heroes Study", Oct. 14-19, 2016, retrieved from the Internet on Sep. 20, 2018 at: https://www.eventscribe.com/2016/ACG/QRcode.asp?Pres=178380, 3 pages.
Dellon, Evan Se., (Apr. 27, 2013) Dig Dis Sci, vol. 58, pp. 1445-1448, "The Pathogenesis of Eosinophilic Esophagitis: Beyond the Eosinophil".

(56) References Cited

OTHER PUBLICATIONS

Desreumaux et al. (Mar. 1, 1996) Gastroenterology 110(3):768-774 "Interleukin 3, Granulocyte-Macrophage Colony-Stimulating Factor, and Interleukin 5 in Eosinophilic Gastroenteritis".
Dupixent (dupilumab) Injection, for Subcutaneous Use, Patient Information, Issued Mar. 2017, 34 pages.
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, mailed Feb. 22, 2019, 34 pages.
Fillon et al. (2009) Immunol Allergy Clin N Am 29(1):171-178 "Epithelial Function in Eosinophilic Gastrointestinal Diseases".
Finkelman, Fred, et al., "Regulation of murine in vivo IgG and IgE responses by a monoclonal anti-IL-4 receptor antibody", Jun. 1991;3(6); 599-607.
Foote and Winter (1992) J. Mol. Biol. 224:487-499 "Antibody Framework Residues Affecting the Conformation of the Hypervariable Loops".
Foroughi et al. (Sep. 1, 2007) J Allergy Clin Immunol 120(3):594-601 "Anti-IgE Treatment of Eosinophil Associated Gastrointestinal Disorders".
Franciosi and Liacouras, (Feb. 2009) Immunol Allergy Clin N Am 29(1):19-27, "Eosinophilic Esophagitis".
Garraud, Olivier, et al., "Regulation of immunoglobulin production in hyper-IgE (Job's) syndrome", J. Allergy Clin. Immunol., Feb. 1999. (2 Pt. 1): 333-340.
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gavett et al. (1997) The American Physiological Society, 16(2):L253-L261, "Interleukin-4 receptor blockade prevents airway responses induced by antigen challenge in mice".
Gevaert et al. (2006) Journal of Allergy and Clinical Immunology 118(5):1133-1141, "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Griffiths, Andrew et al., "Human anti-self antibodies with high specificity from phage display libraries", The EMBO Journal, 1993, 12:725-734.
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Hamilton, Jennifer et al., "Dupilumab Normalizes the Eosinophilic Esophagitis Disease Transcriptome in Adult Patients with Eosinophilic", May 1, 2020, Abstract, retrieved from internet on Aug. 5, 21 at: https://www.sciencedirect.com/science/atricle/pii/S0016508520327669?via%3Dihub, 1 page.
Highlights of Prescribing Information, Dupixent (dupilumab) injection, for subcutaneous use Initial U.S. Approval: 2017, U.S. Food and Drug Administration (FDA), Revised Mar. 2017.
Hijnen et al. (Feb. 2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients with Active Eosinophilic Esophagitis: a Randomized Double-Blind Placebo-Controlled Phase 2 Trial", The World of Congress Gastroenterology ACG, Orlando, FL, Oct. 13-18, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113 Abstract—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490, "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?".
Huang, Evie et al: "Severe Atopic Dermatitis in Children", Current Allergy and Asthma Reports, Current Science, US, vol. 18, No. 6, May 10, 2018, pp. 1-8.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
International Investigative Dermatology, Edinburgh, Conference Posters, May 8-11, 2013, 4 pages.
Ivashkiin, V. T., et al., "Eosinophilic esophagitis," a textbook for physicians, Moscow, "AISPI RAS" JSC, Feb. 14, 2013, pp. 13-21, 57-62, with complete English translation, 50 p. all together.
Ivashkin, V. T., et al., "Eosinophilic esophagitis: literature review and description of own survey," RJGHC, 2012, vol. 22, 1, pp. 71-81.
Jahnz-Rozyk et al. (Apr. 6, 2005) Allergy 60(5):685-688, "Serum thymus and activation-regulated chemokine, macrophage-derived chemokine and eotaxin as marker of severity of atopic dermatitis".
Janeway, Jr. et al., Immunobiology, 3rd Edition, 1997, Garland Publishing Inc., pp. 11:1-11:22.
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608, "Tuning sensitivity to IL-4 and IL-13: differential expression of IL-4Rα, IL-13Rα1, and Yc regulates relative cytokine sensitivity".
Jyonouchi et al., (2013), Basic Mechanisms in Allergic Disease, Clinical & Experimental Allergy, vol. 44, No. 1. pp. 58-68, "Invariant Natural Killer T cells in children with Eosinophilic Esophagitis".
Kagami et al. (2003) Clin. Exp. Immunology 134(2):309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al., (2002) Clin. Exp. Immunol 127(2):270-273 "Serum macrophage-derived chemokine (MDC) levels are closely related with the disease activity of atopic dermatitis".
Kakinuma, Takashi et al., (Mar. 1, 2001) J. Allergy Clin. Immunol. 107(3):535-541, "Thymus and activation-regulated chemokine in

(56) References Cited

OTHER PUBLICATIONS atopic dermatitis: Serum thymus and activation-regulated chemokine level is closely related with disease activity".
Kakkar, Tarundeep et al., (2011) Pharmaceutical Research 28(10):2530-2542, "Population PK and IgE Pharmacodynamic Analysis of a Fully Human Monoclonal Antibody Against IL4 Receptor".
Katial, Rohit, (Feb. 2009) Immunol Allergy Clin N Am 29(1):119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kharkevich, D.A., Pharmacology (Farmakologiya: A Scholarly Manual), 10th Ed., Moscow: GEOTAR-Media, 2010, pp. 73-74 and pp. 846-847, with English translation of cited pages, 12 pages total.
Kim et al., "Engineering of anti-human interleukin-4 receptor alpha antibodies with potent antagonistic activity", Scientific Reports, 2019, vol. 9, Article No. 7772, pp. 1-12.
Kim et al., (Dec. 1, 2004) J Allergy Clin Immunol 114(6):1449-1455, "Rebound eosinophilia after treatment of hypereosinophilic syndrome and eosinophilic gastroenteritis with monoclonal anti-IL-5 antibody SCH55700".
Klimka et al., "Human anti-CD30 recombinant antibodies by guided phage antibody selection using cell planning", British Journal of Cancer, 2000, 83:252-260.
Konikoff et al., (Nov. 1, 2006) Gastroenterology 131(5):1381-1391, "A Randomized, Double-Blind, Placebo-Controlled Trial of Fluticasone Propionate for Pediatric Eosinophilic Esophagitis".
Kopf et al. (1993) Letters to Nature 362:245-248, "Disruption of the murine IL-4 gene blocks Th2 cytokine responses".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Kostic et al. (2010) Clinical Immunology 135:S105-S106, "A Fully Human IL4Rα Antibody for Inhibition of IL-4/IL-13-driven TH2 Responses in Allergic Disease".
Kottyan et al. (Aug. 2014) Nature Genetics, vol. 46, No. 8, pp. 895-900, "Genome-wide association analysis of eosinophilic esophagitis provides insight into the tissue specificity of this allergic disease".
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Kulis et al. (2011) J. Allergy Clin Immunol 127(1):81-88 "Single-tree nut immunotherapy attenuates allergic reactions in mice with hypersensitivity to multiple tree nuts".
Kussie, Paul, et al., "A Single Engineered Amino Acid Substitution Changes Antibody Fine Specificity", Journal of Immunology: 152, pp. 146-152, 1994.
Leung et al. (Apr. 2004) The Journal of Clinical Investigation 113(5): 651-657 "New insights into atopic dermatitis".
Leung et al., (Mar. 13, 2003) The New England Journal of Medicine 348(11):986-993 "Effect of Anti-IgE Therapy in Patients with Peanut Allergy".
Lezcano-Meza et al., (2003) Allergy 58(10):1011-1017, "Interleukin (IL)-4 and to a lesser extent either IL-13 or interferon-gamma regulate the production of eotaxin-2/CCL24 in nasal polyps".
Liacouras et al., (Apr. 8, 2011) J Allergy Clin Immunol 128(1):3-20, "Eosinophilic esophagitis: Updated consensus recommendations for children and adults".
Lin et al.(2007) Clinical Reviews in Allergy & Immunology 33(3):167-177 "Role of Bacterial Pathogens in Atopic Dermatitis".
Linden, Carey et al., "Analysis of allergen specific IgE cut points to cat and dog in the Childhood Allergy Study", Annals of Allergy, Asthma & Immunology, 2011, 106.2: 153-158. e2.
Liu et al., (Aug. 9, 1999) Gene Therapy 6(7):1258-1266 "Hydrodynamics-based transfection in animals by systemic administration of plasmid DNA".
Lucae, S. et al., "IgE responses to exogenous and endogenous allergens in atopic dermatitis patients under long-term systemic cyclosporine A treatment", Allergy 71 (2016); 115-118.
Lucendo and Sanchez-Cazalilla, (Nov. 1, 2012) Expert Rev. Clin. Immunol. 8(8):733-745 "Adult versus pediatric eosinophilic esophagitis: important differences and similarities for the clinician to understand".
Ludmila and Xia, (Feb. 3, 2014) World Allergy Organization Journal 7(1):P8 "Poster 1013: IL-4R alpha antibody inhibits IgE production and airway remodeling in mouse model of house dust mite-induced eosinophilic asthma".
Lwin et al., (Apr. 2011) Modern Pathology 2(4)4:556-563, "Eosinophilic gastritis: histopathological characterization and quantification of the normal gastric eosinophil content".
Maccallum et al. (1996) J. Mol. Biol. 262:732-745 "Antibody-antigen Interactions: Contact Analysis and Binding Site Topography".
Maliszewski et al., (1994) Proc. Soc. Exp. Biol. Med. 206(3):233-237 "In vivo biological effects of recombinant soluble interleukin-4 receptor".
Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.
Mannon et al., (2012) Gut 61(12):1765-1773, "Interleukin 13 and its role in gut defence and inflammation".
Mariuzza et al. (1987) Ann. Rev. Biophys. Biophys. Chem. 16:139-159 "The Structural Basis of Antigen-Antibody Recognition".
Marone et al., Dec. 6, 2019, "The Intriguing Role of Interleukin 13 in the Pathophysiology of Asthma", Frontiers in Pharmacology, vol. 10, pp. 1-13.
Martel, Britta C., et al., "Translational animal Models of Atopic Dermatitis for Preclinical Studies," Yale Journal of Biology and Medicine 90 (2017), pp. 389-402.
Mashkovsky, M.D., Medicinal Drugs: Manual for Physicians, vol. 1, 14th Ed., v1:8-9, Moscow, 2001 Medicines, 7 pgs. (with English translation).
Masterson et al., (Oct. 2011) Curr Opin Gastroenterol. 27(6):515-522, "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg, (Nov. 1, 2003) Gastroenterology 125(5):1419-1427 "Intratracheal IL-13 Induces Eosinophilic Esophagitis by an IL-5, Eotaxin-1, and STAT6-Dependent Mechanism".
Mishra et al., (Jan. 1, 2001) J Clin. Invest. 107(1):83-90 "An etiological role for aeroallergens and eosinophils in experimental esophagitis".
Mishra et al., (Mar. 1, 2002) The Journal of Immunology 168(5):2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al., (Sep. 23, 2011) Clinical & Experimental Allergy 42(5):712-737, "Molecular and clinical rationale for therapeutic targeting of interleukin-5 and its receptor".
Morioka et al., (2009) British Journal of Dermatology 160(6):1172-1179, "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta 1592, (2002), 237-250.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Müller et al. (1993) Journal of Immunology 150:5576-5584 "Th2 cells mediate IL-4-dependent local tissue inflammation".
Nadeau et al., (Jun. 2011) J. Allergy Clin. Immunol 127(6): 1622-1624, Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.

(56) References Cited

OTHER PUBLICATIONS

Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Nguyen et al. (Jul. 2011) Immunological Reviews 242(1):258-271 "Immune modulation for treatment of allergic disease".
Nguyen, Tran Hoai et al., "FutureForms of Immunotherapy and Immunomodulators in Allergic Disease", Immunol Allergy Clin N Am 31 (2011); 343-365.
Nicodeme et al., "Esophageal Distensibility as a Measure of Disease Severity in Patients with Eosinophilic Esophagitis", Clinical Gastroenterology and Hepatology, Sep. 2013, vol. 11, No. 9, pp. 1101-1107.
Niederberger, Verena, (Feb. 2009) Immunology Letters 122, Issue 2:131-133 "Allergen-specific immunotherapy".
Niranjan et al., (2013) Immunology and Cell Biology pp. 1-8, "Pathogenesis of allergen-induced eosinophilic esophagitis is independent of interleukin (IL)-13".
Noel et al. (Aug. 26, 2004) The New England Journal of Medicine 351:940-941 "Eosinophilic Esophagitis".
Nomura, Ichiro et al., "*Staphylococcus aureus* and Atopic Dermatitis", (2000), IRYO vol. 54, No. 2, pp. 62-66, 18 pages with English translation.
Novartis Pharmaceuticals (2013) QAX576, "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell, 171, 217-228.
Oh et al., (2010) Eur Respir Rev 19(115):46-54 "Investigational therapeutics targeting the IL-4/IL-13/STAT-6 pathway for the treatment of asthma".
Ohno et al., (May 1, 1985) Proc. Natl. Acad. Sci. USA 82(9):2945-2949, "Antigen-binding specificities of antibodies are primarily determined by seven residues of VA".
Ong Peck, (2012) Expert Opinion on Emerging Drugs 17(2):129-133 "Editorial update on emerging treatments of atopic dermatitis".
Otani et al., (2013) Journal of Allergy and Clinical Immunology 131(6):1576-1582, "Anti-IL-5 therapy reduces mast cell and IL-9 cell numbers in pediatric patients with eosinophilic esophagitis".
Otulana et al., (2011) Am. J. Respir. Crit. Care Med. 183:A6179, "A Phase 2b Study of Inhaled Pitrakinra, An IL-4R/IL-13 Antagonist, Successfully Identified Responder Subpopulations of Patients with Uncontrolled Asthma".
Oyoshi et al., (Jan. 1, 2009) Advances in Immunology 102:135-226, "Cellular and Molecular Mechanisms in Atopic Dermatitis".
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Pesek, Robert D. et al., "Emerging drugs for eosinophilic esophagitis", Expert Opinion on Emerging Drugs, vol. 23, No. 2, Apr. 3, 2018, 12 pages.
Peserico et al., (2008) British Journal of Dermatology 158(4):801-807, "Reduction of relapses of atopic dermatitis with methylprednisolone aceponate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Phan, N.Q. et al., "Assessment of pruritis intensity: prospective study on validity and reliability of the visual analogue scale, numeric rating scale, and verbal rating scale in 471 patients with chronic pruritis", Acta Dermato-Venereologica, 2012, vol. 92: 502-507.
Prieto and Richter, (May 24, 2013) Curr Gastroenterol Rep 15(6):324, "Eosinophilic Esophagitis in Adults: An Update on Medical Management".
Prussin et al., (Dec. 1, 2009) J Allergy Clin Immunol. 124(6):1326-1332, "Eosinophilic gastrointestinal disease and peanut allergy are alternatively associated with IL-5+ and IL-5-TH2 responses".
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., p. AB158, (made available on Jan. 26, 2013), 2 pgs.
Rafi et al., (Jan. 1, 2010) Allergy and Asthma Proceedings 31(1):76-83 "Effects of omalizumab in patients with food allergy".
Rayapudi et al., (Aug. 2010) Journal of Leukocyte Biology 88(2): 337-346, "Indoor insect allergens are potent inducers of experimental eosinophilic esophagitis in mice".
Receptos, Inc. 2013 Annual Report.
Reed, Craig, et al., "Patient-reported outcomes in esophageal diseases", Clinical Gastroenterology and Hepatology, Elsevier, Amsterdam, NL, vol. 16. No. 3, pp. 305-310.
Regeneron 2011 Annual Report (Apr. 2011), 12 pages.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Ap. 7, 2017), XP055534130, Retrieved from the Internet: URL: https://web.archive.org/web/20170407151633if_/https://www.regeneron.com/sites/default/files/Dupixent_FPI.pdf, 4 pages.
Ring et al., (2012) J. Eur. Acad. Dermatol. Venereol. 26(8):1045-1060, "Guidelines for treatment of atopic eczema (atopic dermatitis) Part 1".
Roitt et al., (2001) Mosby-Harcourt Publishers Limited, Immunology—Sixth Edition "Antigen Presentation" pp. 110-111.
Roll et al., (Jan. 1, 2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, Special Issue, pp. 44-47. (with English translation of the cited portion).
Rothenberg, (2004) J Allergy Clin Immunol 113(1):11-28, "Eosinophilic gastrointestinal disorders (EGID)".
Rothenberg, (2009) Gastroenterology 137(4):1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2014, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, mailed Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), with English translation of the Abstract only, cited in the Japanese Patent Application No. 2015-531149.
Sampson et al., (May 2011) J. Allergy Clin Immunol. 127(5): 1309-1310, Letters to the Editor, "A phase II, randomized, double-blind, parallel-group, placebo-controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.

(56) References Cited

OTHER PUBLICATIONS

Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al., (1993) J. Immunol. 150(7):2717-2723, "Recombinant soluble murine IL-4 receptor can inhibit or enhance IgE responses in vivo".
Scavuzzo et al., (2005) Biomedicine & Pharmacotherapy 59(6):323-329, "Inflammatory mediators and eosinophilia in atopic and non-atopic patients with nasal polyposis".
Schmidt-Weber, (Mar. 13, 2012) Chem Immunol Allergy 96:120-125, "Anti-IL-4 as a New Strategy in Allergy".
Schmitt et al., (Dec. 1, 2007) J. of Allergy and Clinical Immunology 120(6):1389-1398, "What are the best outcome measurements for atopic eczema? A systematic review".
Schneider et al., (Sep. 26, 2013) J. Allergy Clin Immunol 132(6):1368-1374, "A pilot study of omalizumab to facilitate rapid oral desensitization in high-risk peanut-allergic patients".
Sekiya et al., (2002) Allergy 57(2):173-177, "Increased levels of a TH2-type CC chemokine thymus and activation-regulated chemokine (TARC) in serum and induced sputum of asthmatics".
Siegfried et al., "Use of dupilumab in pediatric atopic dermatitis: Access, dosing, and implications for managing severe atopic dermatitis", Pediatric Dermatology, vol. 36, No. 1, Jan. 2019, pp. 172-176.
Silverberg et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA, 1 page.
Silverberg et al., P481, "Dupilumab treatment rapidly improves itch in patients with moderate-to-severe atopic dermatitis" An Allergy Asthma Immunol. 2017;119(suppl 5):S95.
Simpson, E.L., et al., "Two Phase 3 Trials of Dupilumab versus Placebo in Atopic Dermatitis," The New England Journal of Medicine, Oct. 1, 2016, 14 pages, DOI: 10.1056/NEJMoa1610020.
Simpson, Eric L. et al., (Jan. 14, 2016), J. Am. Acad. Dermatol. 74(3):491-498, "Patient burden of moderate to severe atopic dermatitis (AD): Insights from a phase 2b clinical trial of dupilumab in adults".
Simpson, Eric L. et al., (Jun. 4, 2016), J. Am. Acad. Dermatol. 75(3):506-515, "Dupilumab therapy provides clinically meaningful improvement in patient-reported outcomes (PROs): A phase IIb, randomized, placebo-controlled, clinical trial in adult patients with moderate to severe atopic dermatitis (AD)".
Slager et al. (Apr. 26, 2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al., (Dec. 1, 2006) J Allergy Clin Immunol 118(6):1312-1319, "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al., (Dec. 2008) Clinical & Experimental Allergy 38(12):1858-1865, "Immunomodulatory therapy of eosinophil-associated gastrointestinal diseases".
Strauman, (2009) Immunol Allergy Clin N Am 29(1):11-18, "Clinical Evaluation of the Adult who has Eosinophilic Esophagitis".
Straumann et al., (2001) J Allergy Clin Immunol 108(6):954-961 "Idiopathic eosinophilic esophagitis is associated with a $T_H2$-type allergic inflammatory response".
Straumann et al., (2009) Gut vol. 59(1):21-30, "Anti-interleukin-5 antibody treatment (mepolizumab) in active eosinophilic oesophagitis: a randomized, placebo-controlled, double-blind trial".
Straumann, (2005) J Allergy Clin Immunol 115(2):418-419, "Eosinophilic esophagitis: Escalating epidemiology?".
Takashi Yoshike, "Treatment for Atopic Dermatitis", Juntendo Medical Journal, 1999, vol. 45, No. 3, pp. 352-360, 33 pages with English translation.
Tazawa et al., (2004) Arch Dermatol Res 295:459-464, "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Terui, et al., (2000) "Learning from Fungus Allergy in Atopic Dermatitis Patients," Japan J. Med. Mycol, vol. 41, No. 3, 157-160.
Thaci, Diamant et al., Oct. 8, 2015), "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, 387(10013):40-52.
Tomkinson et al., (2001) J. Immunol 166(9):5792-5800, "A Murine IL-4 Receptor Antagonist that Inhibits IL-4- and IL-13-induced Responses Prevents Antigen-Induced Airway Eosinophilia and Airway Hyperresponsiveness".
Tsianakas, Athanasios et al., "Dupilumab: A Milestone in the Treatment of Atopic Dermatitis," The Lancet, (Oct. 8, 2015), 387(10013):4-5.
Ul-Haq, Zaheer et al., "Interleukin-4 receptor signaling and its binding mechanism: A therapeutic insight from inhibitors tool box", Cytokine & Growth Factor Review (2016), 32:3-15.
Vajdos et al. (2002) Journal of Molecular Biology 320(2):415-428 "Comprehensive functional maps of the antigen-binding site of an anti-ErbB2 antibody obtained with shotgun scanning mutagenesis".
Vakharia, Paras P. et al., (2017), "Monoclonal Antibodies for Atopic Dermatitis: Progress and Potential", BioDrugs 31:409-422.
Veerappan et al., (2009) Clinical Gastroenterology and Hepatology 7(4):420-426, "Prevalence of Eosinophilic Esophagitis in an Adult Population Undergoing Upper Endoscopy: A Prospective Study".
Vestergaard et al., (2000) The Journal of Investigative Dermatology 115(4):640-646, "A Th2 Chemokine, TARC, Produced by Keratinocytes May Recruit CLA+CCR4+ Lymphocytes into Lesional Atopic Dermatitis Skin".
Virchow et al., (1994) Lung 172(6):313-334, "Cellular and immunological markers of allergic and intrinsic bronchial asthma".
Waccholz et al., "Detection of Allergen-Specific IgE Antibody Responses", 2005, Journal of Immunotoxicology, 1:3-4, 189-199.
Walker et al., (1993) Clinical and Experimental Allergy 23:145-153, "Atopic dermatitis: correlation of peripheral blood T cell activation, eosinophilia and serum factors with clinical severity".
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Wang and Liu, (2008) Current Opinion in Immunology 20:697-702 "The IL-17 cytokine family and their role in allergic inflammation".
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Ward, E. Sally et al., "Blinding activities of a repertoire of single immunoglobin variable domains secreted from *Escherichia coli*", Nature, 1989, 341:544-546.
Wark et al., (Aug. 7, 2006) Advanced Drug Delivery Reviews 58(5-6):657-670, "Latest technologies for the enhancement of antibody affinity".

(56) References Cited

OTHER PUBLICATIONS

Watson et al. (2011) Allergy, Asthma & Clinical Immunology 7:S4 "Atopic dermatitis".
Wegmann et al., "Targeting Cytokines in Asthma therapy: could IL-37 be a Solution?", Expert Review of Respiratory Medicine, 2017, vol. 11, No. 9, pp. 675-677.
Weihrauch et al., (2005) Cancer Research 65(13):5516-5519 "Elevated Serum Levels of CC Thymus and Activation-Related Chemokine (TARC) in Primary Hodgkin's Disease: Potential for a Prognostic Factor".
Weinbrand-Goichberg et al., (2013) Immunol Res 56(2): 249-260, "Eosinophilic esophagitis: an immune-mediated esophageal disease".
Wenzel et al. (2010) European Respiratory Society, Annual Congress 2010, "ERS—Programme" p. 3980.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Wenzel et al., (2007) Lancet 370(9596):1422-1431, "Effect of an interleukin-4 variant on late phase asthmatic response to allergen challenge in asthmatic patients: results of two phase 2a studies".
Wenzel et al., May 21, 2013, New England Journal of Medicine 368(26):2455-2466, "Dupilumab in Persistent Asthma with Elevated Eosinophil Levels".
Wershil, Barry, (Feb. 1, 2009) Immunol Allergy Clin N Am 29(1):189-195, "Exploring the Role of Mast Cells in Eosinophilic Esophagitis".
Whalley et al., (Feb. 2004) British Journal of Dermatology 150:274-283, "A new instrument for assessing quality of life in atopic dermatitis: international development of the Quality of Life Index for Atopic Dermatitis (QoLIAD)".
Wilhelm and Stockinger, (Nov. 28, 2011) Frontiers in Immunology 2(68):1-4, "Innate lymphoid cells and type 2 (Th2) mediated immune responses-pathogenic or beneficial?"
Wills-Karp and Finkelman, (2008) Science Signaling 1(51):1-5, "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Wong, et al., "Guidelines for the management of atopic dermatitis (eczema) for pharmacists," CPJ/RPC, Sep./Oct. 2017, vol. 150, No. 5, pp. 285-297.
Wu et al. (1999) Journal of Molecular Biology 294:151-162 "Humanization of a murine monoclonal antibody by simultaneous optimization of framework and CDR residues".
Yamanaka et al., (2011) Curr Probl Dermatol 41:80-92, "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Zuo et al., (2010) Journal of Immunology 185:660-669, "IL-13 Induced Esophageal Remodeling and Gene Expression by an Eosinophil-Independent, IL-13R{alpha}2-Inhibited Pathway".
Zurawski et al., (1995) J. Biol. Chem. Am. Society of Biolochemical Biologists 270(23):13869-13878, "The primary binding subunit of the human Interleukin-4 receptor is also a component of the Interleukin-13 receptor".
Kwiatek, Monika et al., "Mechanical properties of the esophagus in eosinophilic esophagitis" Gastroenterology, 2011, vol. 140, No. 1, pp. 82-90.
Abe, Yasuhiko, et al., "Advances in the Diagnosis and Treatment of Eosinophilic Esophagitis", (English abstract), Gastroenterological Endoscopy, 2014, vol. 56, Issue 9, pp. 3378-3393.
Russian Office Action and Search Report in Application 2020140639, mailed Aug. 17, 2022, with English translation, 26 pages.
Blakely, Kim et al., "Dupilumab, a monoclonal antibody for atopic dermatitis: a review of current literature", Skin Therapy Letter, Mar.-Apr. 2016, vol. 21, No. 2, Dupilumab Clinical Trials in AD, 13 pages.
Clinical Trials, Study NCT01859988, phase 2b, "Study of Dupilumab Administered to Adult Patients with Moderate-to-Severe Atopic Dermatitis", study completion date—Sep. 2014, 10 pages.
D'ERME, Angelo et al., "Spotlight on dupilumab in the treatment of atopic dermatitis: design, development, and potential place in therapy", Drug Des Devel Ther, 2017, vol. 11, p. 1473-1480, DOI: 10.2147/DDDT.S113192, Abstract, c.1475-1478, 8 pages.
Grechkina, L.I. et al., "Characteristics for the physical development indices demonstrated by adolescents boring in Magadan", Siberian Medical Journal, 2013, No. 3, Results and discussion, Table 1, obtained from: https://cyberleninka.ru/article/n/harakteristika-pokazateley-fizicheskogo-razvitiya-podrostkov-urozhentsev-magadana/viewer, with English translation, 9 pages.
Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Balabolkin, I. et al., "Modern concepts of pathogenesis and therapy of atopic dermatitis in children", Pharmateka, 2017, No. 1, p. 53-60, with English translation, 14 pages.
Clinical Trials, Study NCT00436670, "Phase II Study to Evaluate the Efficacy of AMG 317", first posted Feb. 19, 2007, Amgen actual study completion date—Feb. 2009, 7 pages.
Vincent, M et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.
"Dupilumab therapy in moderate-to-severe atopic dermatitis provides positive results in the first two phase III clinical trials", J Int Pharm Res, vol. 43, No. 4, Aug. 31, 2016, p. 785 (with English translation).
Konterman, R., Andrew C.R. Martin, "Protein Sequence and Structure Analysis of Antibody Variable Domains", CH. 3, Antibody Engineering, vol. 2, 2010, pp. 33-51, DOI : 10.1007/978-3-642-01147-4_3.
Chiu, Mark et al., "Antibody Structure and Function: The Basis for Engineering Therapeutics", Antibodies, 2019, vol. 8, No. 55, pp. 1-78.
Dumet et al., "Insights into the IgG heavy chain engineering patent landscape as applied to IgG4 antibody development", MABS, 11(8); 1341-1350, 2019.
Center for Drug Evaluation and Research, "Clinical Review, Brenda Carr, MD, BLA, 761055, Dupixent (dupilumab)" Application No. 761055Orig1s000. Reference ID: 4075125 Apr. 9, 2015, 226 pgs.
European Communication of a Notice of Opposition in Application 21167811.5, mailed Jan. 29, 2025, 118 pages.
European Communication of a Notice of Opposition in Application 21167811.5, mailed Jan. 31, 2025, 118 pages.
European Opposition in 75EPD2, "Consolidated List" of cited art references, 21167811.5, 7 pages. (Refs D1-D76).
Silva et al., "The S228P Mutation Prevents in Vivo and in Vitro IgG4 Fab-arm Exchange as demonstrated using a Combination of Novel Quantitative Immunoassays and Physiological Matrix Preparation", The Journal of Biological Chemistry, 290 (9), 5462-5469, Feb. 27, 2015.
Handlogten et al., p. 1, right hand col. first paragraph, "Prevention of Fab-arm exchange and antibody reduction via stabilization of the IgG4 hinge region" Mabs, 12(1): 1779974. 2020.
Emea, Annex I Summary of product characteristics for dupilumab, Sep. 2, 2022, 7 pgs.

(56) References Cited

OTHER PUBLICATIONS

NCT01385657, version 3, "Safety and Tolerability of Dupilumab in Participants with Moderate to Severe Atopic Dermatitis", last update posted Feb. 26, 2020, 12 pgs.
EMEA Guideline for Industry—dose-response information to support drug registration ICH-E4, Nov. 1994, CPMP/ICH/378/95, 10 pages.
Hwang, Ying Khee and Foote, "Immunogenicity of engineered antibodies", 2005, 36:1, 3-10.
Filing Receipts of all US priority applications detailing named applicants in EP Opposition 3889181 (Document TM5), various dates, 24 pgs.
USPTO Pair recordal of assignments of all US priority applications from inventor/applicants to Regeneron, and Sanofi dated Jan. 13, 2019, 8 pgs.
Assignment to Regeneron—reel/frame 030844/0484, dated Jan. 24, 2019, 6 pgs.
Assignment to Sanofi—reel/frame 030931/0570, dated Jan. 28, 2019, 19 pgs.
Assignment to Sanofi Biotech, dated Nov. 5, 2015,—reel/frame 0307055/0414, 9 pgs.
WO 2014039461 Rule 92bis PCT request dated Aug. 27, 2014, 2 pgs.
WO 2014039461 Form PCT/RO/101 and Filing Receipt, filed Sep. 4, 2013, 8 pgs.
Modi, "Dose-Finding Studies in Phase I and Estimation of Maximally Tolerated Dose", Chapter 3 of "Statistics for Biology and Health", 2006, 19 pgs.
Applicant's letter dated Dec. 9, 2011 from EP09744292.5, 3 pgs.
Form PCT/IB/306 Notification of the recording of a change, dated Nov. 12, 2014, 1 page.
Press Release: "Regeneron Reports Fourth Quarter and Full Year Financial and Operating Results", Feb. 13, 2012, 8 pgs.
Amended claims filed Jul. 26, 2012 in U.S. Appl. No. 13/287,151, 3 pgs.
Clinical Study Record for NCT01854047, "An Evaluation of Dupilumab in Patients with Severe Uncontrolled Asthma", Version 1, May 10, 2013, 9 pgs.
Dirks and Meibohm, "Population pharmacokinetics of Therapeutic Monoclonal Antibodies", Clin. Pharmacokinet., vol. 49(10), p. 633-659, 2010.
Schumacher, B., "Neuer Antikorper bessert eosinophiles Asthma", Allergo J 22, 361 (2013), https://doi.org/10.1007/s15007-013-0348-0, published Sep. 1, 2013; followed by translation into English of title and abstract.
Patentee's letter of May 5, 2023 from examination, 6 pgs.
Note of telephone consultation with the examiner—Oct. 31, 2023 in EP Application 21167811.5, 2 pgs.
Patentee's letter of Mar. 25, 2022 from examination, 5 pgs.
Patentee's letter of Oct. 24, 2023 from examination, 9 pgs.
British National Formulary, BNF 60; Sep. 2010, BMA, cover page, pp. 418, 639, 640 and 642, 5 pgs.
Submission of Patentee's Response to Oppositions in EP3107575B1, dated Jan. 2, 2023, Oppo against EP3107575B1, 42 pgs.
Reasons dated Mar. 7, 2023, from Opposition against EP3107575B1, 29 pgs.
Mould and Sweeny, "The pharmacokinetics and pharmacodynamics of monoclonal antibodies—mechanistic modeling applied to drug development", 2007, p. 84-96.
EP Office Action dated Oct. 31, 2023 in EP 21167811.5, 2 pgs.
NCT Clinical Trials.gov Study details tab for NCT01639040, first submitted that met QC criteria on Jul. 11, 2012, 11 pages.
FDA Label Dupixent, Highlights of Prescribing Information, Revised May 2022, 70 pages.
Groves, RW et al., "Inhibition of IL-4 and IL-13 with an IL-4 mutein (Aeroderm) protects against flares in atopic eczema", Abstracts, abstract 320, Journal of Investigative Dermatology (2007), vol. 127, page S54.
NCT Clinical Trials for NCT01859988, "Study of Dupilumab Administered to Adult Patients With Moderate-to-Severe Atopic Dermatitis", Study Record, Version 1, May 21, 2013, 11 pages.
Van Joost, T.H., "Cyclosporin in atopical dermatitis: modulation in the expression of immunologic markers in lesional skin", Journal of the American Academy of Dermatology 27.6 (1992), 922-928.
Birkett, D.J., "Pharmacokinetics made easy 11 Designing dose regiments", Australian Prescriber, Issue Jul. 3, 1996, 7 pages.
Wang et al., "Monoclonal Antibody Pharmacokinetics and Pharmacodynamics", Nature, vol. 84, No. 5, Nov. 2008, pp. 548-558.
Beck et al., "Dupilumab Provides Acceptable Safety and Sustained Efficacy for up to 4 Years in an Open-Label Study of Adults with Moderate-to-Severe Atopic Dermatitis", Am. Journal of Clin Derm (2022) 23:393-408, https://doi.org/10.1007/s40257-022-00685-0.
European Opposition in 75EPD2, "Consolidated List" of cited art references, mailed Jan. 29, 2025, 21167811.5, 7 pages.
Handlogten et al., p. 1, right hand colume first paragraph, "Prevention of Fab-arm exchange and antibody reduction via stabilization of the IgG4 hinge region" Mabs, 12(1): 1779974. 2020.
Recordal of assignments of all US priority applications from inventor/applicants to Regeneron, and Sanofi dated Jan. 13, 2019, 8 pgs.
Submission of Patentee's Response to Oppositions in EP3107575B1, dated Jan. 2, 2023, Opposition against EP3107575B1, 42 pgs.

* cited by examiner

Figure 20
300 mg (n=21)
150 mg (n=22)
75 mg (n=8)
Placebo (n=16)
100
90
80
70
60
50
40
30
10
Day 1
Day 15
Day 29
Day 36
Day 43
Day 57
Day 71
Day 85

| Study Day | -14 | 1 | 4 | 8 | 15 | 22 | 25 | 29 | 36 | 43 | 50 | 57 | 64 | 71 | 85 |
|---|---|---|---|---|---|---|---|---|---|---|---|---|---|---|---|
| Placebo n | 10 | 10 | 9 | 8 | 6 | 6 | 6 | 5 | 5 | 4 | 4 | 4 | 4 | 4 | 4 |
| 150 mg n | 14 | 13 | 13 | 12 | 12 | 12 | 12 | 12 | 12 | 12 | 12 | 12 | 10 | 11 | 10 |
| 300 mg n | 13 | 13 | 13 | 13 | 13 | 13 | 13 | 10 | 9 | 10 | 11 | 11 | 11 | 11 | 10 |

| Study Day | 1 | 8 | 15 | 29 | 36 | 57 | 85 |
|---|---|---|---|---|---|---|---|
| Placebo | 10 | 9 | 6 | 5 | 4 | 4 | 7 |
| 150mg | 14 | 13 | 12 | 12 | 12 | 12 | 11 |
| 300mg | 13 | 13 | 13 | 11 | 8 | 11 | 13 |

* p <0.03 * p <0.04

| Study Day | -15 | 1 | 4 | 8 | 15 | 22 | 25 | 29 | 36 | 43 | 50 | 57 | 64 | 71 | 85 |
|---|---|---|---|---|---|---|---|---|---|---|---|---|---|---|---|
| Placebo n | 9 | 10 | 9 | 8 | 6 | 6 | 6 | 5 | 4 | 4 | 4 | 4 | 4 | 4 | 4 |
| 150 mg n | 13 | 13 | 12 | 11 | 11 | 11 | 11 | 11 | 11 | 11 | 11 | 10 | 9 | 10 | 9 |
| 300 mg n | 13 | 13 | 13 | 13 | 13 | 13 | 13 | 11 | 9 | 10 | 11 | 11 | 11 | 11 | 10 |

| Day | 1 | 8 | 15 | 22 | 29 | 36 | 43 | 50 | 57 | 64 | 71 | 85 | 113 | 141 | 169 | 197 |
|---|---|---|---|---|---|---|---|---|---|---|---|---|---|---|---|---|
| PBO | 53 | 53 | 51 | 46 | 43 | 35 | 31 | 31 | 28 | 29 | 24 | 43 | 8 | 9 | 9 | 25 |
| mAb1 | 53 | 52 | 50 | 50 | 47 | 46 | 46 | 47 | 49 | 46 | 47 | 54 | 22 | 24 | 21 | 42 |

| Day | 1 | 8 | 15 | 22 | 29 | 36 | 43 | 50 | 57 | 64 | 71 | 85 | 113 | 141 | 155 | 169 | 183 | 197 |
|---|---|---|---|---|---|---|---|---|---|---|---|---|---|---|---|---|---|---|
| PBO | 52 | 53 | 49 | 46 | 43 | 34 | 31 | 31 | 29 | 29 | 23 | 42 | 8 | 9 | 7 | 9 | 6 | 25 |
| mAb1 | 53 | 52 | 50 | 49 | 47 | 45 | 46 | 47 | 49 | 45 | 46 | 53 | 22 | 24 | 20 | 21 | 19 | 44 |

METHODS FOR TREATING ATOPIC DERMATITIS BY ADMINISTERING AN IL-4R ANTAGONIST

CROSS-REFERENCE TO RELATED APPLICATIONS

This application is a Continuation of U.S. application Ser. No. 15/610,267, filed on May 31, 2017, which is a Continuation of U.S. application Ser. No. 14/017,333, filed on Sep. 4, 2013, which claims the benefit under 35 U.S.C. § 119(e) of U.S. provisional application No. 61/697,972, filed on Sep. 7, 2012; 61/738,715, filed on Dec. 18, 2012; 61/748,588, filed on Jan. 3, 2013; 61/764,624, filed on Feb. 14, 2013; 61/768,229, filed on Feb. 22, 2013; 61/770,091, filed on Feb. 27, 2013; 61/782,420, filed on Mar. 14, 2013; and 61/816,191, filed on Apr. 26, 2013, and under 35 U.S.C. § 119(b) of French application No. 1356759, filed on Jul. 10, 2013, the disclosures of each herein incorporated by reference in their entireties.

REFERENCE TO A SEQUENCE LISTING XML

This application contains a Sequence Listing which has been submitted electronically in XML format. The Sequence Listing XML is incorporated herein by reference. Said XML file, created on Sep. 19, 2022, is named 40848_0075USC2_SL.xml and is 252,770 bytes in size.

FIELD OF THE INVENTION

The present invention relates to the treatment and/or prevention of atopic dermatitis and related conditions. More specifically, the invention relates to the administration of interleukin-4 receptor (IL-4R) antagonists to treat or prevent atopic dermatitis in a patient in need thereof.

BACKGROUND

Atopic dermatitis (AD) is a chronic/relapsing inflammatory skin disease characterized by intense pruritus (e.g., severe itch) and by scaly and dry eczematous lesions. AD is often associated with other atopic disorders such as allergic rhinitis and asthma. Severe disease can be extremely disabling due to major psychological problems, significant sleep loss, and impaired quality of life, leading to high socioeconomic costs.

The pathophysiology of AD is influenced by a complex interplay between Immunoglobulin E (IgE)-mediated sensitization, the immune system, and environmental factors. The primary skin defect may be an immunological disturbance that causes IgE-mediated sensitization, with epithelial-barrier dysfunction that is the consequence of both genetic mutations and local inflammation. AD often begins in childhood before age 5 and may persist into adulthood.

Typical treatments for AD include topical lotions and moisturizers, topical corticosteroid ointments, creams or injections. Most treatment options, however, offer only temporary, incomplete, symptom relief. Moreover, many patients with moderate-to-severe AD become resistant to treatment by topical corticosteroids or by calcineurin inhibitors. Thus, a need exists in the art for novel targeted therapies for the treatment and/or prevention of AD.

BRIEF SUMMARY OF THE INVENTION

According to certain aspects of the present invention, methods are provided for treating, preventing and/or reducing the severity of symptoms of atopic dermatitis (AD), including moderate-to-severe AD. Certain embodiments of the invention pertain to methods for treating, ameliorating or preventing moderate-to-severe AD in a patient who is resistant to treatment by a topical corticosteroid or a calcineurin inhibitor. In some embodiments, the present invention discloses methods of treating patients with moderate-to-severe AD that is uncontrolled despite treatment with a topical corticosteroid or a calcineurin inhibitor. The methods of the present invention comprise administering to a subject or a patient in need thereof a pharmaceutical composition comprising a therapeutically effective amount of an interleukin-4 receptor (IL-4R) antagonist. According to certain embodiments of the present invention, the IL-4R antagonist is an antibody or antigen-binding fragment thereof that specifically binds IL-4R. Exemplary anti-IL-4R antibodies that can be used in the context of the methods of the present invention are described elsewhere herein, including working Example 1. In certain embodiments, the IL-4R antagonist is an anti-IL-4R antibody having the binding characteristics of the reference antibody referred to herein as "mAb1" (e.g., an antibody or antigen-binding fragment thereof comprising the complementarity determining regions of mAb1). In one embodiment, the antibody or antigen-binding fragment thereof that binds IL-4R comprises complementarity determining regions (CDRs) in a heavy chain variable region (HCVR)/light chain variable region (LCVR) sequence pair of SEQ ID NOs: 162/164.

Some embodiments of the invention are directed to methods for treating, reducing, ameliorating or preventing pruritus in a patient, comprising administration of a pharmaceutical composition comprising a therapeutically effective amount of an IL-4R antagonist. In one embodiment, the patient suffers from moderate-to-severe AD. In some embodiments, the patient suffering from AD is resistant to treatment by either a topical corticosteroid or a calcineurin inhibitor.

In certain embodiments, the present invention includes methods to treat moderate-to-severe AD in a patient, the methods comprising administering a pharmaceutical composition comprising a therapeutically effective amount of an antibody or antigen-binding fragment thereof that binds IL-4R, and determining an improvement in an AD-associated parameter. The improvement can be determined or assayed or quantitated by methods well-known in the art. AD-associated parameters and improvements therein are discussed elsewhere herein, including e.g., in working Example 7.

According to certain exemplary embodiments, the present invention provides methods for improving one or more AD-associated parameter(s) in a subject in need thereof. Improvements in AD-associated parameters include, e.g., a decrease in Investigator's Global Assessment (IGA) score; a decrease in Body Surface Area Involvement of Atopic Dermatitis (BSA) score; a decrease in Eczema Area and Severity Index (EASI) score; a decrease in SCORAD score; a decrease in 5-D Pruritus Scale; and/or a decrease in Pruritus Numeric Rating Scale (NRS) score. In exemplary embodiments, the improvement in an AD-associated parameter is selected from the group consisting of: (i) a decrease from baseline in IGA score of at least 25%; (ii) a decrease from baseline in BSA score of at least 35%; (iii) a decrease from baseline in EASI score of at least 45%; (iv) a decrease from baseline in SCORAD score of at least 30%; (v) a decrease from baseline in 5-D Pruritus scale of at least 15%;

(vi) a decrease from baseline in Pruritus NRS score of at least 25%; and (vii) percent responders with 50% improvement in EASI (EASI50).

In some embodiments, the improvement in an AD-associated parameter comprises a decrease from baseline in IGA of at least 25% on day 22 through at least day 85 after administration of a pharmaceutical composition comprising an antibody or antigen-binding fragment thereof that binds IL-4R. In some embodiments, the improvement in an AD-associated parameter comprises a decrease from baseline in BSA score of at least 40% on day 29 through at least day 85 following administration of the pharmaceutical composition. In some embodiments, the improvement in an AD-associated parameter comprises a decrease from baseline in EASI score of at least 50% on day 29 through at least day 85 after administration of the pharmaceutical composition. In certain embodiments, the improvement in an AD-associated parameter comprises a decrease from baseline in EASI score of at least 50% on day 29 in at least 70% of subjects administered with the pharmaceutical composition. In some embodiments, the improvement in an AD-associated parameter comprises a decrease from baseline in SCORAD score of at least 30% on day 29 through at least day 85 following administration of the pharmaceutical composition. In some embodiments, the improvement in an AD-associated parameter comprises a decrease from baseline in 5-D pruritus Scale of at least 15% on day 15 through at least day 85 after administration of the pharmaceutical composition. In some embodiments, the improvement in an AD-associated parameter comprises a decrease from baseline in NRS score of at least 25% at the end of week 2 through at least the end of week 10 after administration of the pharmaceutical composition.

In some embodiments, the improvement in an AD-associated parameter comprises a decrease from baseline in IGA of at least 45% on day 85 through at least day 197 after administration of a pharmaceutical composition comprising a therapeutically effective amount of an IL-4R antagonist. In some embodiments, the improvement in an AD-associated parameter comprises a decrease from baseline in BSA score of at least 50% on day 85 through at least day 197 after administration of a pharmaceutical composition comprising a therapeutically effective amount of an IL-4R antagonist. In some embodiments, the improvement in an AD-associated parameter comprises a decrease from baseline in EASI score of at least 60% on day 85 through at least day 197 after administration of a pharmaceutical composition comprising a therapeutically effective amount of an IL-4R antagonist. In some embodiments, the improvement in an AD-associated parameter comprises a decrease from baseline in SCORAD score of at least 45% on day 85 through at least day 197 after administration of a pharmaceutical composition comprising a therapeutically effective amount of an IL-4R antagonist. In some embodiments, the improvement in an AD-associated parameter comprises a decrease from baseline in 5-D Pruritus scale of at least 30% on day 85 through at least day 197 after administration of a pharmaceutical composition comprising a therapeutically effective amount of an IL-4R antagonist. In some embodiments, the improvement in an AD-associated parameter comprises a decrease from baseline in NRS score of at least 50% on day 85 through at least day 197 after administration of a pharmaceutical composition comprising a therapeutically effective amount of an IL-4R antagonist.

According to other exemplary embodiments, the present invention provides methods for treating AD in a subject, the methods comprising: (a) selecting a subject who exhibits an elevated level of at least one AD-associated biomarker; and (b) administering to the subject a pharmaceutical composition comprising a therapeutically effective amount of an IL-4R antagonist. In certain embodiments, the IL-4R antagonist is an antibody or antigen-binding fragment thereof that binds IL-4R. Exemplary AD-associated biomarkers that can be evaluated and/or measured in the context of the present invention include, but are not limited to, thymus and activation-regulated chemokine (TARC; also known as CCL17), immunoglobulin E (IgE), eotaxin-3, lactate dehydrogenase (LDH), eosinophils, antigen-specific IgE (e.g., Phadiatop™ test), and periostin. In some embodiments, the methods of the present invention comprise determining the level of an AD-associated biomarker in a patient in need thereof, selecting a patient with an elevated level of the AD-associated biomarker, and administering a therapeutically effective amount of an antibody or antigen-binding fragment thereof that specifically binds IL-4R. In some embodiments, the patient is selected by acquiring information about the level of an AD-associated biomarker in a patient. In some embodiments, the level of an AD-associated biomarker is determined by an assay or test known in the art or as disclosed elsewhere herein. In one embodiment, the patient is selected on the basis of exhibiting an IgE level greater than about 1500 kU/L prior to or at the time of treatment. In one embodiment, the patient is selected on the basis of exhibiting a TARC level of greater than about 1000 pg/mL prior to or at the time of treatment. According to a related aspect of the present invention, methods for treating AD are provided which comprise administering to a subject a pharmaceutical composition comprising a therapeutically effective amount of an IL-4R antagonist, wherein administration of the pharmaceutical composition to the subject results in a decrease in at least one AD-associated biomarker by day 4, 8, 15, 22, 25, 29, 36 or later in the subject following administration. In certain embodiments, the patient exhibits between 5% and 20% decrease in IgE level from the baseline at day 36 or later following administration. In certain embodiments, the patient exhibits between 25% and 70% decrease in TARC level from baseline at day 4 or later following administration.

The present invention also provides methods for decreasing the level of one or more AD-associated biomarker(s) in a subject, or improving one or more AD-associated parameter(s) in a subject, wherein the methods comprise sequentially administering to a subject in need thereof a single initial dose of a pharmaceutical composition comprising an IL-4R antagonist, followed by one or more secondary doses of the pharmaceutical composition comprising the IL-4R antagonist.

According to certain embodiments, the present invention provides methods for decreasing the level of one or more AD-associated biomarker(s) in a subject, or improving one or more AD-associated parameter(s) in a subject, wherein the methods comprise administering to the subject about 50 mg to about 600 mg of a pharmaceutical composition comprising an antibody or antigen-binding fragment thereof that specifically binds IL-4R. In certain embodiments, the initial dose and the one or more secondary doses each comprise about 75 mg to about 300 mg of the antibody or antigen-binding fragment thereof. According to this aspect of the invention, the pharmaceutical composition may be administered to the subject at a dosing frequency of, e.g., once a week. In some embodiments, each secondary dose is administered 1 to 8 weeks after the immediately preceding dose. In certain embodiments, at least 4 doses of the antibody or antigen-binding fragment thereof are administered.

In one embodiment, each secondary dose is administered 1 week after the immediately preceding dose. In certain embodiments, the initial dose comprises a first amount of the antibody or antigen-binding fragment thereof and the one or more secondary doses each comprise a second amount of the antibody or antigen-binding fragment thereof. In some embodiments, the first amount of antibody or fragment thereof is 1.5×, 2×, 2.5×, 3×, 3.5×, 4×, or 5× the second amount of the antibody or antigen-binding fragment thereof. In some embodiments, the pharmaceutical composition is administered subcutaneously or intravenously.

In some embodiments, the present invention provides methods for treating moderate-to-severe AD comprising concomitant administration of an IL-4R antagonist and a topical corticosteroid (TCS). In some embodiments, the methods further comprise assaying for an improvement in an AD-associated parameter. In certain embodiments, the invention provides for methods for improving one or more AD-associated parameters, the methods comprising concomitantly administering an IL-4R antagonist and a TCS, wherein an improvement in an AD-associated parameter is selected from the group consisting of: (i) a decrease from baseline in IGA score of at least 45%; (ii) a decrease from baseline in BSA score of at least 40%; (iii) a decrease from baseline in EASI score of at least 65%; (iv) a decrease from baseline in SCORAD score of at least 50%; (v) a decrease from baseline in 5-D Pruritus scale of at least 25%; and (vi) a decrease from baseline in Pruritus NRS score of at least 60%. In some embodiments, the improvement in an AD-associated parameter is a decrease from baseline in IGA of at least 50% on day 29 after administration of the antibody or antigen-binding fragment thereof that binds IL-4R. In some embodiments, the improvement in an AD-associated parameter is a decrease from baseline in NRS of at least 65% on day 29 after administration. In some embodiments, the improvement in an AD-associated parameter is a decrease from baseline in EASI of at least 70% on day 29 after administration. In some embodiments, the improvement in an AD-associated parameter is a decrease from baseline in SCORAD of at least 60% on day 29 after administration.

In certain embodiments, the TCS is selected from the group consisting of a group I TCS, a group II TCS and a group III TCS. In some embodiments, the TCS is selected from the group consisting of methylprednisolone aceponate, mometasone furoate, fluticasone propionate, betamethasone valerate and hydrocortisone butyrate.

In related embodiments, the invention provides for methods to reduce the dependence on TCS in a patient with moderate-to-severe AD comprising concomitant administration of an IL-4R antagonist and a TCS, wherein the dosage of the TCS is reduced by 50% as compared to subjects without the administration of the IL-4R antagonist. In one embodiment, the invention provides methods to reduce the dosage of a TCS in treatment of moderate-to-severe AD, comprising administration of an IL-4R antagonist concomitantly with a reduced dosage of the TCS. The dosage of the TCS may be reduced by more than, for example, 10%, 20%, 30%, 40%, or 50%. In one embodiment, the dosage of the TCS may be reduced by more than, for example, 10%, 20%, 30%, 40%, or 50% as compared to the dosage used by the subject before treatment with the IL-4R antagonist.

The present invention also includes an IL-4R antagonist as disclosed herein for use in treating or preventing AD, for improving an AD-associated parameter, for decreasing the level of at least one AD-associated biomarker, and/or for treating any of the other indications or conditions disclosed herein.

In certain embodiments, the IL-4R antagonist of the present methods is an antibody or antigen-binding fragment that specifically binds IL-4R and that comprises heavy and light chain CDR sequences from a HCVR/LCVR sequence pair selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260 and 262/264. In one embodiment, the antibody or antigen-binding fragment that specifically binds IL-4R comprises heavy and light chain CDR sequences from the HCVR/LCVR sequence pair of SEQ ID NOs: 162/164. In one embodiment, the antibody or antigen-binding fragment that specifically binds IL-4R comprises three heavy chain complementarity determining region (HCDR) sequences comprising SEQ ID NOs: 148, 150, 152, respectively, and three light chain complementarity determining (LCDR) sequences comprising SEQ ID NO: 156, LGS and SEQ ID NO: 160, respectively.

In some embodiments, the pharmaceutical composition is administered subcutaneously or intravenously to the patient. In some embodiments, the pharmaceutical composition comprises about 50 mg to about 600 mg of the antibody or antigen-binding fragment thereof that binds IL-4R. In further embodiments, the pharmaceutical composition comprises about 75 mg, about 100 mg, about 150 mg, about 200 mg, about 250 mg or about 300 mg of the antibody or fragment thereof that binds IL-4R.

In certain embodiments, the pharmaceutical composition is administered to the patient before, after or concurrent with a second therapeutic agent. In some embodiments, the second therapeutic agent is a topical corticosteroid (TCS) or a calcineurin inhibitor.

In another aspect, the invention provides monitoring the effectiveness of treatment of moderate-to-severe AD in a subject with an IL-4R antagonist, the method comprising: (a) determining the expression level of an AD-associated biomarker, such as TARC or serum IgE in a biological sample acquired from the subject before treatment with the IL-4R antagonist; (b) determining the expression level of one or both of TARC and serum IgE in a biological sample acquired from the subject after treatment with the IL-4R antagonist; (c) comparing the level determined in step (a) with the level in step (b); and (d) concluding that the treatment is effective when the level determined in step (b) is lower than the level determined in step (a), or concluding that the treatment is not effective when the level determined in step (b) is the same or higher than the level determined in step (a). In one embodiment, the level in step (b) is determined 1 week, 2 weeks, 3 weeks, 4 weeks, or 5 weeks after determining the level in step (a). In one embodiment, the biomarker is TARC, and if TARC levels decrease following administration of the IL-4R antagonist, then treatment with the IL-4R antagonist is determined to be effective. In one embodiment, the IL-4R antagonist is an anti-IL-4R antibody or antigen-binding fragment thereof and comprises heavy and light chain CDR sequences from a HCVR/LCVR sequence pair selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260 and 262/264.

The expression level of the biomarker can be determined, for example, 1 week, 2 weeks, 3 weeks, 4 weeks, 5 weeks, or longer after administration of the IL-4R antagonist, and compared to the expression level prior to administration of the antagonist. The dose or the dosing regimen of the IL-4R antagonist (e.g., an anti-IL4R antibody) can be adjusted following the determination. For example, if the expression of the biomarker fails to decrease within 1 week, 2 weeks, 3 weeks, 4 weeks, 5 weeks, or longer following administration of the antagonist, then treatment with the antagonist can be stopped, or the dose of the antagonist can be increased. If expression of the biomarker decreases following administration of the antagonist, the dosage of the antagonist can be maintained or decreased, such as to identify a minimal effective dose. In some embodiments, treatment is maintained at the minimal effective dose.

In another aspect, the invention provides methods for monitoring a subject's response to treatment with an IL-4R antagonist, wherein the subject has moderate-to-severe AD, the method comprising: (a) acquiring information regarding the expression level of one or both of TARC and IgE in a biological sample from the subject following administration of the IL-4R antagonist to the subject; and (b) providing an indication that the treatment should be continued if the expression level of TARC or IgE has decreased as compared to the level before treatment with the IL-4R antagonist. In one embodiment the biomarker is TARC, and if TARC levels are determined to decrease following administration of the antagonist, then an indication is provided to continue treatment with the IL-4R antagonist.

The invention also includes an IL-4R antagonist as disclosed herein for use in the manufacture of a medicament for the treatment and/or prevention of atopic dermatitis (AD) (e.g., moderate to severe eosinophilic AD, extrinsic AD, intrinsic AD, etc.) or for treating any of the other indications or conditions disclosed herein.

The invention also includes an IL-4R antagonist as disclosed herein for use in the treatment and/or prevention of AD (e.g., moderate to severe eosinophilic AD, etc.) or for treating and/or prevention of any of the other indications or conditions disclosed herein.

In one embodiment, the IL-4R antagonist is an anti-IL-4R antibody or antigen-binding fragment thereof.

The invention includes a pharmaceutical composition comprising an anti-IL4R antibody antagonist or an antigen binding fragment thereof for use in the treatment and/or prevention of AD and related conditions.

The invention also includes a pharmaceutical composition comprising an anti-IL4R antibody antagonist or an antigen binding fragment thereof for use in improving one or more AD-associated parameters in a subject in need thereof.

In addition, the invention includes a pharmaceutical composition comprising an anti-IL4R antibody antagonist or an antigen binding fragment thereof for use in reducing the level of one or more AD-associated biomarkers in a subject in need thereof.

The invention includes a pharmaceutical composition comprising an anti-IL-4R antibody antagonist or an antigen binding fragment thereof for use in the treatment of AD in a patient having an elevated level of a biomarker selected from the group consisting of thymus and activation-regulated chemokine (TARC), IgE, eotaxin-3, lactate dehydrogenase (LDH), and periostin.

The invention further includes a pharmaceutical composition comprising an anti-IL-4R antibody antagonist or an antigen binding fragment thereof for use in the treatment of AD in a subject wherein the treatment results in a decrease in an AD-associated biomarker in the subject by day 4, 8, 15, 22, 25, 29 or 36 following treatment as compared to the level of biomarker in the subject prior to treatment. In certain embodiments, the AD-associated biomarker is one or both of TARC and IgE.

The invention further includes a pharmaceutical composition comprising an anti-IL-4R antibody antagonist or an antigen binding fragment thereof for use in improving an AD-associated parameter, or for reducing the level of an AD-associated biomarker in a subject in need thereof, wherein the pharmaceutical composition is sequentially administered to the subject as a single initial dose followed by one or more secondary doses.

In one embodiment, the one or more secondary doses are administered weekly.

In some embodiments, the pharmaceutical composition comprises 75 mg to 600 mg of the anti-IL-4R antibody or antigen-binding fragment thereof. In one embodiment, the pharmaceutical composition comprises 300 mg of the anti-IL-4R antibody or fragment thereof.

In another aspect, the invention provides methods of monitoring whether a therapeutic dose of an interleukin-4 receptor (IL-4R) antagonist administered to a human subject is safe, said method comprising: acquiring information regarding the safety of the antagonist following administration to a human, wherein the information includes the occurrence of one or more events selected from the group consisting of an anaphylactic reaction or acute allergic reaction requiring immediate treatment, severe injection site reaction lasting longer than 24 hours, severe infection, any parasitic infection, alanine aminotransferase (ALT) increase 2 Upper Limit Normal Range (ULN), QTc>=500 ms, pregnancy, overdose, and herpes simplex type II viral infection; determining that the one or more said events has occurred, determining that said therapeutic dose is not safe, and, optionally advising that the therapeutic dose be discontinued or lowered.

In a related aspect, the invention provides methods of monitoring whether a therapeutic dose of an interleukin-4 receptor (IL-4R) antagonist administered to a human subject is safe, said method comprising: acquiring information regarding the safety of the antagonist following administration to a human, wherein the information includes the occurrence of one or more events selected from the group consisting of: anaphylactic reaction or acute allergic reaction requiring immediate treatment, severe injection site reaction lasting longer than 24 hours, severe infection, any parasitic infection, alanine aminotransferase (ALT) increase 2 Upper Limit Normal Range (ULN), QTc>=500 ms, pregnancy, overdose, and herpes simplex type II viral infection; determining that the one or more of said events has not occurred; and determining that said therapeutic dose is safe.

In one embodiment, the infection is upper respiratory tract injection, pharyngitis, or sinusitis. In one embodiment, the injection site reaction is erythema, pain, nodule, hematoma or pruritus. In one embodiment, the pain is greater than 2 mm VAS, e.g., 3 mm to 30 mm VAS. In one embodiment, the erythema diameter is 9 mM.

In one embodiment, the safe therapeutic dose is equal to or less than 500 mg. In one embodiment, the safe therapeutic dose is selected from the group consisting of 75 mg, 150 mg, and 300 mg.

In another aspect, the invention provides methods of quantifying or monitoring an amount of anti-drug antibodies in blood serum of a human subject following administration of drug wherein the drug is an interleukin-4 receptor (IL-4R) antagonist, said method comprising: (a) obtaining a sample of said blood serum from a human subject who was administered a dose of said IL-4R antagonist; and (b) determining the amount of anti-drug antibodies in said serum sample.

In another aspect, the invention provides methods of comparing an interleukin-4 receptor (IL-4R) antagonist manufactured by a first process and proposed equivalent second process, said method comprising: acquiring information regarding the safety of the antagonist following administration of the antagonist manufactured by the first process to a first human, and following administration of the antagonist manufactured by the second process to a second human, wherein the information includes: one or more events selected from the group consisting of an anaphylactic reaction or acute allergic reaction requiring immediate treatment, severe injection site reaction lasting longer than 24 hours, severe infection, any parasitic infection, alanine aminotransferase (ALT) increase ≥2 Upper Limit Normal Range (ULN), QTc>=500 ms, pregnancy, overdose, and herpes simplex type II viral infection; and wherein if the information is not significantly different for the antagonist manufactured by the first process and the antagonist manufactured by the second process, then the two processes are determined to be acceptable for manufacturing equivalent antagonists; and wherein if the information is determined to be significantly different for the antagonist manufactured by the first process and the antagonist manufactured by the second process, then the two processes are determined to be unacceptable for manufacturing equivalent antagonists.

In a related aspect, the invention provides methods of comparing an interleukin-4 receptor (IL-4R) antagonist manufactured by a first process and proposed equivalent second process, said method comprising: acquiring information regarding a therapeutic dose of the antagonist following administration of the dose of the antagonist manufactured by the first process to a first human, and following administration of the dose of the antagonist manufactured by the second process to a second human, wherein the information includes one or more of: (a) area under the plasma concentration versus time curve calculated using the trapezoidal method from time zero to real time ($AUC_{last}$) from about 4 mg-h/ml to about 20 mg-h/ml; (b) maximum plasma concentration observed ($C_{max}$) from about 15 ug/ml to about 42 ug/ml; (c) first time to reach a maximum plasma concentration ($t_{max}$) from about 40 hr to about 280 hr; (d) area under the plasma concentration versus time curve extrapolated to infinity (AUC) from about 5,000,000 ng/h*mL to about 25,000,000 ng/h*mL and (e) time to reach terminal half-life of ($t_{1/2}^{z}$) from about 50 h to about 200 h, wherein if the information is not significantly different for the antagonist manufactured by the first process and the antagonist manufactured by the second process, then the two processes are determined to be acceptable for manufacturing equivalent antagonists; and wherein if the information is determined to be significantly different for the antagonist manufactured by the first process and the antagonist manufactured by the second process, then the two processes are determined to be unacceptable for manufacturing equivalent antagonists.

In another aspect, the invention provides a therapeutic dosage form of a pharmaceutical composition comprising an interleukin-4 receptor (IL-4R) antagonist, wherein administration of the dose form to a human provides one or more of: (a) an area under the plasma concentration versus time curve calculated using the trapezoidal method from time zero to real time ($AUC_{last}$) from about 4 mg-h/ml to about 20 mg-h/ml; (b) a maximum plasma concentration observed ($C_{max}$) from about 15 ug/ml to about 42 ug/ml; (c) a first time to reach a maximum plasma concentration ($t_{max}$) from about 40 hr to about 280 hr; (d) an area under the plasma concentration versus time curve extrapolated to infinity (AUC) from about 5,000,000 ng/h*mL to about 25,000,000 ng/h*mL and (e) a time to reach terminal half-life of ($t_{1/2}^{z}$) from about 50 h to about 200 h.

In one embodiment, the safe therapeutic dose is equal to or less than 500 mg. In one embodiment, the safe therapeutic dose is selected from the group consisting of 75 mg, 150 mg, and 300 mg.

Certain aspects of the invention are related to methods and compositions that are useful in vaccine applications. The present invention provides methods for enhancing or potentiating the immune response against an antigen in a subject. In some embodiments, the methods for enhancing or potentiating the immune response against an antigen in a subject comprise administering a pharmaceutical composition comprising the antigen and an IL-4R antagonist. Some embodiments are related to methods comprising (a) administering a vaccine composition comprising the antigen to the subject; and (b) administering an IL-4R antagonist prior to, concurrent with, and/or subsequent to administration of the vaccine composition to the subject. The present invention also provides for pharmaceutical compositions to enhance or potentiate an immune response against an antigen in a subject, the compositions comprising: (a) the antigen; and (b) an IL-4R antagonist. In one exemplary embodiment, the IL-4R antagonist is an anti-IL-4R antibody (as exemplified in Example 1 herein). In certain embodiments, the IL-4R antagonist is an anti-IL-4R antibody having the binding characteristics of the reference antibody referred to herein as "mAb1" (e.g., an antibody or antigen-binding fragment thereof comprising the complementarity determining regions of mAb1).

Other embodiments of the present invention will become apparent from a review of the ensuing detailed description.

DETAILED DESCRIPTION

Figure 1:
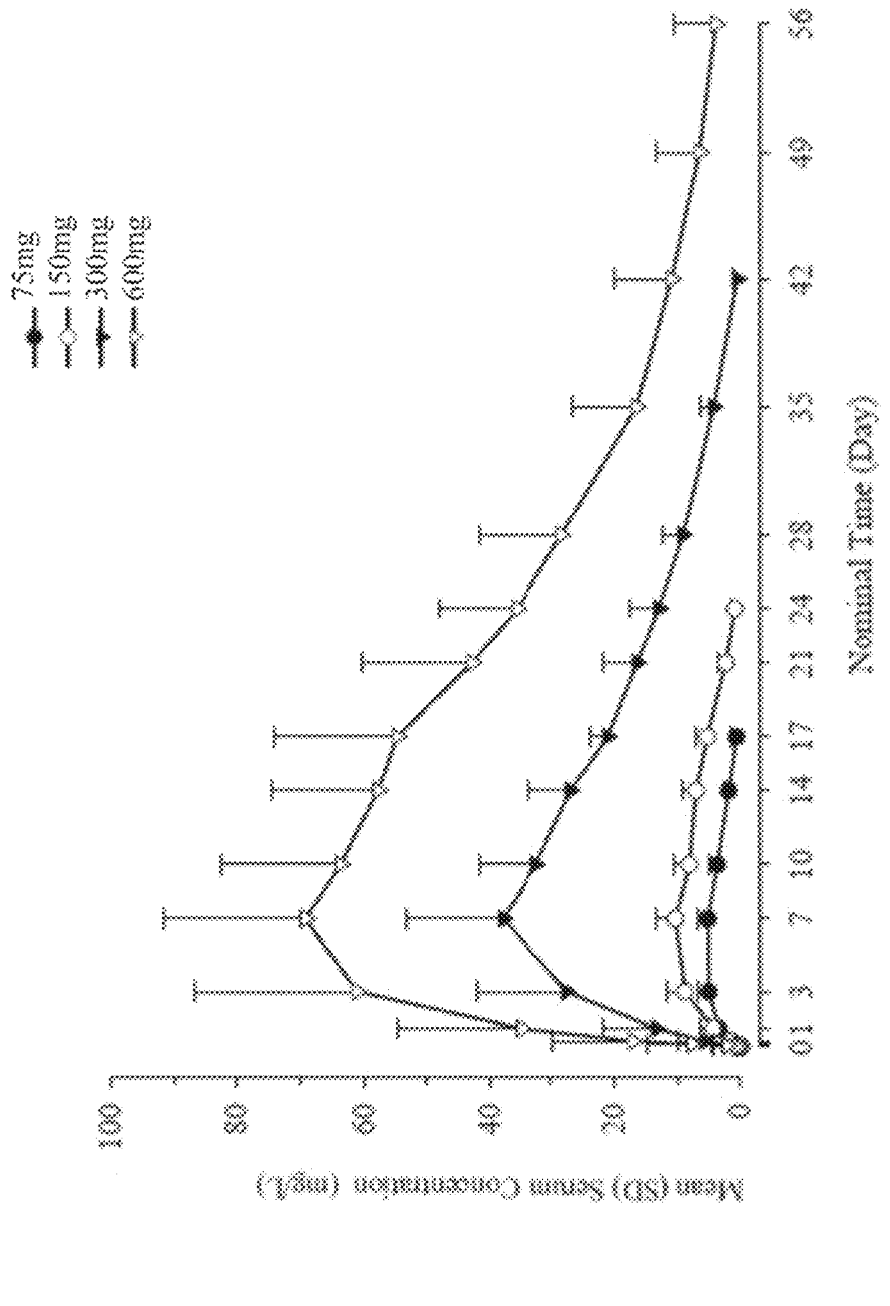
FIG. 1 shows a Cartesian plot of mean (SD) serum functional mAb1 concentration-time profiles following a single subcutaneous dose.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

The present invention includes methods which comprise administering to a subject in need thereof a therapeutic composition comprising an IL-4R antagonist. As used herein, the expression “a subject in need thereof” means a human or non-human animal that exhibits one or more symptoms or indicia of atopic dermatitis, and/or who has been diagnosed with atopic dermatitis. In certain embodiments, the methods of the present invention may be used to treat patients that show elevated levels of one or more AD-associated biomarkers (described elsewhere herein). For example, the methods of the present invention comprise administering an IL-4R antagonist to patients with elevated levels of IgE or TARC or periostin. In some embodiments, the methods herein may be used to treat AD in children who are s 1 year old. For example, the present methods may be used to treat infants who are less than 1 month, 1 month, 2 months, 3 months, 4 months, 5 months, 6 months, 7 months, 8 months, 9 months, 10 months, 11 months or less than 12 months old. In other embodiments, the present methods may be used to treat children and/or adolescents who are s 18 years old. For example, the present methods may be used to treat children or adolescents less than 17 years, 16 years, 15 years, 14 years, 13 years, 12 years, 11 years, 10 years, 9 years, 8 years, 7 years, 6 years, 5 years, 4 years, 3 years, or less than 2 years old.

In the context of the present invention, “a subject in need thereof” may include, e.g., subjects who, prior to treatment, exhibit (or have exhibited) one or more AD-associated parameters such as, e.g., elevated IGA, BSA, EASI, SCORAD, 5D-Pruritus, and/or NRS score, and/or an elevated level of one or more AD-associated biomarker such as, e.g., IgE and/or TARC (as described elsewhere herein). In certain embodiments, “a subject in need thereof” may include a subset of population which is more susceptible to AD or may show an elevated level of an AD-associated biomarker. For example, “a subject in need thereof” may include a subset of population defined by a race or an ethnicity present in the population.

“Atopic dermatitis” (AD), as used herein, means an inflammatory skin disease characterized by intense pruritus (e.g., severe itch) and by scaly and dry eczematous lesions. The term “atopic dermatitis” includes, but is not limited to, AD caused by or associated with epidermal barrier dysfunction, allergy (e.g., allergy to certain foods, pollen, mold, dust mite, animals, etc.), radiation exposure, and/or asthma. The present invention encompasses methods to treat patients with mild, moderate-to-severe or severe AD. As used herein, “moderate-to-severe AD”, is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body’s skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor or any other commonly used therapeutic agent known in the art.

The present invention includes methods to treat both the extrinsic and the intrinsic forms of AD. The extrinsic form of AD associated with IgE-mediated sensitization and increased levels of Th2 cytokines involves 70% to 80% of patients with AD. The intrinsic form without IgE-mediated sensitization involves 20% to 30% of patients with AD; these patients have lower levels of IL-4 and IL-13 than extrinsic AD.

The present invention includes methods to treat AD in patients resistant, non-responsive or inadequately responsive to treatment with a topical corticosteroid (TCS) or a calcineurin inhibitor. The term “resistant, non-responsive or inadequately responsive to a TCS or a calcineurin inhibitor”, as used herein, refers to subjects or patients with AD who have been treated with a TCS or a calcineurin inhibitor and wherein the TCS/calcineurin inhibitor does not have a therapeutic effect. In some embodiments, the term refers to reduced patient compliance and/or toxicity and side effects and/or ineffectiveness of the administered TCS/calcineurin inhibitor to reduce, ameliorate or decrease the symptoms of AD. In some embodiments, the term refers to patients suffering from moderate-to-severe AD who are refractory to treatment by a TCS/calcineurin inhibitor. In some embodiments, the term refers to patients with AD which is uncontrolled despite treatment with a TCS and/or calcineurin inhibitor. In some embodiments, the patients who are “resistant, non-responsive or inadequately responsive to a TCS or a calcineurin inhibitor” may show no improvement in one or more AD-associated parameters. Examples of AD-associated parameters are described elsewhere herein. For example, treatment with a TCS/calcineurin inhibitor may result in no decrease in pruritus or EASI score or BSA score. In some embodiments, the present invention includes methods to treat moderate-to-severe AD in patients who have been treated earlier with a TCS/calcineurin inhibitor for 1 month and do not show a decrease in one or more AD-associated parameters. For example, the present methods may be used to treat a patient with chronic AD who has been on a stable regimen of a TCS/calcineurin inhibitor and has a BSA score of 10% or an IGA score 3.

In alternate embodiments, the term “subject in need thereof” includes patients with moderate-to-severe AD who have been administered one or more TCS for more than 6 months, more than 1 year, more than 2 years, more than about 5 years, more than about 7 years, or more than about 10 years. The patients may desire to minimize or avoid the adverse side effects of the TCS. The present invention includes methods for long-term safer and more effective management of moderate-to-severe AD in a patient, the methods comprising administering an IL-4R antagonist concomitantly with a TCS wherein the dosage is adjusted to minimize or prevent adverse side effects of the TCS. In certain embodiments, the present invention includes methods to reduce dependence on TCS in a patient with moderate-to-severe AD; the methods comprising administering a therapeutically effective amount of an IL-4R antagonist concomitantly with a potent TCS wherein the amount of TCS used by the patient is reduced by about 50% as compared to a patient not administered the IL-4R antagonist. In certain embodiments, the present invention includes methods to reduce dependence on TCS in a patient with moderate-to-severe AD, the methods comprising administering a therapeutically effective amount of an IL-4R antagonist concomitantly with a potent TCS wherein the amount of TCS used by the patient is reduced by about 50% as compared to the amount used by the patient before treatment with the IL-4R antagonist. In certain embodiments, the administration of an IL-4R antagonist and a TCS results in additive or synergistic activity in treating AD as compared to monotherapy.

The term “TCS”, as used herein includes group I, group II, group III and group IV topical corticosteroids. According to the Anatomical Therapeutic Classification System of World Health Organization, the corticosteroids are classified as weak (group I), moderately potent (Group II) and potent (Group III) and very potent (Group IV), based on their activity as compared to hydrocortisone. Group IV TCS (very potent) are up to 600 times as potent as hydrocortisone and include clobetasol propionate and halcinonide. Group III TCS (potent) are 50 to 100 times as potent as hydrocortisone and include, but are not limited to, betamethasone valerate, betamethasone dipropionate, diflucortolone valerate, hydrocortisone-17-butyrate, mometasone furoate, and methylprednisolone aceponate. Group II TCS (moderately potent) are 2 to 25 times as potent as hydrocortisone and include, but are not limited to, clobetasone butyrate, and triamcinolone acetonide. Group I TCS (mild) includes hydrocortisone.

Although any methods and materials similar or equivalent to those described herein can be used in the practice of the present invention, the preferred methods and materials are now described. All publications mentioned herein are incorporated herein by reference to describe in their entirety.

Methods for Improving Atopic Dermatitis (AD)-Associated Parameters

The present invention includes methods for improving one or more atopic dermatitis (AD)-associated parameters in a subject in need thereof, wherein the methods comprise administering a pharmaceutical composition comprising an interleukin-4 receptor (IL-4R) antagonist to the subject.

Examples of "AD-associated parameters" include: (a) Investigators Global Assessment (IGA); (b) Body Surface Area Involvement of Atopic Dermatitis (BSA); (c) Eczema Area and Severity Index (EASI); (d) SCORAD; (e) 5-D Pruritus Scale; and (f) Pruritus Numeric Rating Scale (NRS). An "improvement in an AD-associated parameter" means a decrease from baseline of one or more of IGA, BSA, EASI, SCORAD, 5-D Pruritus Scale, or NRS. As used herein, the term "baseline," with regard to an AD-associated parameter, means the numerical value of the AD-associated parameter for a subject prior to or at the time of administration of a pharmaceutical composition of the present invention.

To determine whether an AD-associated parameter has "improved," the parameter is quantified at baseline and at one or more time points after administration of the pharmaceutical composition of the present invention. For example, an AD-associated parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the AD associated parameter.

Investigator's Global Assessment (IGA).

The IGA is an assessment scale used in clinical settings to determine the severity of AD and clinical response to treatment based on a 6-point scale ranging from 0 (clear) to 5 (very severe). According to certain embodiments of the present invention, administration of an IL-4R antagonist to a patient results in a decrease in IGA score. For example, the present invention includes therapeutic methods which result in a decrease from baseline in IGA score of at least about 10%, 15%, 20%, 25%, 30%, 35%, 40%, 45%, 50%, 55%, 60%, 65%, 70%, 75%, or more at day 4, 8, 15, 22, 25, 29, 36, 43, 50, 57, 64, 71, 85 or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in IGA of at least 25%. In one embodiment of the present invention, administration of an IL-4R antagonist to a subject results in a decrease from baseline in IGA of at least 25% by day 15 after administration. In certain embodiments of the present invention, administration of an IL-4R antagonist to a subject results in a decrease from baseline in IGA of at least 35% by day 22 after administration. In other embodiments, administration of an IL-4R antagonist to a subject results in a decrease from baseline in IGA of at least 40% or at least 45% through day 85 upon treatment.

Body Surface Area Involvement of Atopic Dermatitis (BSA).

BSA is assessed for each major section of the body (head, trunk, arms and legs) and is reported as a percentage of all major body sections combined. According to certain embodiments of the present invention, administration of an IL-4R antagonist to a patient results in a decrease in BSA score. For example, the present invention includes therapeutic methods which result in a decrease from baseline in BSA score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in BSA score of at least 35% after administration. In one embodiment of the present invention, administration of an IL-4R antagonist to a subject results in a decrease from baseline in BSA score of at least 35% by day 29 after administration. In one embodiment of the present invention, administration of an IL-4R antagonist to a subject results in a decrease from baseline in BSA score of at least 40% by day 29 after administration. In some embodiments, administration of an IL-4R antagonist to a subject results in a decrease from baseline in BSA score of at least 40% or at least 50% through day 85 upon treatment.

Eczema Area and Severity Index (EASI).

The EASI is a validated measure used in clinical settings to assess the severity and extent of AD. (Hanifin et al. 2001, *Exp. Dermatol.* 10:11-18). Four AD disease characteristics are assessed for severity by a physician or other qualified medical professional on a scale of 0 (absent) through 3 (severe). In addition, the area of AD involvement is assessed as a percentage by body area of head, trunk, arms and legs and converted to a score of 0 to 6. According to certain embodiments of the present invention, administration of an IL-4R antagonist to a patient results in a decrease in EASI score. For example, the present invention includes therapeutic methods which result in a decrease from baseline in EASI score of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in EASI score of at least 45%. In one embodiment of the present invention, administration of an IL-4R antagonist to a subject results in a decrease from baseline in EASI score of at least 45% by day 15 after administration. In one embodiment of the present invention, administration of an IL-4R antagonist to a subject results in a decrease from baseline in EASI score of at least 50% by day 29 after administration. In some embodiments, administration of an IL-4R antagonist to a subject results in a decrease from baseline in EASI score of at least 55% or at least 60% through day 85 upon treatment.

SCORAD.

SCORing Atopic Dermatitis (SCORAD) is a clinical assessment of the severity (e.g., extent or intensity) of atopic dermatitis developed by the European Task Force on Atopic Dermatitis (Consensus Report of the European Task Force on Atopic Dermatitis, 1993, *Dermatology* (*Basel*) 186(1): 23-31). The extent of AD is assessed as a percentage of each defined body area and reported as the sum of all areas, with a maximum score of 100% (assigned as "A" in the overall SCORAD calculation). The severity of 6 specific symptoms of AD is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the patient or relative on a visual analogue scale (VAS), where 0 is no itch (or sleeplessness) and 10 is the worst imaginable itch (or sleeplessness), with a maximum possible score of 20. This parameter is assigned as "C" in the overall SCORAD calculation. The SCORAD is calculated as: A/5+7B/2+C. According to certain embodiments of the present invention, administration of an IL-4R antagonist to a patient results in a decrease in SCORAD score. For example, the present invention includes therapeutic methods which result in a decrease from baseline in SCORAD of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in SCORAD score of at least 30%. In one embodiment of the present invention, administration of an IL-4R antagonist to a subject results in a decrease from baseline in SCORAD score of at least 30% by day 29 after administration. In one embodiment of the present invention, administration of an IL-4R antagonist to a subject results in a decrease from baseline in SCORAD score of at least 35% by day 29 after administration. In some embodiments, administration of an IL-4R antagonist to a subject results in a decrease from baseline in SCORAD score of at least 40% or at least 45% through day 85 upon treatment.

5-D Pruritus Scale.

The 5-D Pruritus Scale is a 1-page, 5-question tool used in clinical settings to assess 5 dimensions of background itch: degree, duration, direction, disability, and distribution. (Elman and Hynan, 2010, *Brit. J. Dermatol.* 162:587-593). Each question corresponds to 1 of the 5 dimensions of itch; patients rate their symptoms as "present" or on a 1 to 5 scale, with 5 being the most affected. According to certain embodiments of the present invention, administration of an IL-4R antagonist to a patient results in a decrease in 5-D Pruritus Scale. For example, the present invention includes therapeutic methods which result in a decrease from baseline in 5-D Pruritus Scale of at least about 10%, 15%, 20%, 25%, 30%, 35%, 40%, 45%, 50%, 55%, 60%, 65%, 70%, 75% or more at day 4, 8, 15, 22, 25, 29, 36, 43, 50, 57, 64, 71, 85 or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in 5-D Pruritus Scale of at least 15%. In one embodiment of the present invention, administration of an IL-4R antagonist to a subject results in a decrease from baseline in 5-D Pruritus Scale of at least 15% by day 15 after administration. In one embodiment of the present invention, administration of an IL-4R antagonist to a subject results in a decrease from baseline in 5-D Pruritus Scale of at least 20% by day 15 after administration. In some embodiments, administration of an IL-4R antagonist to a subject results in a decrease from baseline in 5-D Pruritus Scale of at least 25% or at least 30% through day 85 upon treatment.

Pruritus Numeric Rating Scale (NRS).

The Pruritus NRS is a single-question assessment tool that is used to assess a subject's worst itch, on a scale of 1 to 10, as a result of AD in the previous 12 hours. According to certain embodiments of the present invention, administration of an IL-4R antagonist to a patient results in a decrease in NRS score. For example, the present invention includes therapeutic methods which result in a decrease from baseline in NRS score of at least about 10%, 15%, 20%, 25%, 30%, 35%, 40%, 45%, 50%, 55%, 60%, 65%, 70%, 75% or more at the end of week 1, 2, 3, 4, 5, 6, 7, 8, 9, 10, 11, 12, or later following administration of the IL-4R antagonist (e.g., following subcutaneous administration of about 75 mg, 150 mg, or 300 mg of an anti-IL-4R antibody or antigen-binding fragment thereof). In certain exemplary embodiments of the present invention, administration of an IL-4R antagonist to a subject results in a decrease from baseline in NRS score of at least 25%. In one embodiment of the present invention, administration of an IL-4R antagonist to a subject results in a decrease from baseline in NRS score of at least 25% by the end of week 2 after administration. In one embodiment of the present invention, administration of an IL-4R antagonist to a subject results in a decrease from baseline in NRS score of at least 30% by the end of week 2 after administration. In some embodiments, administration of an IL-4R antagonist to a subject results in a decrease from baseline in NRS score of at least 45% or at least 50% through day 85 upon treatment.

Global Individual Signs Score (GISS).

Individual components of the AD lesions (erythema, infiltration/population, excoriations, and lichenification) is rate globally (i.e., each assessed for the whole body, not by anatomical region) on a 4-point scale (from 0=none to 3=severe) using the EASI severity grading criteria.

Pruritus Categorical Scale.

The Pruritus categorical scale is a 4-point scale used to assess symptoms that has been used in clinical studies of AD and has less of a "middling" effect (Kaufmann 2006). The scale is rated as follows: 0: absence of pruritus; 1: mild, pruritus (occasional slight itching/scratching); 2: moderate pruritus (constant or intermittent itching/scratching that does not disturb sleep) and 3: severe pruritus (bothersome itching/scratching that disturbs sleep).

Patient Oriented Eczema Measure (POEM).

The POEM is a 7-item, validated questionnaire used in clinical practice and clinical trials to assess disease symptoms in children and adults (Charman 2004). The format is a response to 7 items (dryness, itching, flaking, cracking, sleep loss, bleeding, and weeping) with a scoring system of 0 to 28; a high score is indicative of a poor QOL.

Dermatology Life Quality Index (DLQI).

The DLQI is a 10-item, validated questionnaire used in clinical practice and clinical trials to assess the impact of AD disease symptoms and treatment on QOL (Badia 1999). The format is a simple response to 10 items, which assess QOL over the past week, with an overall scoring system of 0 to 30; a high score is indicative of a poor QOL.

Itchy QOL.

Itchy QOL is a validated pruritus-specific instrument that addresses the symptom, emotional, and functional impact of pruritus. There is an overall score as well as subscale scores to address the 3 types of impact. This is a reliable, valid, and responsive questionnaire (Desai 2008).

EQ-5D.

The EQ-5D is a standardized measure of health status developed by the EuroQOI Group in order to provide a simple, generic measure of health for clinical and economic appraisal. The EQ-5D as a measure of health related QOL, defines health in terms of 5 dimensions: mobility, self-care, usual activities, pain/discomfort, and anxiety/depression. Each dimension has 3 ordinal levels of severity: "no problem" (1), "some problems" (2), "severe problems" (3). Overall health state is defined as a 5-digit number. Health states defined by the 5-dimensional classification can be converted into corresponding index scores that quantify health status, where 0 represents "death" and 1 represents "perfect health."

HADS.

The HADS is a general Likert scale used to detect states of anxiety and depression (Bjelland 2002). The 14 items on the questionnaire include 7 that are related to anxiety and 7 that are related to depression. Each item on the questionnaire is scored; a person can score between 0 and 21 for either anxiety or depression.

Patient Global Assessment of Disease Status and Treatment Effect.

Patients rate their overall wellbeing based on a 5-point Likert scale from poor to excellent. Patients are asked: "Considering all the ways in which your eczema affects you, indicate how well you are doing". Response choices are: "Poor"; "Fair"; "Good"; "Very Good"; "Excellent".

For treatment effect, patients rate their satisfaction with the study treatment based on a 5-point Likert scale from poor to excellent. Patients are asked: "How would you rate the way your eczema responded to the study medication?" Response choices are: "Poor"; "Fair"; "Good"; "Very Good"; "Excellent".

Methods for Long-Term Management of Atopic Dermatitis

The present invention includes methods for long term management of moderate-to-severe AD in a patient. In certain embodiments, the methods comprise administering an IL-4R antagonist concomitantly with a conventional therapeutic agent such as a topical corticosteroid (TCS). In further embodiments, the IL-4R antagonist may be an anti-IL-4R antibody as described herein.

The term "conventional therapeutic agent", as used herein, refers to therapeutic agents and drugs commonly or routinely used to treat AD in patients. Conventional therapeutic agents include systemic as well as topical therapeutics. For example, the most commonly or frequently prescribed drugs are the topical corticosteroids (TCS). Other examples of such agents include, but are not limited to, topical calcineurin inhibitors, anti-histamines, oral immunosuppressants, and glucocorticoids, systemic immunosuppressants such as methotrexate, cyclosporine, and azathioprine. Conventional therapeutic agents are used to relieve the symptoms of AD; however have numerous and considerable adverse side effects including diabetes, hypertension, osteoporosis, myelosuppression, nephrotoxicity, hepatotoxicity, leucopenia, an increased risk of microbial infections. Topical agents such as corticosteroids and calcineurin inhibitors are not recommended for long-term application due to the risk of irreversible skin atrophy, dyspigmentation, acneiform eruptions and risks associated with systemic absorption including skin malignancies and lymphomas. Also repetitive application of any topical therapies over a long period of time can erode patient compliance.

The term "long-term management of AD", as used herein, refers to treatment or containment of one or more symptoms or disease conditions of AD over a long period of time, typically more than about 2 years, more than about 5 years, more than about 10 years, or more than about 20 years. Long-term management of AD includes methods of treatment or methods to improve one or more AD-associated parameters over a period of more than 6 months, more than 1 year, more than 2 years, or more than about 5 years, the methods comprising administering an anti-IL-4R antibody in combination with a conventional therapeutic agent such as TCS. The administration regimen and dosage of the IL-4R antibody and the TCS is adjusted or varied such that one or more AD-associated parameters is significantly improved as well as the toxicity due to the conventional agent is prevented or minimized. In some embodiments, the IL-4R antibody may be administered in higher loading doses for significant improvement in an AD-associated parameter followed by lower regular doses to sustain or maintain the improvement. The concomitantly administered TCS may be administered at a reduced dose, typically reduced by about 20%, about 30%, about 40%, about 50% or about 60% as compared to a patient not treated with the IL-4R antibody. The administration regimens and dosage amounts are described elsewhere herein. In some embodiments, the present invention includes methods to reduce dependence on TCS in a patient with moderate-to-severe AD.

In certain embodiments, the present invention includes methods to treat patients who have AD for more than 1 year, more than about 5 years, more than about 10 years, or more than about 15 years, the methods comprising administering a therapeutically effective amount of an IL-4R antagonist in combination with a conventional therapeutic agent such as TCS.

In another aspect, the present invention includes methods for a safer and/or more effective therapy in the long-term management of moderate-to-severe AD in patients. The term "safer and/or more effective therapy", as used herein, refers to methods of treatment comprising administering an IL-4R antagonist in combination with a conventional therapeutic agent such as TCS such that one or more AD-associated parameters is significantly improved as well as the side effects and toxicity due to the conventional agent is minimized or prevented. In certain embodiments, the improvement in an AD-associated parameter is selected from the group consisting of: (a) a decrease from baseline in Investigator's Global Assessment (IGA) score of at least 50%; (b) a decrease from baseline in Pruritus Numeric Rating Scale (NRS) score of at least 65%; (c) a decrease from baseline in Eczema Area and Severity Index (EASI) score of at least 70%; and (d) a decrease from baseline in SCORAD score of at least 60%. In some embodiments, the dosage of the conventional agent is reduced or lowered to minimize the adverse side effects. In some embodiments, the methods of treatment as described herein may reduce or eliminate the risk of rebound after steroid reduction or discontinuation.

The present invention includes methods for more effective and safer therapy in long-term management of AD in patients including in children or young adults who may be more susceptible or sensitive to a conventional therapeutic agent.

In another aspect of the invention, methods for reducing or eliminating an AD patient's dependence on conventional therapeutics such as TCS during the treatment of moderate-to-severe AD are provided. In embodiments of the invention, the methods comprise: selecting a patient with moderate-to-severe AD that is uncontrolled or partially controlled with a background therapy; administering to the patient a defined dose of an IL-4R antagonist, preferably an anti-IL-4R antibody, for an initial treatment period while maintaining the patient's background therapy for the initial treatment period; and gradually reducing the dosage of one or more components of the background therapy over a subsequent period of treatment, while continuing to administer the IL-4R antagonist. The term "background therapy" as used herein, refers to standard or conventional therapeutic agents known in the art which are used for treating AD (described elsewhere herein). In certain embodiments, the background therapy comprises a TCS, or a topical calcineurin inhibitor. In one embodiment, the background therapy is a potent Group III TCS such as mometasone furoate or methylprednisolone aceponate. In some embodiments, the dosage of the conventional therapeutic such as TCS is eliminated or completely withdrawn upon the initial treatment period. For example, a TCS is administered in an initial treatment period and completely stopped or withdrawn in the subsequent treatment period. In certain embodiments, the TCS is reduced by about 10%, about 20%, about 30%, about 40%, about 50%, or more as compared to the dose during the initial treatment period.

In one example of a treatment regimen for a patient with moderate-to-severe AD wherein an IL-4R antagonist is administered to a patient with moderate-to-severe AD, during an initial treatment period (also called the "stable phase"), a conventional therapeutic such as a TCS administered to the patient as background therapy. During a subsequent treatment period (also called "withdrawal phase"), the administration of the TCS is gradually reduced by about 5-60% as compared to the initial treatment period. In one embodiment, the TCS is stopped, i.e., the TCS is gradually reduced over the subsequent treatment period until it is withdrawn or eliminated.

In a related aspect of the invention, methods of treating AD comprising an add-on therapy to background therapy with systematic background therapy withdrawal are provided. In certain embodiments of the invention, an IL-4R antagonist is administered as an add-on therapy to an AD patient who is on background therapy for a certain period of time (e.g., 1 week, 2 weeks, 3 weeks, 1 month, 2 months, 5 months, 12 months, 18 months, 24 months, or longer) (also called the "stable phase"). In some embodiments, the background therapy comprises a TCS. The stable phase is followed by a background therapy withdrawal phase, wherein one or more components comprising the background therapy are withdrawn, or reduced or eliminated, while the add-on therapy continues. In some embodiments, the background therapy may be reduced by about 5%, about 10%, about 20%, about 30%, about 40%, about 50% or by more during the withdrawal phase. The withdrawal phase may last 1 week, 2 weeks, 3 weeks, 4 weeks, 5 weeks, 6 weeks, 7 weeks, 8 weeks, 9 weeks, 10 weeks, 11 weeks, 12 weeks, or more.

Atopic Dermatitis-Associated Biomarkers

The present invention also includes methods involving the use, quantification, and analysis of AD-associated biomarkers. As used herein, the term "AD-associated biomarker" means any biological response, cell type, parameter, protein, polypeptide, enzyme, enzyme activity, metabolite, nucleic acid, carbohydrate, or other biomolecule which is present or detectable in an AD patient at a level or amount that is different from (e.g., greater than or less than) the level or amount of the marker present or detectable in a non-AD patient. In some embodiments, the term "AD-associated biomarker" includes a biomarker associated with Type 2 helper T-cell (Th2)-driven inflammation. Exemplary AD-associated biomarkers include, but are not limited to, e.g., thymus and activation-regulated chemokine (TARC; also known as CCL17), immunoglobulin E (IgE), eotaxin-3 (also known as CCL26), lactate dehydrogenase (LDH), eosinophils, antigen-specific IgE (e.g., Phadiatop™ test), and periostin. The term "AD-associated biomarker" also includes a gene or gene probe known in the art which is differentially expressed in a subject with AD as compared to a subject without AD. For example, genes which are significantly up-regulated in a subject with AD include, but are not limited to, T-helper 2 (Th2)-associated chemokines such as CCL13, CCL17, CCL18 and CCL26, markers of epidermal proliferation such as K16, Ki67, and T-cell and dendritic cell antigens CD2, CD1b, and CD1c (Tintle et al 2011; J. Allergy Clin. Immunol. 128: 583-593). Alternatively, "AD-associated biomarker" also includes genes which are down regulated due to AD such as terminal differentiation proteins (e.g., loricrin, filaggrin and involucrin) (Tintle et al 2011; J. Allergy Clin. Immunol. 128: 583-593). Certain embodiments of the invention pertain to use of these biomarkers for monitoring disease reversal with the administration of the IL-4R antagonist. Methods for detecting and/or quantifying such AD-associated biomarkers are known in the art; kits for measuring such AD-associated biomarkers are available from various commercial sources; and various commercial diagnostic laboratories offer services which provide measurements of such biomarkers as well.

According to certain aspects of the invention, methods for treating AD are provided which comprise: (a) selecting a subject who exhibits a level of at least one AD-associated biomarker prior to or at the time of treatment which signifies the disease state; and (b) administering to the subject a pharmaceutical composition comprising a therapeutically effective amount of an IL-4R antagonist. In certain embodiments, the patient is selected by determining if the level of an AD-associated biomarker is elevated. The level of an AD-associated biomarker is determined or quantified by acquiring a sample from the patient for a biomarker assay known in the art. In certain other embodiments, a patient is selected by acquiring information relating to an elevated level of an AD-associated biomarker from the patient. In certain embodiments of this aspect of the invention, the subject is selected on the basis of an elevated level of IgE or TARC or periostin.

For purposes of the present invention, a normal IgE level in healthy subjects is less than about 114 kU/L (e.g., as measured using the ImmunoCAP® assay [Phadia, Inc. Portage, MI]). Thus, the present invention involves methods comprising selecting a subject who exhibits a serum IgE level greater than about 114 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L, and administering to the subject a pharmaceutical composition comprising a therapeutically effective amount of an IL-4R antagonist.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, MN.) Thus, the present invention involves methods comprising selecting a subject who exhibits a serum TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, and administering to the subject a pharmaceutical composition comprising a therapeutically effective amount of an IL-4R antagonist.

Another AD-associated biomarker is antigen-specific IgE. Phadiatop™ is a commercially available variant of serum specific or antigen-specific IgE assay test that was introduced for the screening of allergic sensitization (Merrett et al 1987, Allergy 17: 409-416). The test provides for simultaneous testing for serum specific IgE to a mixture of relevant allergens causing common inhalant allergies. The test gives a qualitative result, either positive or negative depending upon a fluorescence response obtained. When a patient sample gives a fluorescence response higher than or equal to the reference, a positive test result is indicated. A patient sample with a lower fluorescence response indicates a negative test result. The present invention includes methods comprising selecting a subject who exhibits a positive test result and administering to the subject a therapeutically effective amount of an IL-4R antagonist.

Periostin is an extracellular matrix protein involved in the Th2-mediated inflammatory processes. Periostin levels are found to be up regulated in patients with AD (Masuoka et al 2012 *J Clin Invest.* 122(7):2590-2600. doi:10.1172/JCI58978). The present invention includes methods comprising administering an IL-4R antagonist to treat patients with elevated levels of periostin.

Lactate dehydrogenase (LDH) is used as a marker of tissue damage and is found to be elevated in patients with AD (Kou et al 2012; Arch. Dermatol. Res. 304: 305-312). The present invention includes methods comprising administering an IL-4R antagonist to treat patients with elevated levels of LDH.

According to other aspects of the invention, methods for treating AD are provided which comprise administering to a subject a pharmaceutical composition comprising a therapeutically effective amount of an IL-4R antagonist, wherein administration of the pharmaceutical composition to the subject results in a decrease in at least one AD-associated biomarker (e.g., IgE, TARC, eosinophils, eotaxin-3, antigen-specific IgE, LDH, etc.) at a time after administration of the pharmaceutical composition, as compared to the level of the biomarker in the subject prior to the administration.

As will be appreciated by a person of ordinary skill in the art, an increase or decrease in an AD-associated biomarker can be determined by comparing (i) the level of the biomarker measured in a subject at a defined time point after administration of the pharmaceutical composition comprising an IL-4R antagonist to (ii) the level of the biomarker measured in the patient prior to the administration of the pharmaceutical composition comprising an IL-4R antagonist (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more after administration of the of the pharmaceutical composition comprising an IL-4R antagonist.

According to certain particular embodiments of the present invention, a subject may exhibit a decrease in the level of one or more of TARC and/or IgE following administration of a pharmaceutical composition comprising an IL-4R antagonist (e.g., an anti-IL-4R antibody). For example, at about day 4, day 8, day 15, day 22, day 25, day 29, day 36, day 43, day 50, day 57, day 64, day 71 or day 85, following administration of a first, second, third or fourth dose of a pharmaceutical composition comprising about 75, 150 or 300 mg of an anti-hIL-4R antibody (e.g., mAb1), the subject, according to the present invention, may exhibit a decrease in TARC of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of TARC in the subject just prior to the first administration). Similarly, at about day 4, day 8, day 15, day 22, day 25, day 29, day 36, day 43, day 50, day 57, day 64, day 71 or day 85, following administration of a first, second, third or fourth dose of a pharmaceutical composition comprising about 75, 150 or 300 mg of an anti-hIL-4R antibody (e.g., mAb1), the subject, according to the present invention, may exhibit a decrease in IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IgE in the subject just prior to the first administration).

The present invention also includes methods for determining whether a subject is a suitable subject for whom administration of a pharmaceutical composition comprising an IL-4R antagonist would be beneficial. For example, if an individual, prior to receiving a pharmaceutical composition comprising an IL-4R antagonist, exhibits a level of an AD-associated biomarker which signifies the disease state, the individual is therefore identified as a suitable patient for whom administration of a pharmaceutical composition of the invention (a composition comprising an anti-IL-4R antibody) would be beneficial. In a related embodiment, the present invention includes methods for treating suitable subjects, wherein a suitable subject may be more susceptible to AD, for example, due to race or ethnicity. For example, the present invention includes methods comprising administering an IL-4R antagonist to African-American subjects who may be more susceptible to AD. Such a subject population may have an elevated level of an AD-associated biomarker.

According to certain exemplary embodiments, an individual may be identified as a good candidate for anti-IL-4R therapy if the individual exhibits one or more of the following: (i) an IgE level greater than about 114 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L; or (ii) a TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L; or (iii) a positive Phadiatop™ test. Additional criteria, such as other clinical indicators of AD (e.g., an elevated IGA, BSA, EASI, SCORAD, 5-D Pruritus, and/or NRS score indicative of AD), may be used in combination with any of the foregoing AD-associated biomarkers to identify an individual as a suitable candidate for anti-IL-4R therapy as described elsewhere herein.

Interleukin-4 Receptor Antagonists

As disclosed in detail above, the present invention includes methods which comprise administering to a subject in need thereof a therapeutic composition comprising an interleukin-4 receptor (IL-4R) antagonist. As used herein, an "IL-4R antagonist" is any agent which binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R.

The terms "IL-4R," "hIL-4R," and the like, as used herein, are intended to refer to the alpha chain of the human cytokine receptor that specifically binds interleukin-4 (IL-4), IL-4Rα (SEQ ID NO:274). Unless specifically designated as being from a non-human species, the term "IL-4R", as used herein, shall be understood to mean the human interleukin-4 receptor alpha chain.

The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$, (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (Xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as used in the context of the present invention, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-IL-4R antibodies comprising variants of any of the HCVR, LCVR, and/or CDR amino acid sequences disclosed herein having one or more conservative substitutions. For example, the present invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance," as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$," as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used in the context of the present invention to make human antibodies that specifically bind to human IL-4R.

Using VelocImmune™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VelocImmune® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VelocImmune® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind IL-4R which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258 and 262. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260 and 264. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260 and 262/264.

In certain embodiments of the present invention, the antibody or antigen-binding fragment thereof comprises six CDRs (HCDR1/HCDR2/HCDR3/LCDR1/LCDR2/LCDR3) having the amino acid sequences selected from the group consisting of SEQ ID NOs: 4/6/8/12/AAS/16; 28/30/32/36/AAS/40; 52/54/56/60/AVS/64; 76/78/80/84/LGS/88; 100/102/104/108/AAS/112; 124/126/128/132/SAS/136; 148/150/152/156/LGS/160; 172/174/176/180/AAS/184; 196/198/200/204/VAS/208; 220/222/224/228/DAS/232; and 244/246/248/252/DAS/256.

In certain embodiments of the present invention, the antibody or antigen-binding fragment thereof comprises HCVR/LCVR amino acid sequence pairs selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260 and 262/264.

Pharmaceutical Compositions

The present invention includes methods which comprise administering an IL-4R antagonist to a patient, wherein the IL-4R antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell, et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to Autopen® (Owen Mumford, Inc., Woodstock, UK), Disetronic® pen (Disetronic Medical Systems, Bergdorf, Switzerland), Humalog™ Mix 75/25pen, Humalog® pen, Humulin® 70/30pen (Eli Lilly and Co., Indianapolis, Ind.), NovoPen® I, II and III (Novo Nordisk, Copenhagen, Denmark), NovoPen® Junior (Novo Nordisk, Copenhagen, Denmark), BD™ pen (Becton Dickinson, Franklin Lakes, N.J.), OptiPen®, OptiPen Pro®, OptiPen Starlet™ and OptiClik® (sanofi-aventis, Frankfurt, Germany), to name only a few. Examples of disposable pen delivery devices having applications in subcutaneous delivery of a pharmaceutical composition of the present invention include, but are not limited to the SoloSTAR® pen (Sanofi-Aventis), the FlexPen® (Novo Nordisk), and the KwikPen™ (Eli Lilly), the SureClick® Autoinjector (Amgen, Thousand Oaks, Calif.), the Penlet® (Haselmeier, Stuttgart, Germany), the EpiPen® (Dey, L.P.), and the HUMIRA® Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in US Patent Application Publication No. 2012/0097565.

Dosage

The amount of IL-4R antagonist (e.g., anti-IL-4R antibody) administered to a subject according to the methods of the present invention is, generally, a therapeutically effective amount. As used herein, the phrase "therapeutically effective amount" means an amount of IL-4R antagonist that results in one or more of: (a) an improvement in one or more AD-associated parameters (as defined elsewhere herein); and/or (b) a detectable improvement in one or more symptoms or indicia of atopic dermatitis. A "therapeutically effective amount" also includes an amount of IL-4R antagonist that inhibits, prevents, lessens, or delays the progression of AD in a subject.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 75 mg, 150 mg, or 300 mg of an anti-IL-4R antibody is administered to a subject.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods of the present invention, according to certain embodiments, comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. The term "in combination with" also includes sequential or concomitant administration of IL-4R antagonist and a second therapeutic agent.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" or with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a TNF antagonist, an IL-8 antagonist, an IL-9 antagonist, an IL-17 antagonist, an IL-5 antagonist, an IgE antagonist, a CD48 antagonist, an IL-31 antagonist (including, e.g., as set forth in U.S. Pat. No. 7,531,637), a thymic stromal lymphopoietin (TSLP) antagonist (including, e.g., as set forth in US 2011/027468), interferon-gamma (IFNγ) antibiotics, topical corticosteroids, tacrolimus, pimecrolimus, cyclosporine, azathioprine, methotrexate, cromolyn sodium, proteinase inhibitors, or combinations thereof. In certain embodiments, the pharmaceutical composition comprising an anti-IL4R antagonist is administered to a subject in conjunction with a non-pharmaceutical therapy such as ultraviolet (UV) light therapy.

The methods of the invention comprise administering an IL-4R antagonist in combination with a second therapeutic agent for additive or synergistic activity to treat AD. In one embodiment, the invention includes methods to treat moderate-to-severe AD. Certain embodiments of the invention include methods to treat moderate-to-severe AD by administering an IL-4R antagonist concomitantly with a TCS. The TCS may be a potent TCS such as a Group III TCS. Examples of Group II TCS include methylprednisolone aceponate, mometasone furoate, fluticasone propionate and betamethasone valerate. In some embodiments, the TCS may be a moderate TCS such as Group II TCS or a weak TCS such as Group I TCS.

Administration Regimens

The present invention includes methods comprising administering to a subject a pharmaceutical composition comprising an IL-4R antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-4R antibody, once a week dosing at an amount of about 75 mg, 150 mg, or 300 mg, can be employed.

According to certain embodiments of the present invention, multiple doses of an IL-4R antagonist may be administered to a subject over a defined time course. The methods according to this aspect of the invention comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a patient with AD at a loading dose of about 300 mg or about 600 mg followed by one or more maintenance doses of about 75 mg to about 300 mg. In one embodiment, the initial dose and the one or more secondary doses each include 50 mg to 600 mg of the IL-4R antagonist, e.g., 100 mg to 400 mg of the IL-4R antagonist, e.g., 100 mg, 150 mg, 200 mg, 250 mg, 300 mg, 400 mg or 500 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of the IL-4R antagonist.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

The methods according to this aspect of the invention may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an IL-4R antagonist and a second therapeutic agent, to a patient to treat AD. In some embodiments, the present methods comprise administering one or more doses of an IL-4R antagonist followed by one or more doses of a second therapeutic agent. For example, one or more doses of about 75 mg to about 300 mg of the IL-4R antagonist may be administered after which one or more doses of a second therapeutic agent (e.g., a topical corticosteroid or a calcineurin inhibitor or any other therapeutic agent, as described elsewhere herein) may be administered to treat, alleviate, reduce or ameliorate one or more symptoms of AD. In some embodiments, the IL-4R antagonist is administered at one or more doses resulting in an improvement in one or more AD-associated parameters followed by the administration of a second therapeutic agent to prevent recurrence of at least one symptom of AD. Alternative embodiments of the invention pertain to concomitant administration of an IL-4R antagonist and a second therapeutic agent. For example, one or more doses of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

IL-4R Antagonists as Vaccine Adjuvants

The present invention also includes compositions and methods that are useful in vaccine applications. For example, an IL-4R antagonist (e.g., an anti-IL-4R antibody disclosed herein) may be administered to a subject in conjunction with a vaccine to improve or potentiate the immune response (including humoral and cellular immune responses) elicited by the vaccine, i.e., as a vaccine adjuvant. In certain embodiments, an IL-4R antagonist is administered just prior to, concurrent with, and/or subsequent to administration of a vaccine composition to a subject. For example, the present invention includes methods of eliciting or enhancing an immune response to an antigen in a subject by first administering to the subject a pharmaceutical composition comprising an IL-4R antagonist, followed by administering to the subject a vaccine composition comprising the antigen (by itself or in combination with the IL-4R antagonist), and optionally administering additional doses of the IL-4R antagonist for a period of time following administration of the vaccine antigen to the subject.

The IL-4R antagonists of the present invention may be administered as adjuvants with any type of vaccine including, e.g., live vaccines, live/attenuated vaccines, killed vaccines, subunit vaccines, DNA vaccines, and cancer immunotherapeutic vaccines. The vaccines that may be used in connection with the IL-4R antagonists of the invention include vaccines against bacterial pathogens, viruses, parasites, and other infectious agents. Non-limiting examples of infectious agents and diseases against which the vaccine compositions and methods of the invention may be targeted include, e.g., HIV, HCV, RSV, *Neisseria meningitides, streptococcus*, tuberculosis, malaria, smallpox, diphtheria, pertussis, tetanus, polio, measles, rubella, mumps, influenza, Anthrax, SARS, Ebola virus, Hanta virus, Dengue virus, etc.

The present invention also includes pharmaceutical compositions comprising an IL-4R antagonist and one or more vaccine antigen. The pharmaceutical compositions according to this aspect of the invention may comprise one or more additional immune potentiators such as MPL, MDP, CpG oligonucleotides, lipopeptides, saponins, dsRNA, small molecule immune potentiators, etc.

Besides IL-4R antagonists, other inhibitors of the IL-4/IL-13 signaling pathway (e.g., anti-IL-4 antibodies, anti-IL-13 antibodies, bispecific anti-IL-4/anti-IL-13 antibodies, etc.) may be used in the context of vaccine methods and compositions as disclosed herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human IL-4R

Human anti-hIL-4R antibodies were generated as described in U.S. Pat. No. 7,608,693. Table 1 sets forth the sequence identifiers for the heavy and light chain variable region amino acid sequence pairs, and CDR amino acid sequences, of selected anti-IL-4R antibodies and their corresponding antibody designations.

TABLE 1

| | SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 (sequence) | LCDR3 |
| H1H095-a | 2 | 4 | 6 | 8 | 10 | 12 | AAS | 16 |
| H1H095-b | 18 | 4 | 6 | 8 | 20 | 12 | AAS | 16 |
| H1H095-c | 22 | 4 | 6 | 8 | 24 | 12 | AAS | 16 |
| H1H097-a | 26 | 28 | 30 | 32 | 34 | 36 | AAS | 40 |
| H1H097-b | 42 | 28 | 30 | 32 | 44 | 36 | AAS | 40 |
| H1H097-c | 46 | 28 | 30 | 32 | 48 | 36 | AAS | 40 |
| H1H093-a | 50 | 52 | 54 | 56 | 58 | 60 | AVS | 64 |
| H1H093-b | 66 | 52 | 54 | 56 | 68 | 60 | AVS | 64 |
| H1H093-c | 70 | 52 | 54 | 56 | 72 | 60 | AVS | 64 |
| H1H093-d | 74 | 76 | 78 | 80 | 82 | 84 | LGS | 88 |
| H1H093-e | 90 | 76 | 78 | 80 | 92 | 84 | LGS | 88 |
| H1H093-f | 94 | 76 | 78 | 80 | 96 | 84 | LGS | 88 |
| H1H094-a | 98 | 100 | 102 | 104 | 106 | 108 | AAS | 112 |
| H1H094-b | 114 | 100 | 102 | 104 | 116 | 108 | AAS | 112 |
| H1H094-c | 118 | 100 | 102 | 104 | 120 | 108 | AAS | 112 |
| H1H096-a | 122 | 124 | 126 | 128 | 130 | 132 | SAS | 136 |
| H1H096-b | 138 | 124 | 126 | 128 | 140 | 132 | SAS | 136 |
| H1H096-c | 142 | 124 | 126 | 128 | 144 | 132 | SAS | 136 |
| H1H098-a | 146 | 148 | 150 | 152 | 154 | 156 | LGS | 160 |
| H1H098-b | 162 | 148 | 150 | 152 | 164 | 156 | LGS | 160 |
| H1H098-c | 166 | 148 | 150 | 152 | 168 | 156 | LGS | 160 |
| H1H099-a | 170 | 172 | 174 | 176 | 178 | 180 | AAS | 184 |
| H1H099-b | 186 | 172 | 174 | 176 | 188 | 180 | AAS | 184 |

TABLE 1-continued

| | SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 (sequence) | LCDR3 |
| H1H099-c | 190 | 172 | 174 | 176 | 192 | 180 | AAS | 184 |
| H4H083-a | 194 | 196 | 198 | 200 | 202 | 204 | VAS | 208 |
| H4H083-b | 210 | 196 | 198 | 200 | 212 | 204 | VAS | 208 |
| H4H083-c | 214 | 196 | 198 | 200 | 216 | 204 | VAS | 208 |
| H4H121-a | 218 | 220 | 222 | 224 | 226 | 228 | DAS | 232 |
| H4H121-b | 234 | 220 | 222 | 224 | 236 | 228 | DAS | 232 |
| H4H121-c | 238 | 220 | 222 | 224 | 240 | 228 | DAS | 232 |
| H4H118-a | 242 | 244 | 246 | 248 | 250 | 252 | DAS | 256 |
| H4H118-b | 258 | 244 | 246 | 248 | 260 | 252 | DAS | 256 |
| H4H118-c | 262 | 244 | 246 | 248 | 264 | 252 | DAS | 256 |

The exemplary IL-4R antagonist used in the following Examples is the human anti-IL-4R antibody designated in Table 1 as H1H098-b (also referred to herein as "mAb1").

Example 2: Single Ascending Dose Clinical Trial of Intravenously and Subcutaneously Administered Anti-IL-4R Antibody (mAb1) in Healthy Subjects A. Study Design This study was a randomized, double-blind, placebo-controlled, sequential, single ascending-dose study of intravenous (IV) and subcutaneous (SC) administered mAb1 in healthy subjects. The main purpose of this study was to evaluate the safety and tolerability of intravenously and subcutaneously administered mAb1 in healthy subjects.

Screening occurred from day −21 to day −3. On day 1 (baseline), subjects were randomized to receive either IV or SC study drug (mAb1 or placebo) infused over a 2-hour period. Subjects returned on days 4, 8, 11, 15, 22, 29, 43, 57 and 85 (end-of-study) for safety assessments and blood sampling for clinical laboratory testing.

Forty-eight total subjects participated in the study. Four sequential ascending dose cohorts (1.0, 3.0, 8.0, and 12.0 mg/kg) were planned for IV dosing and 2 sequential ascending dose cohorts (150 and 300 mg) were planned for SC dosing. Each dose cohort consisted of 8 subjects (if there was no cohort expansion): 6 randomized to receive mAb1 and 2 randomized to receive placebo. In order to optimize safety, the first 3 subjects in IV cohort 1 (1.0 mg/kg) were dosed at least 24 hours apart and the remaining 5 subjects were dosed 5 to 7 days later. In subsequent IV cohorts, 3 of the 8 subjects were dosed on day 1 and the remaining 5 subjects were dosed 5 to 7 days later. All 8 subjects in SC dose cohort 1 (150 mg) were dosed on the same day, and all 8 subjects in the subsequent SC cohort (300 mg) were dosed on the same day. The SC cohorts were administered after the IV cohorts were completed.

Inclusion criteria for the study were as follows: (1) Male or female 18 to 65 years of age; (2) Weight >50 kg and <120 kg; (3) For women of childbearing potential, a negative serum pregnancy test at the screening visit (visit 1) and a negative urine pregnancy test on day −1; (4) Willingness to refrain from the consumption of more than 2 standard alcoholic drinks in any 24-hour period during the duration of the study. A standard alcoholic drink was considered to be the equivalent of 12 ounces of beer, 5 ounces of wine, or 1.5 ounces of hard liquor; (5) Willingness to refrain from the consumption of alcohol for 24 hours prior to each study visit; (6) For men and women of childbearing potential, willingness to utilize adequate contraception and not become pregnant (or have their partner[s] become pregnant) during the full duration of the study. Adequate contraceptive measures include intrauterine device (IUD); bilateral tubal ligation; vasectomy; condom or diaphragm plus either contraceptive sponge, foam or jelly; and (7) Willingness, commitment, and ability to return for all clinic visits and complete all study-related procedures.

Exclusion criteria for the study were as follows: (1) Onset of a new exercise routine or major change to a previous exercise routine within 4 weeks prior to screening (visit 1). Subjects had to be willing to maintain a similar level of exercise for the duration of the study and to refrain from unusually strenuous exercise for the duration of the trial; (2) Pregnant or breast-feeding women; (3) Significant concomitant illness or history of significant illness such as cardiac, renal, neurological, endocrinological, metabolic or lymphatic disease, or any other illness or condition that would have adversely affected the subject's participation in this study; (4) Any clinically significant abnormalities observed during the screening visit; (5) Hospitalization for any reason within 60 days of screening (visit 1); (6) Known history of human immunodeficiency virus (HIV), hepatitis B or hepatitis C, and/or positive hepatitis B surface antigen, positive hepatitis C antibody or positive HIV serology at the screening visit; (7) History of or positive drug screen for drug or alcohol abuse within a year prior to the screening visit; (8) History of a hypersensitivity to doxycycline or similar compound; (9) Participation in any clinical research study evaluating another investigational drug or therapy within 30 days or at least 5 half-lives (whichever was longer), of the investigational drug prior to the screening visit; (10) Previous exposure to any therapeutic or investigational biological agent; (11) Any medical or psychiatric condition which, in the opinion of the investigator, would have placed the subject at risk; interfered with participation in the study or interfered with the interpretation of study results; (12) Subjects with a positive QuantiFERON® tuberculosis (TB) test; (13) History of a parasitic infection or recent (within the previous 6 months) travel to a parasitic endemic area; (14) History of alcohol or substance abuse within previous 5 years; (15) Positive urine drug screen result at screening (visit 1) or baseline (visit 2); and/or (16) Live/attenuated vaccinations within 12 weeks of screening or during the study.

B. Investigational Treatment mAb1 drug product was supplied as a lyophilized powder in a 20 ml glass vial for either IV or SC administration. When delivered IV, mAb1 drug product was reconstituted in a single use vial with 7.8 ml of sterile water for injection yielding a solution containing 50 mg/mL of mAb1. The pharmacist or designee withdrew the required amount of reconstituted mAb1 (dependent upon the subject's dose and weight) or placebo, and injected it into an infusion bag with 0.9% saline for IV delivery. The infusion was given over a 2-hour period.

When delivered SC, the mAb1 drug product was reconstituted with 2.3 ml of sterile water for injection, yielding a solution containing 150 mg/mL of mAb1. The pharmacist or designee administered the injections in the abdomen; administration to the extremities was not allowed due to the possibility of different absorption and bioavailability. If administration of multiple injections were required on the same day, each injection was delivered at a different injection site.

The dose levels of mAb1 tested were: 1.0, 3.0, 8.0, and 12.0 mg/kg for IV administration, and 150 and 300 mg for SC administration.

Placebo matching mAb1 was prepared in the same formulation as mAb1, but without addition of antibody.

C. Results and Conclusions mAb1 was generally well-tolerated with a favorable safety profile. The overall adverse event (AE) profile was characteristic of a healthy population. Less than 55% of subjects treated with mAb1 (19/36) experienced 1 or more treatment-emergent adverse event (TEAE) as compared to less than 59% for the subjects treated with placebo (7/12). The most frequently reported TEAEs were: Blood creatine phosphokinase (CPK) Increased, Blood Pressure Increased, Nasopharyngitis, and Toothache. Most subjects experienced an intensity of TEAEs as mild or moderate; only 3 subjects reported TEAEs that were considered severe. Only 1 severe TEAE (Blood CPK Increased) was considered by the investigator to be related to treatment. One serious adverse event (SAE) was reported during the study, which was considered by the investigator to be unrelated to the study drug. No subjects were withdrawn from the study due to an AE and no deaths were reported. No other clinically significant laboratory test results (blood chemistry, hematology, or urinalysis) were reported during the study. No trends were seen in mean/median baseline in any laboratory parameter. There were no significant trends in mean or median changes from baseline in temperature or pulse throughout the study. No clinically significant abnormalities were seen on physical examination results, ECGs or vital signs.

This study was significant in that the subject population consisted of a high proportion of Black/African-American subjects (Table 2).

Although the subjects were healthy volunteers, African-Americans as a group may be more susceptible to atopic diseases (Caggana et al 1999; Genet. Med. 1: 267-271), and this population may therefore be considered appropriate for evaluation of proof of mechanism based on the exploratory biomarker analysis.

With regard to pharmacokinetic (PK) analysis, nonlinear kinetics were observed. The target-mediated pathway of elimination appeared saturated at IV doses of 8 and 12 mg/kg, when concentrations of functional mAb1 were above about 30 mg/L. Low anti-drug antibody (ADA) titers were observed in 9 subjects. No sudden and persistent drop in concentrations of functional mAB1 was observed indicating that the ADAs did not have a major impact on PK.

Example 3: Clinical Trial of Two Different Drug Products of Anti-IL-4R Antibody (mAb1) Following Subcutaneous Administration of Anti-IL-4R Antibody (mAb1) in Healthy Patients A. Study Design This study was a single-center, single-dose, double-blind, randomized, no placebo-controlled study to assess the safety and pharmacokinetic profile of subcutaneous administration of two different anti-IL-4R mAb (mAb1) drug products generated from different cell lines and manufacturing processes. The drug products were provided in 150 mg/mL 2 mL doses, and 300 mg (2 mL) were administered subcutaneously to 30 healthy adults in two parallel groups (15 subjects per group). Subjects included 30 subjects represented by 22 males (73.3%) and 8 females (26.7%) aged 19 to 45 years old, with weights ranging from 54.8 to 94.3 kg.

Serum concentration of mAb1 was used to determine the following PK parameters: maximum serum concentration ($C_{max}$), area under the [serum concentration versus time] curve from time 0 to the real time corresponding to the last concentration above the lower limit of quantification ($t_{last}$ ($AUC_{last}$), and area under the serum concentration versus time curve from time zero extrapolated to infinity (AUC). Also measured with the time to reach maximum concentration ($t_{max}$) and terminal half-life ($t_{1/2z}$).

B. Criteria for Evaluation and Methods

Safety was assessed by measuring adverse events, including treatment-emergent adverse events (TEAEs) up to two months postdose, clinical laboratory evaluations (biochemistry, hematology, urinalysis), vital signs, electrocardiograms (ECGs) with automatic reading, anti-mAb1 antibodies (negative or titer), and local tolerability assessments (including injection site pain using a Visual Analog Scale

TABLE 2

Demographic Characteristics of the Treatment Groups

| | | Intravenous dose | | | | Subcutaneous dose | |
|---|---|---|---|---|---|---|---|
| Variable | Placebo (n = 12) | 1 mg/kg (n = 6) | 3 mg/kg (n = 6) | 8 mg/kg (n = 6) | 12 mg/kg (n = 6) | 150 mg (n = 6) | 300 mg (n = 6) |
| Age, years, mean (SD) | 35.8 (10.1) | 34.3 (9.4) | 37.7 (9.8) | 35.7 (12.3) | 37.2 (9.7) | 35.0 (10.4) | 33.3 (8.3) |
| Sex, n (%) | | | | | | | |
| Male | 5 (41.7) | 5 (83.3) | 2 (33.3) | 4 (66.7) | 5 (83.3) | 4 (66.7) | 4 (66.7) |
| Female | 7 (58.3) | 1 (16.7) | 4 (66.7) | 2 (33.3) | 1 (16.7) | 2 (33.3) | 2 (33.3) |
| Race, n (%) | | | | | | | |
| White | 4 (33.3) | 2 (33.3) | 1 (16.7) | 2 (33.3) | 1 (16.7) | 0 | 1 (16.7) |
| Black/African American | 8 (66.7) | 4 (66.7) | 5 (83.3) | 4 (66.7) | 5 (83.3) | 6 (100) | 5 (83.3) |

[VAS; 100 mm ungraduated line], Erythema [diameter in mm at injection site], and edema [diameter in mm at injection site]).

Adverse events of special interest (AESI) were AEs (serious or nonserious) of scientific and medical concern that needed specific monitoring, documentation, and management as described in the protocol. The following AEs were defined as AESI: hypersensitivity/anaphylaxis: anaphylactic reaction or acute allergic reaction requiring immediate treatment, severe injection site reaction lasting longer than 24 hours, severe infection, any parasitic infection, alanine aminotransferase (ALT) increase ≥2 ULN, QTc≥500 ms, pregnancy, or overdose.

Blood samples for hematology and biochemistry evaluations were collected predose on Day−1 and on Days 2 (i.e., 24 hours postdose) and 57, and biochemistry limited to liver function on Days 8, 15, 22, 29, 36, 43, and 50.

Blood samples for the determination of anti-mAb1 antibodies in serum were collected on Day 1 and on Days 15, 29 and 57.

Local tolerability assessments were performed at predose on Day 1 and at 2 minutes, 2 hours, 6 hours and 12 hours postdose and on Days 2 (i.e., 24 hours postdose), 3, 4 and 8 following mAb1 administration.

For pharmacokinetic and pharmacogenetic sampling, blood samples were collected at predose on Day 1 and 12 hours post-dose, and on Days 2, 3, 4, 8, 11, 15, 22, 29, 36, 43, 50, and 57 following mAb1 administration. Serum concentrations of functional mAb1 were determined using a validated enzyme-linked immunosorbent assay (ELISA) with a lower limit of quantification (LLOQ) of 78 ng/mL.

Samples were collected at baseline (Day 1 predose) for optional pharmacogenetic analyses.

Pharmacokinetic parameters of serum functional mAb1 were summarized by treatment group using descriptive statistics (mean, geometric mean, median, standard deviation (SD), coefficient of variation [CV], minimum, and maximum). For log transformed $C_{max}$, $AUC_{last}$, and AUC, the test/reference treatment ratios were assessed using a linear fixed effects model with gender and treatment as fixed effects, and with weight as covariate. Estimates and 90% confidence intervals (CIs) for treatment ratios were provided for $C_{max}$, $AUC_{last}$, and AUC.

Evaluation of safety was based on the review of individual values and descriptive statistics. All AEs were coded using Medical Dictionary for Regulatory Activities (MedDRA) version 15.0, and frequencies of treatment emergent adverse events (TEAEs) were classified and tabulated (counts and percents) by primary system organ class, preferred term, and treatment group. Potentially clinically significant abnormalities (PCSAs; definitions according to version 2.0 dated 14 Sep. 2009) for clinical laboratory data, vital signs, and ECG values and out of normal range values for clinical laboratory data were flagged and summarized by treatment group.

Anti-mAb1 antibody results were listed as either negative or with a titer value if positive in the confirmation assay by treatment group, subject and visit. Data were summarized as number of subjects (counts and percent) with negative or positive anti-drug antibody (ADA) response by treatment group.

Descriptive statistics (mean, SD, minimum, median, and maximum) of the pain VAS, erythema diameter, and edema diameter were provided by treatment group for each scheduled time point. Each of these measurements was further summarized by treatment group as time-averaged (from study drug administration to Day 8 assessment included) and peak values (using post-dose assessments).

C. Pharmacokinetic Results

TABLE 3

Mean ± SD (geometric mean) [CV %] of serum functional mAb1 PK parameters

| PK Parameters | Serum mAb1 Drug product A | Serum mAb1 Drug Product B |
|---|---|---|
| N | 15 | 13 |
| $C_{max}$ (ng/mL) | 28900 ± 9110 (27300) [31.6] | 27200 ± 9950 (25300) [36.6] |
| $t_{max}{}^{a}$ (h) | 168.00 (72.00-240.00) | 168.00 (48.00-240.00) |
| $AUC_{last}$ (ng · h/mL) | 11700000 ± 4790000 (10500000) [41.0] | 12000000 ± 4300000 (11200000) [35.7][c] |
| AUC (ng · h/mL) | 13300000 ± 3910000 (12800000) [29.4][b] | 12500000 ± 4770000 (11600000) [38.2][c] |
| $t_{1/2}{}^{z}$ (h) | 137 ± 46.3 (129) [33.8][b] | 131 ± 47.4 (124) [36.2][c] |

[a]Median (Min-Max),
[b]N = 13 since terminal log-linear phase could not be determined in 2 subjects,
[c]N = 11 since 2 subjects discontinued from the study.

TABLE 4

Point estimates of treatment ratios with 90% confidence interval

| Comparison | Parameter | Estimate | 90% CI |
|---|---|---|---|
| Drug Product A vs. Drug Product B | $C_{max}$ | 1.10 | (0.89 to 1.35) |
| | $AUC_{last}$ | 0.90 | (0.71 to 1.16) |
| | AUC | 1.05 | (0.86 to 1.29) |

Drug Product A: Group A (test), 150 mg/mL (Drug Product 1) x 2.0 mL (300 mg of mAb1); Drug Product B: Group B (reference), 150 mg/mL (Drug Product 2) x 2.0 mL (300 mg of mAb1).

The estimates are based on the linear fixed effect model with fixed terms for gender, weight, and treatment.

D. Safety Results

Twelve out of 15 subjects (80.0%) on Drug Product A (test drug product) versus 8 out of 15 subjects (53.3%) on Drug Product B (reference drug product) had TEAEs. The apparent treatment imbalance appeared in some primary system organ classes only and appeared to be due to events not related to the IMP as often another cause was identified. Four SAEs were reported in two subjects during the study.

A 23 years old male subject in the Drug Product 1 treatment group experienced a “herpes simplex type II viral infection” with symptoms of blurred vision, diaphoresis, fever, and headache starting 4 days after dosing, followed by a swollen tongue (6 days after dosing) and cough, chest congestion, and muscle cramps in both calves (7 days after dosing). During the course of this event, the subject went to the emergency room on several occasions and received multiple treatments including SoluMedrol® (3 IV doses), prednisone (for 9 days), Rocephin® (1 IV dose), Zithromax® (for 5 days). It is noteworthy that the subject had a tongue barbell piercing placed 3 months before dosing. All symptoms had resolved 19 days after dosing. Initial Herpes Simplex Virus (HSV) II Ig G titers performed 10 days after dosing were negative which converted to positive when re-assessed 7 weeks after dosing. This SAE was judged as related to the IMP by the Investigator and the company. More than 4 weeks after dosing, the subject was diagnosed with “Bell’s palsy” on the left side that was considered by the Investigator to be consequent to the HSV II infection. This event was treated with prednisone (for 6 days) and acyclovir (for 10 days). This SAE was deemed to be not related to the IMP by the Investigator due to the multiple and repeated steroids administrations in the acute state of the HSV II infection, which were considered an alternative explanation. The company considered that a causal relationship to the IMP could not be excluded. Both events were recovering at the end of the study. This subject did not develop ADA at any time during the study.

A 22 years old male subject in the Drug Product A treatment group experienced "elevated ALT" (ALT up to 11.4 ULN) together with "rhabdomyolysis" (creatine phosphokinase up to 392 ULN) both discovered by routine laboratory exams 7 weeks after dosing. These events followed a physical challenge (consisting of swimming, push-ups, pull-ups, sit-ups and other endurance type exercises; subject is a life guard) and an injury to his triceps muscle (NSAE). The subject was admitted to the hospital for hydration. Liver causes of the increased liver function tests were ruled out, and the elevated ALT (as well as the aspartate aminotransferase [AST] elevation, up to 50.5 ULN) was judged as related to the rhabdomyolysis. Creatinine and glomerular function remained within normal ranges during the course of the events. Both events resolved within 3 weeks. These 2 SAEs were deemed to be not related to the IMP by the Investigator. This subject also developed ADA with positive titers detected on Day 29 (titer value=120) and at EOSV on Day 58 (titer value=30).

Apart from the ALT increase, no other AESI were observed during the study.

Four (4) subjects experienced infection during the study. Apart from the herpes simplex infection described above, cases of mild upper respiratory tract infection, pharyngitis, and sinusitis (1 case each) were observed 54, 7 and 1 day after dosing, respectively. These 3 latter events were observed in subjects treated with C1P2.

Fifteen (15) cases of injection site reaction occurred in 12 subjects: erythema (8 cases in 8 subjects, 4 in each group), pain (3 cases, 2 on C2P1 and 1 on C1P2), nodule (2 cases, 1 in each group), haematoma (1 case on C1P2), and pruritus (1 case on C2P1). All were mild and resolved within 24 hours of injection.

Other TEAEs were not observed in more than 1 subject in each treatment group, except for 2 cases of pruritus (not at injection site) in 2 subjects treated with C2P1 and 3 cases of headache (in 1 subject treated with C2P1 and 2 subjects treated with C1P2).

Apart from the laboratory abnormalities already described, there were no other laboratory increases above the predefined thresholds for PCSAs.

Anti-mAb1 antibodies were positive in 6 out of 27 (22.22%) subjects who completed the study (no subject who did not complete the study had any detected ADA). Among the 6 subjects with positive ADA titers, 4 were treated with C2P1 and 2 were treated with C1P2. No association was observed between ADA development and TEAEs.

E. Specific Local Tolerability Assessments

On the pain VAS, the mean peak values were 4.4 and 4.2 mm (on the 100 mm scale) in the C2P1 and C1P2 treatment groups, respectively, with a median value at 2.0 mm in both groups. Five (5) out of 15 subjects in each group had "no pain" (peak value at 0 mm). The highest measurements were 17 and 18 mm in the C2P1 and C1P2 treatment groups, respectively, and were generally observed 2 minutes after dosing (range between 2 minutes and 12 hours postdose).

The mean peak values for erythema diameters measured were 12.5 and 10.9 mm in the C2P1 and C1P2 treatment groups, respectively. Nine (9) out of 15 subjects in each group had no erythema at any time. The maximum values observed were 40 mm in both groups, and were all observed 2 minutes after dosing, except for one subject whose maximum (3 mm) was observed 48 hours post-dose.

The mean peak values for edema diameters measured were 1.1 and 0 mm in the C2P1 and C1P2 treatment groups, respectively. Thirteen (13) out of 15 subjects and 15 out of 15 subjects in the C2P1 and C1P2 treatment groups, respectively, had no edema at any time. The maximum values were 15 and 1 mm in 2 subjects in the C2P1 treatment group, and were observed 2 hours post-dose.

F. Conclusions

After a single subcutaneous dose of 300 mg of mAb1 to healthy subjects, serum functional mAb1 exposure was similar in the two test drug products. The geometric mean treatment ratios (DP1/DP2) with 90% CIs were 1.10 (0.89 to 1.35) for $C_{max}$, 0.90 (0.71 to 1.16) for $AUC_{last}$, and 1.05 (0.86 to 1.29) for AUC.

mAb1 was generally well-tolerated. One subject administered with DP1 experienced a serious adverse event of "herpes simplex type II viral infection" followed by "Bell's Palsy".

There were no clinically important local tolerability issues and no apparent differences in local tolerability parameters (i.e., pain, erythema, and edema) between treatment groups.

The most common TEAE was erythema at injection site (8 out of 30 subjects) and was observed with the same incidence in both treatment groups (4 out of 15 subjects [26.7%] in each group).

In conclusion, after a single 300 mg SC administration of mAb1 in healthy subjects, there was no clinically important difference identified in the PK profiles, safety, and local tolerability of the two different drug products.

Example 4: Clinical Trial of Safety, Tolerability and Pharmacokinetics of Ascending Single Subcutaneous Dose of Anti-IL-4R Antibody in Healthy Japanese Adult Male Subjects A. Study Design This study was a randomized, double-blind, placebo-controlled study of ascending, single subcutaneous doses of an anti-IL-4R antibody (mAb1) in healthy Japanese adult male subjects. The primary objective was to assess the safety and tolerability of mAb1 after ascending single subcutaneous doses in healthy Japanese male subjects. The secondary objectives were to assess the pharmacokinetics, the immunogenicity and exploratory pharmacodynamics of ascending single subcutaneous doses of mAb1 in healthy Japanese male subjects.

mAb1 was derived from cell line 2 and supplied in liquid formulation of either 75 mg/mL or 150 mg/mL concentration in vials. Single ascending doses of 75, 150, 300, and 600 mg of mAb1 were administered subcutaneously on day 1 (1 injection for 75 mg and for 150 mg; 2 injections for 300 mg; and 4 injections for 600 mg). Duration of observation was for approximately 11 weeks (including a screening period of 2 to 21 days prior to dosing, 5 days in the clinic [day −1 to day 4 with 1 treatment day], and outpatient follow-up visits up to 57 days after dosing) for each subject.

B. Criteria for Evaluation

Safety: Adverse events (AEs), physical examination, clinical laboratory evaluations (hematology, biochemistry, urinalysis), vital signs (supine and standing blood pressure and heart rate, body temperature), 12-lead electrocardiograms (ECGs), and anti-mAb1 antibodies Pharmacokinetics: The following mAb1 serum functional pharmacokinetics parameters were calculated with non-compartmental analysis—maximum observed serum concentration ($C_{max}$), time to reach maximum serum concentration ($t_{max}$), dose normalized $C_{max}$ ($C_{max}$/Dose), area under the serum concentration versus time curve from time zero to the real time corresponding to the last concentration above the lower limit of quantification $t_{last}$ ($AUC_{last}$), dose normalized $AUC_{last}$ ($AUC_{last}$/Dose), area under the serum concentration versus time curve from time zero extrapolated to infinity (AUC), apparent volume of distribution at steady state ($V_{ss}$/F), apparent total body clearance (CL/F), mean residence time (MRT), and terminal half-life ($t_z$)

Pharmacodynamics (PD): pharmacodynamics effects of mAb1 on total IgE and TARC

Blood samples for PK evaluation were collected at pre-dose (Day 1) and days 1, 2, 4, 8, 11, 15, 18, 22, 25, 29, 36, 43, 50, and 57 (±1 day for days 15 to 25; 2 days for days 29 to 57) following mAb1 administration. Serum concentrations of mAb1 were determined using a validated ELISA with a lower limit of quantification (LLOQ) of 78 ng/mL (0.078 mg/mL). Blood samples for PD evaluation were collected prior to dosing at Day −1 and on day 1, then on days 8, 15, 22, 29, 43, and 57 (±1 day for days 15 to 25; 2 days for days 29 to 57) following mAb1 administration. Serum screens for total IgE and TARC were determined using a validated method.

C. Statistical Methods

Evaluation of safety was based on the review of individual values and descriptive statistics. All adverse events were coded using MedDRA version 15.1, and frequencies of treatment-emergent adverse events (TEAEs) were classified and tabulated (counts and percentages) by primary system organ class, preferred term, and treatment group. Potentially clinically significant abnormalities for clinical laboratory data, vital signs, and ECG data and out of normal range values for clinical laboratory data were flagged and summarized by treatment group. In addition, raw data and changes from baseline for vital signs, ECGs, and limited laboratory parameters were summarized in descriptive statistics.

Pharmacokinetic parameters of serum functional mAb1 were summarized for each dose group using descriptive statistics (mean, geometric mean, standard error of the mean [SEM], median, standard deviation [SD], and coefficient of variation [CV], minimum and maximum). Dose proportionality was assessed using a power model for $C_{max}$, $AUC_{last}$, and AUC. The dose effect on $t_{1/2z}$ was assessed with a linear fixed effect model. The distribution of $t_{max}$ values was represented by histogram plots. mAb1 PD biomarkers (total IgE and TARC: CCL17) were summarized for each dose group using descriptive statistics.

D. Safety Results mAb1 administration of a single subcutaneous dose of up to 600 mg was well tolerated in healthy Japanese adult male subjects with a median weight of 65.1 kg. No serious TEAEs or premature discontinuations were reported during the study. During the 57-day period of observation after dosing, a total of 3 TEAEs were reported among the 32 study subjects as follows: 1 out of 8 subjects in the placebo group (influenza), 1 out of 6 subjects in the 150 mg group (influenza) and 1 out of 6 subjects in the 600 mg group (orthostatic hypotension).

There were no local cutaneous reactions or discomfort at the site on injection at volumes up to 2.0 mL×4 sites (600 mg).

Anti-mAb1 antibodies (ADAs) were positive in 5 out of 32 subjects with low titer levels (1 in 75 mg group, 2 in 150 mg group, 1 in 300 mg group, and 1 in 600 mg group). ADAs were undetectable at baseline and in the placebo group in all subjects. No ADA positive subject experienced any TEAE.

Very few PCSAs in hematology and biochemistry values were identified in the mAb1 treatment group without any dose-incidence relationship. In particular, there were no changes in liver enzymes observed. There were few PCSAs for vital signs or ECG, with no dose relationship. No subjects experienced a prolonged QTcB (>450 ms) and no changes from baseline over 60 ms were observed during the study.

E. Pharmacokinetic Results

Mean (SD) serum functional mAb1 concentration-time profiles following single subcutaneous doses are shown in FIG. 1. Pharmacokinetic parameters for serum functional mAb1 are summarized for all subjects treated with mAb1 in Table 5.

TABLE 5

| Mean ± SD (geometric mean) [CV %] of serum mAb1 PK parameters | | | | |
|---|---|---|---|---|
| PK parameter | mAb1 75 mg | mAb1 150 mg | mAb1 300 mg | mAb1 600 mg |
| N | 6 | 6 | 6 | 6 |
| Cmax | 5.33 ± 1.50 | 10.4 ± 2.95 | 38.3 ± 15.3 | 70.1 ± 24.1 |
| (mg/L) | (5.09) [28.2] | (10.1) [28.2] | (36.1) [40.1] | (66.8) [34.4] |
| $t_{max}$[a] (day) | 7.01 (3.00-7.03) | 7.01 (3.00-7.03) | 7.01 (6.99-10.00) | 7.01 (3.00-7.02) |
| $t_{last}$[a] (day) | 17.02 (14.01-21.05) | 24.03 (21.01-24.04) | 42.00 (35.00-42.02) | 52.51 (42.00-56.02) |
| $AUC_{last}$ | 59.2 ± 20.8 | 150 ± 41.3 | 700 ± 234 | 1780 ± 699 |
| (mg · day/L) | (55.2) [35.2] | (146) [27.5] | (667) [33.5] | (1680) [39.3] |
| AUC | 72.4 ± 10.6 [b] | 155 ± 41.6 | 709 ± 231 | 1870 ± 852 |
| (mg · day/L) | (71.9) [14.6] | (151) [26.8] | (677) [32.6] | (1740) [45.5] |
| $V_{ss}$/F (L) | 7.96 ± 0.673 [b] | 10.7 ± 3.04 | 6.67 ± 2.34 | 6.60 ± 1.78 |
| | (7.94) [8.5] | (10.3) [28.4] | (6.32) [35.1] | (6.41) [26.9] |
| CL/F | 1.05 ± 0.144 [b] | 1.02 ± 0.238 | 0.464 ± 0.155 | 0.366 ± 0.126 |
| (L/day) | (1.04) [13.7] | (0.993) [23.4] | (0.443) [33.5] | (0.344) [34.4] |
| $t_{1/2z}$ (day) | 2.77 ± 0.567 [b] | 3.18 ± 0.805 | 5.13 ± 1.42 | 8.77 ± 5.18 |
| | (2.72) [20.5] | (3.11) [25.3] | (4.96) [27.7] | (7.66) [59.1] |

[a]Median (Min-Max);
[b]N = 4 since terminal log-linear phase could not be determined in 2 subjects Median $t_{max}$ of mAb1 was 7 days at all doses. Mean terminal elimination half-life ($t_{1/2z}$) was dose-dependent ($p<0.01$) and ranged from 2.77 days at 75 mg to 8.77 days at 600 mg. An 8-fold increase in dose from 75 mg to 600 mg resulted in 13.1-, 30.4-, and 24.2-fold increase in geometric mean $C_{max}$, $AUC_{last}$, and AUC respectively.

F. Pharmacodynamics Results

Serum IgE and TARC values were highly variable within the treatment groups. Regarding the serum IgE (percent change from baseline), no drug-related effect was observed over time at single administrations of subcutaneous doses at 75 mg and 150 mg. At 300 mg and 600 mg, there was a trend of decreasing serum IgE post-treatment. A treatment effect was observed on TARC. Single administrations of subcutaneous doses between 75 mg and 600 mg were associated with reduced serum TARC levels as compared to placebo. A more sustained reduction was associated with increasing dose.

G. Conclusions mAb1 with single subcutaneous dose up to 600 mg was well tolerated in healthy Japanese male subjects. No serious TEAEs or premature discontinuations were reported during the study. A total of 3 TEAEs were reported among the 32 study subjects. There were no local cutaneous reactions or discomfort at the site on injection at volumes up to 2.0 mL×4 sites (600 mg). Overall, the reported TEAEs and laboratory, vital signs and ECG assessments did not suggest dose-related effects.

After single doses to healthy Japanese adult males, mAb1 was absorbed with a median $t_{max}$ of 7 days and eliminated with a dose-dependent mean terminal elimination half-life ($t_{1/2z}$) ranging from 2.77 days at 75 mg to 8.77 days at 600 mg. Mean serum functional mAb1 exposure increased in a greater than dose proportional manner, with an 8-fold increase in dose from 75 mg to 600 mg resulting in a 13.1-, 30.4-, and 24.2-fold increase in geometric mean $C_{max}$, $AUC_{last}$, and AUC, respectively.

A pharmacodynamic effect was observed. Serum levels of TARC were reduced post-treatment with mAb1. A more sustained decline was associated with increasing dose. Low titers of ADA were detected in 5 out of 32 subjects. ADAs were undetectable at baseline and in the placebo group in all subjects. No ADA positive subject experienced any TEAE.

Example 5: Clinical Trial to Assess the Effect of Injection Rate on Safety and Tolerability of mAb1 Administered Subcutaneously to Healthy Volunteers A. Overview and Study Design This study was conducted to support the development of a large volume injection device for administering mAb1. The study assessed comparatively two different injection rates approximating the corresponding attributes of two different subcutaneous (SC) delivery devices: A fast injection representing an autoinjector and a slow injection representing a microinfuser. The primary objective of the study was to assess the comparative safety and tolerability of a single 300 mg/2 mL dose of mAb1 administered SC at 2 different rates to normal healthy volunteers. The secondary objectives of the study were: to compare the pharmacokinetic (PK) profiles of a single 300 mg/2 mL dose of mAb1 administered SC at 2 different rates in two separate cohorts of NHV; and to assess the comparative immunogenicity of a single 300 mg/2 mL dose of mAb1 administered SC at 2 different rates in NHV.

This was an open label, randomized, parallel-group, single-dose study of the safety, tolerability, PK and immunogenicity of mAb1 administered SC at 2 different injection rates. The study was randomized to avoid any potential bias in assigning subjects to study treatment and to minimize systematic differences between treatment groups with respect to baseline variables that could affect the outcome. Injection method and duration could not be effectively blinded, so the study was open-label. Thirty-six subjects (18 subjects per treatment group) were recruited and randomized at 1 site in the US. The sample size for this study was selected empirically. No formal sample size or power calculations based on the primary endpoint were used. However, it was estimated that the enrollment of 18 subjects per group would provide 80% power to detect the difference of 20 in pain VAS between 2 groups, assuming the common standard deviation is 20.8 in pain VAS with a 2-sided test at the 0.05 significance level.

Subjects underwent screening between day −14 and day −2. On day −1, subjects were admitted to the clinic for training and familiarization with the injection procedure, and were randomized to either group 1 (fast injection) or group 2 (slow injection):

- Group 1 (Fast injection): subjects received study drug via manual SC injection administered over 30 seconds.
- Group 2 (Slow injection): subjects received study drug via a SC infusion set connected to a syringe pump programmed to deliver 2 mL in 10 minutes.

On day −1, all subjects underwent a mock injection, in which the SC infusion set was briefly attached to the skin. The process included the insertion of a 27 G 6-mm needle, which was left in place for about 10-15 seconds and then removed. Subjects rated their pain/discomfort related to each respective step of the mock injection procedure as follows:

- Immediately (within 10 seconds) of needle insertion and needle removal, subjects rated their pain/discomfort related to each respective step of the procedure.
- Global assessment (GA): 1 minute after needle removal subjects were asked to provide a GA by recalling and rating the pain/discomfort experienced during the entire procedure.
- Comparative assessment (CA): approximately 1 minute after needle removal (immediately post GA), in addition to the visual analog scale (VAS), subjects provided a CA by relating their global pain/discomfort to familiar experiences, like a bee sting or a flu shot.

Figure 2:
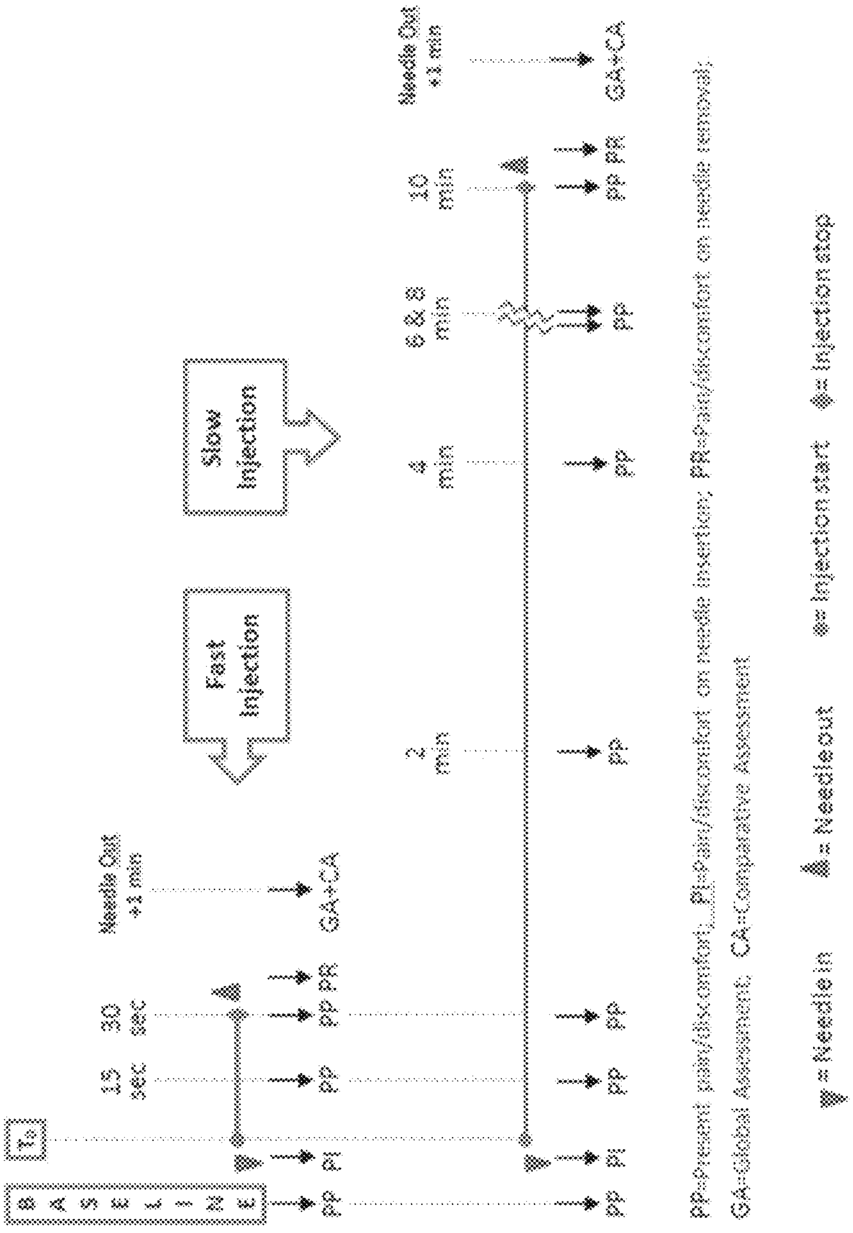
FIG. 2 shows a diagrammatic representation of the injection procedure and pain assessments as described in Example 5.
Figure 3:
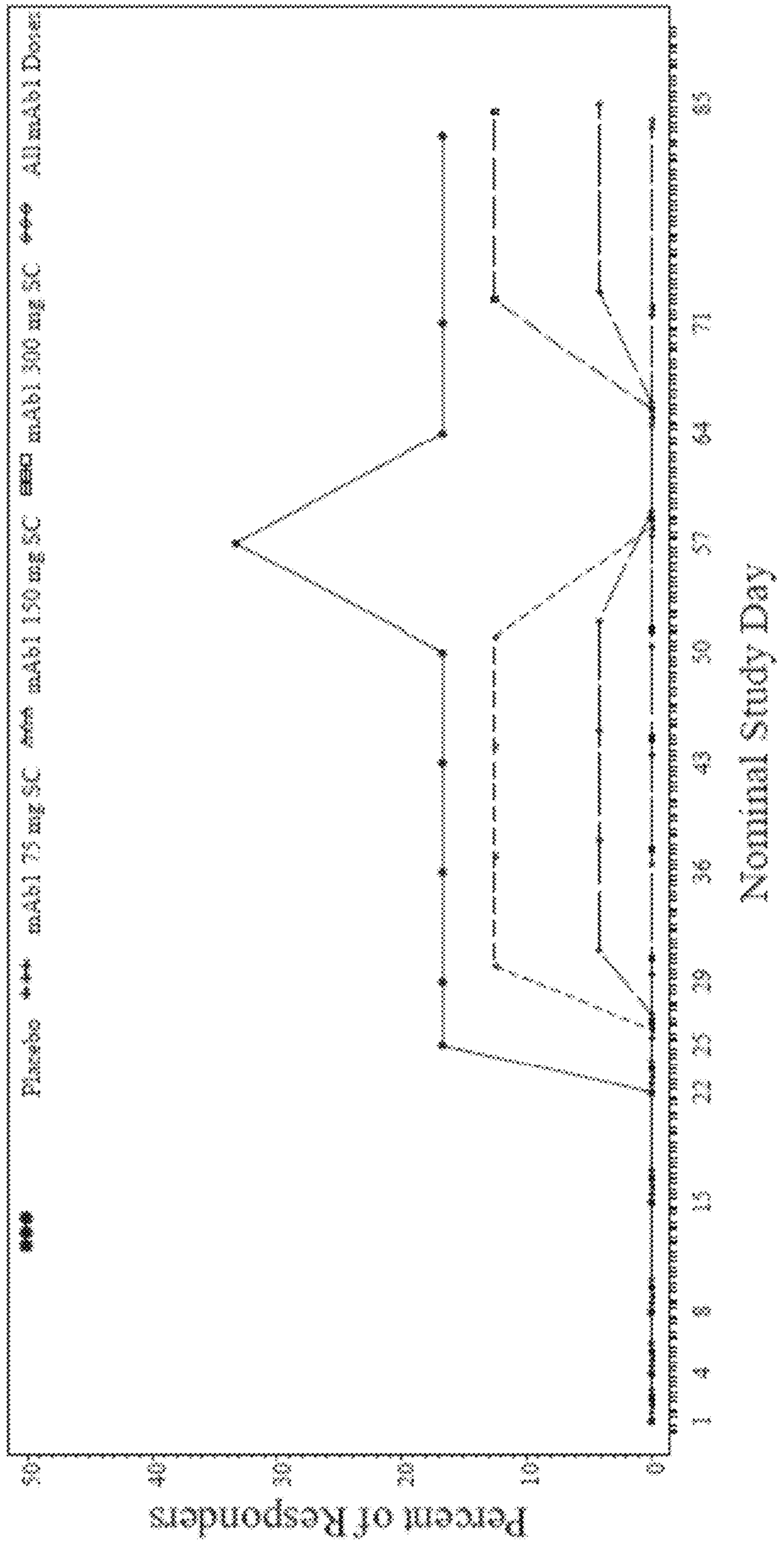
FIG. 3 shows the IGA score responder rate (score of 0 or 1)—last observation carried forward (LOCF) for the study in Example 6.
Figure 4:
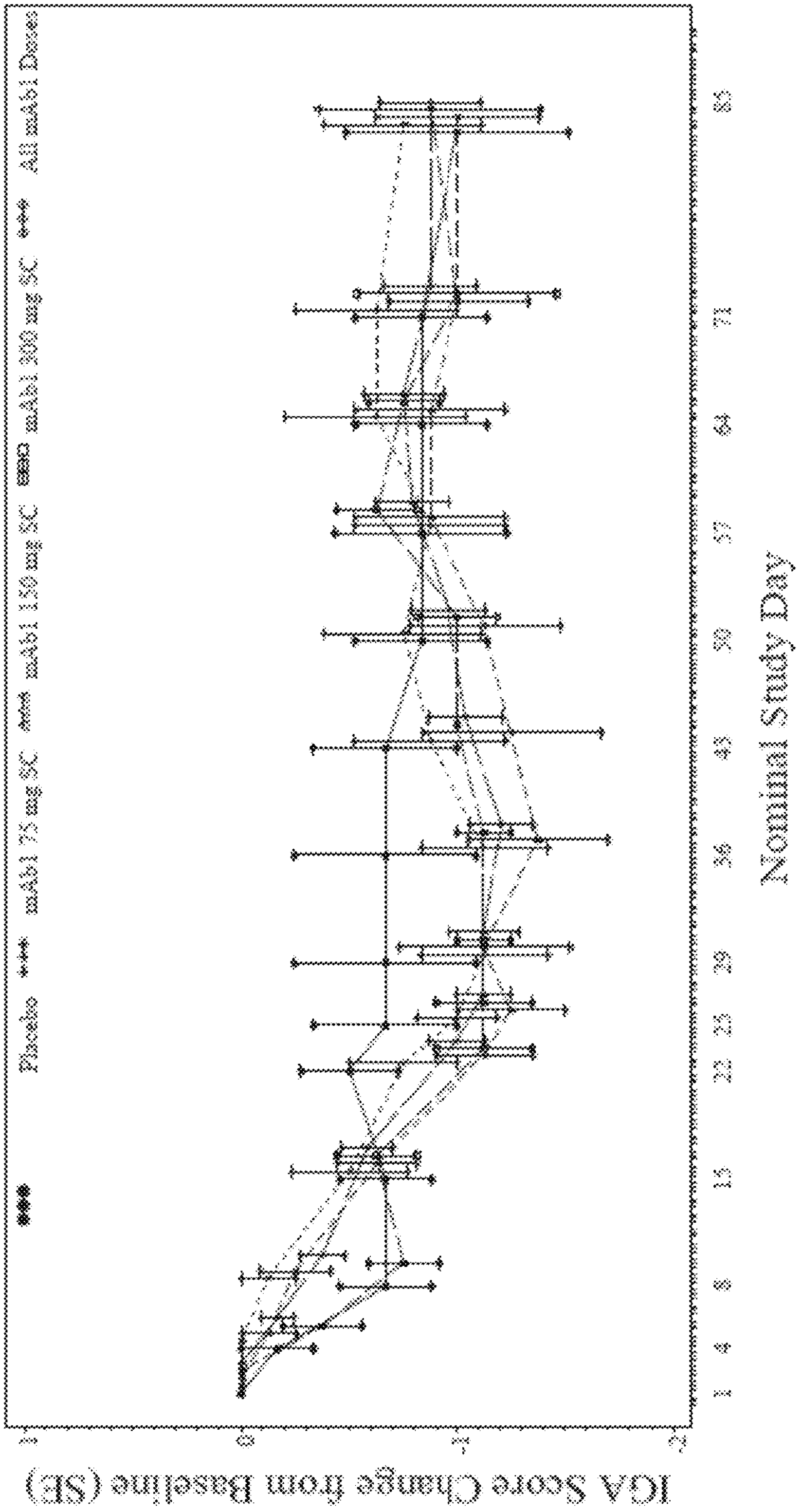
FIG. 4 shows the mean IGA score change from baseline—LOCF for the study in Example 6.
Figure 5:
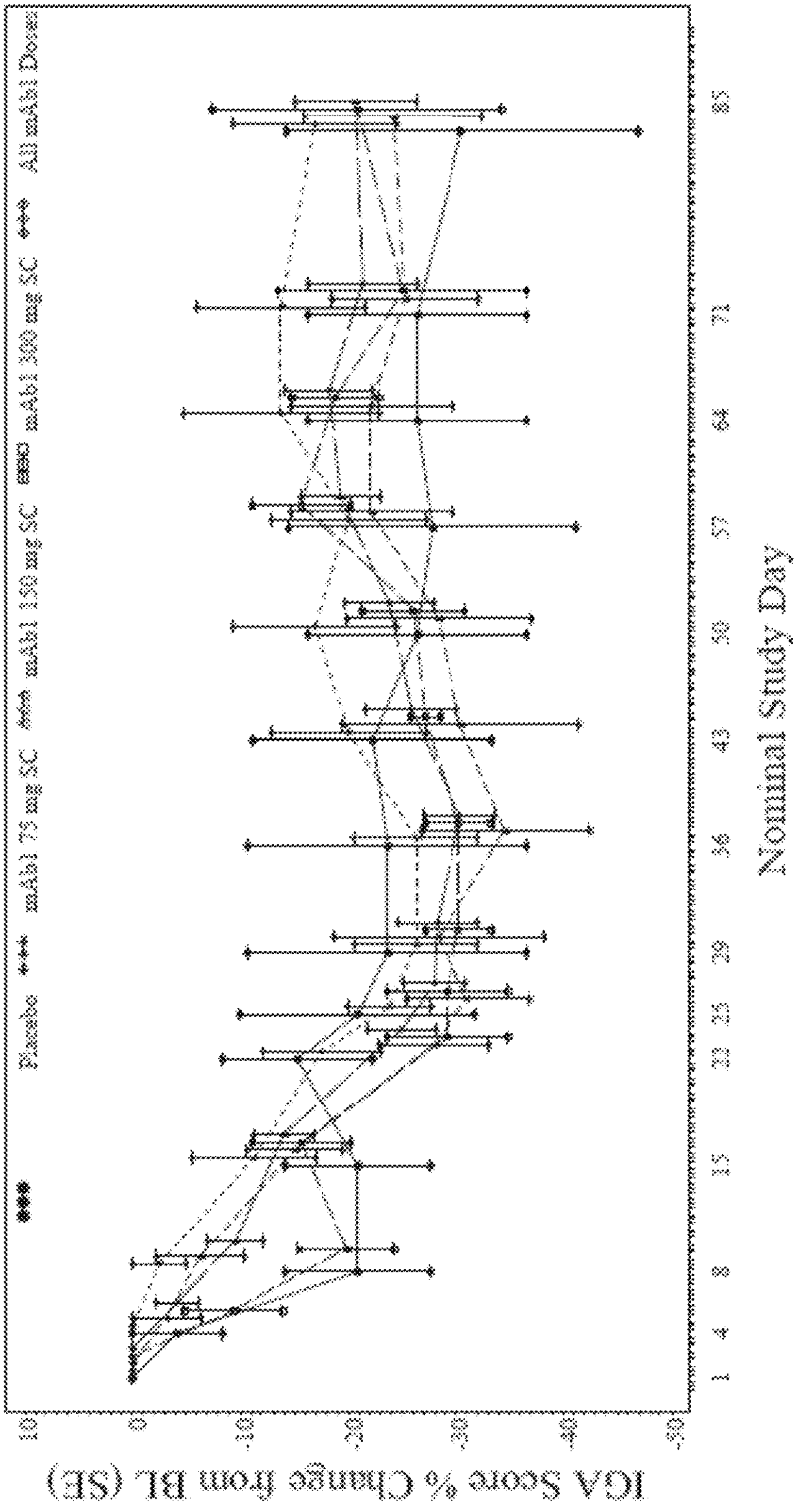
FIG. 5 shows the mean IGA score percent change from baseline—LOCF for the study in Example 6.
Figure 6:
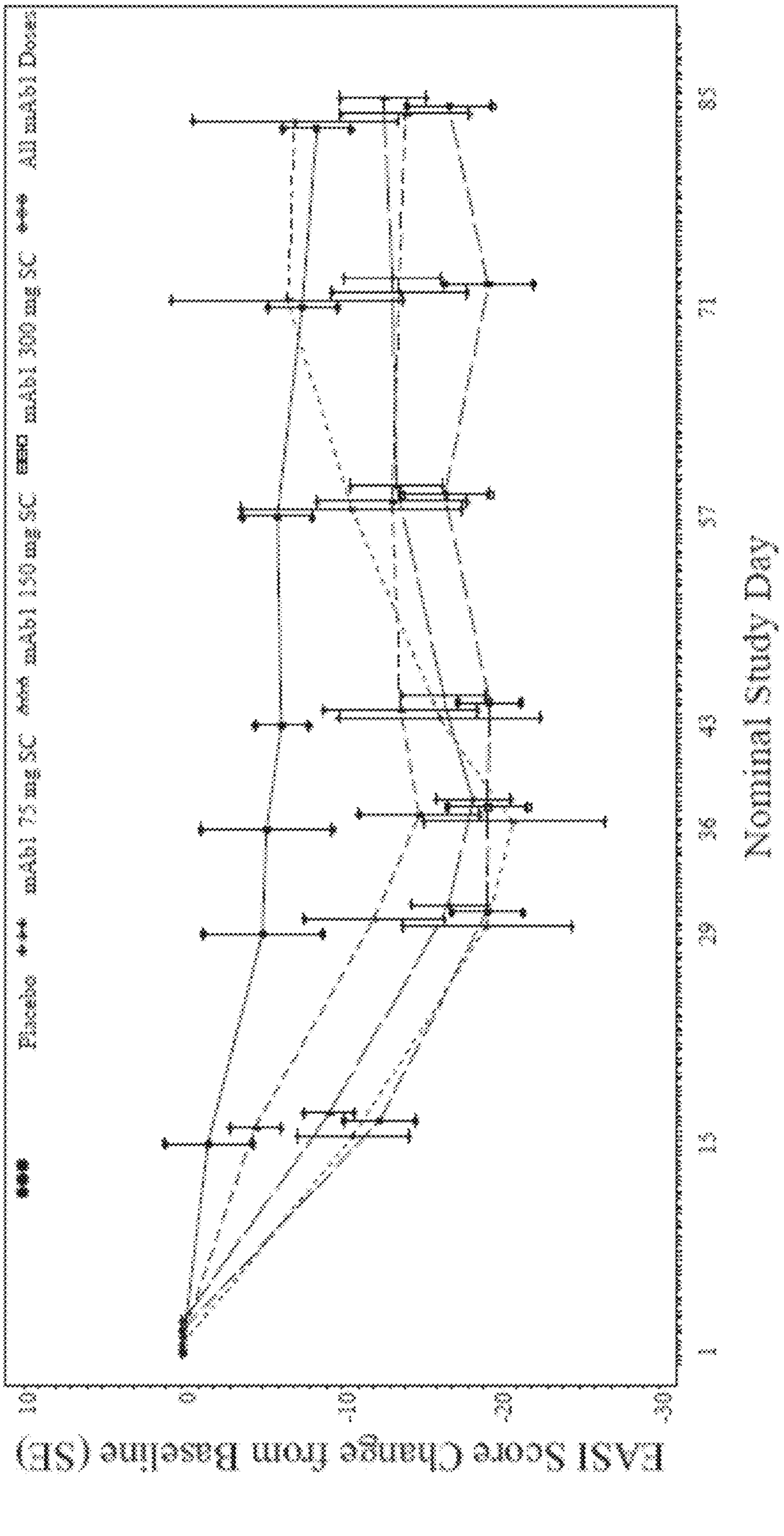
FIG. 6 shows mean EASI score change from baseline—LOCF for the study in Example 6.
Figure 7:
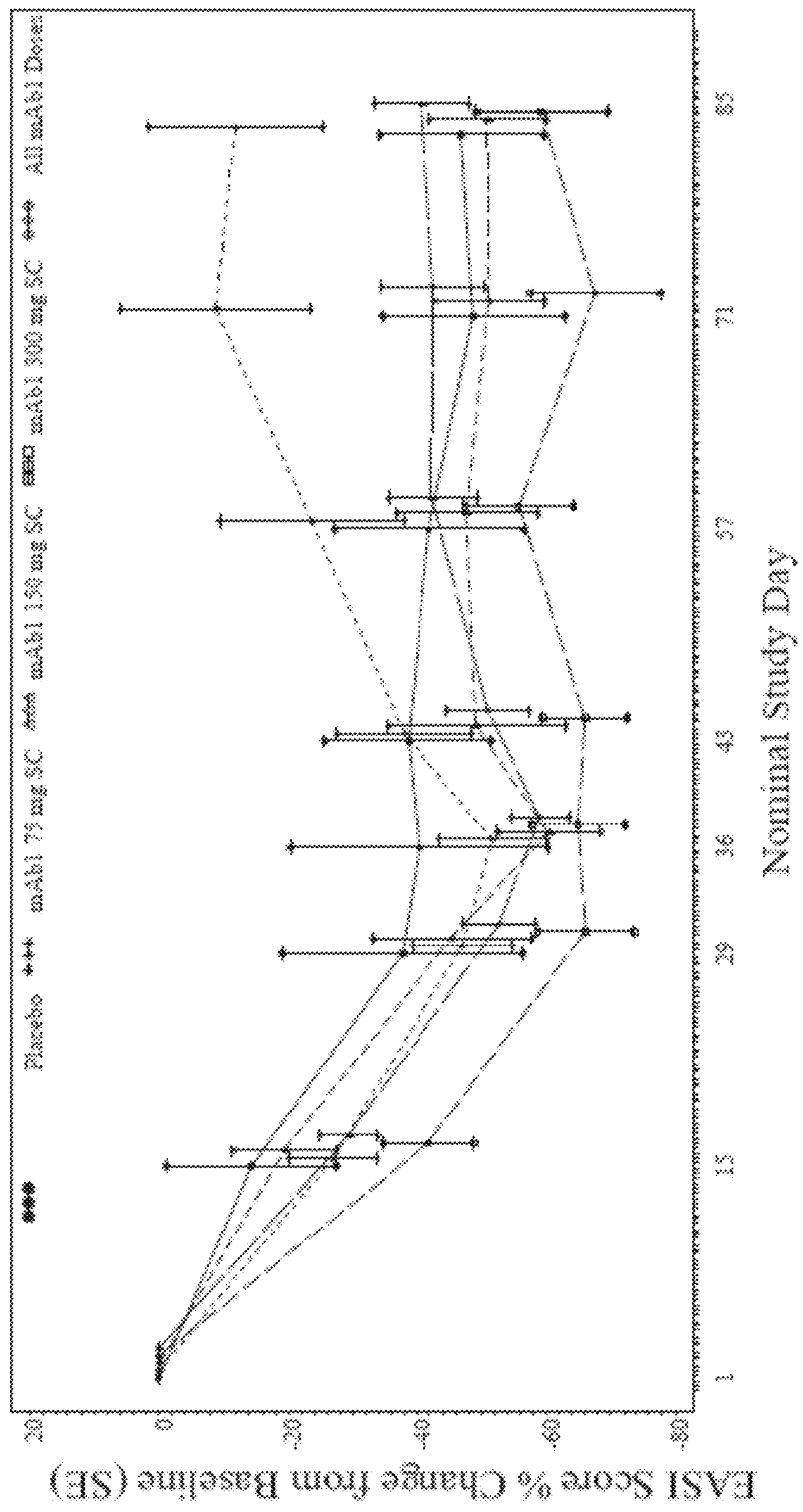
FIG. 7 shows mean EASI score percent change from baseline—LOCF for the study in Example 6.
Figure 8:
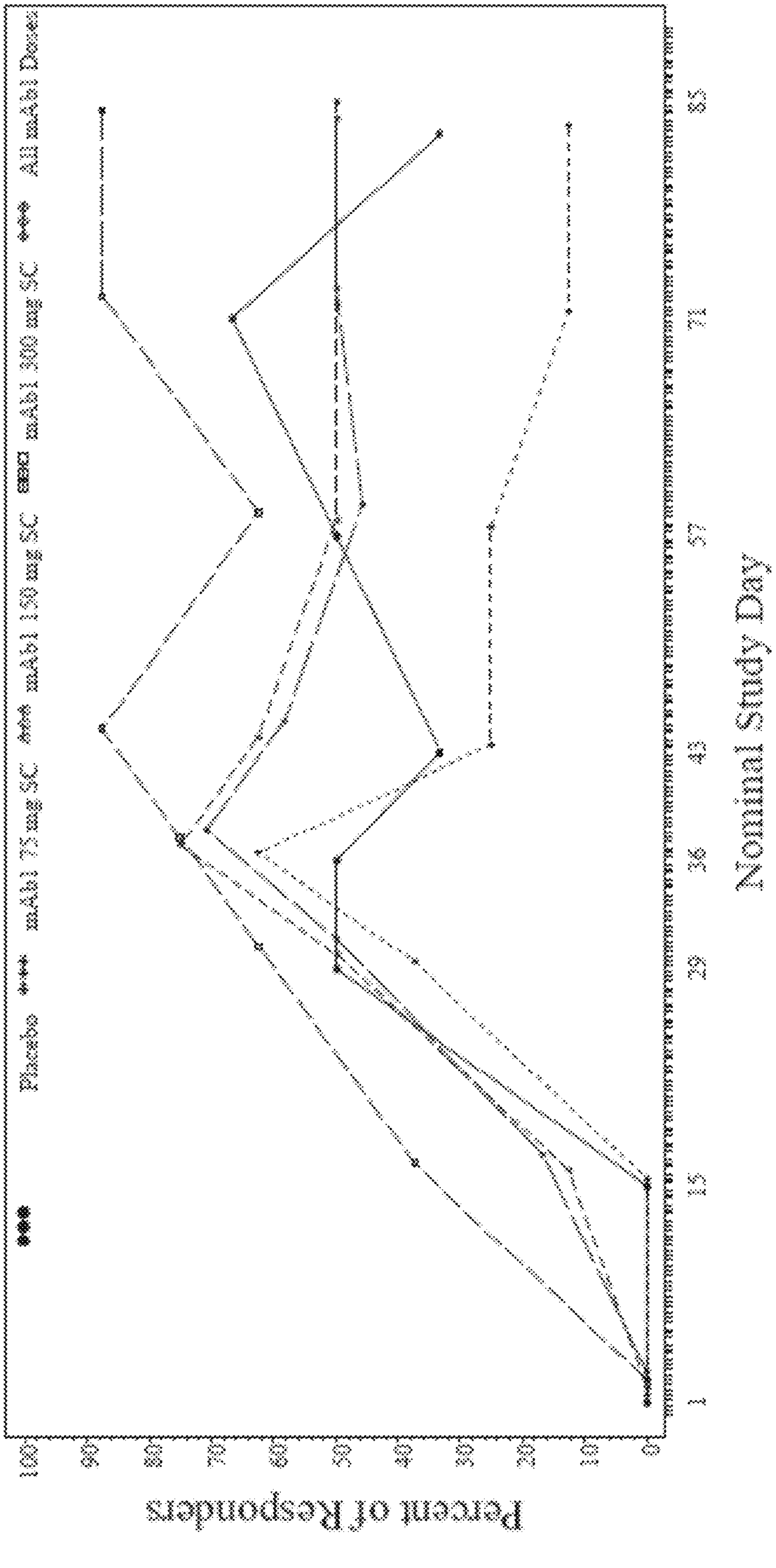
FIG. 8 shows EASI50 responder rate—LOCF for the study in Example 6.
Figure 9:
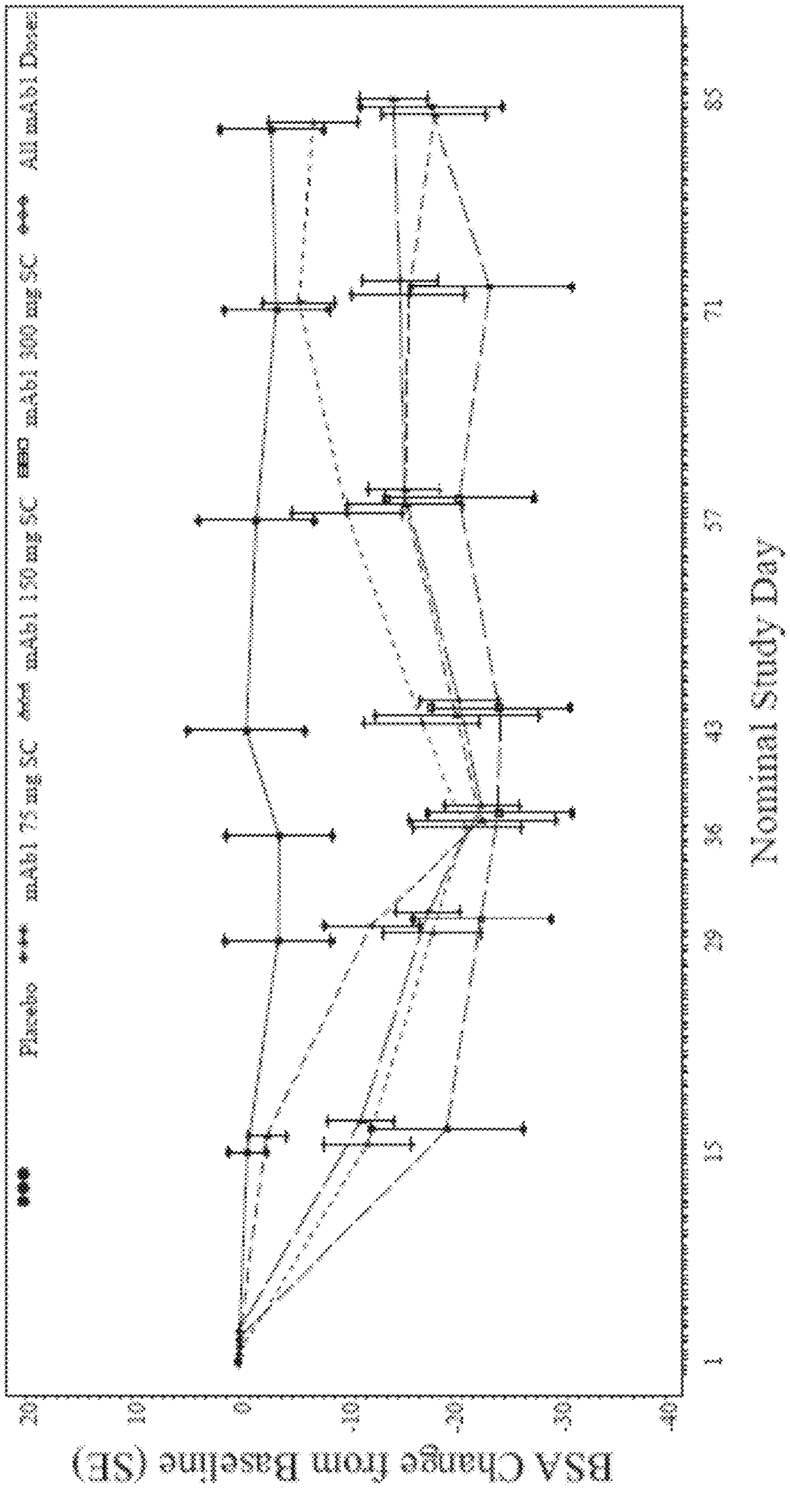
FIG. 9 shows mean BSA change from baseline—LOCF for the study in Example 6.
Figure 10:
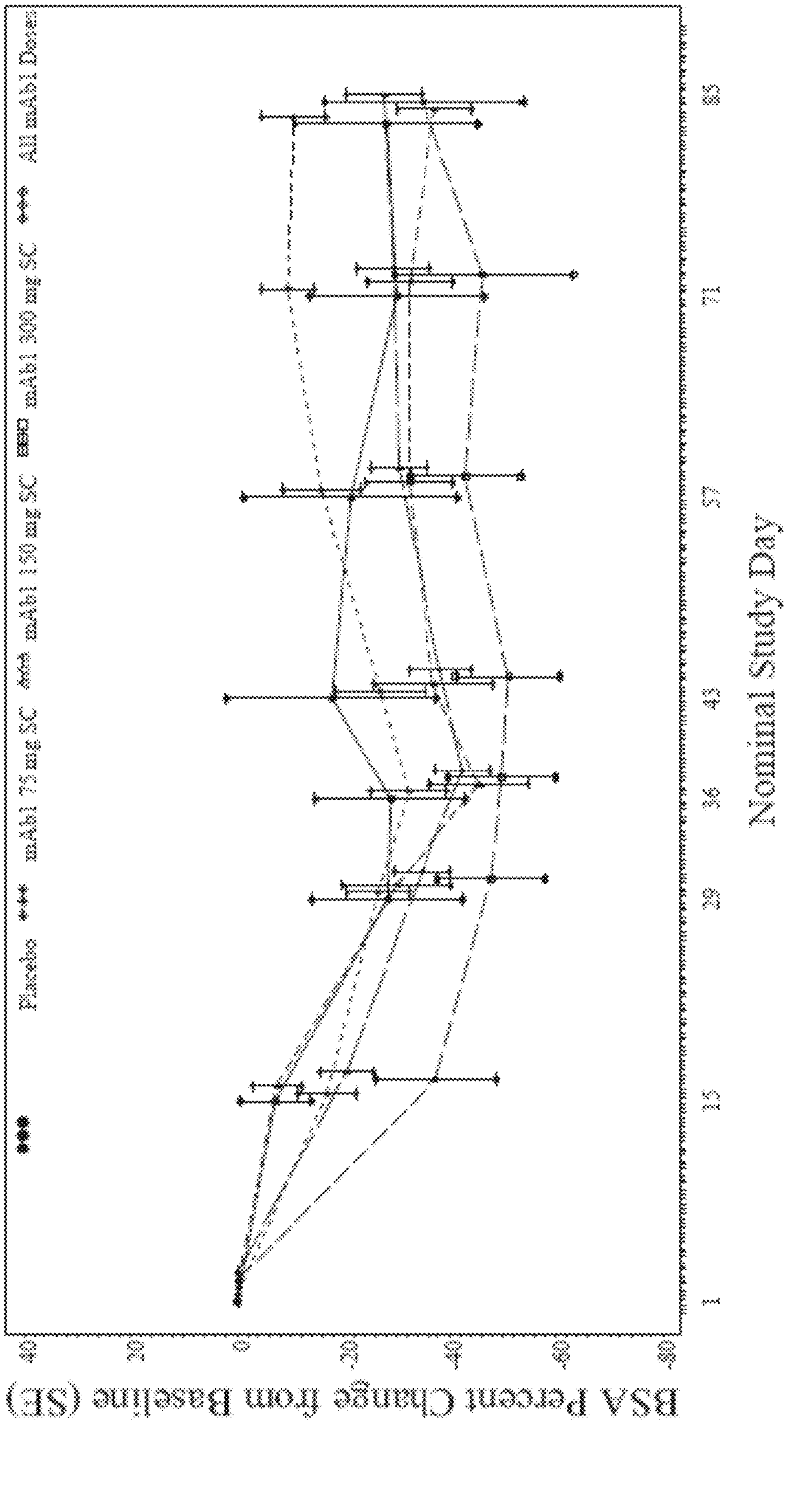
FIG. 10 shows mean BSA percent change from baseline—LOCF for the study in Example 6.
Figure 11:
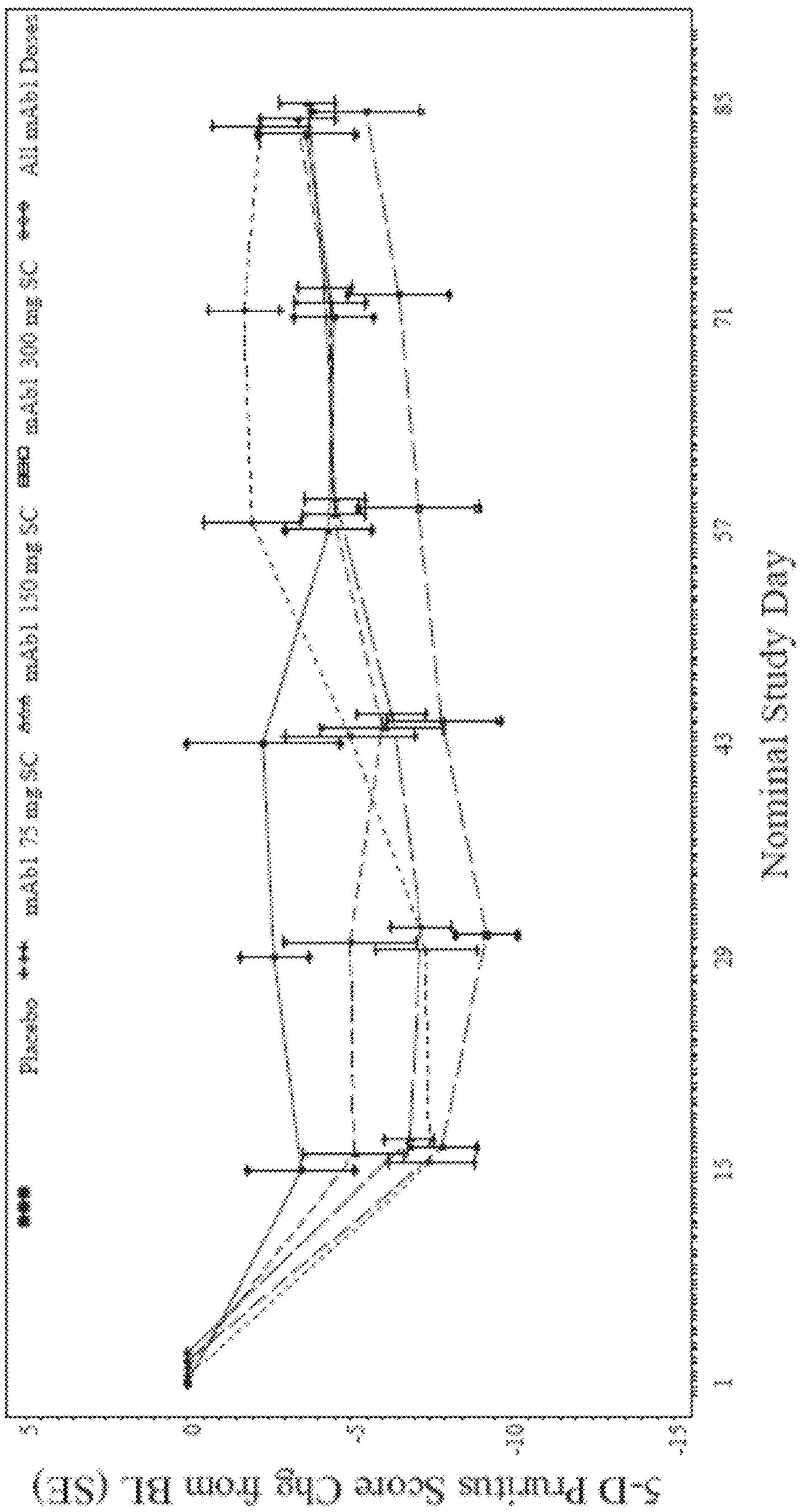
FIG. 11 shows mean 5-D change from baseline—LOCF for the study in Example 6.
Figure 12:
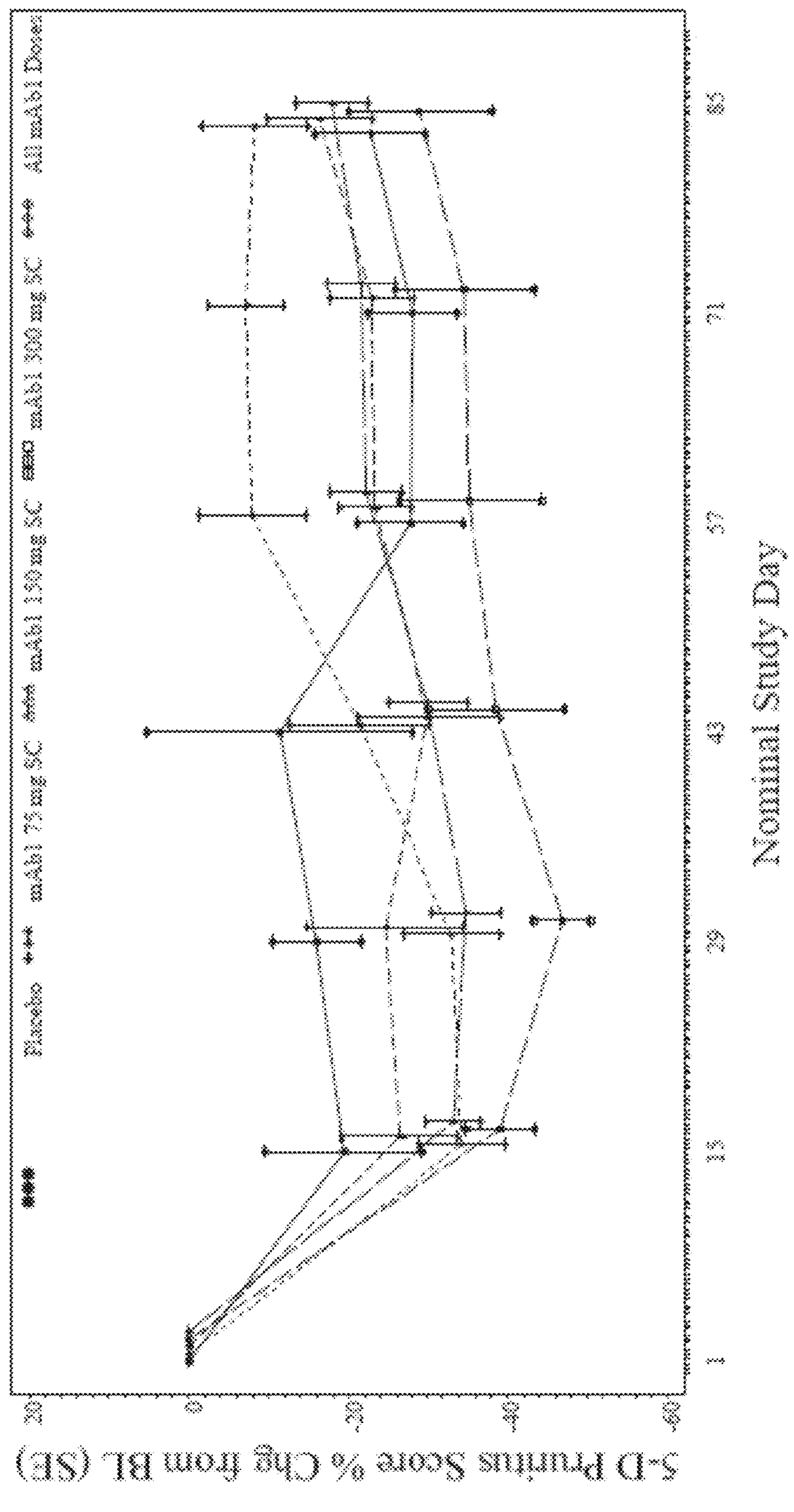
FIG. 12 shows mean 5-D percent change from baseline—LOCF for the study in Example 6.
Figure 13:
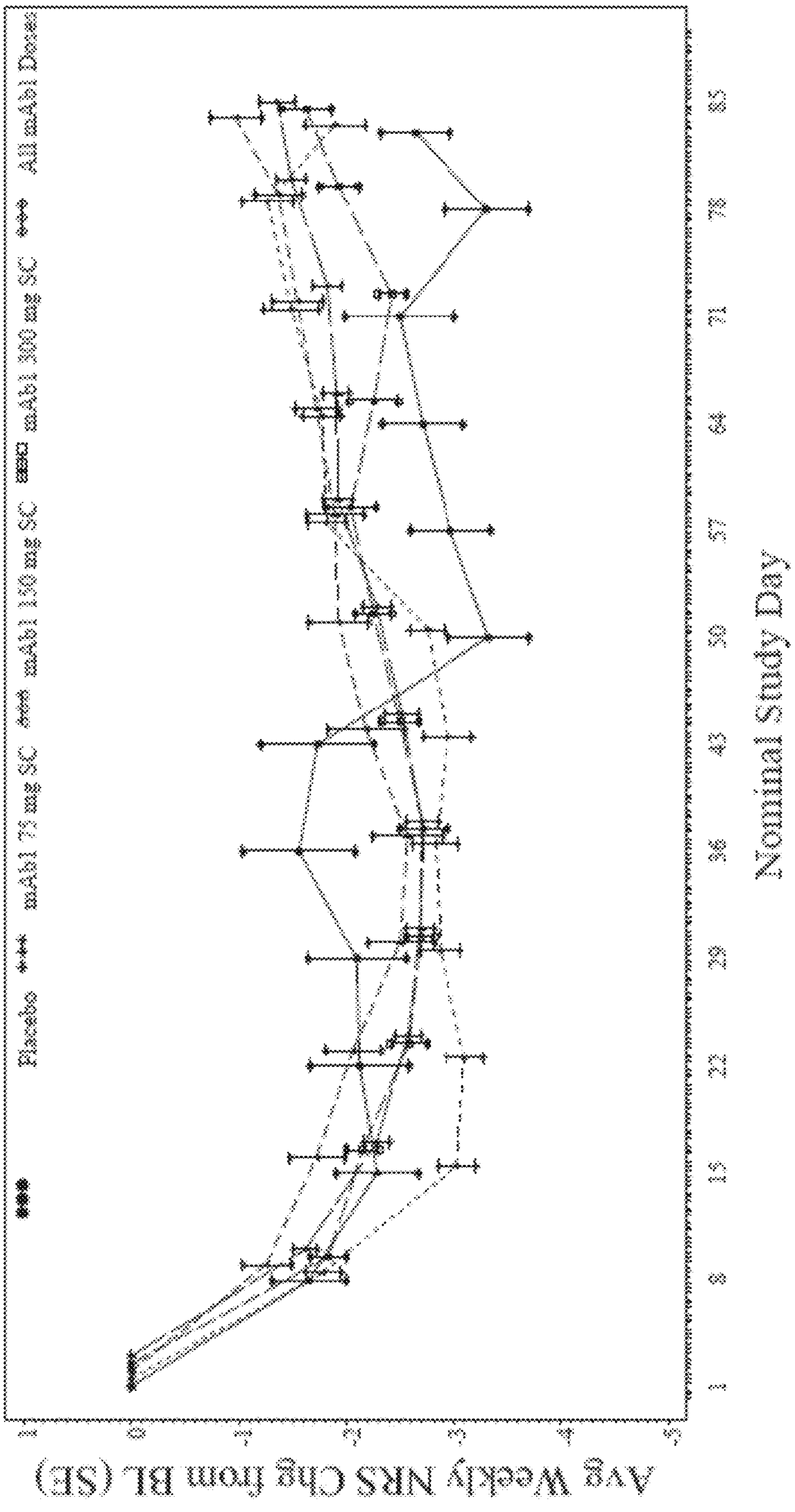
FIG. 13 shows mean NRS change from baseline—LOCF for the study in Example 6.
Figure 14:
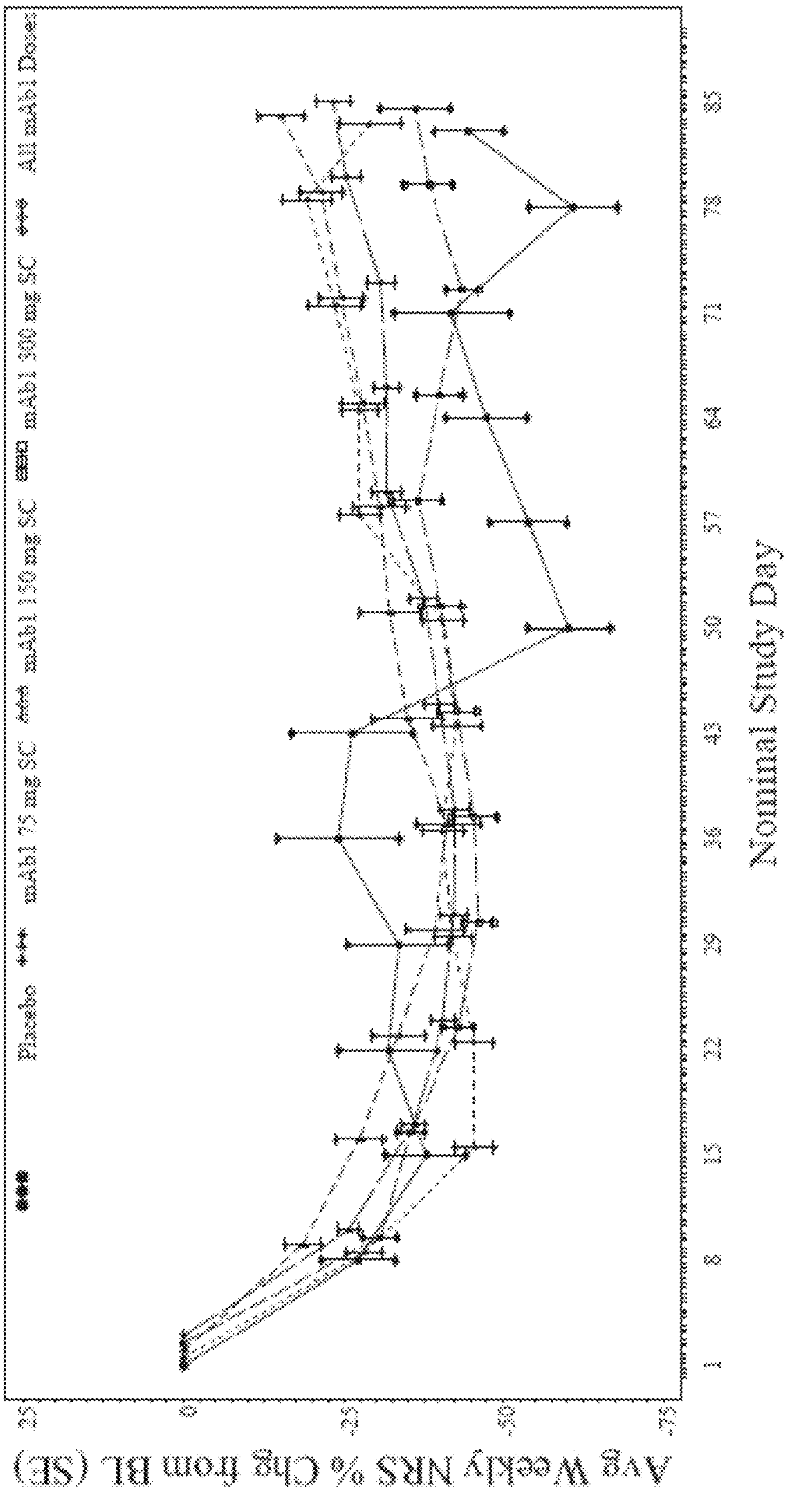
FIG. 14 shows mean NRS percent change from baseline—LOCF for the study in Example 6.
Figure 15:
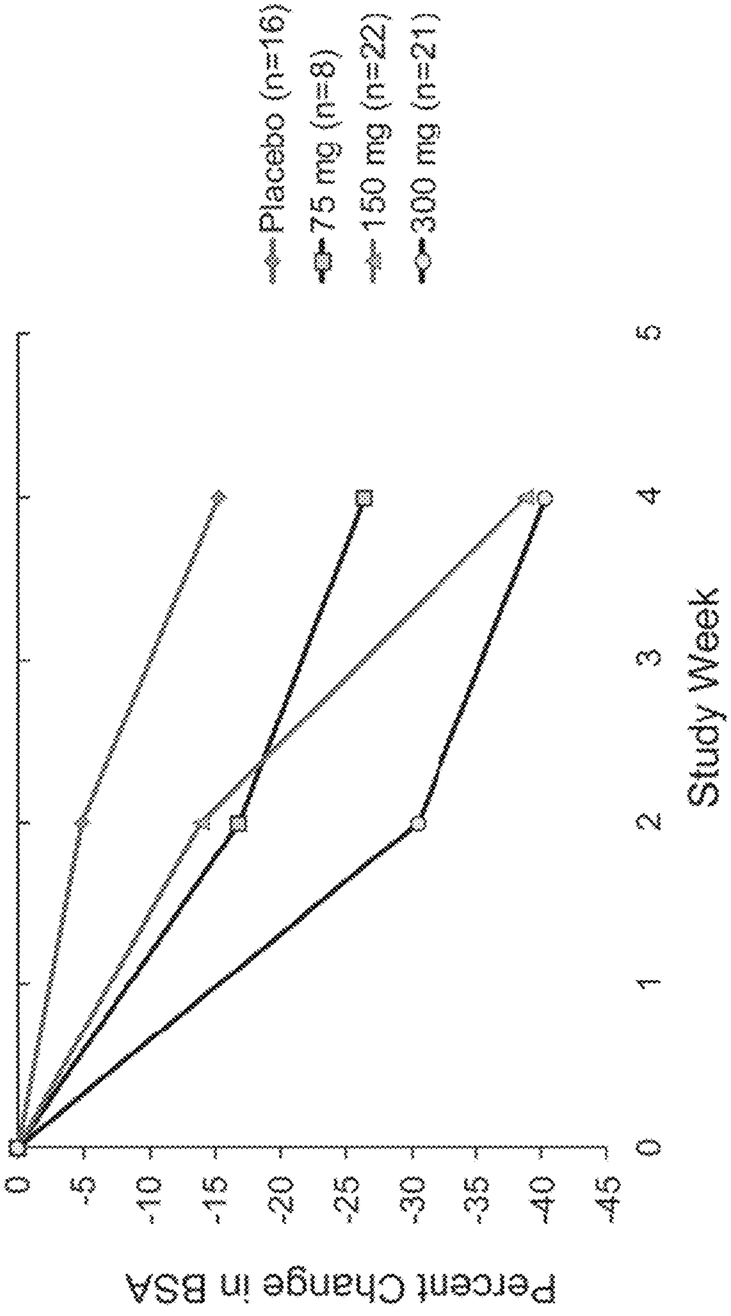
FIG. 15 shows percent change from baseline in BSA in patients administered 75 mg, 150 mg or 300 mg of anti-IL-4R antibody vs. placebo for the study in Example 8.
Figure 16:
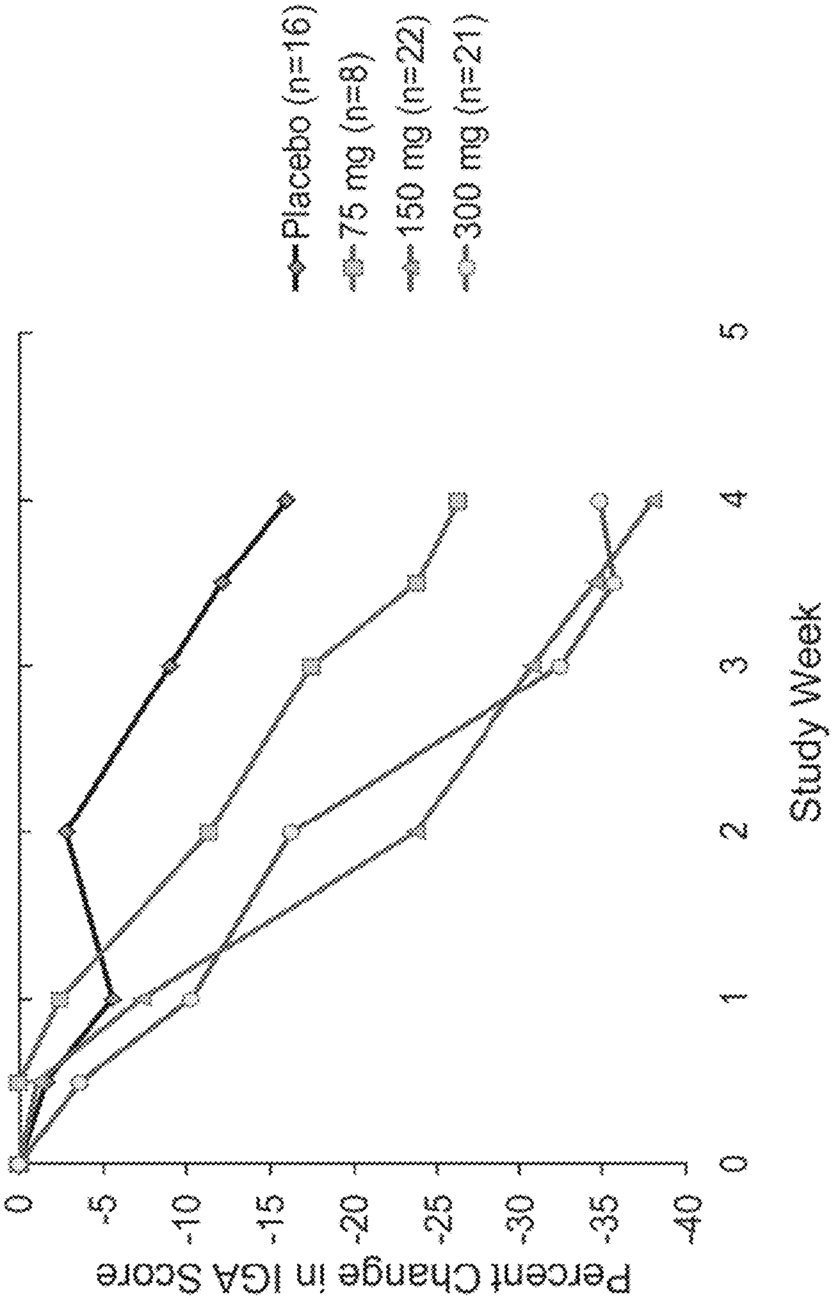
FIG. 16 shows percent change from baseline in IGA in patients administered 75 mg, 150 mg or 300 mg of anti-IL-4R antibody vs. placebo for the study in Example 8.
Figure 17:
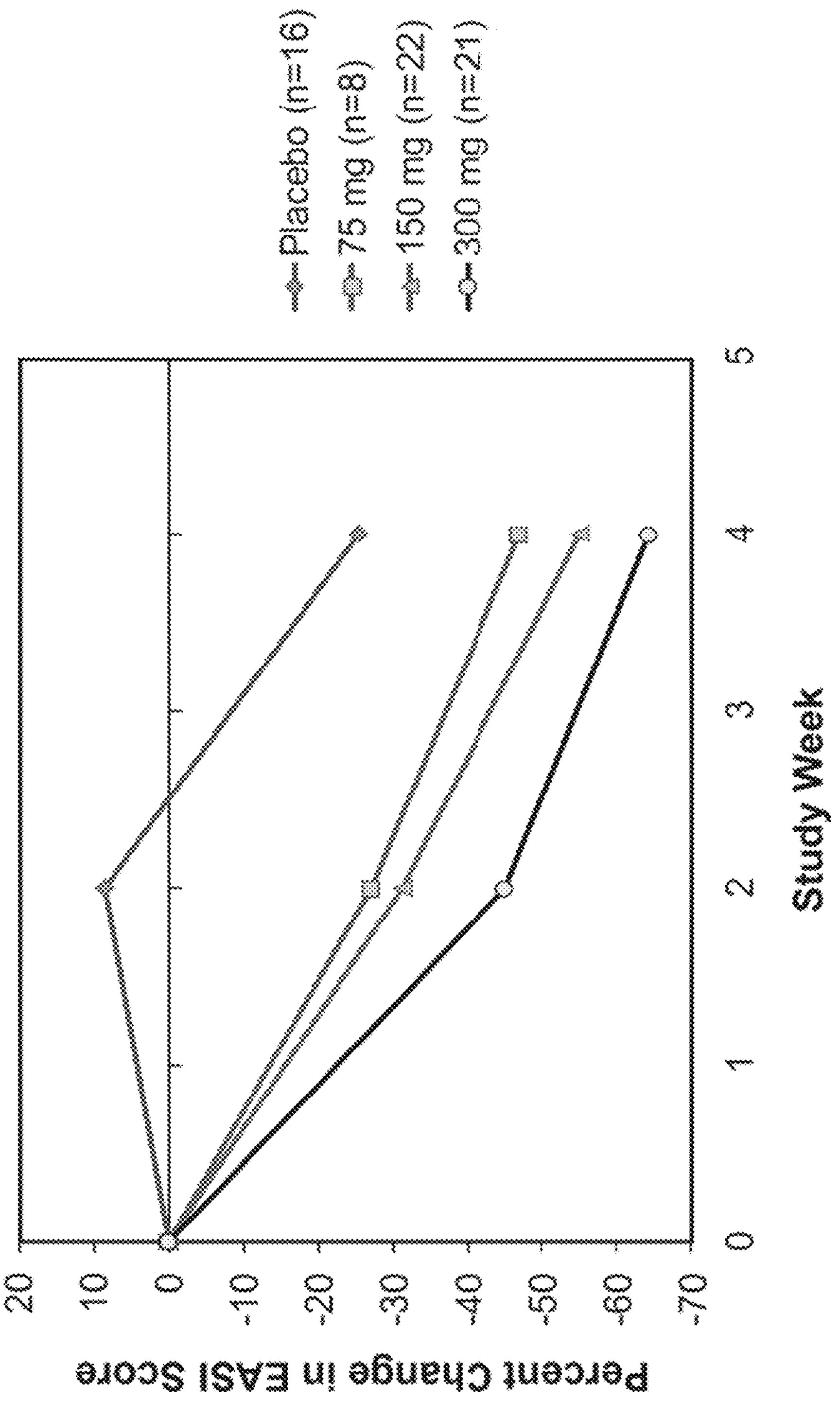
FIG. 17 shows percent change from baseline in EASI in patients administered 75 mg, 150 mg or 300 mg of anti-IL-4R antibody vs. placebo for the study in Example 8.

On day 1, all subjects received 300 mg mAb1 in 2 mL volume and completed VAS assessments according to the diagram in FIG. 2.

Information on the incidence, extent, and severity of injection site reactions (ISRs), such as erythema, edema, induration, tenderness, and itching, were monitored for all subjects (in groups 1 and 2). The extent (largest diameter in mm) of erythema, edema, and induration, as well as the severity of erythema and edema, were assessed 1, 2, 4, and 8 hours post completion of the injection and at follow-up visits through the end of the study or until the injection site appeared normalized at 2 consecutive assessments, based on all parameters evaluated. Subjects were also asked to rate any pruritus (itching) and tenderness (pain on palpation) present using VAS.

Subjects were discharged from the clinic on day 2. Subjects returned to the clinic for outpatient follow-up visits on days 4, 8, 11, 15, 22, 29, 36, 43, 50, 57, and 64 (end of study). Day 8, 11, and 15 clinic visits could have occurred within a window of +/−1 day. Visits from day 22 through day 64 could have occurred within a window of +/−2 days. The total observation period for each subject was 9 weeks following day 1 dosing.

B. Analysis Variables and Statistical Methods

The following demographic and Baseline characteristics variables were summarized: Age at screening (year), Gender, Ethnicity, Race, Baseline Weight (kg), Height (m), and BMI (kg/m2), Pain/discomfort VAS. Primary variables include the following measurements for safety and tolerability: (i) incidence and severity of treatment-emergent adverse events (TEAEs) through day 64 (end of study); Incidence, extent, severity and duration of ISRs through day 64; (ii) overall pain/discomfort associated with the injection procedure (GA); (iii) individual pain/discomfort components on needle insertion, while injecting study drug and on needle removal; and (iv) residual pain/discomfort over time: present pain/discomfort at 5 minutes, 10 minutes, 15 minutes, 30 minutes, 1, 2, 4, and 8 hours after study administration, and at subsequent study visits.

Information on the incidence, extent, and severity of ISRs, such as erythema, edema, induration, tenderness, and itching, were monitored for all subjects (in groups 1 and 2). The extent (largest diameter in mm) of erythema, edema and induration were assessed. In addition, the severity of erythema and edema were qualitatively assessed using standard 0-4 dermal tolerability scales (Draize) 1, 2, 4, and 8 hours post completion of the injection, and at follow-up visits through the end of the study or until the injection site appeared normalized at 2 consecutive assessments, based on all parameters evaluated.

The following scales were used to grade the severity of erythema and edema:

Erythema:

0=no erythema
1=very slight erythema (barely perceptible)
2=well defined erythema
3=moderate to severe erythema
4=severe erythema (beet redness) to slight eschar formation (injuries in depth)

Edema:

0=no edema
1=very slight edema (barely perceptible)
2=slight edema (edges well defined)
3=moderate edema (raised >1 mm)
4=severe edema (raised >1 mm and beyond area of exposure)

The VAS is a continuous rating scale (0-100 mm) used by patients to rate their pain/discomfort related to study drug injection. The VAS was anchored by "no pain/discomfort" on the left and "worst possible pain/discomfort" on the right. The same scale was used to quantify injection site itching and tenderness, which were assessed as part of ISR.

Safety and tolerability of mAb1 were assessed by physical examination, vital signs, electrocardiograms (ECGs), and clinical laboratory evaluations. Subjects were asked to monitor and report all adverse events (AEs) experienced from the time the informed consent is signed until the end of study visit on day 64. Adverse events, serious adverse events, and treatment-emergent adverse events have been defined elsewhere herein.

Blood samples were collected for PK analyses at every study visit starting at baseline (day 1, pre-dose and post-dose [at the end of the injection and 1, 2, 4, 8, and 12 hours post dose]). Blood samples were collected for the analysis of anti-mAb1 antibody levels on day 1 (pre-dose), and on days 29 and 64 (end of study).

For continuous variables, descriptive statistics included the following: the number of patients reflected in the calculation (n), mean, median, standard deviation, minimum, and maximum. For categorical or ordinal data, frequencies and percentages were displayed for each category.

C. Results

Pain on Injection and Residual Pain:

Both injection modalities—fast and slow—were well tolerated and associated with relatively low levels of pain on injection. For both modalities, pain peaked approximately 15-30 seconds after the start of injection. Mean peak pain levels were below 15 mm on the 0-100 mm VAS. Mean pain scores, including the global assessment (overall pain recalled at 1 minute after the injection), as well as residual pain over time, were comparable between the fast and slow injection; differences observed were not clinically relevant (i.e., $\Delta<10$ on the 0-100 VAS scale). More subjects on slow injection reported little to no pain (VAS<5 mm), compared to those who received the fast injection. Overall, injection pain profile seemed slightly more favorable for the slow injection, but did not clearly differentiate the two injection modalities.

Injection Site Reactions:

ISR incidence overall was similar between the two study groups (89% for the fast injection, versus 94% for the slow injection). However, incidence of objective ISR findings (erythema and/or induration) was higher in the in the slow injection group (83%) compared with the fast injection group (44%), especially for injection site erythema (61% vs. 11%, respectively). Subjective ISRs included tenderness and pruritus at the injection site and their incidence was somewhat higher for the fast injection (72%) compared with the slow injection (56%), especially for injection site tenderness (72% vs. 39%, respectively). ISR onset was noted from 1 hour to several days after the injection. Time to ISR resolution was also reported from 1 hour to several days after onset. Overall, the ISR profile appeared somewhat more favorable to the fast injection group, but did not provide a clear differentiation between the two injection modalities.

Adverse Events:

The number and incidence of treatment emergent adverse events were higher in the slow-injection group (35 TEAEs reported in 15 subjects) compared with the fast-injection group (19 TEAEs reported in 11 subjects). Most TEAEs were ISRs that were reported as adverse events based on investigator's assessment of clinical relevance. No TEAE led to discontinuation. There were 3 serious TEAEs related to a single case which were not related to the study drug or injection modality. Overall, the adverse event profile appeared slightly more favorable to the fast-injection group, mostly on the account of ISRs reported as adverse events.

D. Conclusion

The study achieved the primary and secondary objectives stated in the protocol. mAb1 was safe and well tolerated when administered by either fast or slow injection. The results of the study did not provide a clear differentiation between the two injection modalities.

Example 6: Sequential Ascending Repeat-Dose Clinical Trial of Subcutaneously Administered Anti-IL-4R Antibody (mAb1) in Patients with Moderate-to-Severe Atopic Dermatitis A. Study Design This study was a phase 1b, randomized, double-blind, placebo-controlled, sequential ascending, repeat-dose study of mAb1 subcutaneously administered in patients with moderate-to-severe extrinsic atopic dermatitis (AD). Thirty patients were randomized into the study (6 in placebo, 8 each in of 75 mg, 150 mg and 300 mg groups). Twenty-eight patients received all the treatments. The treatment period was 4 weeks in duration; patients were followed for 8 weeks after end of the treatment period. Patients were randomized in a 4:1 ratio to receive mAb1 or placebo in each of 3 ascending dose cohorts (75, 150, or 300 mg mAb1). The primary objective of the trial was to access the safety and tolerability, with PK as a secondary objective. Exploratory objectives included efficacy and biomarker endpoints. The exploratory efficacy variables included: (i) proportion of patients who achieved an IGA score of 0 or 1 through week 4 and each study visit; (ii) change and percent change in BSA, EASI, and 5-D pruritus scale from baseline to each visit; and (iii) weekly change from baseline in NRS scale.

B. Efficacy Variables

The efficacy variables IGA, BSA, EASI, SCORAD, 5-D pruritus scale, and pruritus NRS rating have been described elsewhere herein (see, for example, Example 7).

The IGA, BSA, EASI and SCORAD scores were assessed at every clinic visit. Patients underwent 5-D pruritus assessment at the following visits: screening, day 1/baseline (pre-dose), and days 15, 29, 43, 57, 71, and 85 (end of study) or early termination. Patients used the IVRS to record their Pruritus NRS score twice daily through the last study visit.

Baseline for efficacy variable is defined as the last non-missing value on or before the date of randomization. For the patient who has no value on or before his/her randomization date the last non-missing value on or before the date of first dose injection will be used as baseline.

C. Statistical Methods

Summary of safety and exploratory efficacy variables was generated by dose group and overall. The summary of safety and tolerance were performed based on the safety analysis set (SAF). The safety analyses were based on the reported adverse events (AEs), clinical laboratory evaluations, vital signs, and 12-lead ECG.

All the categorical variables were analyzed using the Fisher's exact test with nominal p-value and confidence intervals reported.

All continuous variables were analyzed by the ANalysis of COVAriance (ANCOVA). Unless otherwise specified, assessments of changes from baseline and construction of confidence intervals for continuous measures were based on an ANCOVA model which included treatment as the main factor and baseline value as covariates. Point estimate and 95% CI of the difference in adjusted mean change from baseline between two treatment groups were provided. Due to small sample size of this study, p-values from the tests of the exploratory efficacy variables were provided for descriptive purpose. Missing values were imputed by the last observation carried forward (LOCF).

D. Patient Disposition

The patients in placebo group were the youngest, and 33% of patients in placebo group were Hispanic or Latino compared to the treatment groups where all the patients were non-Hispanic. Table 6 summarizes the demographic characteristics of the patient population.

TABLE 6

Summary of Demographic Characteristics

| | Placebo (N = 6) | 75 mg (N = 8) | 150 mg (N = 8) | 300 mg (N = 8) | All Doses (N = 24) |
|---|---|---|---|---|---|
| Mean age, years (SD) | 23.0 (4.00) | 35.8 (12.51) | 45.6 (10.78) | 46.1 (11.36) | 42.5 (12.09) |
| Ethnicity, n (%) | | | | | |
| Hispanic or Latino | 2 (33.3%) | 0 | 0 | 0 | 0 |
| Non-Hispanic | 4 (66.7%) | 8 (100%) | 8 (100%) | 8 (100%) | 24 (100%) |
| Race, n (%) | | | | | |
| American-Indian/Alaska Native | 0 | 0 | 0 | 1 (12.5%) | 1 (4.2%) |
| Asian | 0 | 0 | 0 | 1 (12.5%) | 1 (4.2%) |
| African-American | 2 (33.3%) | 4 (50.0%) | 2 (25.0%) | 2 (25.0%) | 8 (33.3%) |
| White | 4 (66.7%) | 4 (50.0%) | 5 (62.5%) | 4 (50.0%) | 13 (54.2%) |
| Other | 0 | 0 | 1 (12.5%) | 0 | 1 (4.2%) |
| Gender, n (%) | | | | | |
| Male | 3 (50.0%) | 6 (75.0%) | 5 (62.5%) | 2 (25.0%) | 13 (54.2%) |
| Female | 3 (50.0%) | 2 (25.0%) | 30 (37.5%) | 6 (75.0%) | 11 (45.8%) |
| Mean BMI, kg/m$^3$ (SD) | 26.81 (8.191) | 26.41 (4.489) | 27.32 (5.285) | 31.60 (12.890) | 24.45 (8.399) |

Table 7 summarizes the baseline disease characteristics of the patient population.

TABLE 7

Baseline Disease Characteristics

| | Placebo (N = 6) | 75 mg (N = 8) | 150 mg (N = 8) | 300 mg (N = 8) | All Doses (N = 24) |
|---|---|---|---|---|---|
| Duration of chronic AD, years | 17.8 (6.82) | 24.5 (16.95) | 27.5 (16.34) | 33.9 (17.92) | 28.6 (16.80) |

TABLE 7-continued

| Baseline Disease Characteristics | | | | | |
|---|---|---|---|---|---|
| | Placebo (N = 6) | 75 mg (N = 8) | 150 mg (N = 8) | 300 mg (N = 8) | All Doses (N = 24) |
| EASI score | 18.1 (7.17) | 36.9 (11.75) | 25.6 (13.84) | 29.8 (6.44) | 30.8 (11.65) |
| IGA score | 3.2 (0.41) | 4.1 (0.35) | 3.9 (0.64) | 3.8 (0.46) | 3.9 (0.50) |
| % BSA of AD | 31.6 (24.27) | 64.4 (17.03) | 46.9 (28.20) | 47.0 (20.49) | 52.84 (22.99) |
| 5-D pruritus scale | 15.5 (3.83) | 21.5 (3.55) | 19.3 (2.92) | 19.6 (2.97) | 20.1 (3.18) |
| Pruritus NRS score | 5.8 (1.60) | 7.0 (1.78) | 6.7 (1.62) | 6.0 (1.18) | 6.6 (1.54) |

The mean baseline IGA, EASI, BSA, and pruritus NRS for the study participants was approximately 3.8, 28.2, 48.5, and 6.4 respectively.

E. Results

Subcutaneous administration of mAb1 to patients with moderate-to-severe AD was safe and well tolerated in this study. A single serious adverse event was recorded for a patient in the 150 mg group, who was diagnosed with exercise-associated CPK increase. No deaths were reported. 25 of the treated patients or 83% reported at least one treatment emergent adverse event (TEAE). The most frequent TEAE from the treatment groups were infections and infestations (n=7 [29%] vs. 1 [17%] for placebo), and headaches in patients dosed with mAb1 (n=3 [13%] vs. 1 [17%] for placebo).

The baseline and exploratory efficacy results obtained from the study are summarized in FIGS. 3-14. mAb1 administration did not induce statistically significant improvement in any exploratory endpoints of AD. This may be due to the small sample size and the fact that the placebo patients were less severe and younger than active treatment groups.

Example 7: Clinical Trial of Subcutaneously Administered Anti-IL-4R Antibody (mAb1) in Patients with Moderate-to-Severe Atopic Dermatitis A. Study Design This study was a 12-week, double-blind, randomized, placebo-controlled, sequential ascending, repeated-dose study to assess the safety and pharmacokinetic profile of subcutaneous administration of the anti-IL-4R mAb, referred to herein as "mAb1," in adult patients with moderate-to-severe atopic dermatitis. Patients with moderate-to-severe AD had an Eczema Area and Severity Index (EASI) ≥12 and minimum 10% body surface area involvement. The treatment period was four weeks in duration, with patients being followed for 8 weeks after the end of the treatment period. Patients were withdrawn from topical agents (e.g., pimecrolimus, tacrolimus, and topical corticosteroids) for at least 1 week prior to baseline. Oral corticosteroids and immunosuppressives (e.g., cyclosporine, mycophenolate-mofetil, IFNγ) were also prohibited from ≥4 weeks prior to baseline.

Patients were randomized in a 3:1 ratio to receive mAb1 or placebo in each of two ascending dose cohorts (150 mg or 300 mg). The study consisted of a screening period (day −14 through day −3), a treatment period (day 1 through day 29) (topical steroids were not allowed), and a follow-up period (day 29 through day 85) (topical steroids were allowed). During the treatment period, patients were seen in the clinic at least once weekly for safety, laboratory, and clinical effect assessments on days 1, 4, 8, 15, 22, 25 and 29 (week 4). Patients received a dose of study drug on days 1, 8, 15 and 22. Patients were monitored at the study site for 2 hours after each dose of study drug. The end of the treatment period study visit occurred on day 29 (week 4). During the follow-up period patients were seen in the clinic for follow-up assessments at days 36, 43, 50, 57, 64, 71 and 85 (end of study visit).

B. Efficacy Variables

The exploratory efficacy variables measured in this study included: (1) proportion of patients who achieved an investigator's global assessment (IGA) score of 0 or 1 through week 4 and each study visit; (2) change and percent change in body surface area involvement of atopic dermatitis (BSA), eczema area and severity index (EASI), SCORAD, and 5-D pruritus scale from baseline to each visit; (3) weekly change from baseline in pruritus numeric rating scale (NRS); (4) change from baseline in circulating eosinophils, TARC, eotaxin-3, and total IgE through week 4; (5) change from baseline in circulating eosinophils, TARC, eotaxin-3, and total IgE through week 12; and (6) change from baseline in eosinophils, TARC, eotaxin-3, Phadiatop™ results, and total IgE associated with response through week 4.

Baseline for efficacy variable is defined as the last non-missing value on or before the date of randomization. For the patient who has no value on or before his/her randomization date the last non-missing value on or before the date of first dose injection will be used as baseline.

Investigator's Global Assessment (IGA):

The IGA is an assessment scale used in clinical studies to determine severity of AD and clinical response to treatment based on a 6-point scale ranging from 0 (clear) to 5 (very severe). The IGA score was assessed at every clinic visit.

Body Surface Area Involvement of Atopic Dermatitis (BSA):

BSA affected by AD was assessed for each major section of the body (head, trunk, upper extremities, and lower extremities) and was reported as the total of percentage from each body sections. Patients were assessed for BSA at the following visits: screening, day1/baseline (pre-dose), and days 15, 29, 36, 43, 57, 71, and 85 (end of study) or early termination.

Eczema Area and Severity Index (EASI):

The EASI is a validated measure used in clinical practice and clinical trials to assess the severity and extent of AD (Hanifin et al 2001, Exp. Dermetol. 10: 11-18). The EASI score calculation is based upon the Physician's Assessment of Individual Signs [erythema (E), induration/papulation (I), excoriation (X), and lichenification (L)], where each sign is scored as 0=Absent, 1=Mild, 2=Moderate, or 3=Severe, and also upon the Area Score [based on the % (BSA) affected] where 0=0% BSA, 1=1-9% BSA, 2=10-29% BSA, 3=30-49% BSA, 4=50-69% BSA, 5=70-89% BSA, 6=90-100% BSA.

For each of major section of the body (head, upper extremities, trunk and lower extremities), EASI score=(E+I+X+L)×Area Score. The total EASI score is the weighted total of the section EASI using the weights 10%=head, 20%=upper extremities, 30%=trunk, 40%=lower extremities. The minimum possible EASI score is 0 and the maximum possible EASI score is 72 where a higher score indicates increased severity of atopic dermatitis. Achieving an EASI 50 (50% or greater improvement in EASI score is considered by dermatology investigators to a clinically significant level of improvement to use as an endpoint.

Patients underwent EASI score assessment at the following visits: screening, day 1/baseline (pre-dose), and days 15, 29, 36, 43, 57, 71, and 85 (end of study) or early termination.

SCORAD:

The SCORAD is a validated tool used in clinical research and clinical practice that was developed to standardize the evaluation of the extent and severity of AD (Dermatology 1993, 186: 23-31). The extent of AD is assessed as a percentage of each defined body area and reported as the sum of all areas, with a maximum score of 100% (assigned as "A" in the overall SCORAD calculation). The severity of 6 specific symptoms (erythema, oedema/papulation, excoriations, lichenification, oozing/crusts and dryness) of AD is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the patient or relative on a visual analogue scale (VAS), where 0 is no itch (or sleeplessness) and 10 is the worst imaginable itch (or sleeplessness), with a maximum possible score of 20. This parameter is assigned as "C" in the overall SCORAD calculation. The SCORAD score is calculated as A/5+7B/2+C. The maximum SCORAD score is 103.

Patients underwent SCORAD assessment at the following visits: screening, day 1/baseline (pre-dose), and days 15, 29, 36, 43, 57, 71, and 85 (end of study) or early termination.

5-D Pruritus Scale:

The 5-D Pruritus Scale is a 5-question tool used in clinical trials to assess 5 dimensions of background itch: degree, duration, direction, disability, and distribution (Elman et. al. 2010, Brit. J. Dermatol. 162: 587-593). Patients rate their symptoms over the preceding 2-week period as "present" or on a 1 to 5 scale, with 5 being the most affected for each question in degree, duration, direction and disability. Single-item domain scores (duration, degree and direction) are equal to the value indicated below the response choice (range 1-5).

The disability domain includes four items that assess the impact of itching on daily activities: sleep, leisure/social activities, housework/errands and work/school. The score for the disability domain is achieved by taking the highest score on any of the four items.

For the distribution domain, the number of affected body parts is tallied (potential sum 0-16) and the sum is sorted into five scoring bins: sum of 0-2=score of 1, sum of 3-5=score of 2, sum of 6-10=score of 3, sum of 11-13=score of 4, and sum of 14-16=score of 5.

The scores of each of the five domains are achieved separately and then summed together to obtain a total 5-D score. 5-D scores can potentially range between 5 (no pruritus) and 25 (most severe pruritus).

Patients underwent 5-D pruritus assessment at the following visits: screening, day 1/baseline (pre-dose), and days 15, 29, 43, 57, 71, and 85 (end of study) or early termination.

Pruritus Numeric Rating Scale (NRS):

The Pruritus NRS is a single-question assessment tool that was used to assess the patient's worst itch as a result of AD in the previous 12 hours. Patients call in to the IVRS twice daily from the evening of the screening visit and be asked the following question, "on a scale of 0-10, with 0 being 'no itch' and 10 being the 'worst itch imaginable', how would you rate your worst degree of itch experienced during the previous 12 hours?" Patients are instructed on using the IVRS to record their Pruritus NRS score at the screening visit and are queried for compliance at each following clinic visit. Patients complete the rating scale twice daily through the last study visit.

The baseline NRS is defined as the average of the reported NRSs during right after the screening visit and right before the baseline visit. For post-baseline NRS, The mean weekly NRS is calculated as the average of the reported daily NRS within the week (prorated mean).

C. Safety Assessment

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

In addition, laboratory safety variables, vital sign variables, 12-lead electrocardiography (ECG) variables, and physical examination variables were measured throughout the study.

The clinical laboratory data consists of hematology, blood chemistry and urinalysis. Blood samples for hematology testing were collected at every study visit; blood samples for serum chemistry testing and urine samples for urinalysis were collected to measure overall patient health at screening, day 1/baseline (pre-dose), day 8, day 15, day 29, day 36, day 57, day 85 (end-of-study) or early termination if subject is discontinued from the study.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 4, 8, 15, 22, 25, 29, 36, and 85 (end of study) or early termination. Vital signs were taken at 1 and 2 hours post-injection following the study drug dose on days 1, 8, 15, and 22.

12-Lead ECG parameters include: Ventricular HR, PR interval, QRS interval, corrected QT interval (QTcF=QT/[$RR^{0.33}$] and QTcB=QT/[$RR^{0.5}$]) ECG status: normal, abnormal not clinical significant or abnormal clinical significant. A standard 12-lead ECG was performed at screening, day 29, and day 85 (end of study) or early termination.

A thorough and complete physical examination was performed at screening, day 29, and day 85 (end of study) or early termination.

D. Data Analysis

1. Analyses of Exploratory Efficacy Variables

All categorical variables were analyzed using the Fisher's Exact test with nominal p-value and confidence intervals reported. All continuous variables were analyzed by the ANalysis of COVAriance (ANCOVA). Unless otherwise specified, assessments of changes from baseline and construction of confidence intervals for continuous measures were based on an ANCOVA model which includes treatment as the main factor and baseline value as covariates. Point estimate and 95% CI of the difference in adjusted mean change from baseline between two treatment groups are provided. Missing values were imputed by the last observation carried forward (LOCF) approach. In the event that the model assumptions were not warranted, the Rank-based analysis of covariates was used. Correlation analyses were performed using Spearman's correlation coefficient.

2. Analysis of Safety Data

The safety analysis is based on the reported AEs, clinical laboratory evaluations, vital signs, and 12-lead ECG. Thresholds for Potentially Clinically Significant Values (PCSV) in laboratory variables, vital signs and ECG are defined in SAP. The time interval to detect any event or abnormality is between the infusion of study medication and end of study. Data collected outside this interval are excluded from the calculation of descriptive statistics and identification of abnormalities for laboratory evaluations, vital sign and ECG.

E. Results

As noted above, patients were treated either with 150 mg or 300 mg subcutaneous mAb1 once a week for four weeks, or with placebo. Except for a higher age at diagnosis in the 300 mg treatment group, demographic and clinical characteristics were generally similar among treatments (Table 8). The study population was primarily male (62.2%), white (94.6%), with a mean age of 43.6 (15.4) years. Of the 37 patients, 31 (83.8%) completed treatments and 25 (67.6%) completed the whole study. The most frequent reason for withdrawal was lack of efficacy (4 placebo patients and 1 in each treatment group). There were no withdrawals due to adverse events with the administered mAb1.

The baseline and exploratory efficacy results obtained from the study are summarized in Tables 9-14.

TABLE 8

Summary of Baseline Characteristics-all values represented as Mean (SD)

| | | mAb1 | | | |
|---|---|---|---|---|---|
| | Placebo | 150 mg | 300 mg | All Doses Combined | All Subjects Combined |
| No. Patients | 10 | 14 | 13 | 27 | 37 |
| Age, years, mean (SD) | 46.0 (16.2) | 40.6 (11.7) | 45.0 (18.6) | 42.7 (15.3) | 43.6 (15.4) |
| Gender, n (%) | | | | | |
| Male | 8 (80.0) | 7 (50.0) | 8 (61.5) | 15 (55.6) | 23 (62.2) |
| Female | 2 (20.0) | 7 (50.0) | 5 (38.5) | 12 (44.4) | 14 (37.8) |
| Race, n (%) | | | | | |
| White | 9 (90.0) | 14 (100) | 12 (92.3) | 26 (96.3) | 35 (94.6) |
| Black/African-American | 0 | 0 | 1 (7.7) | 1 (3.7) | 1 (2.7) |
| Other | 1 (10.0) | 0 | 0 | 0 | 1 (2.7) |
| BMI, kg/m$^2$ mean (SD) | 25.0 (4.6) | 24.7 (2.8) | 25.3 (3.5) | 25.0 (3.1) | 25.0 (3.5) |
| Chronic Atopic Dermatitis Diagnosis Age | 5.8 (10.50) | 5.9 (11.92) | 16.2 (23.79) | 10.9 (18.98) | 9.5 (17.11) |
| BSA | 45.5 (26.43) | 51.4 (29.98) | 49.0 (24.08) | 50.2 (26.80) | 48.9 (26.42) |
| EASI Score | 25.6 (13.73) | 32.6 (18.56) | 25.9 (13.38) | 29.4 (16.32) | 28.3 (15.56) |
| IGA Score | 3.9 (0.74) | 3.9 (0.73) | 3.3 (0.48) | 3.6 (0.69) | 3.7 (0.70) |
| NRS Score | 5.8 (1.92) | 5.6 (1.87) | 5.4 (1.69) | 5.5 (1.75) | 5.6 (1.78) |
| SCORAD Score | 65.3 (11.09) | 66.2 (17.07) | 58.6 (13.93) | 62.6 (15.81) | 63.3 (14.59) |
| Pruritus 5-D Score | 17.8 (3.94) | 18.9 (3.05) | 18.1 (3.99) | 18.5 (3.49) | 18.3 (3.58) |
| CCL17, ng/mL, mean (SD) | 7001 (2669.8) | 9162.2 (4851.7) | 4601.4 (1957.3) | 6881.8 (2280.4) | 6914.9 (2001.3) |

TABLE 9

Summary of Percentage and Absolute Change in IGA Score from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline IGA Score | 3.9 (0.74) | 3.9 (0.73) | 3.3 (0.48) | 3.6 (0.69) |
| Day 4 IGA Score | 3.9 (0.74) | 3.9 (0.73) | 3.3 (0.48) | 3.6 (0.69) |
| % Change from Baseline to Day 4 | 0.0 (0.00) | 0.0 (0.00) | 0.0 (0.00) | 0.0 (0.00) |
| Absolute change from Baseline to Day 4 | 0.0 (0.00) | 0.0 (0.00) | 0.0 (0.00) | 0.0 (0.00) |
| Day 8 IGA Score | 3.9 (0.60) | 3.6 (0.93) | 3.2 (0.55) | 3.4 (0.80) |
| % Change from Baseline to Day 8 | 4.6 (18.22) | −8.0 (13.46) | −4.5 (11.08) | −6.3 (12.27) |
| Absolute change from Baseline to Day 8 | 0.1 (0.60) | −0.3 (0.47) | −0.2 (0.38) | −0.2 (0.42) |

TABLE 9-continued

Summary of Percentage and Absolute Change in IGA Score from Baseline-all values represented as Mean (SD)

| | | mAb1 | | |
|---|---|---|---|---|
| | Placebo | 150 mg | 300 mg | All Doses Combined |
| Day 15 IGA Score | 4.0 (0.71) | 2.9 (1.19) | 2.8 (0.83) | 2.8 (1.01) |
| % Change from Baseline to Day 15 | 9.3 (29.89) | −27.2 (18.24) | −16.7 (21.25) | −21.9 (20.13) |
| Absolute change from Baseline to Day 15 | 0.2 (0.97) | −1.0 (0.71) | −0.5 (0.66) | −0.8 (0.71) |
| Day 22 IGA Score | 3.5 (0.55) | 2.7 (0.89) | 2.2 (0.90) | 2.4 (0.91) |
| % Change from Baseline to Day 22 | −2.8 (21.52) | −32.8 (11.68) | −34.6 (28.23) | −33.7 (21.49) |
| Absolute change from Baseline to Day 22 | −0.2 (0.75) | −1.3 (0.45) | −1.2 (0.90) | −1.2 (0.71) |
| Day 25 IGA Score | 3.5 (0.55) | 2.6 (1.00) | 2.0 (1.00) | 2.3 (1.02) |
| % Change from Baseline to Day 25 | −1.4 (28.59) | −34.4 (18.73) | −39.7 (29.30) | −37.2 (24.44) |
| Absolute change from Baseline to Day 25 | −0.2 (0.98) | −1.3 (0.78) | −1.3 (0.95) | −1.3 (0.85) |
| Day 29 IGA Score | 3.3 (0.52) | 2.2 (0.94) | 2.1 (0.95) | 2.1 (0.93) |
| % Change from Baseline to Day 29 | −8.3 (12.91) | −44.4 (19.86) | −37.8 (26.05) | −41.0 (23.05) |
| Absolute change from Baseline to Day 29 | −0.3 (0.52) | −1.8 (0.87) | −1.2 (0.83) | −1.5 (0.87) |
| Day 36 IGA Score | 3.5 (0.58) | 2.0 (0.74) | 2.1 (0.35) | 2.1 (0.60) |
| % Change from Baseline to Day 36 | −6.3 (12.50) | −48.9 (15.51) | −36.5 (8.84) | −43.9 (14.39) |
| Absolute change from Baseline to Day 36 | −0.3 (0.50) | −1.9 (0.67) | −1.3 (0.46) | −1.7 (0.67) |
| Day 43 IGA Score | 3.0 (1.10) | 2.2 (1.03) | 1.7 (0.79) | 2.0 (0.93) |
| % Change from Baseline to Day 43 | −20.0 (29.15) | −45.1 (23.40) | −47.7 (22.39) | −46.4 (22.44) |
| Absolute change from Baseline to Day 43 | −0.8 (1.17) | −1.8 (0.87) | −1.5 (0.69) | −1.7 (0.78) |
| Day 50 IGA Score | 3.2 (1.48) | 2.3 (1.14) | 1.6 (0.67) | 2.0 (0.98) |
| % Change from Baseline to Day 50 | −10.0 (37.91) | −42.1 (25.51) | −50.0 (21.08) | −45.9 (23.32) |
| Absolute change from Baseline to Day 50 | −0.4 (1.52) | −1.7 (1.07) | −1.6 (0.67) | −1.7 (0.88) |
| Day 57 IGA Score | 3.5 (0.58) | 2.2 (1.01) | 1.7 (0.79) | 2.0 (0.93) |
| % Change from Baseline to Day 57 | 2.1 (23.94) | −42.6 (24.94) | −47.0 (23.65) | −44.6 (23.93) |
| Absolute change from Baseline to Day 57 | 0.0 (0.82) | −1.7 (1.03) | −1.5 (0.82) | −1.6 (0.92) |
| Day 64 IGA Score | 3.2 (0.45) | 2.5 (1.13) | 1.7 (0.65) | 2.1 (0.97) |
| % Change from Baseline to Day 64 | −10.0 (13.69) | −36.8 (27.24) | −47.0 (18.36) | −41.9 (23 . . . 26) |
| Absolute change from Baseline to Day 64 | −0.4 (0.55) | −1.5 (1.04) | −1.5 (0.69) | −1.5 (0.86) |
| Day 71 IGA Score | 3.0 (.071) | 2.8 (0.87) | 1.6 (0.90) | 2.2 (1.07) |
| % Change from Baseline to Day 71 | −16.7 (15.59) | −25.6 (31.74) | −52.8 (26.67) | −39.8 (31.72) |
| Absolute change from Baseline to Day 71 | −0.6 (0.55) | −1.2 (1.33) | −1.8 (0.87) | −1.5 (1.12) |
| Day 85 IGA Score | 3.3 (0.96) | 2.8 (1.08) | 2.2 (0.94) | 2.5 (1.04) |
| % Change from Baseline to Day 85 | −6.3 (29.95) | −26.5 (35.84) | −33.3 (29.09) | −30.1 (31.92) |
| Absolute change from Baseline to Day 85 | −0.3 (0.96) | −1.2 (1.33) | −1.1 (0.90) | −1.1 (1.10) |

TABLE 10

Summary of Percentage and Absolute Change in EASI Score from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline EASI Score | 25.6 (13.73) | 32.6 (18.56) | 25.9 (13.38) | 29.4 (16.32) |
| Day 15 EASI Score | 31.4 (22.59) | 20.6 (16.87) | 14.1 (9.62) | 17.5 (14.00) |
| % Change from Baseline to Day 15 | 23.9 (79.60) | −35.6 (28.97) | −47.2 (20.13) | −41.2 (25.32) |
| Absolute change from Baseline to Day 15 | 5.7 (17.21) | −11.9 (14.03) | −11.8 (7.53) | −11.9 (11.16) |
| Day 29 EASI Score | 21.4 (15.36) | 12.7 (13.52) | 11.7 (14.25) | 12.2 (13.62) |
| % Change from Baseline to Day 29 | −13.1 (15.14) | −61.5 (26.54) | −63.1 (29.00) | −62.3 (27.27) |
| Absolute change from Baseline to Day 29 | −2.2 (5.14) | −19.6 (15.59) | −14.2 (8.00) | −16.8 (12.29) |
| Day 36 EASI Score | 13.9 (2.11) | 8.7 (10.94) | 10.6 (11.30) | 9.4 (10.83) |
| % Change from Baseline to Day 36 | −10.7 (19.60) | −74.7 (20.64) | −58.9 (25.75) | −68.3 (23.54) |
| Absolute change from Baseline to Day 36 | −1.9 (3.08) | −23.7 (16.13) | −12.9 (8.44) | −19.4 (14.36) |
| Day 43 EASI Score | 13.9 (5.85) | 9.5 (12.71) | 8.6 (9.96) | 9.0 (11.23) |
| % Change from Baseline to Day 43 | −29.1 (27.93) | −71.3 (25.68) | −66.7 (25.72) | −69.1 (25.22) |
| Absolute change from Baseline to Day 43 | −6.3 (5.61) | −22.8 (16.59) | −14.9 (8.88) | −19.0 (13.78) |
| Day 57 EASI Score | 14.1 (12.14) | 12.1 (14.93) | 8.2 (10.22) | 10.3 (12.87) |
| % Change from Baseline to Day 57 | −15.2 (78.20) | −63.3 (34.42) | −65.5 (27.26) | −64.3 (30.70) |
| Absolute change from Baseline to Day 57 | −4.7 (15.74) | −21.6 (19.92) | −15.3 (10.72) | −18.7 (16.36) |
| Day 71 EASI Score | 13.3 (8.00) | 13.7 (12.01) | 7.2 (8.61) | 10.5 (10.75) |
| % Change from Baseline to Day 71 | −42.3 (29.40) | −56.8 (36.08) | −73.7 (21.83) | −65.3 (30.41) |
| Absolute change from Baseline to Day 71 | −12.2 (10.91) | −18.6 (16.96) | −18.9 (11.33) | −18.8 (14.11) |
| Day 85 EASI Score | 10.1 (3.73) | 15.9 (17.57) | 7.9 (8.31) | 11.8 (13.85) |
| % Change from Baseline to Day 85 | −41.6 (33.96) | −51.2 (44.04) | −68.6 (25.00) | −60.3 (35.68) |
| Absolute change from Baseline to Day 85 | −10.5 (11.97) | −18.1 (20.78) | −15.5 (8.12) | −16.7 (15.20) |

TABLE 11

Summary of Percentage and Absolute Change in BSA Score from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline BSA Score | 45.5 (26.43) | 51.4 (29.98) | 49.0 (24.08) | 50.2 (26.80) |
| Day 15 BSA Score | 42.8 (26.62) | 42.3 (27.46) | 38.7 (24.88) | 40.6 (25.81) |
| % Change from Baseline to Day 15 | −3.0 (14.43) | −16.6 (24.86) | −26.4 (23.61) | −21.3 (24.30) |
| Absolute change from Baseline to Day 15 | −2.4 (6.25) | −9.1 (17.98) | −10.3 (9.10) | −9.7 (14.15) |
| Day 29 BSA Score | 34.3 (25.78) | 28.8 (31.01) | 36.0 (29.38) | 32.6 (29.76) |
| % Change from Baseline to Day 29 | −2.5 (22.46) | −44.7 (41.65) | −35.6 (37.02) | −40.0 (38.76) |
| Absolute change from Baseline to Day 29 | −0.5 (10.41) | −22.0 (30.09) | −13.0 (13.81) | −17.3 (23.05) |
| Day 36 BSA Score | 21.0 (5.48) | 25.2 (25.27) | 29.5 (29.51) | 26.9 (26.37) |
| % Change from Baseline to Day 36 | 10.1 (37.06) | −51.5 (35.29) | −38.6 (41.01) | −46.4 (37.18) |
| Absolute change from Baseline to Day 36 | 1.3 (7.23) | −25.7 (27.96) | −11.5 (14.60) | −20.0 (24.12) |
| Day 43 BSA Score | 29.0 (19.79) | 27.8 (31.69) | 28.9 (25.09) | 28.3 (28.08) |
| % Change from Baseline to Day 43 | −4.2 (31.32) | −46.4 (47.42) | −44.4 (32.77) | −45.4 (40.17) |
| Absolute change from Baseline to Day 43 | −3.2 (8.35) | −23.1 (32.26) | −16.4 (10.04) | −19.9 (24.04) |
| Day 57 BSA Score | 27.3 (28.19) | 31.2 (31.48) | 28.3 (22.40) | 29.8 (27.15) |
| % Change from Baseline to Day 57 | −31.6 (31.63) | −40.5 (52.06) | −42.7 (34.66) | −41.5 (44.01) |
| Absolute change from Baseline to Day 57 | −11.0 (20.58) | −22.6 (34.40) | −17.0 (13.33) | −20.0 (26.51) |
| Day 71 BSA Score | 26.6 (20.63) | 30.6 (24.59) | 23.2 (20.72) | 26.9 (22.56) |
| % Change from Baseline to Day 71 | −27.9 (35.30) | −38.3 (44.29) | −55.7 (26.21) | −47.0 (36.69) |
| Absolute change from Baseline to Day 71 | −12.2 (23.53) | −20.3 (26.80) | −26.2 (17.24) | −23.2 (22.24) |
| Day 85 BSA Score | 20.0 (14.00) | 32.2 (32.71) | 18.1 (14.85) | 24.8 (25.46) |
| % Change from Baseline to Day 85 | −41.5 (6.32) | −38.5 (54.33) | −62.6 (19.64) | −51.1 (41.06) |
| Absolute change from Baseline to Day 85 | −16.3 (15.88) | −22.2 (36.78) | −27.2 (12.77) | −24.8 (26.51) |

TABLE 12

Summary of Percentage and Absolute Change in SCORAD Score from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline SCORAD score | 65.3 (11.09) | 66.2 (17.07) | 58.6 (13.93) | 62.6 (15.81) |
| Day 15 SCORAD score | 68.9 (17.01) | 52.5 (18.61) | 41.4 (13.78) | 47.1 (17.01) |
| % Change from Baseline to Day 15 | 8.1 (22.20) | −21.0 (15.53) | −29.4 (14.80) | −25.1 (15.49) |
| Absolute change from Baseline to Day 15 | 5.0 (13.08) | −13.7 (10.94) | −17.3 (9.27) | −15.4 (10.14) |
| Day 29 SCORAD score | 56.2 (17.51) | 38.8 (17.39) | 32.9 (20.53) | 35.7 (18.94) |
| % Change from Baseline to Day 29 | −10.1 (17.58) | −38.9 (19.00) | −46.5 (26.30) | −42.9 (22.94) |
| Absolute change from Baseline to Day 29 | −5.5 (11.20) | −24.3 (13.06) | −25.8 (15.03) | −25.1 (13.85) |
| Day 36 SCORAD score | 53.8 (8.97) | 28.6 (14.79) | 34.0 (12.78) | 30.8 (13.93) |
| % Change from Baseline to Day 36 | −8.9 (8.74) | −54.7 (17.10) | −44.6 (15.77) | −50.7 (16.93) |
| Absolute change from Baseline to Day 36 | −5.4 (5.33) | −34.5 (14.35) | −27.2 (10.64) | −31.6 (13.20) |
| Day 43 SCORAD score | 46.4 (10.88) | 31.3 (17.18) | 25.9 (14.30) | 28.7 (15.75) |
| % Change from Baseline to Day 43 | −25.3 (15.86) | −50.3 (22.09) | −55.9 (18.41) | −53.0 (20.15) |
| Absolute change from Baseline to Day 43 | −16.6 (10.29) | −31.8 (16.14) | −30.8 (10.69) | −31.3 (13.15) |
| Day 57 SCORAD score | 49.3 (22.19) | 36.2 (21.67) | 27.6 (15.77) | 32.3 (19.29) |
| % Change from Baseline to Day 57 | −19.0 (33.04) | −44.4 (27.74) | −49.9 (24.92) | −46.9 (26.06) |
| Absolute change from Baseline to Day 57 | −11.2 (20.24) | −29.0 (19.89) | −29.1 (15.70) | −29.0 (17.71) |
| Day 71 SCORAD score | 46.4 (14.80) | 41.9 (17.40) | 28.6 (18.83) | 35.3 (18.98) |
| % Change from Baseline to Day 71 | −27.5 (18.86) | −34.0 (23.47) | −53.4 (23.21) | −43.7 (24.88) |
| Absolute change from Baseline to Day 71 | −17.2 (11.67) | −21.2 (14.43) | −29.9 (12.18) | −25.5 (13.78) |
| Day 85 SCORAD score | 48.8 (21.01) | 42.3 (21.07) | 31.2 (19.86) | 36.5 (20.77) |
| % Change from Baseline to Day 85 | −19.7 (37.22) | −33.4 (26.47) | −48.4 (27.53) | −41.2 (27.49) |
| Absolute change from Baseline to Day 85 | −12.8 (22.14) | −22.3 (20.81) | −25.8 (12.96) | −24.1 (16.85) |

TABLE 13

Summary of Percentage and Absolute Change in 5-D Pruritus Scale from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline 5-D Pruritus Scale | 17.8 (3.94) | 18.9 (3.05) | 18.1 (3.99) | 18.5 (3.49) |
| Day 15 5-D Pruritus Scale | 17.0 (4.61) | 14.3 (4.68) | 13.0 (5.03) | 13.7 (4.8) |
| % Change from Baseline to Day 15 | 3.6 (30.77) | −24.8 (19.73) | −28.2 (19.49) | −26.5 (19.31) |
| Absolute change from Baseline to Day 15 | 0.0 (6.18) | −4.6 (3.97) | −5.1 (4.15) | −4.9 (3.99) |
| Day 29 5-D Pruritus Scale | 16.7 (3.50) | 12.2 (5.02) | 11.4 (5.97) | 11.8 (5.45) |
| % Change from Baseline to Day 29 | 8.1 (18.85) | −35.4 (20.28) | −37.1 (26.40) | −36.3 (23.30) |
| Absolute change from Baseline to Day 29 | 1.2 (3.19) | −6.5 (4.25) | −6.7 (5.57) | −6.6 (4.91) |
| Day 43 5-D Pruritus Scale | 14.5 (2.17) | 11.8 (4.43) | 10.0 (5.44) | 11.0 (4.91) |
| % Change from Baseline to Day 43 | −9.4 (23.24) | −37.1 (19.61) | −42.5 (24.75) | −39.7 (21.86) |
| Absolute change from Baseline to Day 43 | −2.3 (5.20) | −7.0 (3.95) | −7.5 (5.26) | −7.2 (4.52) |
| Day 57 5-D Pruritus Scale | 14.5 (2.74) | 13.4 (5.45) | 11.2 (5.40) | 12.4 (5.43) |
| % Change from Baseline to Day 57 | −7.8 (28.55) | −29.6 (25.38) | −36.2 (22.7) | −32.6 (23.90) |
| Absolute change from Baseline to Day 57 | −2.0 (5.14) | −5.5 (4.75) | −6.3 (4.71) | −5.9 (4.65) |
| Day 71 5-D Pruritus Scale | 16.4 (2.88) | 16.2 (5.47) | 12.3 (5.66) | 14.3 (5.79) |
| % Change from Baseline to Day 71 | 8.1 (22.85) | −15.4 (21.50) | −31.6 (24.97) | −23.5 (24.25) |
| Absolute change from Baseline to Day 71 | 1.0 (3.24) | −2.7 (3.70) | −5.6 (4.87) | −4.1 (4.48) |
| Day 85 5-D Pruritus Scale | 17.5 (3.00) | 15.3 (4.92) | 14.0 (5.83) | 14.6 (5.33) |
| % Change from Baseline to Day 85 | 20.6 (34.03) | −19.1 (23.10) | −21.4 (26.23) | −20.3 (24.25) |
| Absolute change from Baseline to Day 85 | 2.5 (5.00) | −3.7 (4.50) | −3.7 (4.66) | −3.7 (4.48) |

TABLE 14

Summary of Percentage and Absolute Change in Average Weekly NRS Score from Baseline-all values represented as Mean (SD)

| | | mAb1 | | |
|---|---|---|---|---|
| | Placebo | 150 mg | 300 mg | All Doses Combined |
| No. Patients | 10 | 14 | 13 | 27 |
| Baseline NRS Score | 5.8 (1.92) | 5.6 (1.87) | 5.4 (1.69) | 5.5 (1.75) |
| Week 1 NRS Score | 5.5 (1.46) | 5.1 (1.88) | 4.3 (1.59) | 4.7 (1.75) |
| % Change from Baseline to Week 1 | −2.9 (14.99) | −9.1 (15.88) | −16.5 (28.61) | −12.8 (22.98) |
| Absolute change from Baseline to Week 1 | −0.3 (0.99) | −0.5 (0.93) | −1.1 (1.76) | −0.8 (1.42) |
| Week 2 NRS Score | 5.4 (1.42) | 4.2 (2.41) | 3.5 (1.83) | 3.9 (2.13) |
| % Change from Baseline to Week 2 | 1.3 (25.45) | −26.6 (31.37) | −31.9 (31.90) | −29.3 (31.11) |
| Absolute change from Baseline to Week 2 | −0.1 (1.50) | −1.3 (1.67) | −1.9 (2.01) | −1.6 (1.84) |
| Week 3 NRS Score | 5.5 (2.02) | 3.6 (1.80) | 3.2 (1.35) | 3.4 (1.57) |
| % Change from Baseline to Week 3 | 2.9 (16.38) | −35.7 (17.81) | −37.2 (30.15) | −36.4 (24.23) |
| Absolute change from Baseline to Week 3 | 0.2 (0.83) | −1.8 (0.92) | −2.2 (1.87) | −2.0 (1.45) |
| Week 4 NRS Score | 4.5 (1.33) | 3.7 (2.18) | 2.9 (2.18) | 3.3 (2.17) |
| % Change from Baseline to Week 4 | −1.1 (28.49) | −35.0 (25.50) | −45.4 (40.95) | −40.2 (33.78) |
| Absolute change from Baseline to Week 4 | −0.1 (1.35) | −1.8 (1.37) | −2.5 (2.18) | −2.1 (1.81) |
| Week 5 NRS Score | 4.4 (1.68) | 3.2 (2.08) | 2.8 (1.92) | 3.0 (1.96) |
| % Change from Baseline to Week 5 | −5.4 (34.34) | −44.6 (26.15) | −43.1 (37.67) | −43.9 (31.42) |
| Absolute change from Baseline to Week 5 | −0.3 (1.60) | −2.3 (1.54) | −2.3 (2.10) | −2.3 (1.79) |
| Week 6 NRS Score | 3.8 (1.89) | 3.2 (1.98) | 2.7 (2.08) | 3.0 (2.00) |
| % Change from Baseline to Week 6 | −19.0 (35.26) | −43.6 (23.27) | −49.7 (33.29) | −46.3 (27.72) |
| Absolute change from Baseline to Week 6 | −0.9 (1.72) | −2.3 (1.37) | −2.6 (1.98) | −2.4 (1.64) |
| Week 7 NRS Score | 3.8 (2.18) | 3.2 (2.52) | 2.3 (1.84) | 2.7 (2.21) |
| % Change from Baseline to Week 7 | −17.3 (42.69) | −45.0 (33.78) | −55.2 (35.03) | −49.9 (33.99) |
| Absolute change from Baseline to Week 7 | −0.8 (2.06) | −2.3 (1.90) | −3.1 (2.13) | −2.7 (2.00) |
| Week 8 NRS Score | 3.5 (2.01) | 3.2 (2.10) | 2.5 (1.93) | 2.9 (2.00) |
| % Change from Baseline to Week 8 | −22.1 (38.80) | −43.0 (35.08) | −50.7 (34.39) | −46.7 (34.18) |
| Absolute change from Baseline to Week 8 | −1.0 (1.90) | −2.3 (1.84) | −2.8 (2.18) | −2.6 (1.98) |
| Week 9 NRS Score | 3.7 (1.93) | 3.6 (2.12) | 2.5 (2.34) | 3.1 (2.25) |
| % Change from Baseline to Week 9 | −20.7 (34.06) | −34.2 (36.64) | −52.9 (39.71) | −43.1 (38.47) |
| Absolute change from Baseline to Week 9 | −0.9 (1.65) | −1.8 (1.74) | −2.8 (2.25) | −2.3 (2.02) |
| Week 10 NRS Score | 3.7 (1.86) | 4.3 (2.39) | 3.1 (2.38) | 3.7 (2.40) |
| % Change from Baseline to Week 10 | −19.7 (31.94) | −25.1 (32.66) | −43.6 (38.72) | −34.4 (36.22) |
| Absolute change from Baseline to Week 10 | −0.8 (1.54) | −1.2 (1.30) | −2.3 (2.10) | −1.7 (1.80) |
| Week 11 NRS Score | 3.9 (2.18) | 4.9 (2.45) | 2.9 (1.92) | 3.9 (2.39) |
| % Change from Baseline to Week 11 | −17.1 (37.62) | −10.1 (43.91) | −43.4 (37.56) | −26.0 (43.46) |
| Absolute change from Baseline to Week 11 | −0.7 (1.77) | −0.5 (1.85) | −2.2 (1.93) | −1.4 (2.03) |

TABLE 14-continued

Summary of Percentage and Absolute Change in Average Weekly NRS Score from Baseline-all values represented as Mean (SD)

| | Placebo | mAb1 150 mg | mAb1 300 mg | mAb1 All Doses Combined |
|---|---|---|---|---|
| Week 12 NRS Score | 3.9 (1.88) | 4.3 (2.68) | 3.4 (2.59) | 3.9 (2.60) |
| % Change from Baseline to Week 12 | −13.6 (29.53) | −21.1 (39.41) | −38.0 (35.65) | −29.1 (37.65) |
| Absolute change from Baseline to Week 12 | −0.5 (1.35) | −1.1 (2.00) | −1.9 (1.93) | −1.5 (1.96) |

F. Conclusions

Subcutaneous administration of an anti-IL-4R antibody (mAb1) to adult patients with moderate-to-severe atopic dermatitis was generally safe and well tolerated after 4 weekly doses of 150 or 300 mg with an adverse event (AE) rate similar to placebo and no dose limiting toxicities or serious AEs. The most common AEs with mAb1 were nasopharyngitis and headache. The mAb1 rapidly (by Day 8) reduced pruritus and improved skin disease in a dose-dependent fashion. Administration of mAb1 at 150 and 300 mg resulted in significant improvement in IGA, EASI, BSA, SCORAD and NRS pruritus as early as Day 8 through day 85 in both mean and absolute and percent change, as compared to baseline (see Tables 9-14). In the 300 mg arm at day 29, proportion of patients who achieved an EAS150 response was 71.4% vs 18.8% for placebo (p=0.0025) and NRS pruritus score decreased by 45.4% vs 18.6% for placebo (p=0.0016). The effect was sustained through day 85 for EAS150 and day 75 for NRS pruritus. For the 300 mg treatment group, the difference from placebo was significant for an additional 6 weeks after end of treatment period. The mAb significantly improved other clinical outcomes at day 29, mean % change IGA (p=0.0002), EASI (p<0.0001), BSA (p=0.0037), and 5D pruritus (p<0.0001). These improvements were generally observed by Day 8 and persisted after end of treatment. No rebound phenomena were observed after end of treatment.

The results shown in this Example therefore demonstrate that mAb1 is safe and effective for the treatment of atopic dermatitis.

Example 8: Treatment of Patients with Moderate-to-Severe Atopic Dermatitis with Anti-IL-4R Antibody: Analysis of Pooled Phase 1b Studies AD efficacy parameters were measured and pooled for analysis from two separate clinical trials in patients with moderate-to-severe AD. "Study A" was a 12-week, double-blind, randomized, placebo-controlled, sequential ascending dose study to assess the safety and tolerability of administered anti-IL-4R antibody (mAb1) in patients with atopic dermatitis. The treatment period was 4 weeks with patients being followed for 8 weeks after the end of the treatment period. Patients were randomized in a 4:1 ratio to receive mAb1 or placebo in each of the three ascending dose cohorts (75 mg, 150 mg, or 300 mg). The study consisted of a screening period (day −14 to day −3), a treatment period (day 1 through day 29), and a follow-up period (day 29 through day 85). During the treatment period, patients were seen in the clinic once weekly for safety, laboratory and clinical effect assessments on days 1, 4, 8, 15, 22, 25 and 29 (week 4). Patients received a dose of mAb1 or placebo on days 1, 8, 15 and 22. The end of the treatment period study was on day 29 (week 4). Patients were monitored at the study site for 6 hours after the injection (of mAb1 or placebo) on day 1, and for 3 hours after the injection on days 8, 15 and 22. During the follow-up period, patients were seen in the clinic for follow-up assessments at days 36, 43, 50, 57, 64, 71, and 85 (end of study visit).

"Study B" was a 12-week, double-blind, randomized, placebo-controlled, sequential ascending, repeated-dose study in patients with moderate-to-severe AD. AD subjects were administered 150 mg or 300 mg of mAb1, or placebo on days 1, 8, 15 and 22 of the study (four weekly doses) (See Example 3 herein). All administrations for both studies were subcutaneous.

The patient inclusion criteria for the studies were: (1) should be male or female 18 years; (2) have chronic atopic dermatitis for 3 years; (3) have EASI 12; (4) IGA 3; (5) 15% BSA of AD involvement (in the US) or 10% BSA of AD involvement (ex-US); and (6) history of inadequate response to stable regimen of topical corticosteroids (TCS) or calcineurin inhibitors.

The patient exclusion criteria for the study were: (1) WBC<$3.5\times10^3/\mu l$; (2) platelets <$125\times10^3/\mu l$; (3) neutrophils <$1.75\times10^3/\mu l$; (4) AST/ALT>1.5×ULN; (5) positive for hepatitis B or hepatitis C; and (6) treatment with TCS or calcineurin inhibitors within 1 week of baseline.

The primary endpoint of the studies was to monitor incidence of treatment-emergent adverse events (TEAEs) from baseline through week 12. The exploratory endpoints for efficacy variables were: (i) % achieving an IGA of 0 or 1 through week 4; (ii) % improvement in BSA and EASI from baseline; and (iii) change from baseline in NRS scale.

The efficacy variables IGA, BSA, EASI, SCORAD, 5-D Pruritus scale, and Pruritus NRS rating have been described elsewhere herein (see, e.g., Example 4).

The IGA, BSA, EASI and SCORAD scores were assessed at every clinic visit. Patients underwent 5-D pruritus assessment at the following visits: screening, day 1/baseline (predose), and days 15, 29, 43, 57, 71, and 85 (end of study) or early termination. Patients used the IVRS to record their Pruritus NRS score twice daily through the last study visit.

Baseline for efficacy variable is defined as the last non-missing value on or before the date of randomization. For the patient who has no value on or before his/her randomization date the last non-missing value on or before the date of first dose injection will be used as baseline.

The baseline demographics for the patient population are presented below in Table 15.

TABLE 15

| Baseline Demographics | | | | | |
|---|---|---|---|---|---|
| | Placebo (N = 16) | 75 mg (N = 8) | 150 mg (N = 22) | 300 mg (N = 21) | All Doses (N = 51) |
| Mean age, years (SD) | 37.4 (17.16) | 35.8 (12.51) | 42.5 (11.37) | 45.4 (15.92) | 42.6 (13.73) |
| Race, n (%) | | | | | |
| Caucasian | 13 (81.3%) | 4 (50.0%) | 19 (86.4%) | 16 (76.2%) | 39 (76.5%) |
| Non-Caucasian | 3 (18.7%) | 4 (50.0%) | 3 (13.6%) | 5 (23.8%) | 12 (23.5%) |
| Gender, n (%) | | | | | |
| Male | 11 (68.8%) | 6 (75.0%) | 12 (54.5%) | 10 (47.6%) | 28 (54.9%) |
| Female | 5 (31.3%) | 2 (25.0%) | 10 (45.5%) | 11 (52.4%) | 23 (45.1%) |
| Mean BMI, $kg/m^3$ (SD) | 25.69 (5.993) | 26.41 (4.489) | 25.68 (3.991) | 27.71 (8.667) | 26.63 (6.361) |

The mean baseline disease characteristics are given in Table 16.

TABLE 16

| Mean Baseline Disease Characteristics | | | | | |
|---|---|---|---|---|---|
| | Placebo (N = 16) | 75 mg (N = 8) | 150 mg (N = 22) | 300 mg (N = 21) | All Doses (N = 51) |
| Duration of chronic AD, years | 31.8 (18.67) | 24.5 (16.95) | 32.1 (15.44) | 30.7 (16.95) | 30.4 (16.19) |
| EASI score | 22.8 (12.02) | 36.9 911.75) | 30.0 (17.00) | 27.4 (11.21) | 30.0 (14.19) |
| IGA score | 3.6 (0.72) | 4.1 (0.35) | 3.9 (0.68) | 3.5 (0.51) | 3.8 (0.62) |
| % BSA of AD | 40.3 (25.77) | 64.4 917.03) | 49.8 (28.75) | 48.2 (22.26) | 51.4 (24.87) |
| 5-D pruritus scale | 16.9 (3.94) | 21.5 (3.55) | 19.0 (2.94) | 18.7 (3.64) | 19.3 (3.41) |
| Pruritus NRS score | 5.8 (1.75) | 7.0 (1.78) | 6.0 (1.82) | 5.7 (1.51) | 6.0 (1.72) |

The exploratory efficacy results obtained from the pooled studies are summarized in Tables 17-25 and in FIGS. 15-22.

TABLE 17

| Summary of subjects achieving IGA ≤1 at Day 29 and all study visits | | | | | |
|---|---|---|---|---|---|
| | Number and % subjects with IGA ≤1 | | | | |
| | Placebo (N = 16) | 75 mg (N = 8) | 150 mg (N = 22) | 300 mg (N = 21) | All Doses Combined (N = 51) |
| Week 4, Day 29 | 1 (6.3%) | 0 | 4 (18.2%) | 2 (9.5%) | 6 (11.8%) |
| Day 4 | 0 | 0 | 0 | 0 | 0 |
| Week 1, Day 8 | 0 | 0 | 0 | 0 | 0 |
| Week 2, Day 15 | 0 | 0 | 0 | 1 (4.8%) | 1 (2.0%) |
| Week 3, Day 22 | 0 | 0 | 0 | 2 (9.5%) | 2 (3.9%) |
| Week 3, Day 25 | 1 (6.3%) | 0 | 1 (4.5%) | 4 (19.0%) | 5 (9.8%) |
| Week 5, Day 36 | 1 | 0 | 4 (18.2%) | 2 (9.5%) | 6 (11.8%) |
| Week 6, Day 43 | 2 (12.5%) | 0 | 5 (22.7%) | 3 (14.3%) | 8 (15.7%) |
| Week 7, Day 50 | 2 (12.5%) | 0 | 4 (18.2%) | 3 (14.3%) | 7 (13.7%) |
| Week 8, Day 57 | 2 (12.5%0 | 0 | 3 (13.6%) | 5 (23.8%) | 8 (15.7%) |
| Week 9, Day 64 | 1 (6.3%) | 0 | 3 (13.6%) | 4 (19.0%) | 7 (13.7%) |
| Week 10, Day 71 | 1 (6.3%) | 0 | 1 (4.5%) | 5 (23.8%) | 6 (11.8%) |
| Week 12, Day 85 | 1 (6.3%) | 0 | 0 | 3 (14.3%) | 3 (5.9%) |

TABLE 18

Summary of Percentage and Absolute Change in BSA Score from Baseline-all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline BSA Score | 40.3 (25.77) | 64.4 (17.03) | 49.8 (28.75) | 48.2 (22.26) | 51.4 (24.87) |
| Day 15 BSA Score | 37.6 (26.61) | 52.3 (12.54) | 40.9 (25.66) | 34.4 (22.66) | 40.0 (23.23) |
| % Change from Baseline to Day 15 | −4.8 (14.80) | −16.8 (15.17) | −13.9 (21.77) | −30.5 (27.09) | −21.4 (24.27) |
| Absolute change from Baseline to Day 15 | −1.7 (5.37) | −12.1 (11.58) | −7.0 (15.07) | −13.9 (14.73) | −10.7 (14.51) |
| Day 29 BSA Score | 31.1 (29.69) | 46.3 (12.42) | 31.1 (28.78) | 31.5 925.33) | 33.8 (25.47) |
| % Change from Baseline to Day 29 | −15.3 (31.02) | −26.4 (16.41) | −38.8 (37.00) | −40.3 (33.78) | −37.4 (32.88) |
| Absolute change from Baseline to Day 29 | −2.1 (10.93) | −18.1 (13.14) | −18.2 (24.61) | −16.7 (16.05) | −17.5 (19.31) |
| Day 36 BSA Score | 25.1 (26.81) | 41.2 (15.59) | 24.9 (24.15) | 26.0 (22.67) | 28.0 (22.70) |
| % Change from Baseline to Day 36 | −13.3 (39.22) | −33.7 (21.53) | −48.6 (32.13) | −44.2 (34.61) | −44.4 (31.41) |
| Absolute change from Baseline to Day 36 | −1.8 (10.33) | −22.4 (15.26) | −24.3 (25.07) | −18.0 (17.82) | −21.6 (20.85) |
| Day 43 BSA Score | 29.9 (27.04) | 48.4 (21.56) | 24.8 (26.36) | 26.2 (21.03) | 29.1 (24.42) |
| % Change from Baseline to Day 43 | −11.0 (39.52) | −29.2 (24.87) | −43.3 (42.81) | −47.2 (30.07) | −42.7 (35.05) |
| Absolute change from Baseline to Day 43 | −2.0 (10.74) | −19.0 (15.63) | −22.2 (29.35) | −19.8 (14.41) | −20.7 (21.52) |
| Day 57 BSA Score | 27.2 (31.12) | 57.5 (23.40) | 31.2 (28.60) | 28.3 (20.11) | 33.7 (26.24) |
| % Change from Baseline to Day 57 | −33.6 (32.95) | −18.7 (23.06) | −37.4 (42.74) | −41.9 (29.38) | −36.6 (35.90) |
| Absolute change from Baseline to Day 57 | −8.3 (16.62) | −12.4 (16.36) | −20.0 (28.38) | −17.6 (13.86) | −18.0 (21.99) |
| Day 71 BSA Score | 27.4 (28.13) | 58.4 (19.79) | 30.7 (24.56) | 23.2 (19.85) | 31.1 (24.32) |
| % Change from Baseline to Day 71 | −29.0 (36.38) | −13.2 (11.92) | −35.7 (37.54) | −52.0 (35.43) | −39.9 (36.13) |
| Absolute change from Baseline to Day 71 | −7.5 (17.71) | −8.5 (8.10) | −18.4 (23.12) | −25.2 (18.53) | −20.1 (20.14) |
| Day 85 BSA Score | 25.1 (27.73) | 58.0 (19.52) | 30.7 (28.38) | 23.6 (17.95) | 30.7 (25.04) |
| % Change from Baseline to Day 85 | −33.4 (32.68) | −16.9 (16.63) | −37.8 (43.59) | −49.0 (37.34) | −40.4 (39.14) |
| Absolute change from Baseline to Day 85 | −8.4 (14.45) | −11.9 (11.45) | −20.6 (29.67) | −22.7 (15.74) | −20.5 (22.31) |

TABLE 19

Summary of Percentage and Absolute Change in EASI Score from Baseline-all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline EASI Score | 22.8 (12.02) | 36.9 (11.75) | 30.0 (17.00) | 27.4 (11.21) | 30.0 (14.19) |
| Day 15 EASI Score | 25.4 (20.13) | 26.2 (7.72) | 19.8 (15.05) | 15.4 (8.57) | 19.0 (12.06) |
| % Change from Baseline to Day 15 | 8.7 (66.05) | −26.9 (19.29) | −31.1 (27.24) | −45.1 (19.90) | −36.3 (24.02) |
| Absolute change from Baseline to Day 15 | 2.8 (14.11) | −10.7 (9.83) | −9.7 (12.02) | −12.0 (6.93) | −10.8 (9.67) |
| Day 29 EASI Score | 17.2 (15.11) | 17.7 (6.05) | 13.1 (11.89) | 11.3 (11.84) | 13.1 (11.17) |
| % Change from Baseline to Day 29 | −25.4 (34.98) | −47.0 (21.93) | −55.0 (30.36) | −64.3 (25.83) | −57.7 (27.45) |
| Absolute change from Baseline to Day 29 | −3.6 (7.25) | −19.2 (15.11) | −16.6 (14.58) | −16.1 (7.69) | −16.8 (11.97) |
| Day 36 EASI Score | 13.2 (11.97) | 16.3 (7.74) | 9.4 (10.27) | 10.5 (8.69) | 11.0 (9.42) |
| % Change from Baseline to Day 36 | −28.4 (41.10) | −51.5 (25.53) | −69.6 (22.46) | −61.9 (22.69) | −63.6 (23.41) |
| Absolute change from Baseline to Day 36 | −3.9 (7.94) | −21.5 (17.30) | −20.5 (14.98) | −16.1 (8.23) | −19.0 (13.13) |
| Day 43 EASI Score | 12.9 97.13) | 19.8 (10.41) | 9.6 (11.01) | 9.3 (8.29) | 11.1 (10.32) |
| % Change from Baseline to Day 43 | −33.8 (28.94) | −39.4 (31.87) | −64.2 (33.89) | −66.4 (22.39) | −61.2 (29.98) |
| Absolute change from Baseline to Day 43 | −6.2 (4.71) | −17.0 (19.33) | −19.7 (16.63) | −16.8 (7.84) | −18.0 (13.76) |
| Day 57 EASI Score | 13.0 (11.95) | 27.0 (16.46) | 12.2 (12.88) | 10.4 (9.40) | 13.5 (13.11) |
| % Change from Baseline to Day 57 | −28.7 (62.63) | −24.5 (47.21) | −57.3 (33.38) | −61.1 (24.91) | −54.3 (33.99) |
| Absolute change from Baseline to Day 57 | −5.4 (11.79) | −11.9 (22.95) | −18.4 (17.88) | −15.8 (9.69) | −16.5 (15.81) |
| Day 71 EASI Score | 11.8 (9.22) | 28.3 (13.06) | 13.0 (10.86) | 8.5 (9.21) | 13.1 (12.06) |
| % Change from Baseline to Day 71 | −45.8 (31.06) | −14.5 (41.14) | −54.9 (32.01) | −71.3 (24.14) | −56.8 (34.68) |
| Absolute change from Baseline to Day 71 | −9.6 (8.23) | −9.4 (22.16) | −16.9 (15.41) | −19.1 (9.88) | −16.9 (14.32) |
| Day 85 EASI Score | 9.8 (4.87) | 27.1 (11.99) | 14.2 (14.30) | 10.5 (9.26) | 14.0 (12.77) |
| % Change from Baseline to Day 85 | −44.8 (30.60) | −28.3 (29.69) | −51.3 (37.58) | −63.0 (25.55) | −53.9 (32.86) |
| Absolute change from Baseline to Day 85 | −9.3 (8.01) | −13.4 (18.94) | −16.6 (17.67) | −15.4 (7.57) | −15.7 (13.81) |

TABLE 20

Summary of Percentage and Absolute Change in 5-D Pruritus Scale from Baseline-all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline 5-D Pruritus Scale | 16.9 (3.94) | 21.5 (3.55) | 19.0 (2.94) | 18.7 (3.64) | 19.3 (3.41) |
| Day 15 5-D Pruritus Scale | 15.0 (4.66) | 14.0 (3.55) | 14.0 (4.46) | 12.5 (4.08) | 13.4 (4.15) |
| % Change from Baseline to Day 15 | −5.6 (29.83) | −34.3 (15.43) | −26.6 (19.26) | −32.4 (17.60) | −30.3 (17.95) |
| Absolute change from Baseline to Day 15 | −1.4 (5.55) | −7.5 (3.82) | −5.0 (3.97) | −6.1 (3.93) | −5.9 (3.94) |
| Day 29 5-D Pruritus Scale | 14.8 93.77) | 14.1 (3.31) | 13.1 (5.03) | 11.0 (4.86) | 12.3 (4.79) |
| % Change from Baseline to Day 29 | −3.9 (20.07) | −33.0 (17.25) | −30.8 (23.71) | −40.8 (21.83) | −35.6 (22.02) |
| Absolute change from Baseline to Day 29 | −0.8 (3.41) | −7.4 (4.47) | −5.9 (4.84) | −7.7 (4.78) | −6.9 (4.73) |
| Day 43 5-D Pruritus Scale | 13.8 (3.71) | 16.5 (4.54) | 12.1 (4.64) | 10.7 (4.83) | 12.3 (5.04) |
| % Change from Baseline to Day 43 | −10.4 (31.60) | −21.4 (25.01) | −35.0 (22.07) | −40.8 (23.87) | −35.0 (23.86) |
| Absolute change from Baseline to Day 43 | −2.3 (5.25) | −5.0 (5.66) | −6.6 (4.45) | −7.6 (5.04) | −6.8 (4.90) |
| Day 57 5-D Pruritus Scale | 12.3 (3.35) | 19.9 (3.98) | 13.9 94.75) | 11.6 (5.18) | 14.0 (5.46) |
| % Change from Baseline to Day 57 | −19.0 (25.37) | −9.0 (20.15) | −27.2 (21.28) | −37.2 (21.68) | −28.1 (22.85) |
| Absolute change from Baseline to Day 57 | −3.4 (4.43) | −2.3 (4.46) | −5.1 (4.03) | −6.8 (4.61) | −5.3 (4.49) |
| Day 71 5-D Pruritus Scale | 13.5 (4.03) | 19.4 (3.51) | 15.3 (4.78) | 12.9 (5.61) | 14.7 (5.36) |
| % Change from Baseline to Day 71 | −11.6 (25.71) | −8.3 (14.91) | −18.9 (19.50) | −31.7 (24.53) | −23.3 (22.58) |
| Absolute change from Baseline to Day 71 | −2.0 (4.12) | −2.0 (3.39) | −3.4 (3.56) | −5.8 (4.70) | −4.3 (4.24) |
| Day 85 5-D Pruritus Scale | 14.1 (4.48) | 18.6 (1.34) | 15.2 (3.99) | 14.6 (5.26) | 15.3 (4.53) |
| % Change from Baseline to Day 85 | −5.4 (32.44) | −10.0 (22.58) | −18.5 (21.29) | −21.9 (23.41) | −19.0 (22.18) |
| Absolute change from Baseline to Day 85 | −1.2 (5.09) | −2.8 (4.92) | −3.7 (4.04) | −4.1 (4.52) | −3.7 (4.27) |

TABLE 21

Summary of Percentage and Absolute Change in Average Weekly NRS Score from Baseline-all values represented as Mean (SD)

| | | mAb1 | | | |
|---|---|---|---|---|---|
| | Placebo | 75 mg | 150 mg | 300 mg | All Doses Combined |
| No. Patients | 10 | 8 | 22 | 21 | 51 |
| Baseline NRS Score | 5.8 (1.75) | 7.0 (1.78) | 6.0 (1.82) | 5.7 (1.51) | 6.0 (1.72) |
| Week 1 NRS Score | 5.1 (1.73) | 5.2 (2.50) | 5.2 (1.91) | 4.3 (1.52) | 4.8 (1.88) |
| % Change from Baseline to Week 1 | −11.9 (23.13) | −27.3 (20.25) | −12.7 (18.26) | −21.6 (26.03) | −18.8 (22.42) |
| Absolute change from Baseline to Week 1 | −0.8 (1.40) | −1.7 (1.22) | −0.8 (1.30) | −1.4 (1.59) | −1.2 (1.44) |
| Week 2 NRS Score | 4.7 (2.00) | 4.0 (2.36) | 4.5 (2.38) | 3.7 (1.59) | 4.1 (2.07) |
| % Change from Baseline to Week 2 | −14.8 (36.13) | −44.6 (21.90) | −26.9 (29.96) | −33.3 (26.69) | −32.4 (27.63) |
| Absolute change from Baseline to Week 2 | −1.0 (2.16) | −3.0 (1.350 | −1.5 (1.76) | −2.0 (1.71) | −1.9 (1.73) |
| Week 3 NRS Score | 5.0 (2.29) | 3.9 (2.12) | 4.0 (2.12) | 3.3 (1.30) | 3.7 (1.81) |
| % Change from Baseline to Week 3 | −10.2 (33.75) | −45.6 (21.67) | −35.4 (23.84) | −39.4 (25.92) | −38.8 (24.17) |
| Absolute change from Baseline to Week 3 | −0.7 (2.01) | −3.1 (1.30) | −2.0 (1.49) | −2.4 (1.65) | −2.3 (1.55) |
| Week 4 NRS Score | 4.1 (2.03) | 4.1 (1.95) | 3.9 (2.38) | 3.1 (1.84) | 3.6 (2.10) |
| % Change from Baseline to Week 4 | −18.6 (40.12) | −42.3 (22.62) | −36.7 (29.33) | −45.4 (32.89) | −41.3 (29.63) |
| Absolute change from Baseline to Week 4 | −1.2 (2.29) | −2.9 (1.38) | −2.1 (1.85) | −2.6 (1.77) | −2.4 (1.74) |
| Week 5 NRS Score | 4.2 (2.29) | 4.1 (2.03) | 3.5 (2.36) | 3.0 (1.80) | 3.4 (2.09) |
| % Change from Baseline to Week 5 | −18.9 (43.93) | −41.9 (24.53) | −43.4 (30.89) | −44.2 (32.74) | −43.5 (30.09) |
| Absolute change from Baseline to Week 5 | −1.2 (2.43) | −2.9 (1.55) | −2.5 (1.97) | −2.5 (1.92) | −2.6 (1.85) |
| Week 6 NRS Score | 4.0 (2.40) | 4.1 (2.22) | 3.7 (2.38) | 3.0 (1.84) | 3.5 (2.14) |
| % Change from Baseline to Week 6 | −24.9 (42.63) | −42.7 (24.23) | −40.0 (30.52) | −46.9 (28.41) | −43.3 (28.31) |
| Absolute change from Baseline to Week 6 | −1.4 (2.36) | −2.8 (1.44) | −2.2 (1.86) | −2.6 (1.68) | −2.5 (1.71) |
| Week 7 NRS Score | 3.4 (2.59) | 4.4 (2.39) | 3.7 (2.56) | 2.8 (1.78) | 3.4 (2.26) |
| % Change from Baseline to Week 7 | −35.5 (42.70) | −41.3 (21.96) | −40.3 (33.56) | −49.9 (30.73) | −44.5 (30.73) |
| Absolute change from Baseline to Week 7 | −1.9 (2.33) | −2.8 (1.10) | −2.2 (1.90) | −2.8 (1.83) | −2.5 (1.77) |
| Week 8 NRS Score | 3.5 (2.61) | 5.4 (2.40) | 3.7 (2.24) | 3.0 (1.98) | 3.7 (2.24) |
| % Change from Baseline to Week 8 | −33.9 (38.63) | −27.8 (21.17) | −38.2 (33.09) | −45.6 (32.23) | −39.8 (31.29) |
| Absolute change from Baseline to Week 8 | −1.8 (2.19) | −1.9 (1.19) | −2.2 (1.80) | −2.6 (1.99) | −2.3 (1.80) |
| Week 9 NRS Score | 3.6 (2.26) | 5.5 (2.44) | 4.1 (2.10) | 3.0 (2.27) | 3.9 (2.32) |
| % Change from Baseline to Week 9 | −32.8 (35.28) | −26.1 (17.08) | −31.5 (32.14) | −46.2 (36.56) | −36.9 (32.95) |
| Absolute change from Baseline to Week 9 | −1.7 (2.01) | −1.7 (1.02) | −1.8 (1.59) | −2.5 (2.10) | −2.1 (1.77) |
| Week 10 NRS Score | 3.7 (2.51) | 5.3 (2.33) | 4.6 (2.18) | 3.2 (1.99) | 4.1 (2.21) |
| % Change from Baseline to Week 10 | −30.3 (41.78) | −21.7 (24.33) | −24.6 (28.77) | −43.4 (31.24) | −32.5 (30.36) |
| Absolute change from Baseline to Week 10 | −1.6 (2.31) | −1.4 (1.51) | −1.3 (1.37) | −2.4 (1.70) | −1.8 (1.59) |
| Week 11 NRS Score | 2.8 (2.03) | 5.8 (2.11) | 5.0 (2.19) | 3.2 (1.81) | 4.4 (2.23) |
| % Change from Baseline to Week 11 | −40.2 (40.04) | −13.1 (26.33) | −14.2 (36.88) | −41.2 (31.87) | −25.1 (35.60) |
| Absolute change from Baseline to Week 11 | −2.0 (2.26) | −0.9 (1.61) | −0.8 (1.72) | −2.2 (1.64) | −1.4 (1.76) |

TABLE 21-continued

Summary of Percentage and Absolute Change in Average Weekly NRS Score from Baseline-all values represented as Mean (SD)

| | | mAb1 | | | |
|---|---|---|---|---|---|
| | Placebo | 75 mg | 150 mg | 300 mg | All Doses Combined |
| Week 12 NRS Score | 3.5 (1.48) | 5.2 (2.37) | 4.8 (2.47) | 3.5 (2.37) | 4.4 (2.44) |
| % Change from Baseline to Week 12 | −28.9 (29.54) | −25.4 (25.39) | −17.9 (33.42) | −35.5 (33.02) | −25.4 (32.53) |
| Absolute change from Baseline to Week 12 | −1.5 (1.66) | −1.7 (1.50) | −1.0 (1.77) | −1.7 (1.73) | −1.3 (1.71) |

TABLE 22

Summary of Percentage and Absolute Change in IGA Score from Baseline-all values represented as Mean (SD)

| | | mAb1 | | | |
|---|---|---|---|---|---|
| | Placebo | 75 mg | 150 mg | 300 mg | All Doses Combined |
| No. Patients | 16 | 8 | 22 | 21 | 51 |
| Baseline IGA Score | 3.6 (0.72) | 4.1 (0.35) | 3.9 (0.68) | 3.5 (0.51) | 3.8 (0.62) |
| Day 4 IGA Score | 3.6 (0.73) | 4.1 (0.35) | 3.9 (0.71) | 3.3 (0.48) | 3.7 (0.65) |
| % Change from Baseline to Day 4 | −1.6 (6.25) | 0.0 (0.00) | −1.1 (5.33) | −3.6 (8.96) | −2.0 (6.79) |
| Absolute change from Baseline to Day 4 | −0.1 (0.25) | 0.0 (0.00) | 0.0 (0.21) | −0.1 (0.36) | −0.1 (0.27) |
| Day 8 IGA Score | 3.3 (0.90) | 4.0 (0.00) | 3.6 (0.85) | 3.1 (0.54) | 3.5 (0.73) |
| % Change from Baseline to Day 8 | −5.6 (21.28) | −2.5 (7.07) | −7.3 (12.55) | −10.3 (13.67) | −7.8 (12.46) |
| Absolute change from Baseline to Day 8 | −0.2 (0.68) | −0.1 (0.35) | −0.3 (0.46) | −0.4 (0.50) | −0.3 (0.46) |
| Day 15 IGA Score | 3.4 (0.99) | 3.6 (0.52) | 3.0 (0.97) | 2.9 (0.70) | 3.1 (0.83) |
| % Change from Baseline to Day 15 | −2.8 (28.98) | −11.3 (16.20) | −23.7 (16.69) | −16.3 (18.16) | −18.5 (17.55) |
| Absolute change from Baseline to Day 15 | −0.1 (0.92) | −0.5 (0.76) | −0.9 (0.64) | −0.6 (0.60) | −0.7 (0.65) |
| Day 22 IGA Score | 3.1 (0.67) | 3.4 (0.52) | 2.7 (0.73) | 2.3 (0.80) | 2.7 (0.80) |
| % Change from Baseline to Day 22 | −9.0 (19.61) | −17.5 (15.35) | −30.8 (12.76) | −32.5 (23.99) | −29.4 (19.17) |
| Absolute change from Baseline to Day 22 | −0.3 (0.65) | −0.8 (0.710 | −1.2 (0.52) | −1.1 (0.79) | −1.1 (0.68) |
| Day 25 IGA Score | 3.0 (0.89) | 3.1 (0.35) | 2.5 (0.87) | 2.2 (0.89) | 2.5 (0.86) |
| % Change from Baseline to Day 25 | −12.1 (29.43) | −23.8 (10.94) | −34.5 (18.64) | −35.7 (25.16) | −33.2 (21.05) |
| Absolute change from Baseline to Day 25 | −0.5 (0.93) | −1.0 (0.53) | −1.4 (0.790 | −1.2 (0.83) | −1.2 (0.77) |
| Day 29 IGA Score | 2.9 (1.08) | 3.0 (0.53) | 2.4 (0.99) | 2.3 (0.85) | 2.4 (0.89) |
| % Change from Baseline to Day 29 | −16.0 (24.48) | −26.3 (16.20) | −38.0 (24.02) | −34.9 (21.18) | −34.8 (21.68) |
| Absolute change from Baseline to Day 29 | −0.5 (0.80) | −1.1 (0.83) | −1.5 (1.00) | −1.2 (0.68) | −1.3 (0.85) |
| Day 36 IGA Score | 2.9 (1.20) | 3.0 (0.58) | 2.2 (0.76) | 2.4 (0.50) | 2.4 (0.70) |
| % Change from Baseline to Day 36 | −16.7 (26.35) | −26.4 (17.49) | −44.1 (19.38) | −33.3 (9.13) | −37.1 (16.97) |
| Absolute change from Baseline to Day 36 | −0.5 (0.85) | −1.1 (0.90) | −1.7 (0.81) | −1.2 (0.40) | −1.4 (0.74) |
| Day 43 IGA Score | 2.8 (1.06) | 3.3 (0.76) | 2.3 (1.02) | 2.2 (0.83) | 2.4 (0.97) |
| % Change from Baseline to Day 43 | −21.1 (26.91) | −19.3 (21.88) | −40.8 (28.04) | −39.0 (19.85) | −36.6 (24.53) |
| Absolute change from Baseline to Day 43 | −0.8 (0.97) | −0.9 (1.07) | −1.6 (1.04) | −1.3 (0.58) | 1.4 (0.89) |
| Day 50 IGA Score | 2.7 (1.19) | 3.3 (0.82) | 2.4 (1.07) | 2.1 (0.80) | 2.4 (1.00) |

TABLE 22-continued

Summary of Percentage and Absolute Change in IGA Score from Baseline-all values represented as Mean (SD)

| | Placebo | mAb1 75 mg | mAb1 150 mg | mAb1 300 mg | mAb1 All Doses Combined |
|---|---|---|---|---|---|
| % Change from Baseline to Day 50 | −18.9 (30.98) | −18.3 (23.80) | −37. 2 (25.87) | −40.7 (21.93) | −36.0 (24.57) |
| Absolute change from Baseline to Day 50 | −0.6 (1.12) | −0.8 (1.17) | −1.5 (1.07) | −1.4 (0.70) | −1.3 (0.95) |
| Day 57 IGA Score | 2.8 (1.20) | 3.2 (0.75) | 2.5 (1.03) | 2.2 (0.97) | 2.5 (1.00) |
| % Change from Baseline to Day 57 | −17.6 (33.45) | −22.5 (22.08) | −34.8 (25.21) | −36.3 (24.99) | −33.7 (24.60) |
| Absolute change from Baseline to Day 57 | −0.6 (1.01) | −1.0 (1.10) | −1.4 (1.07) | −1.2 (0.83) | −1.3 (0.97) |
| Day 64 IGA Score | 2.7 (0.79) | 3.5 (1.05) | 2.7 (1.08) | 2.1 (0.81) | 2.6 (1.06) |
| % Change from Baseline to Day 64 | −18.9 (21.44) | −14.2 (29.23) | −30.9 (26.08) | −38.5 (20.61) | −31.5 (25.22) |
| Absolute change from Baseline to Day 64 | −0.6 (0.67) | −0.7 (1.37) | −1.2 (1.06) | −1.3 (0.70) | −1.2 (0.98) |
| Day 71 IGA Score | 2.6 (0.81) | 3.4 (0.89) | 2.8 (0.86) | 2.1 (1.15) | 2.5 (1.10) |
| % Change from Baseline to Day 71 | −22.0 (20.84) | −17.0 (26.36) | −25.5 (27.32) | −41.7 (31.65) | −32.0 (30.18) |
| Absolute change from Baseline to Day 71 | −0.7 (0.65) | −0.8 (1.300 | −1.1 (1.18) | −1.5 (1.10) | −1.2 (1.15) |
| Day 85 IGA Score | 2.6 (1.17) | 3.2 (0.84) | 2.8 (0.99) | 2.6 (0.96) | 2.8 (0.96) |
| % Change from Baseline to Day 85 | −20.8 (36.69) | −22.0 (24.65) | −25.6 (31.31) | −24.6 (28.66) | −24.7 (28.77) |
| Absolute change from Baseline to Day 85 | −0.7 (1.16) | −1.0 (1.22) | −1.1 (1.23) | −0.8 (0.90) | −1.0 (1.07) |

TABLE 23

Number (%) of subjects achieving EASI-50 at Day 29 and every study visit-LOCF

| Number and % subjects with EASI50 | Placebo (N = 16) | 75 mg (N = 8) | 150 mg (N = 22) | 300 mg (N = 21) | All Doses Combined (N = 51) |
|---|---|---|---|---|---|
| Week 4, Day 29 | 3 (18.8%) | 3 (37.5%) | 12 (54.5%) | 15 (71.4%) | 30 (58.8%) |
| Week 2, Day 15 | 0 | 0 | 6 (27.3%) | 11 (52.4%) | 17 (33.3%) |
| Week 5, Day 36 | 3 (18.8%) | 5 (62.5%) | 16 (72.7%) | 15 (71.4%) | 36 (70.6%) |
| Week 6, Day 43 | 3 (18.8%) | 2 (25.0%) | 14 (63.6%) | 16 (76.2%) | 32 (62.7%) |
| Week 8, Day 57 | 5 (31.3%) | 2 (25.0%) | 12 (54.5%) | 13 (61.9%) | 27 (52.9%) |
| Week 10, Day 71 | 6 (37.5%) | 1 (12.5%) | 13 (59.1%) | 16 (76.2%) | 30 (58.8%) |
| Week 12, Day 85 | 3 (18.8%) | 1 (12.5%) | 12 (54.5%) | 17 (81.0%) | 30 (58.8%) |

TABLE 24

Number (%) of subjects achieving EASI-25 at Day 29 and every study visit-LOCF

| Number and % subjects with EASI50 | Placebo (N = 16) | 75 mg (N = 8) | 150 mg (N = 22) | 300 mg (N = 21) | All Doses Combined (N = 51) |
|---|---|---|---|---|---|
| Week 4, Day 29 | 4 (25.0%) | 7 (87.5%) | 16 (72.7%) | 18 (85.7%) | 41 (80.4%) |
| Week 2, Day 15 | 3 (18.8%) | 5 (62.5%) | 13 (59.1%) | 16 (76.2%) | 34 (66.7%) |
| Week 5, Day 36 | 6 (37.5%) | 7 (87.5%) | 19 (86.4%) | 18 (85.7%) | 44 (86.3%) |
| Week 6, Day 43 | 7 (43.8%) | 5 (62.5%) | 19 (86.4%) | 18 (85.7%) | 42 (82.4%) |
| Week 8, Day 57 | 8 (50.0%) | 4 (40.0%) | 16 (72.7%) | 17 (81.0%) | 37 (72.5%) |
| Week 10, Day 71 | 8 (50.0%) | 3 (37.5%) | 17 (77.3%) | 19 (90.5%) | 39 (76.5%) |
| Week 12, Day 85 | 9 (56.3%) | 3 (37.5%) | 16 (72.7%) | 20 (95.2%) | 39 (76.5%) |

TABLE 25

Figure 18:
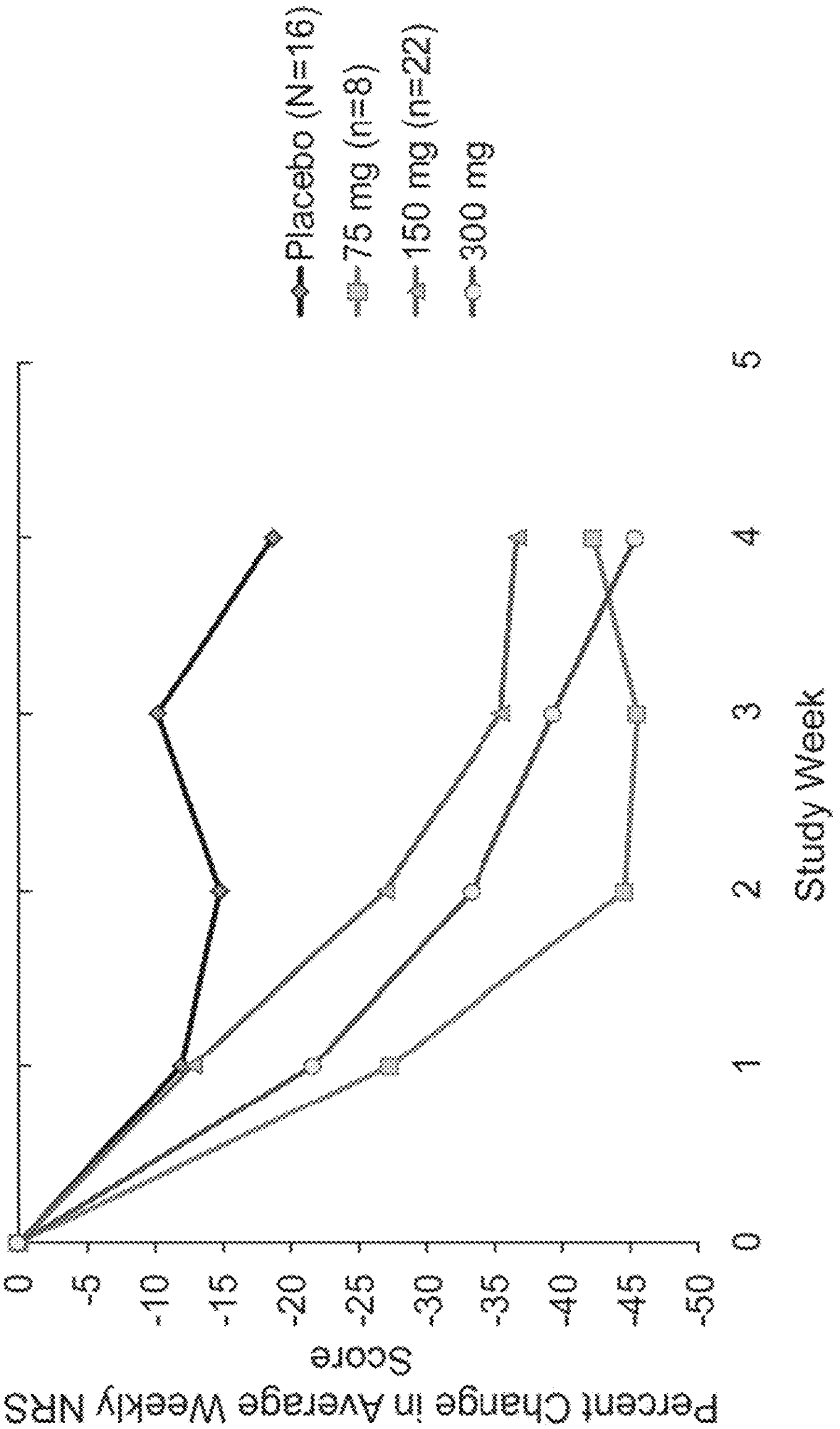
FIG. 18 shows percent change from baseline in Pruritus NRS in patients administered 75 mg, 150 mg or 300 mg of anti-IL-4R antibody vs. placebo for the study in Example 8.
Figure 19:
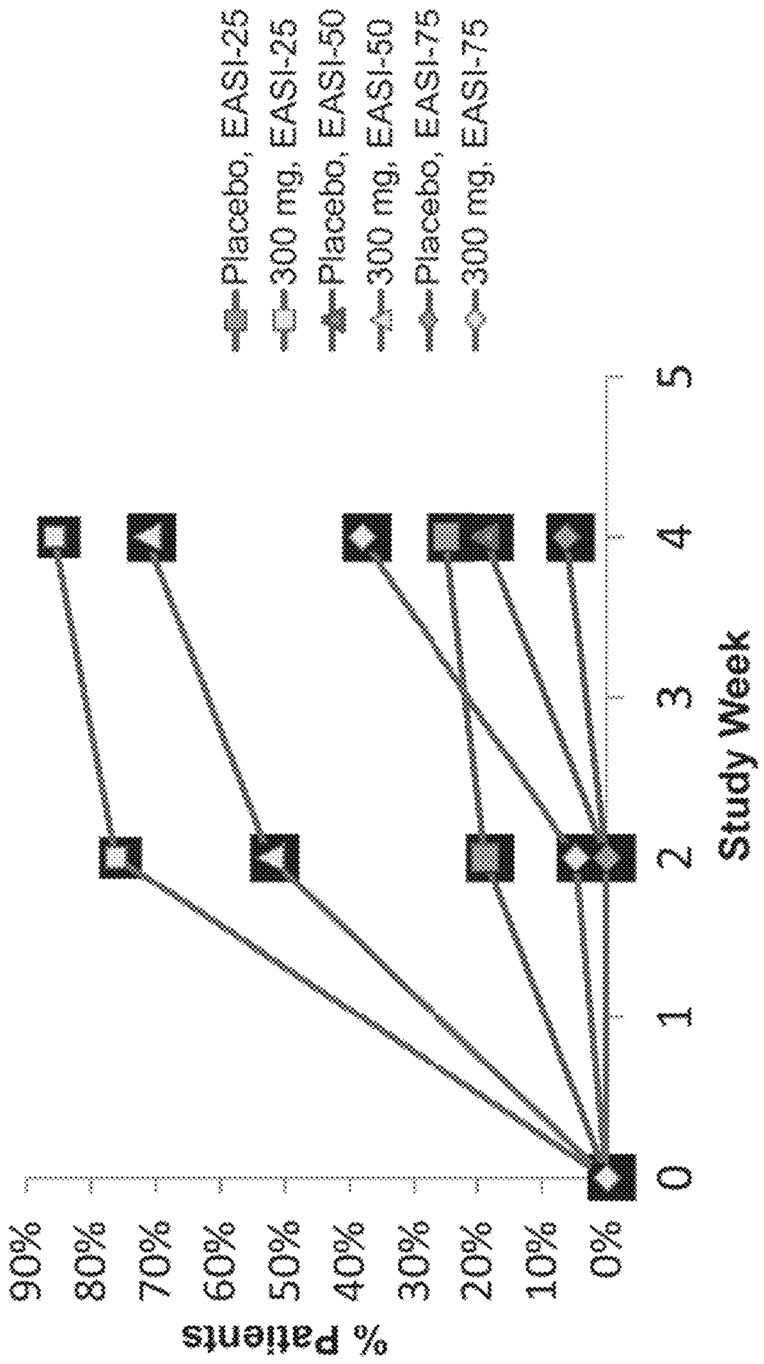
FIG. 19 shows EASI response time course in patients with moderate-to-severe AD to 300 mg anti-IL-4R antibody for the study in Example 8.
Figure 20:
FIG. 20 shows the percent responders in the EASI score administered with 75 mg, 150 mg or 300 mg anti-IL-4R antibody vs. placebo for the study in Example 8.
Figure 21:
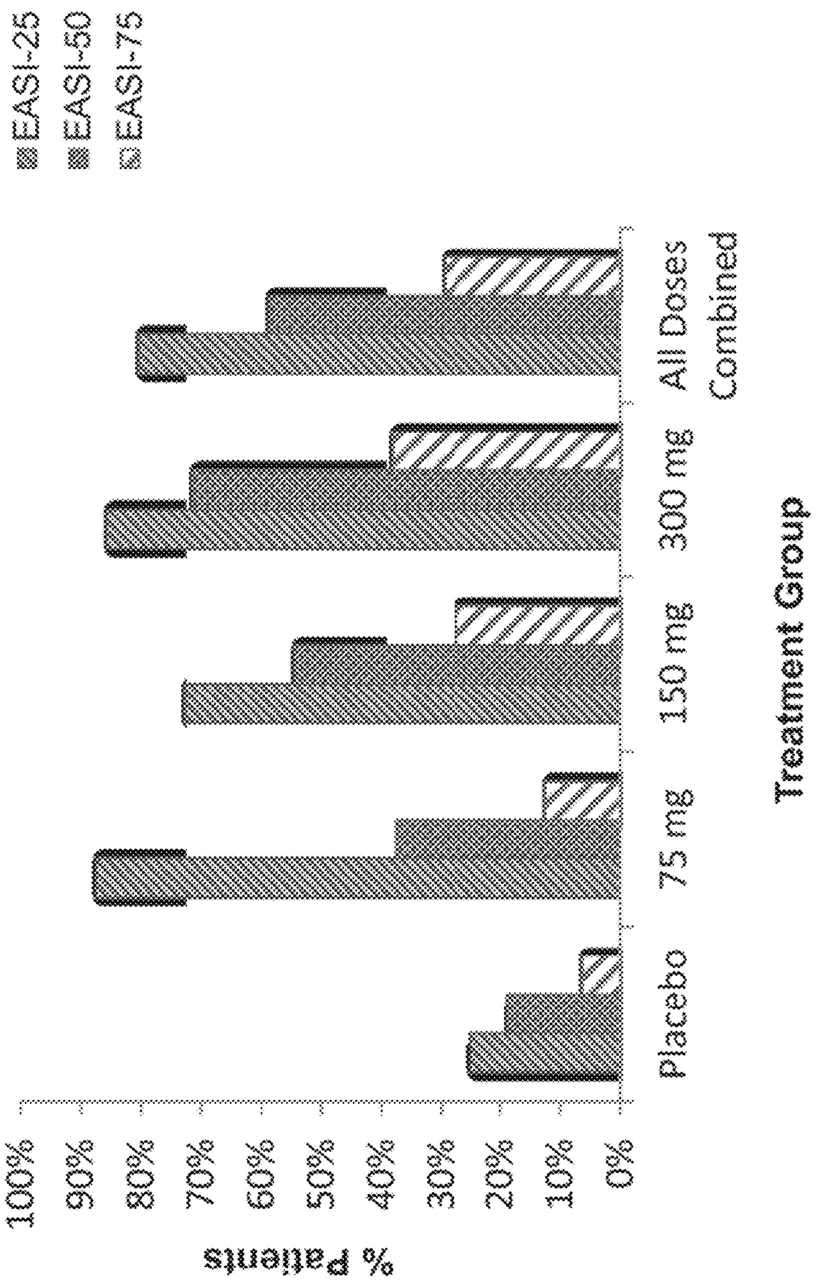
FIG. 21 shows EASI responses at week 4 (day 29) to anti-IL-4R antibody administered at 75 mg, 150 mg or 300 mg doses vs. placebo for the study in Example 8.

| Number (%) of subjects achieving EASI-75 at Day 29 and every study visit-LOCF | | | | | |
|---|---|---|---|---|---|
| Number and % subjects with EASI50 | Placebo (N = 16) | 75 mg (N = 8) | 150 mg (N = 22) | 300 mg (N = 21) | All Doses Combined (N = 51) |
| Week 4, Day 29 | 1 (6.3%) | 1 (12.5%) | 6 (27.3%) | 8 (38.1%) | 15 (29.4%) |
| Week 2, Day 15 | 0 | 0 | 1 (4.5%) | 1 (4.8%) | 2 (3.9%) |
| Week 5, Day 36 | 1 (6.3%) | 1 (12.5%) | 9 (40.9%) | 7 (33.3%) | 17 (33.3%) |
| Week 6, Day 43 | 1 (6.3%) | 1 (12.5%) | 8 (36.4%) | 6 (28.6%) | 15 (29.4%) |
| Week 8, Day 57 | 2 (12.5%) | 1 (12.5%) | 9 (40.9%) | 6 (28.6%) | 16 (31.4%) |
| Week 10, Day 71 | 2 (12.5%) | 1 (12.5%) | 6 (27.3%) | 11 (52.4%) | 18 (35.5%) |
| Week 12, Day 85 | 2 (12.5%) | 1 (12.5%) | 6 (27.3%) | 7 (33.3%) | 14 (27.5%) |

mAb1 was well-tolerated and effective in adults with moderate-to-severe AD. mAb1 administration significantly improved AD disease activity and severity. At 4 weeks, 150 mg and 300 mg mAb1 achieved significant improvements vs. placebo for change from baseline in % BSA ($p<0.05$) (FIG. 15), IGA ($p<0.001$) (FIG. 16), EASI ($p<0.001$) (FIG. 17), and pruritus NRS ($p<0.01$, 300 mg) (FIG. 18). More patients had 50% reduction in EASI score with 150 mg mAb1 (54.5%) and with 300 mg (71.4%) vs. placebo (18.8%; $p<0.05$ for both) (FIGS. 19 and 20). More patients achieved EASI-25, EASI-50, and EASI-75 with mAb1 over placebo at week 4 (FIG. 21).

Figure 22:
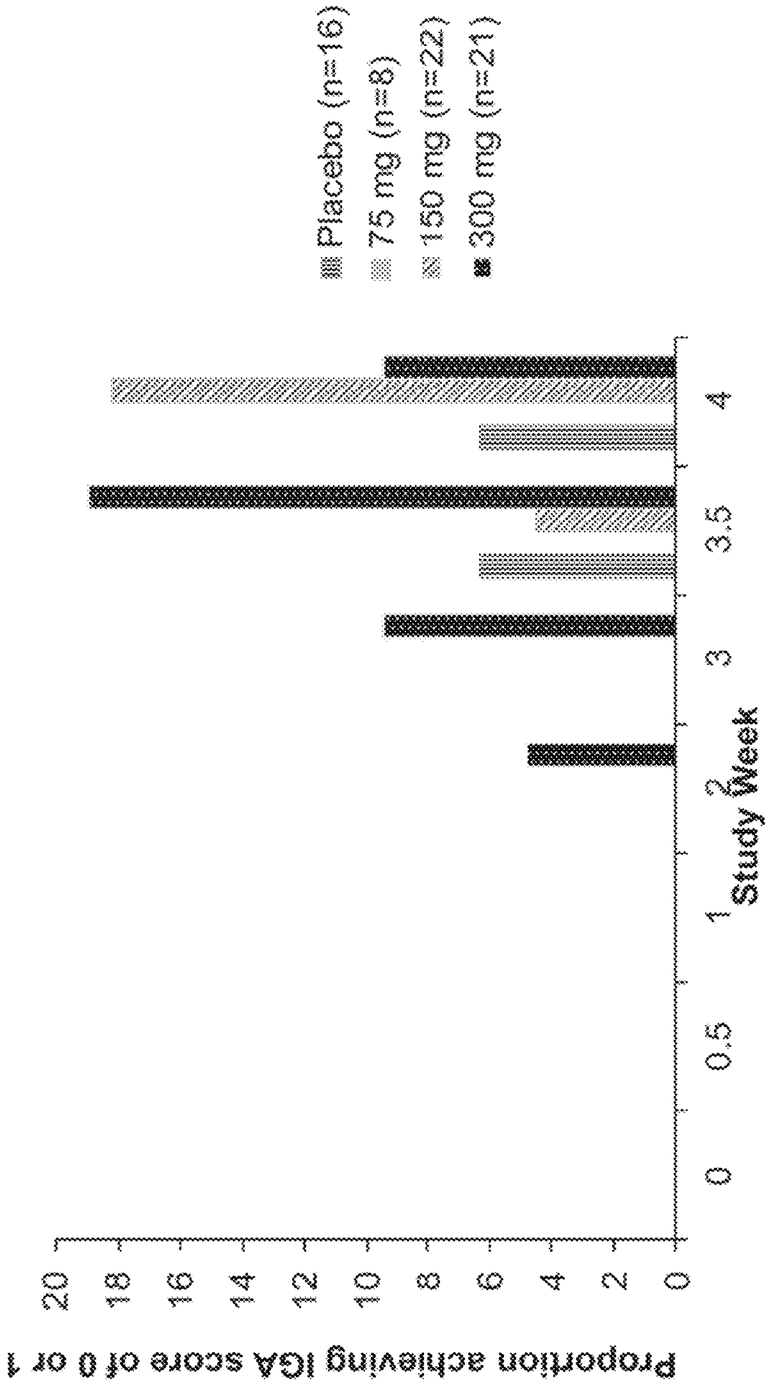
FIG. 22 shows proportion of patients achieving IGA s 1 for the study in Example 8.
Figure 23:
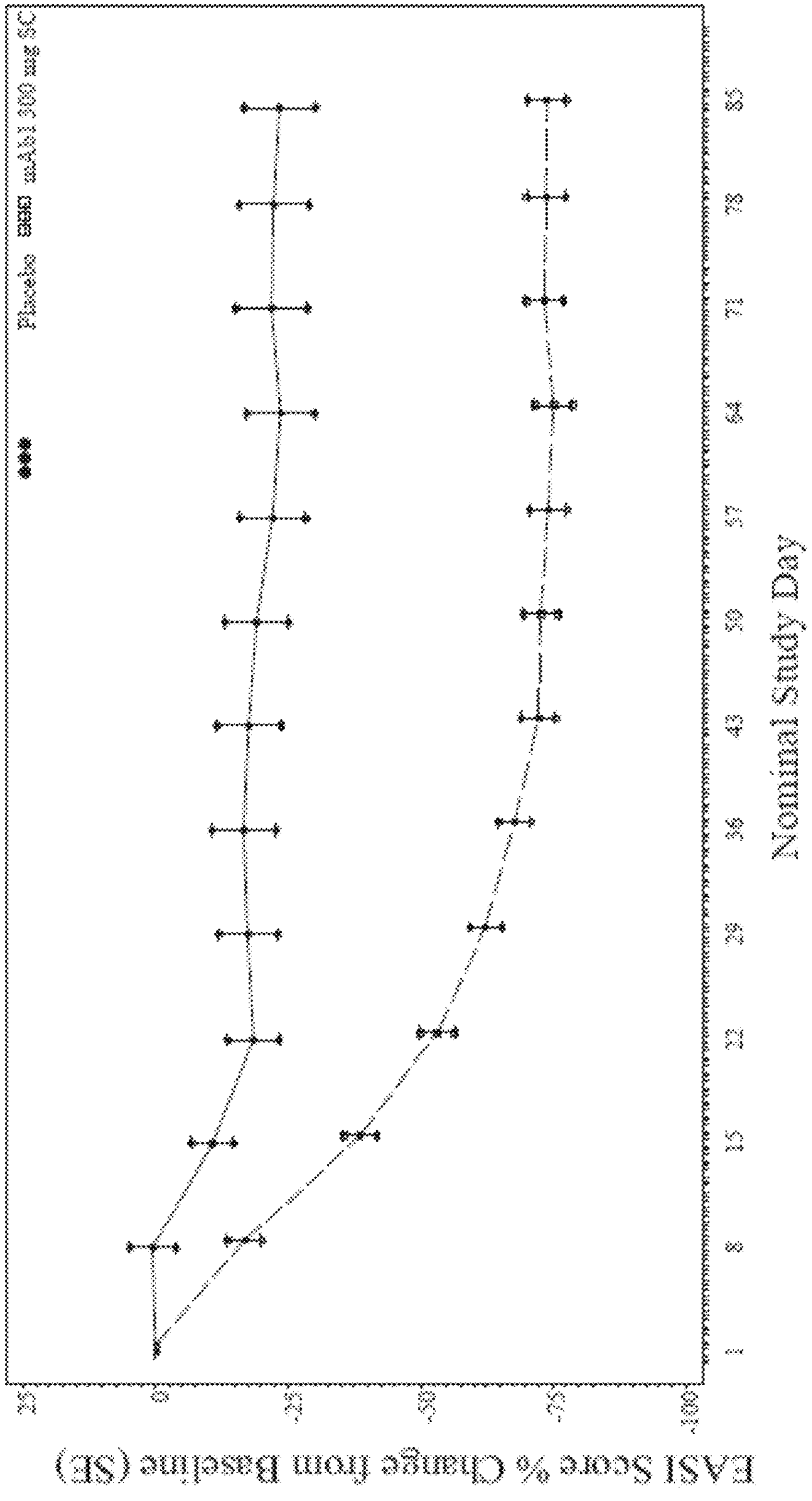
FIG. 23 shows mean EASI score percent change from baseline to the last observation carried forward (LOCF) for the study in Example 10.
Figure 24:
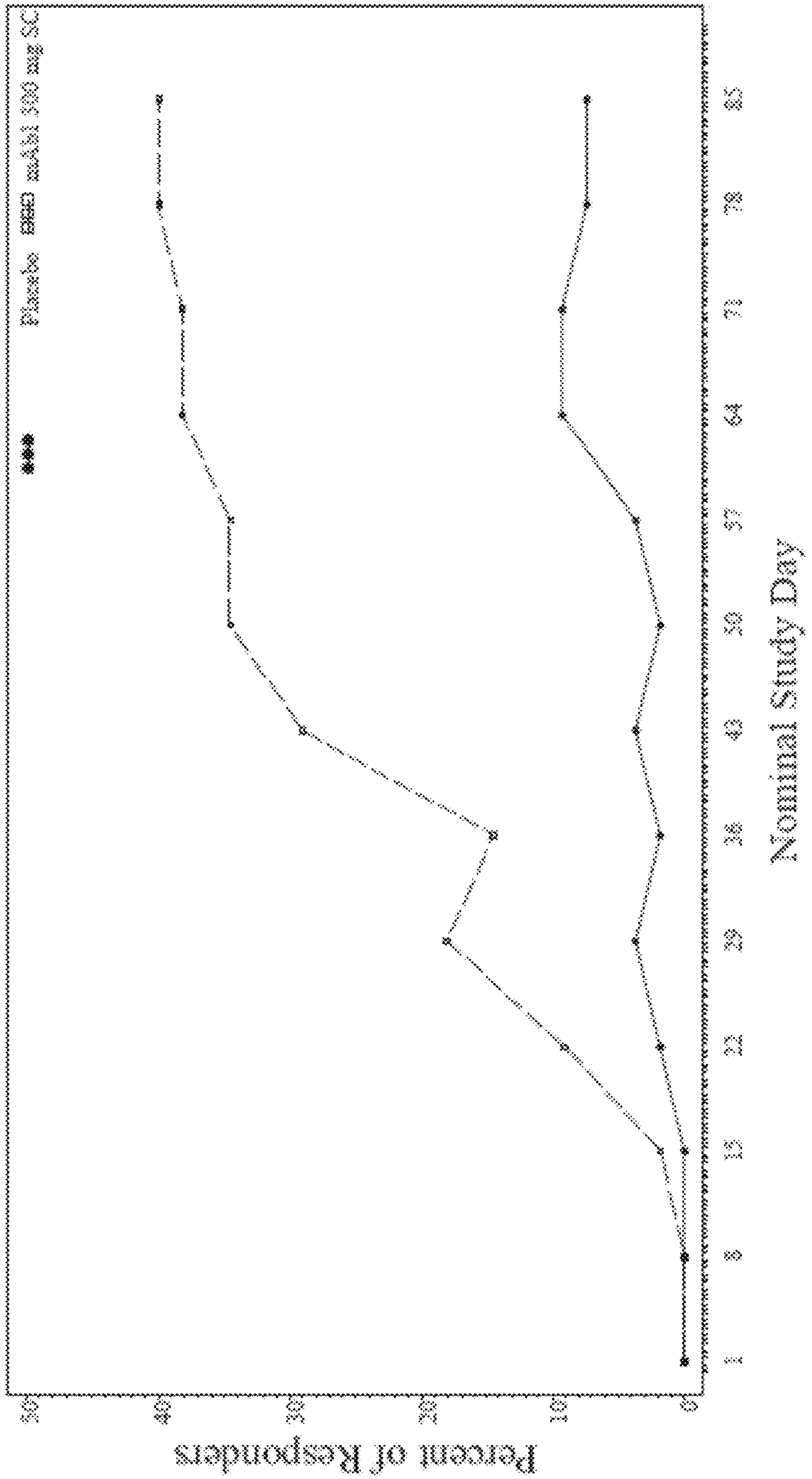
FIG. 24 shows IGA score responder rate 9 score of 0 or 1) up to LOCF for the study in Example 10.
Figure 25:
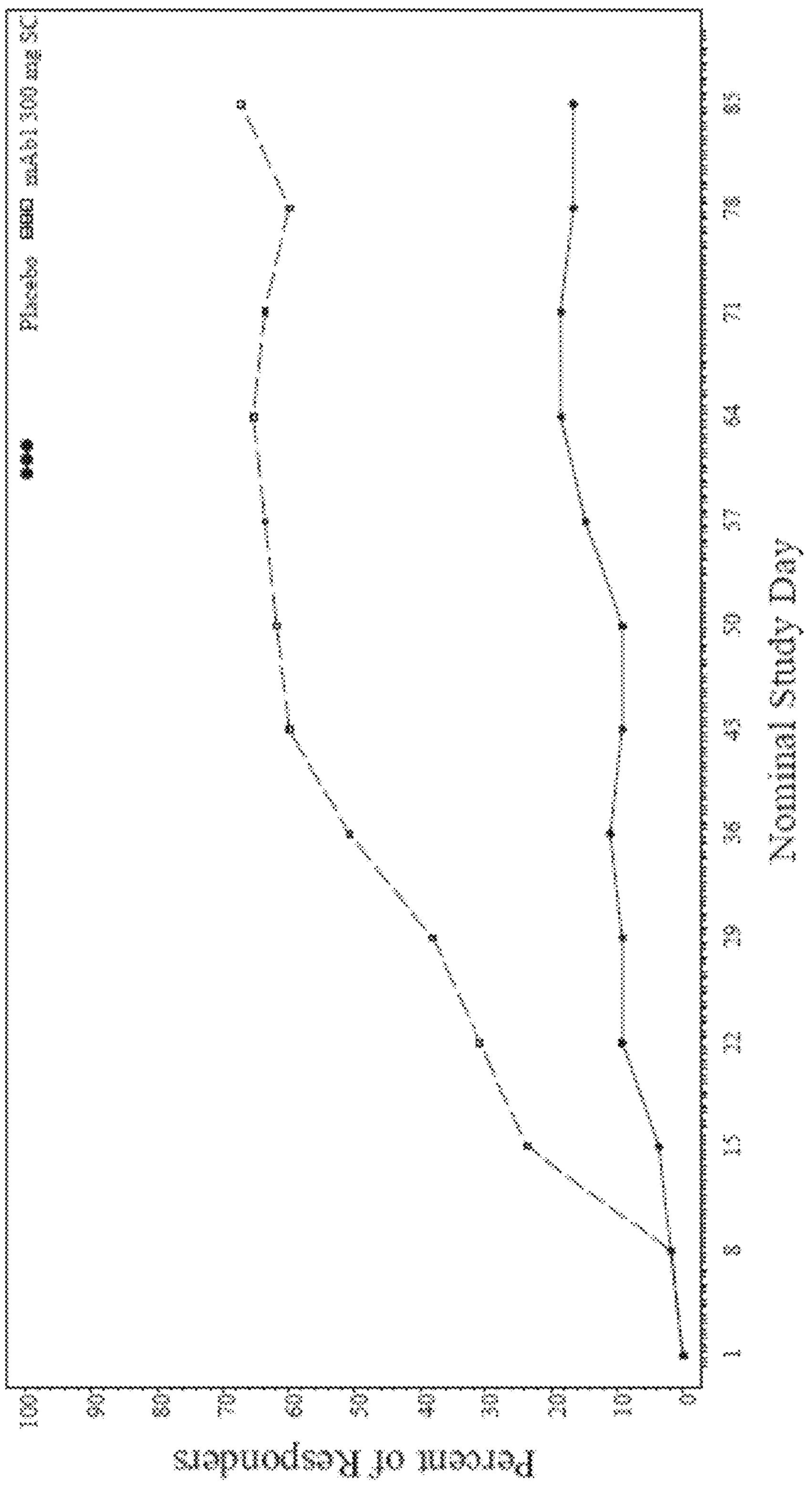
FIG. 25 shows IGA score responder rate (reduction in score of 2 or more) up to LOCF for the study in Example 10.
Figure 26:
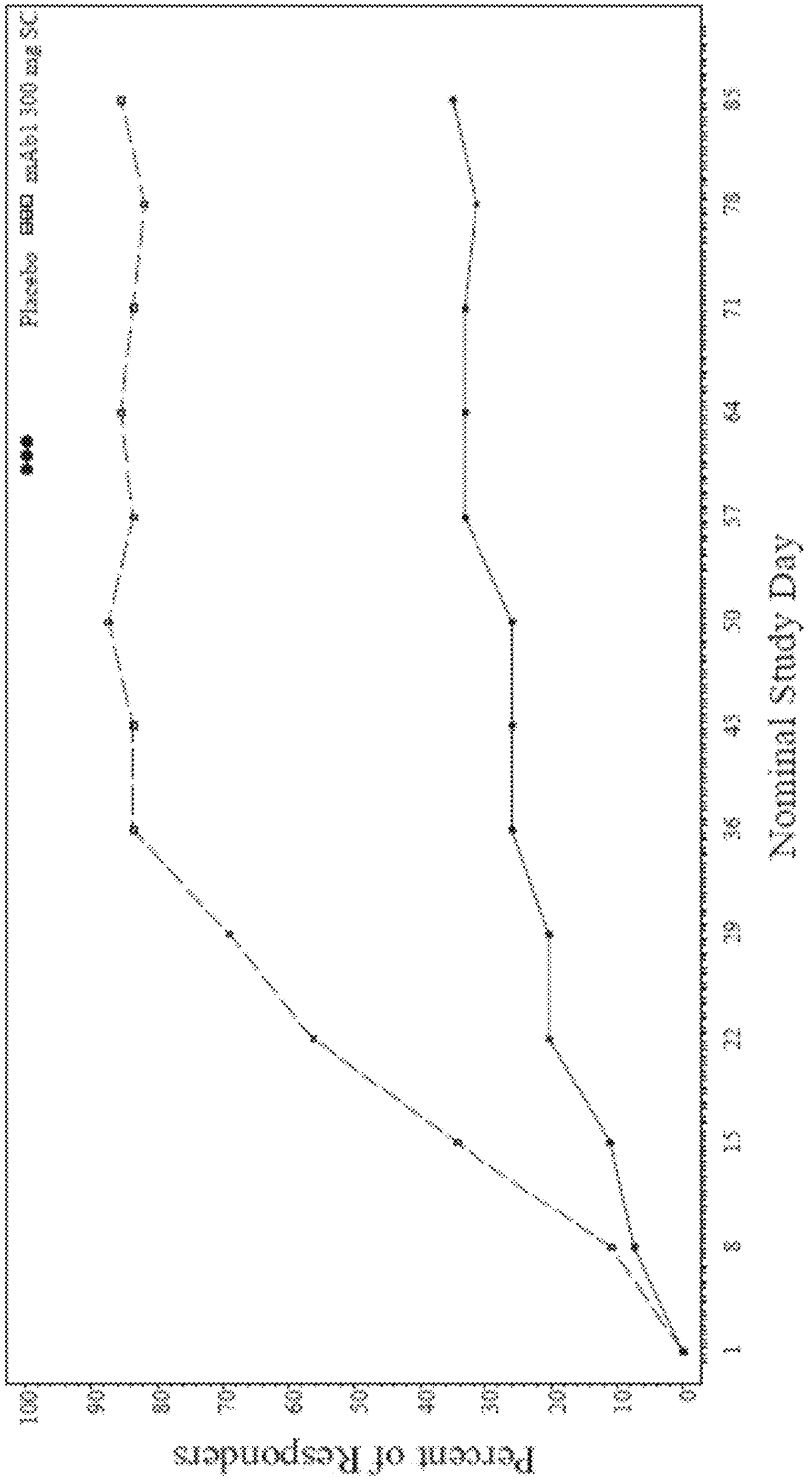
FIG. 26 shows EASI score responder rate (50% score reduction from baseline) up to LOCF for the study in Example 10.
Figure 27:
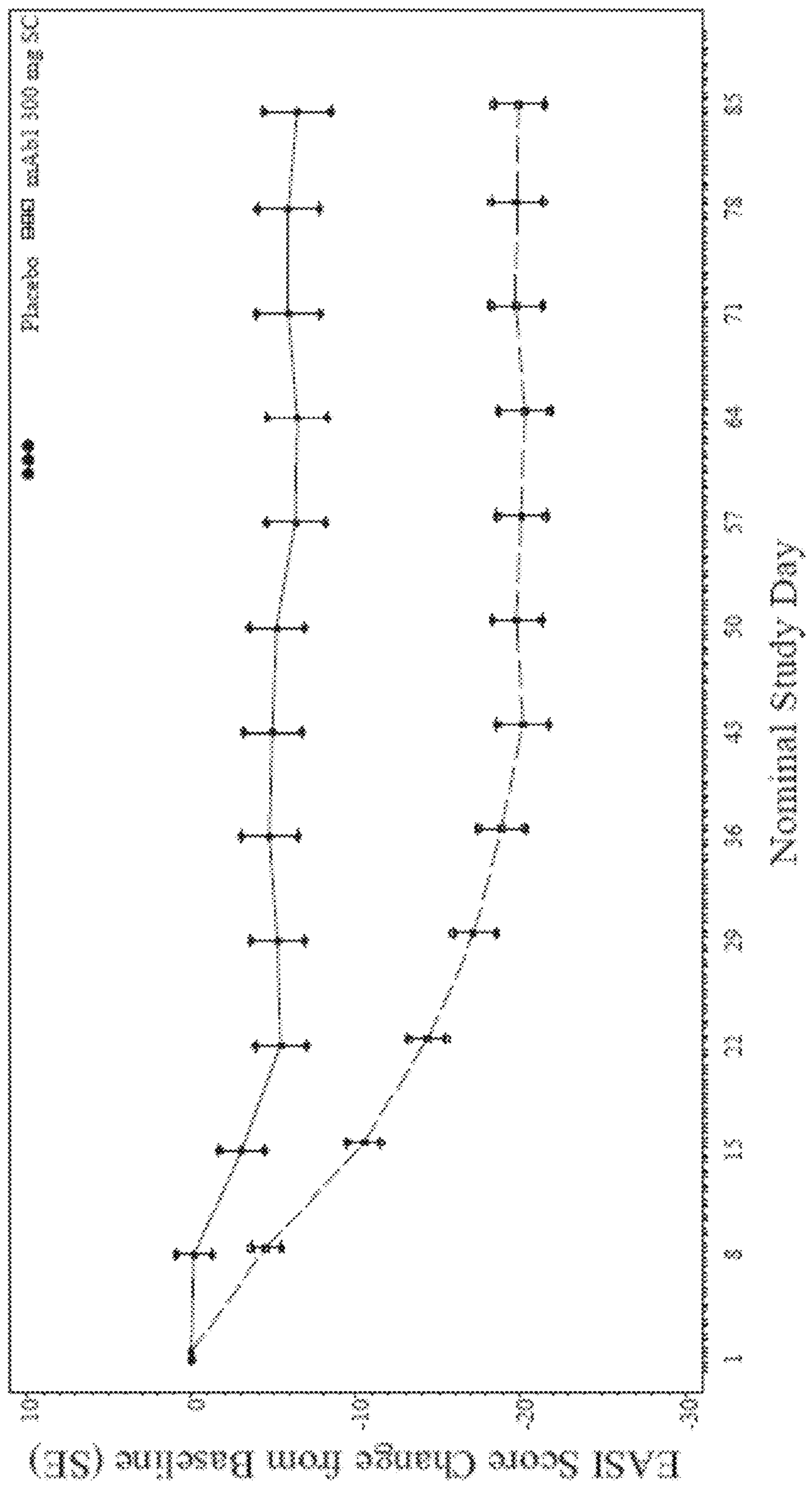
FIG. 27 shows mean EASI score change from baseline up to LOCF for the study in Example 10.
Figure 28:
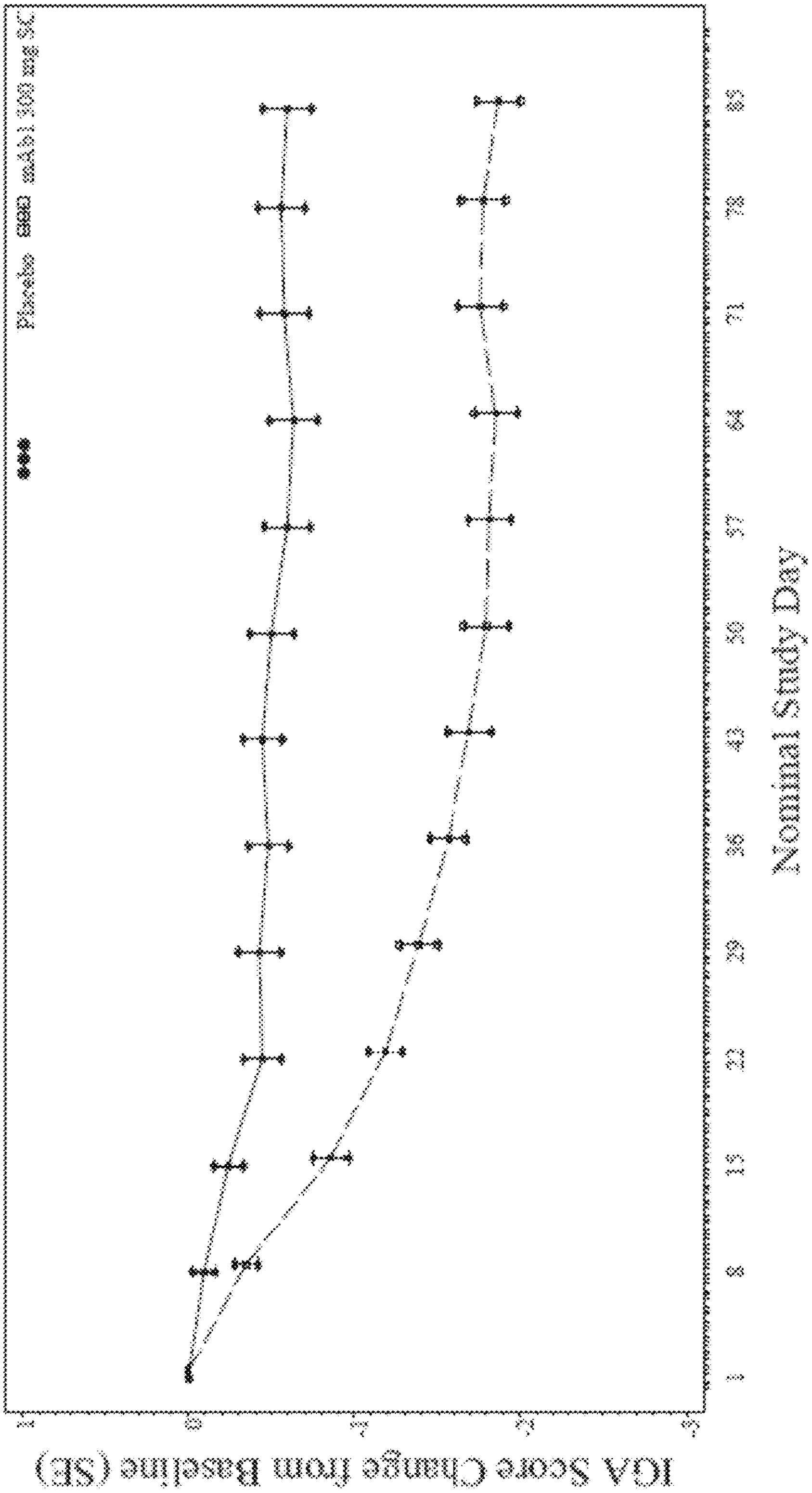
FIG. 28 shows mean IGA score change from baseline up to LOCF for the study in Example 10.
Figure 29:
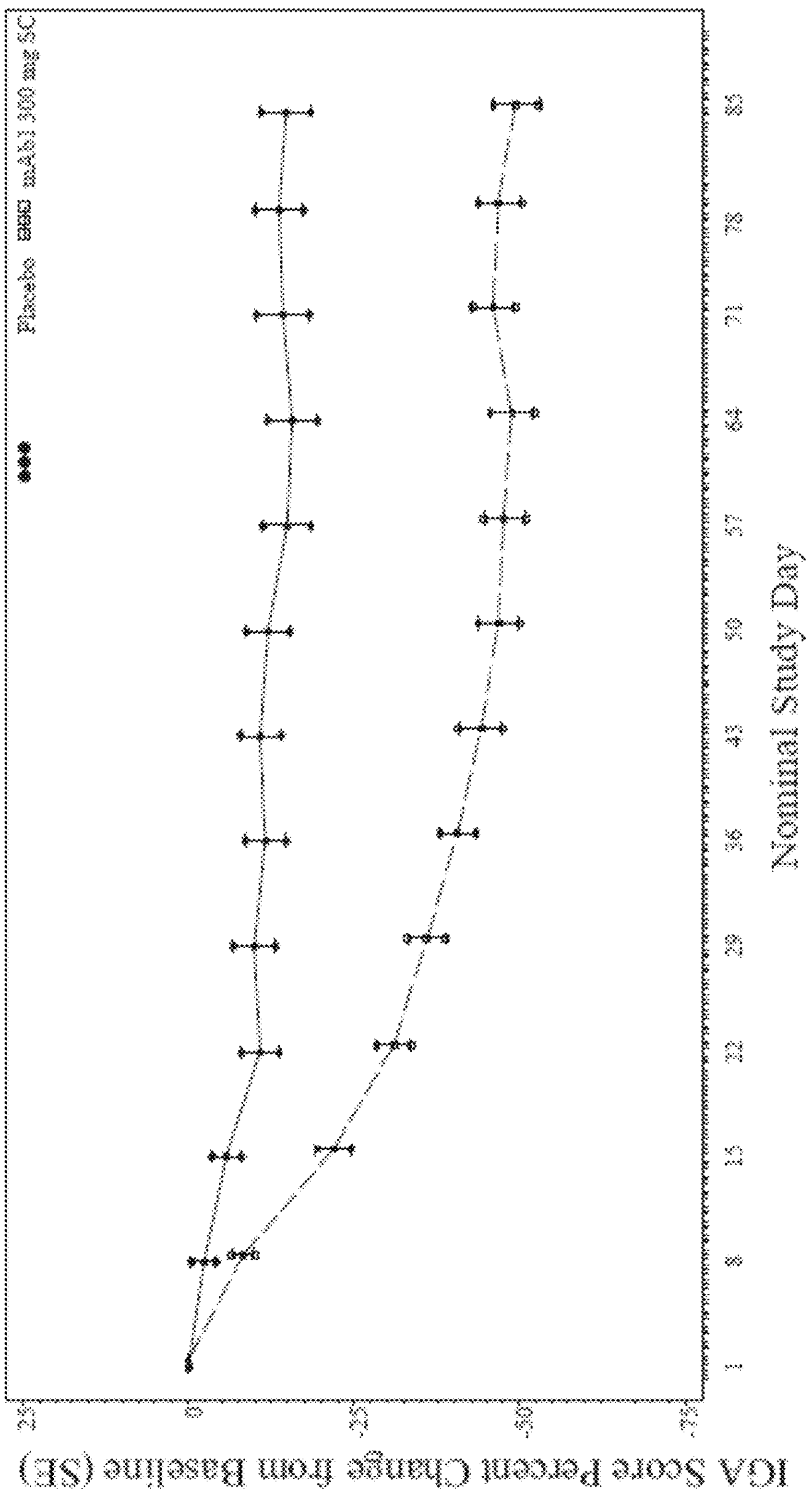
FIG. 29 shows mean IGA score percent change from baseline up to LOCF for the study in Example 10.
Figure 30:
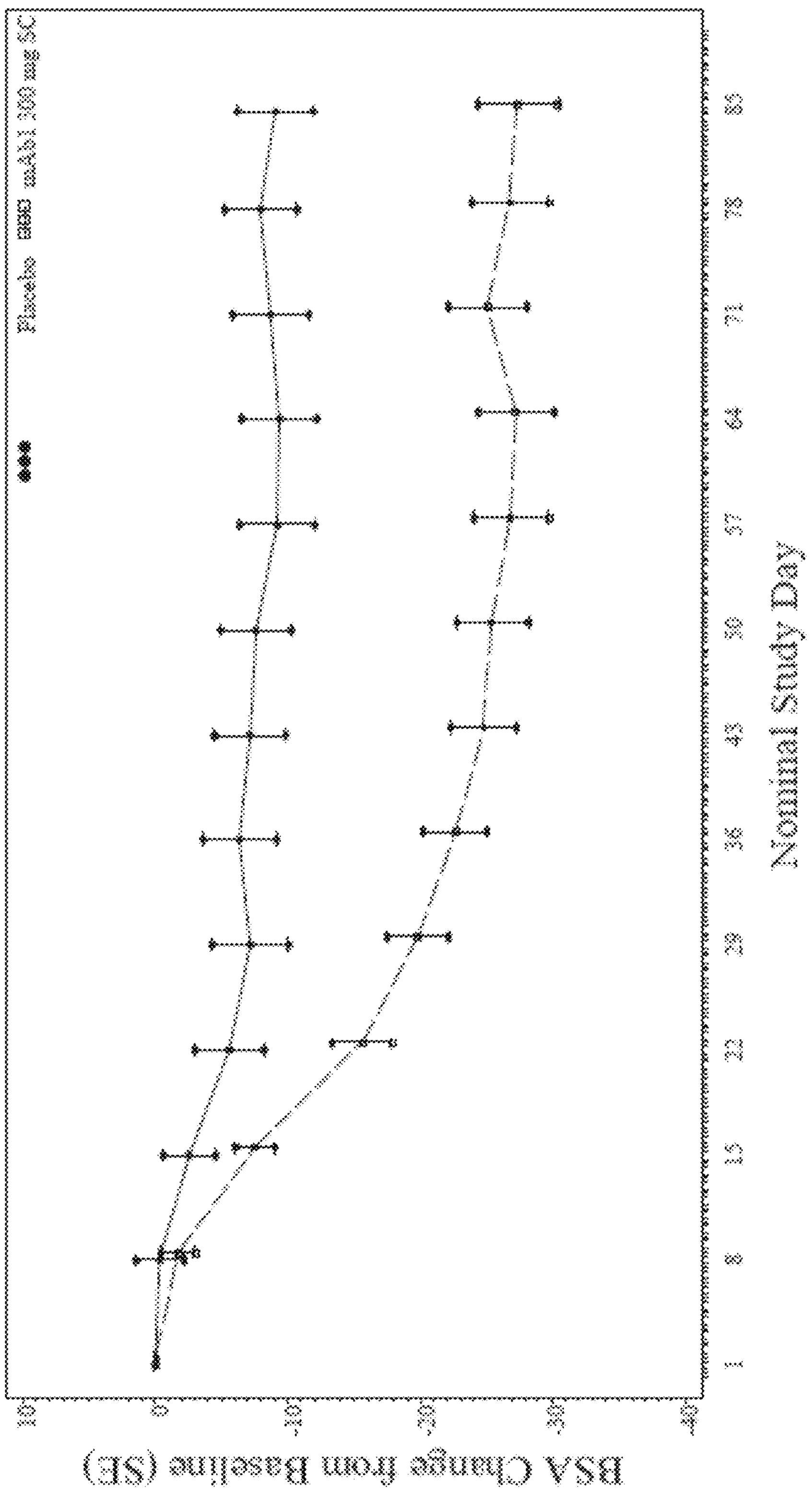
FIG. 30 shows mean BSA change from baseline up to LOCF for the study in Example 10.
Figure 31:
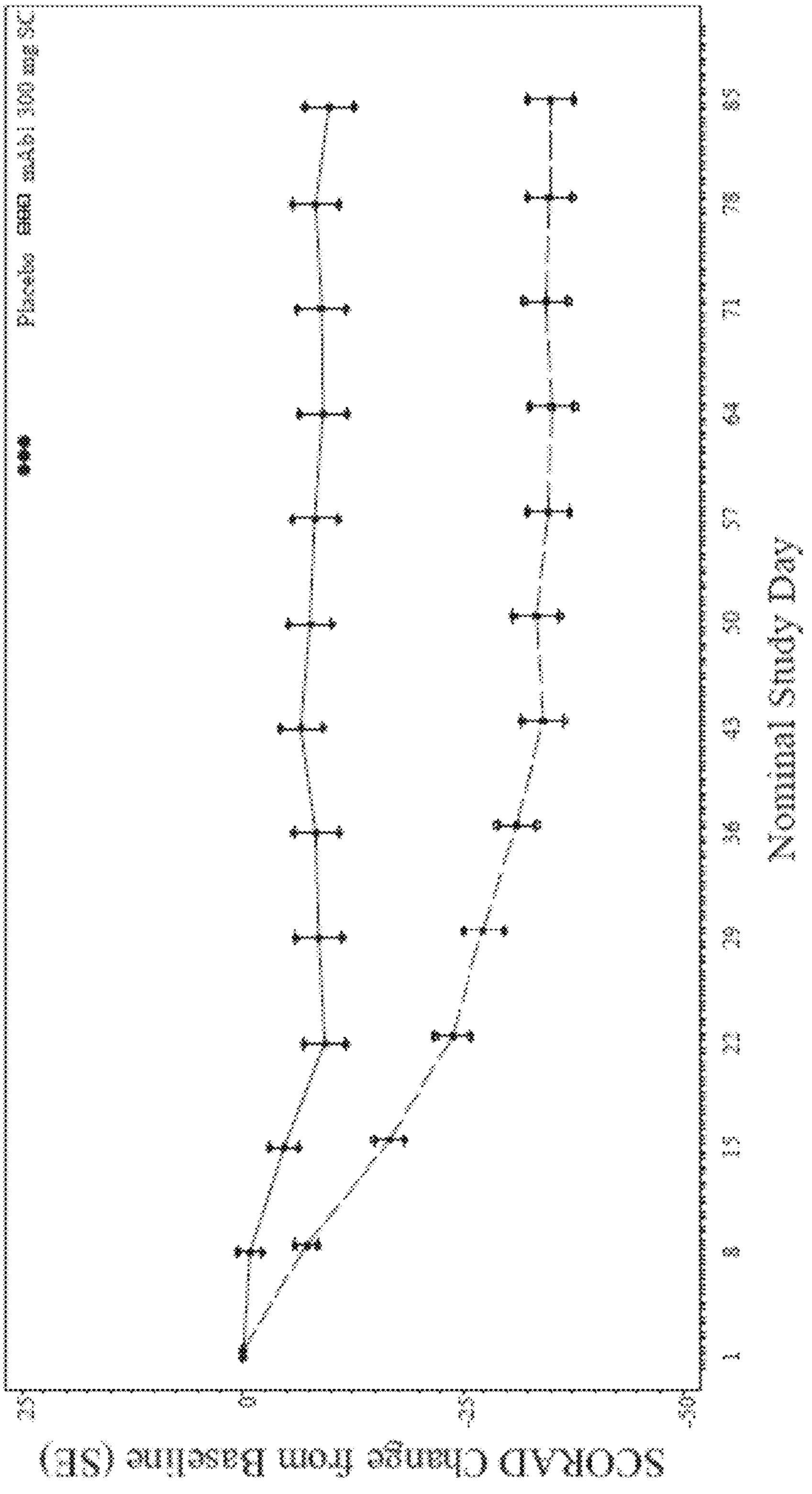
FIG. 31 shows mean SCORAD score change from baseline up to LOCF for the study in Example 10.
Figure 32:
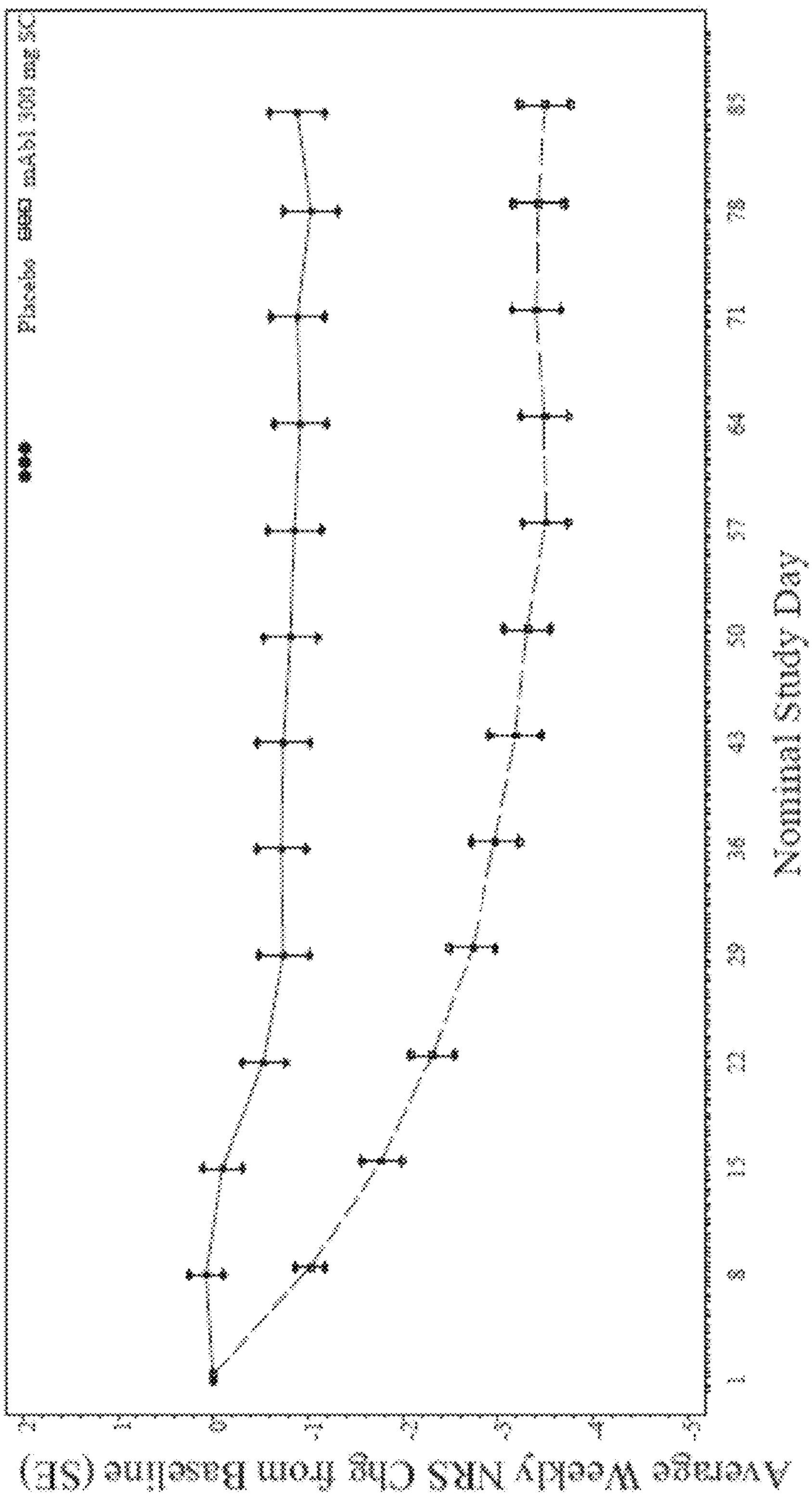
FIG. 32 shows mean NRS score change from baseline up to LOCF for the study in Example 10.
Figure 33:
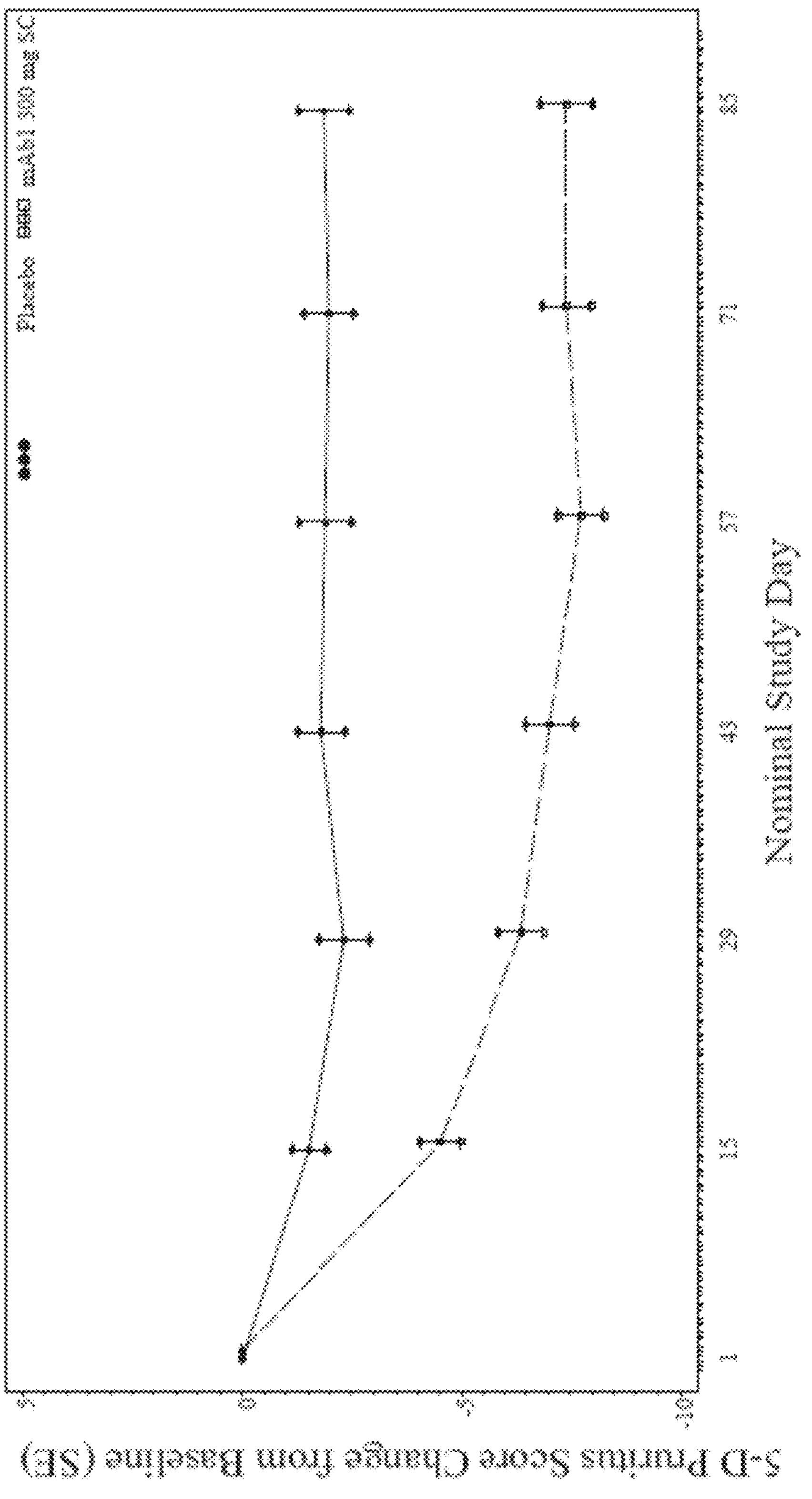
FIG. 33 shows mean 5-D Pruritus score change from baseline up to LOCF for the study in Example 10.
Figure 34:
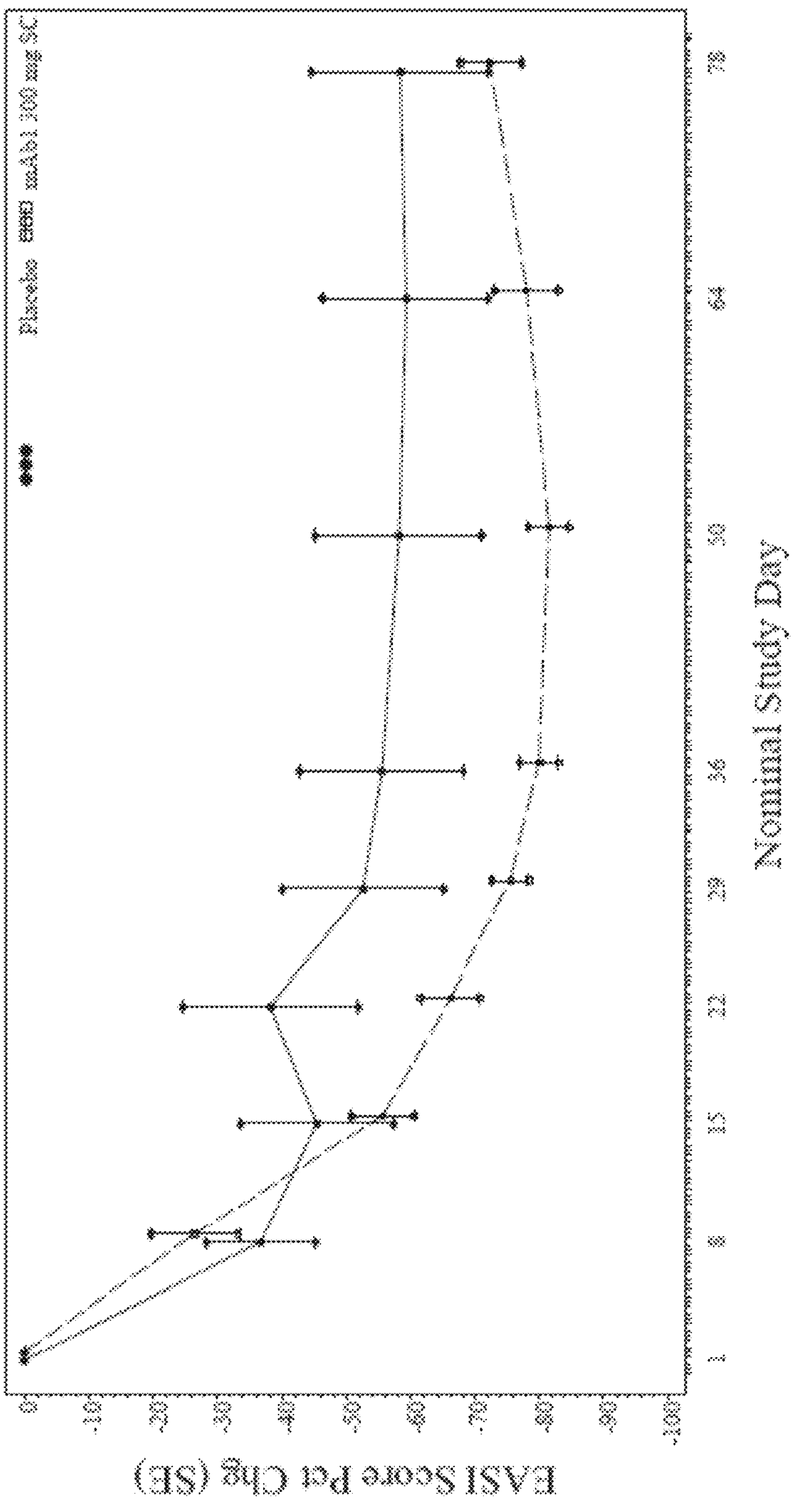
FIG. 34 shows mean EASI score percent change from baseline—censored LOCF, for the study in Example 11.
Figure 35:
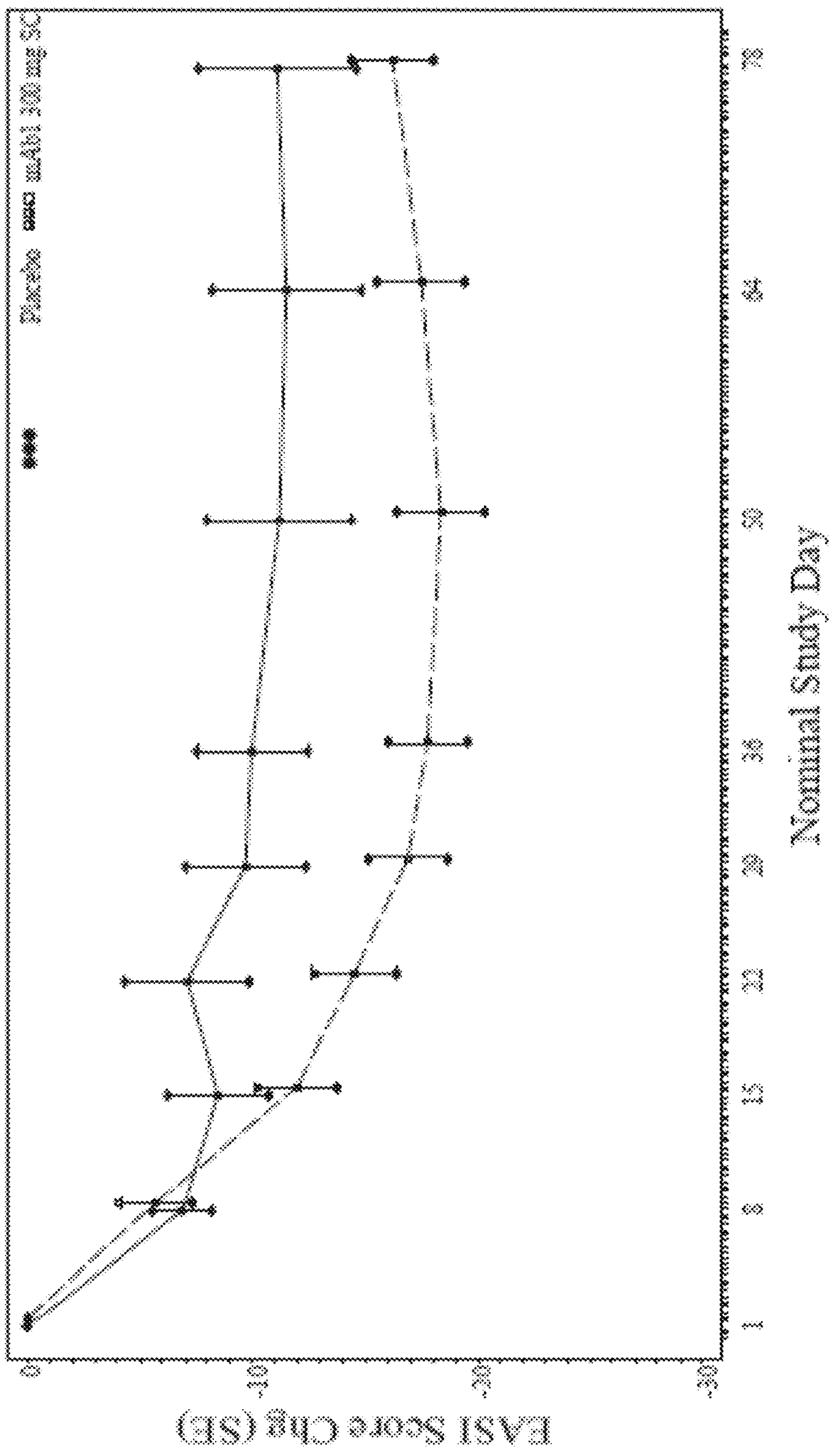
FIG. 35 shows mean EASI score change from baseline—censored LOCF, for the study in Example 11.
Figure 36:
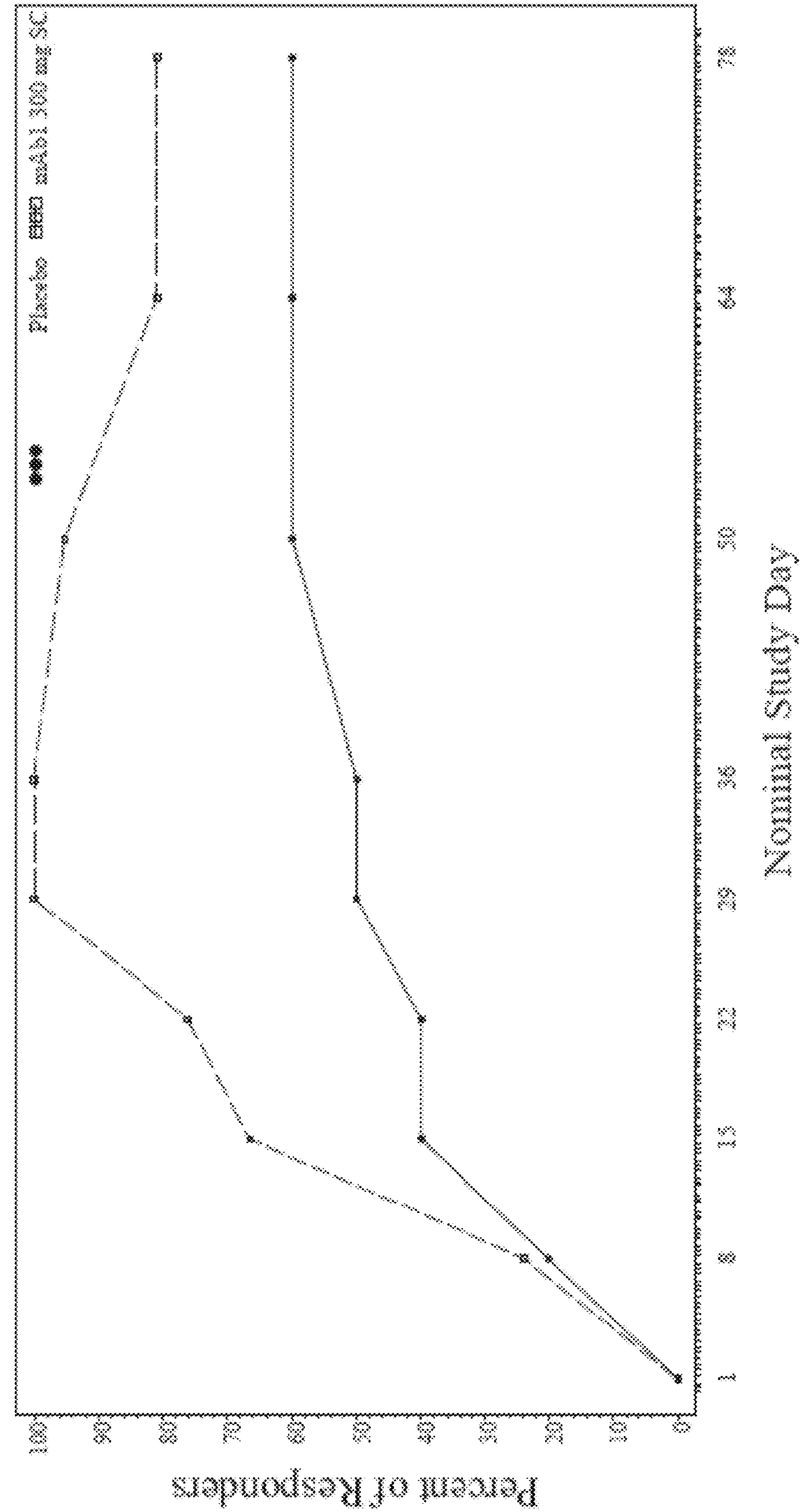
FIG. 36 shows EASI50 responder rate—censored LOCF, for the study in Example 11.
Figure 37:
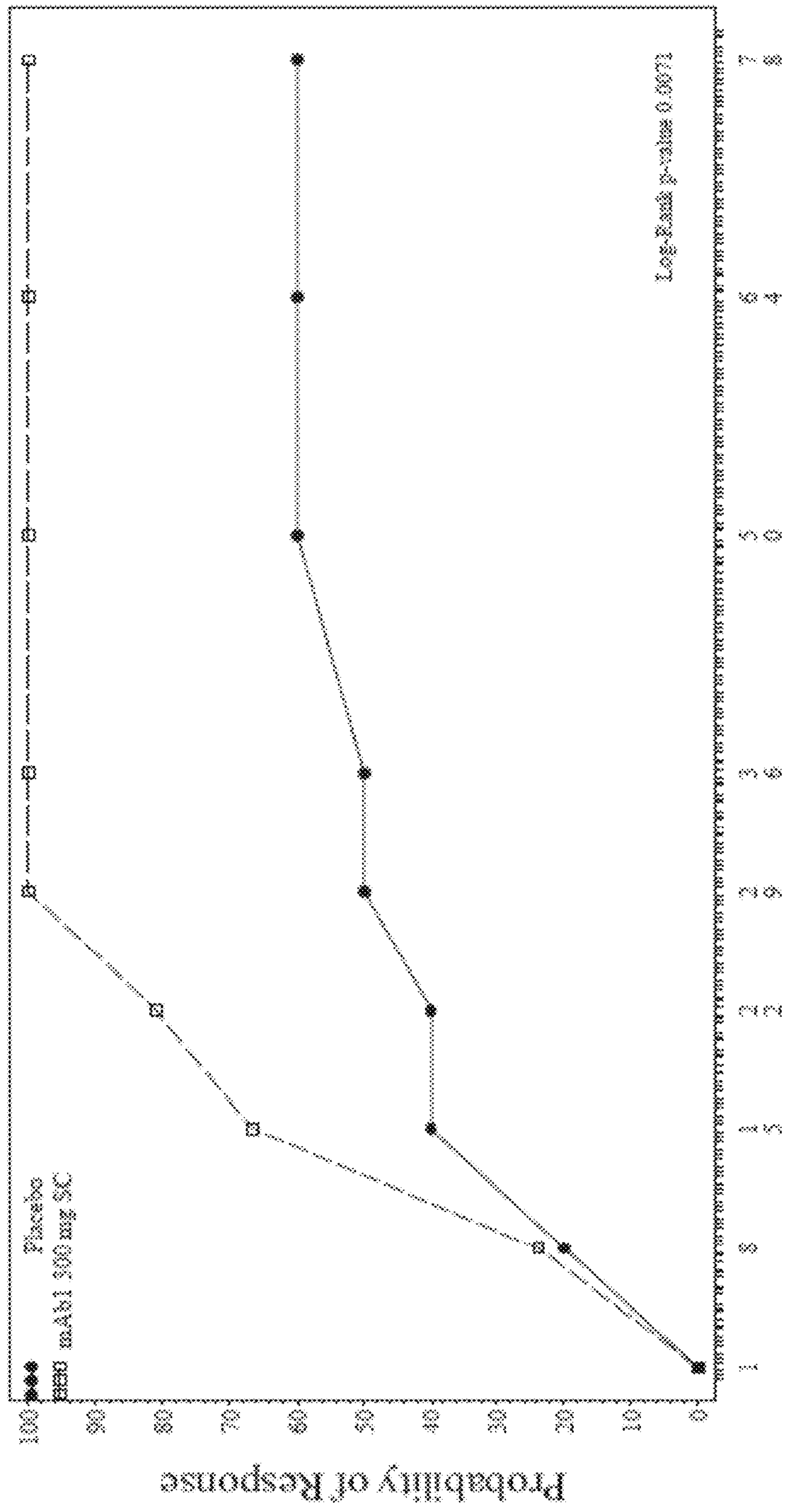
FIG. 37 shows a Kaplan-Meier plot of Time to first EASI50—censored LOCF, for the study in Example 11.
Figure 38:
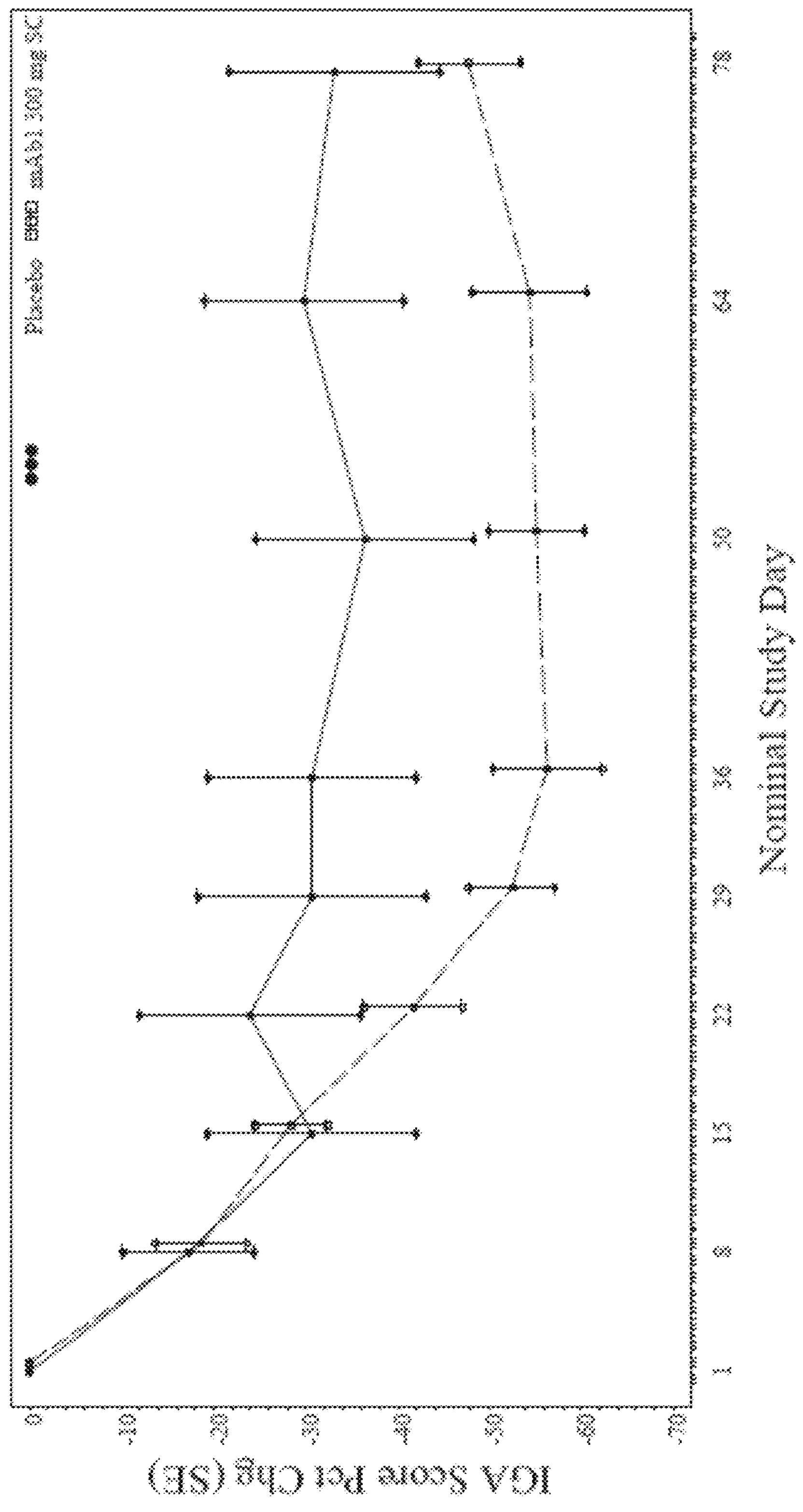
FIG. 38 shows mean IGA score percent change from baseline—censored LOCF, for the study in Example 11.
Figure 39:
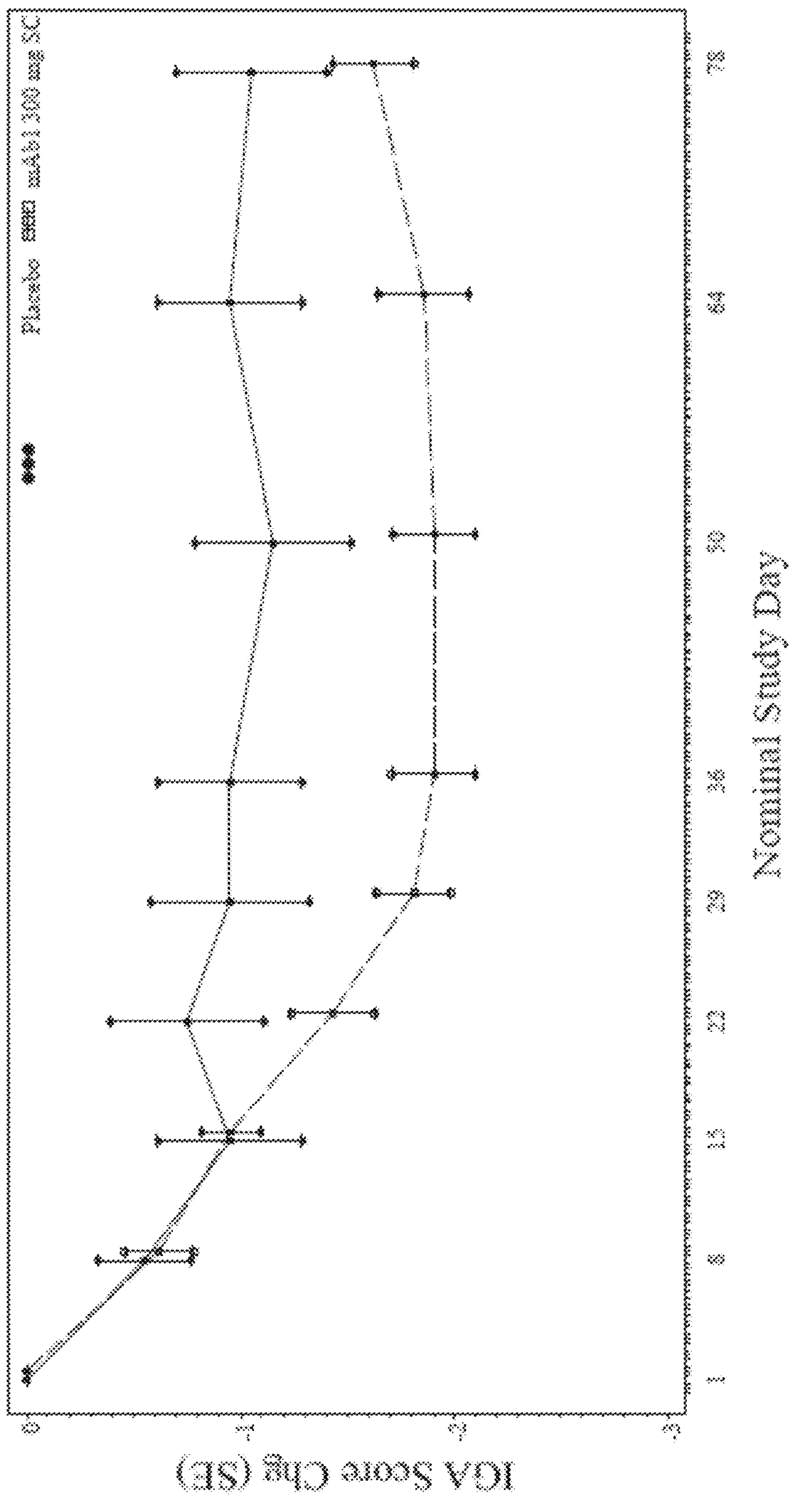
FIG. 39 shows mean IGA score change from baseline—censored LOCF, for the study in Example 11.
Figure 40:
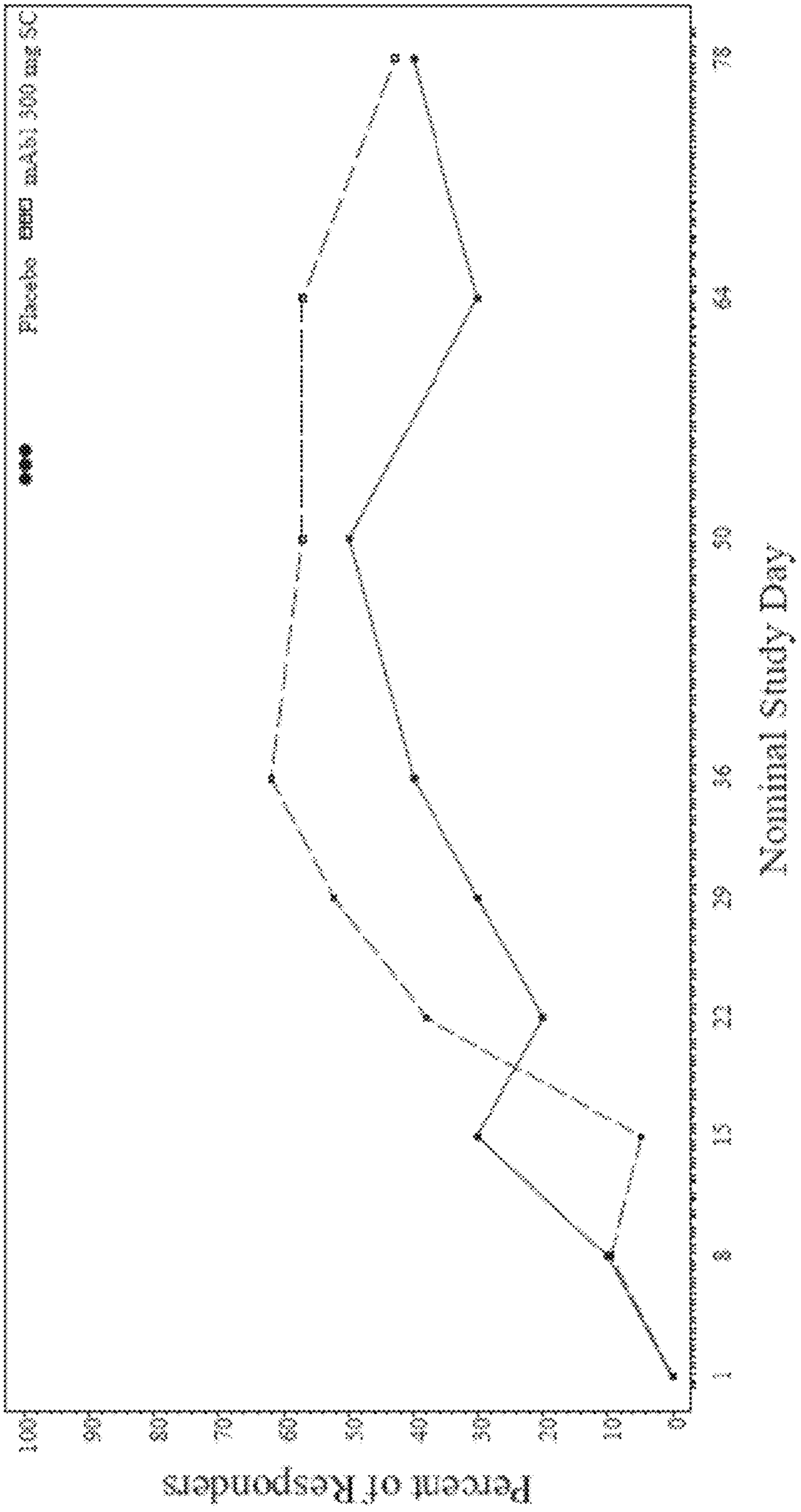
FIG. 40 shows IGA score responder rate (score of 0 or 1)—censored LOCF, for the study in Example 11.
Figure 41:
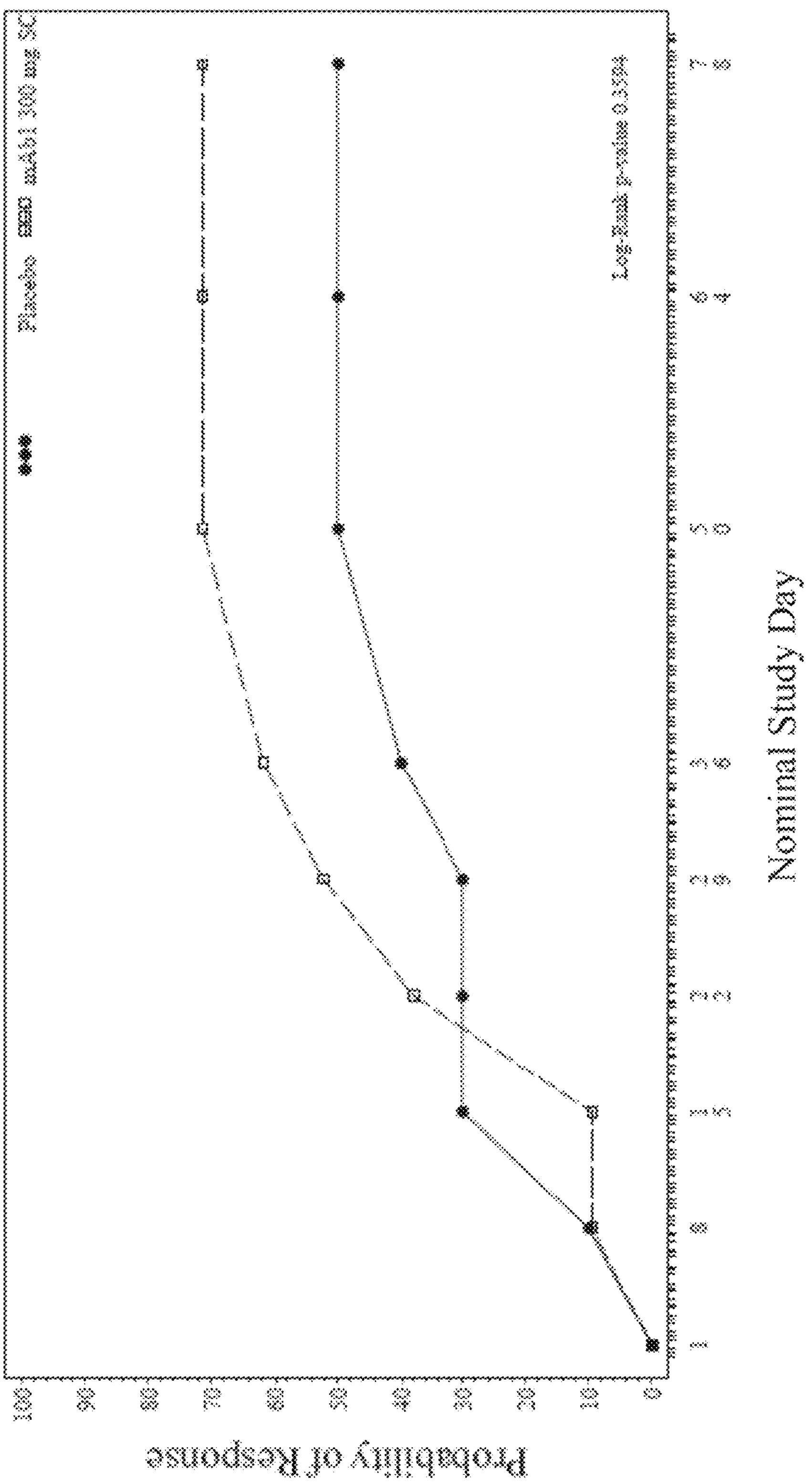
FIG. 41 shows a Kaplan-Meier plot of time to first IGA≤1—censored LOCF, for the study in Example 11.
Figure 42:
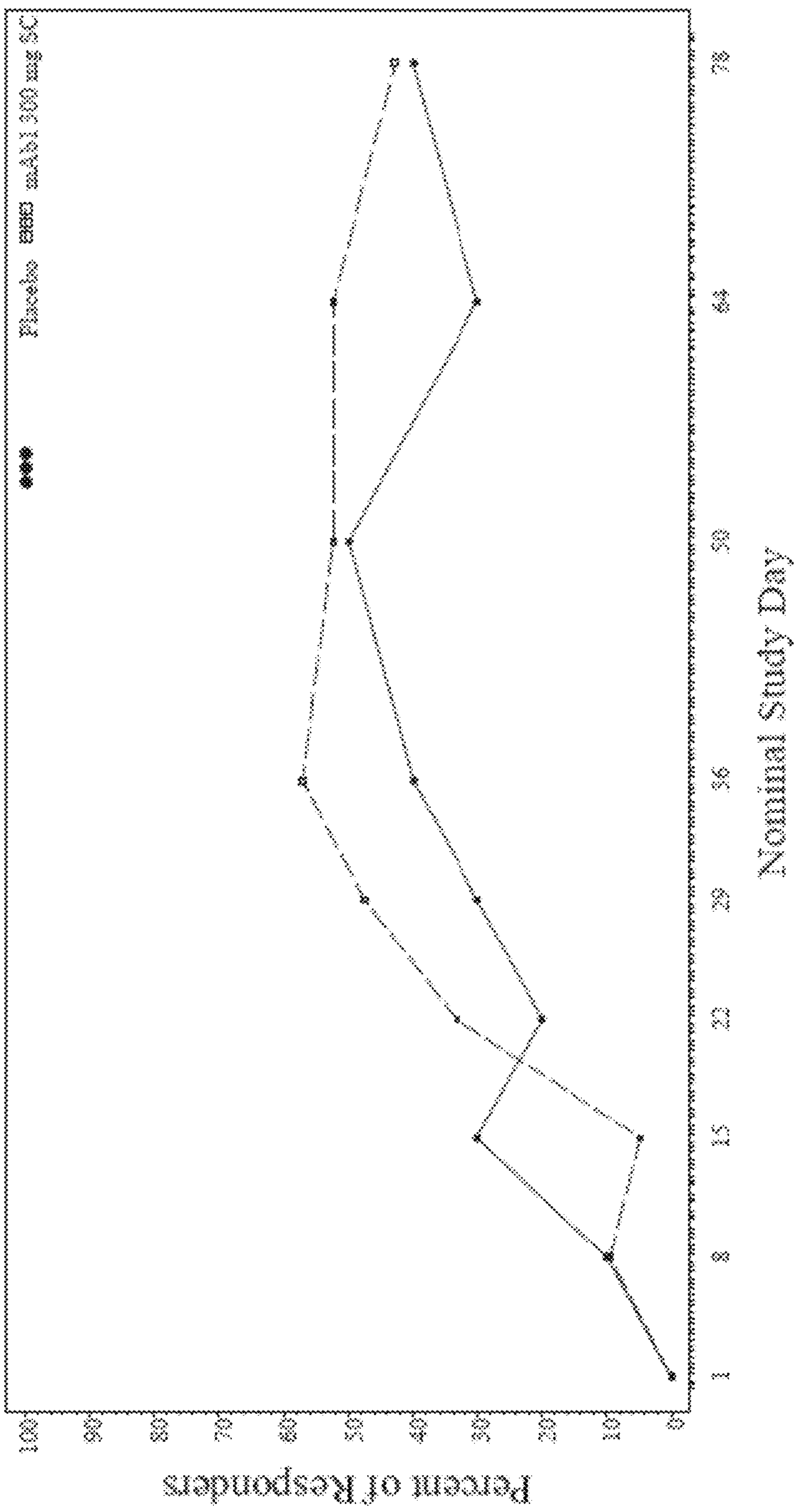
FIG. 42 shows proportion of patients with IGA≤1 at each visit who remained relapse-free—censored LOCF, for the study in Example 11.
Figure 43:
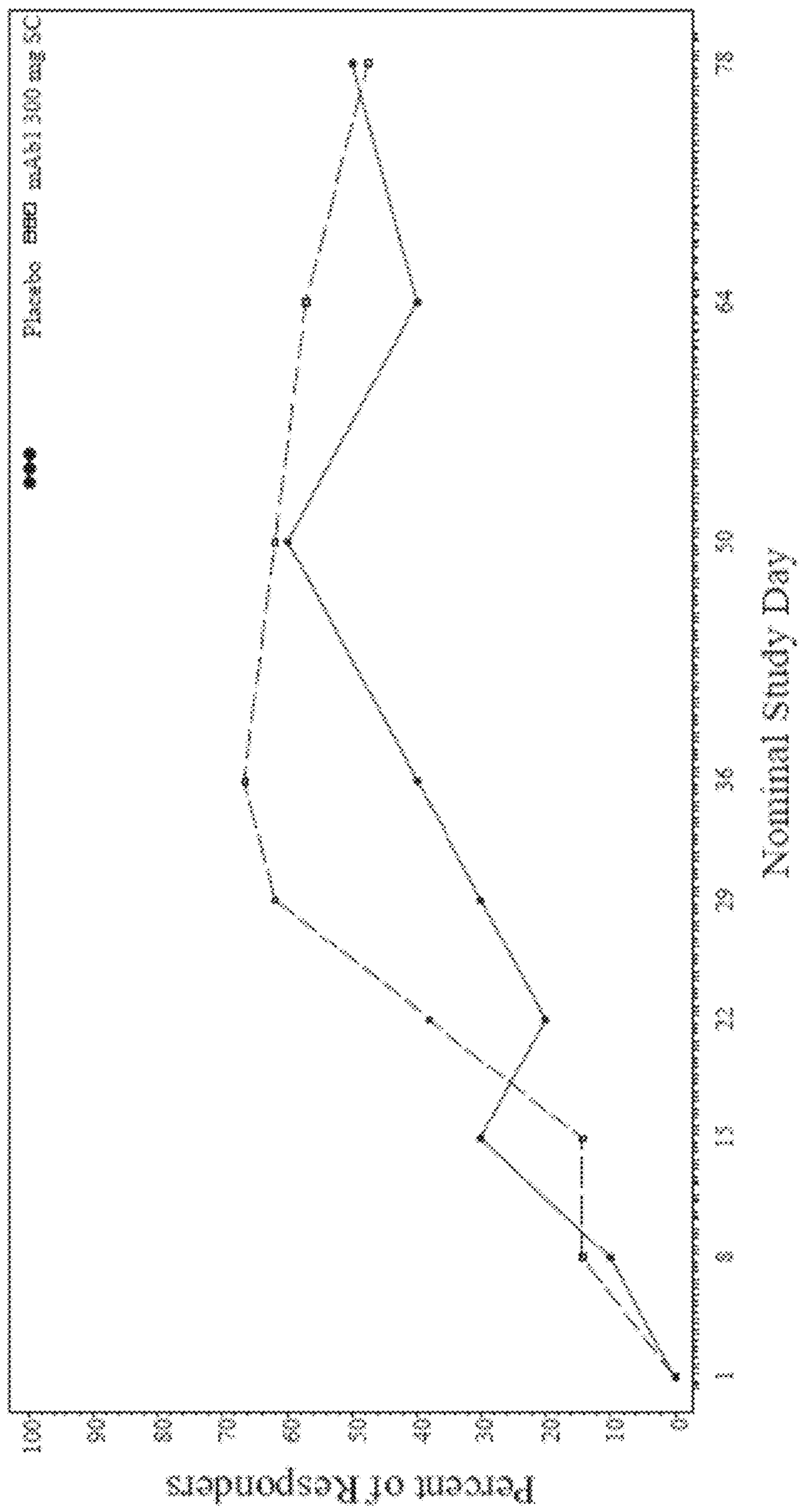
FIG. 43 shows proportion of patients with reduction from baseline in IGA≥2 at each visit—censored LOCF, for the study in Example 11.
Figure 44:
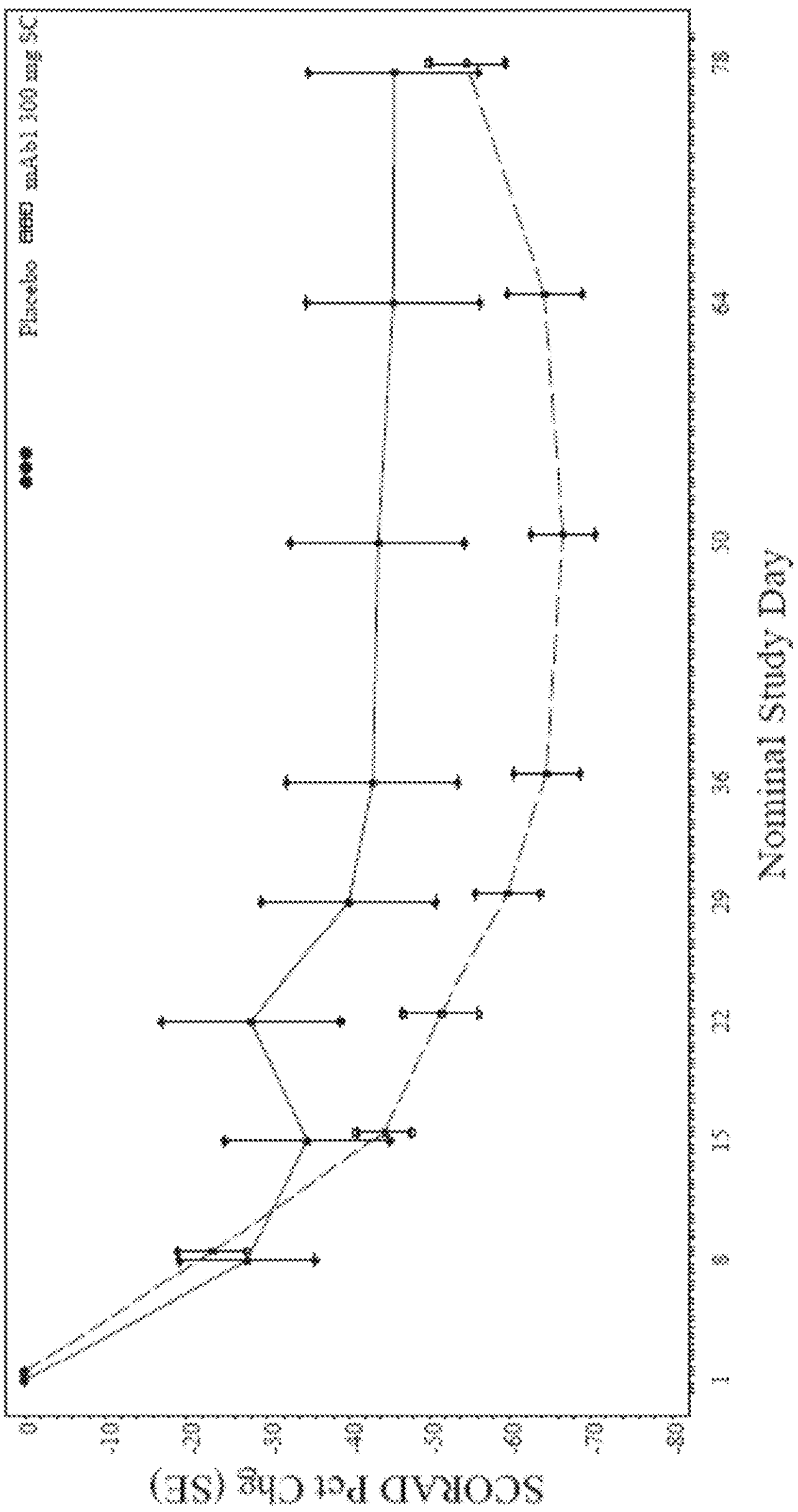
FIG. 44 shows mean SCORAD score percent change from baseline—censored LOCF, for the study in Example 11.
Figure 45:
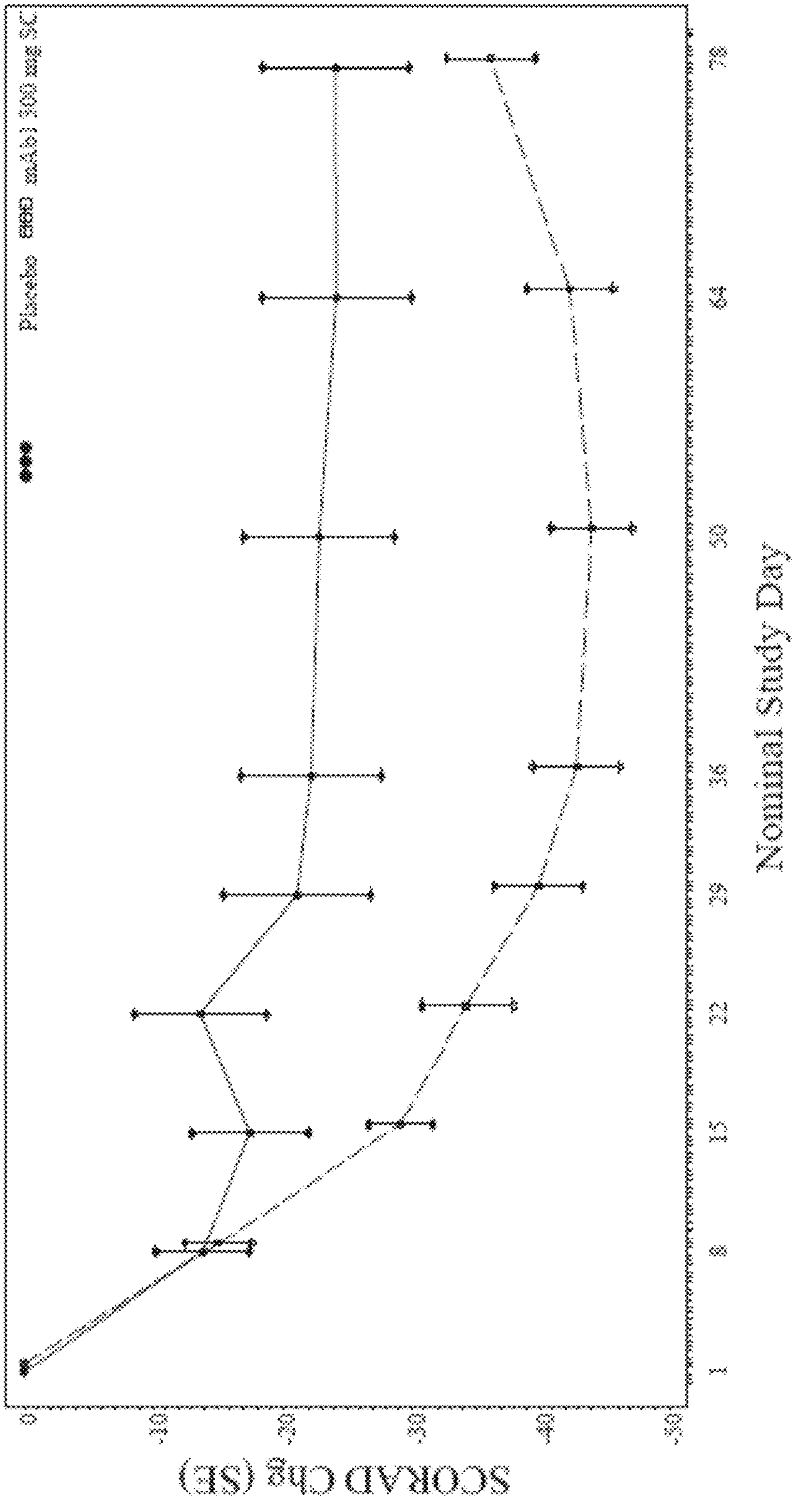
FIG. 45 shows mean SCORAD score change from baseline—censored LOCF, for the study in Example 11.
Figure 46:
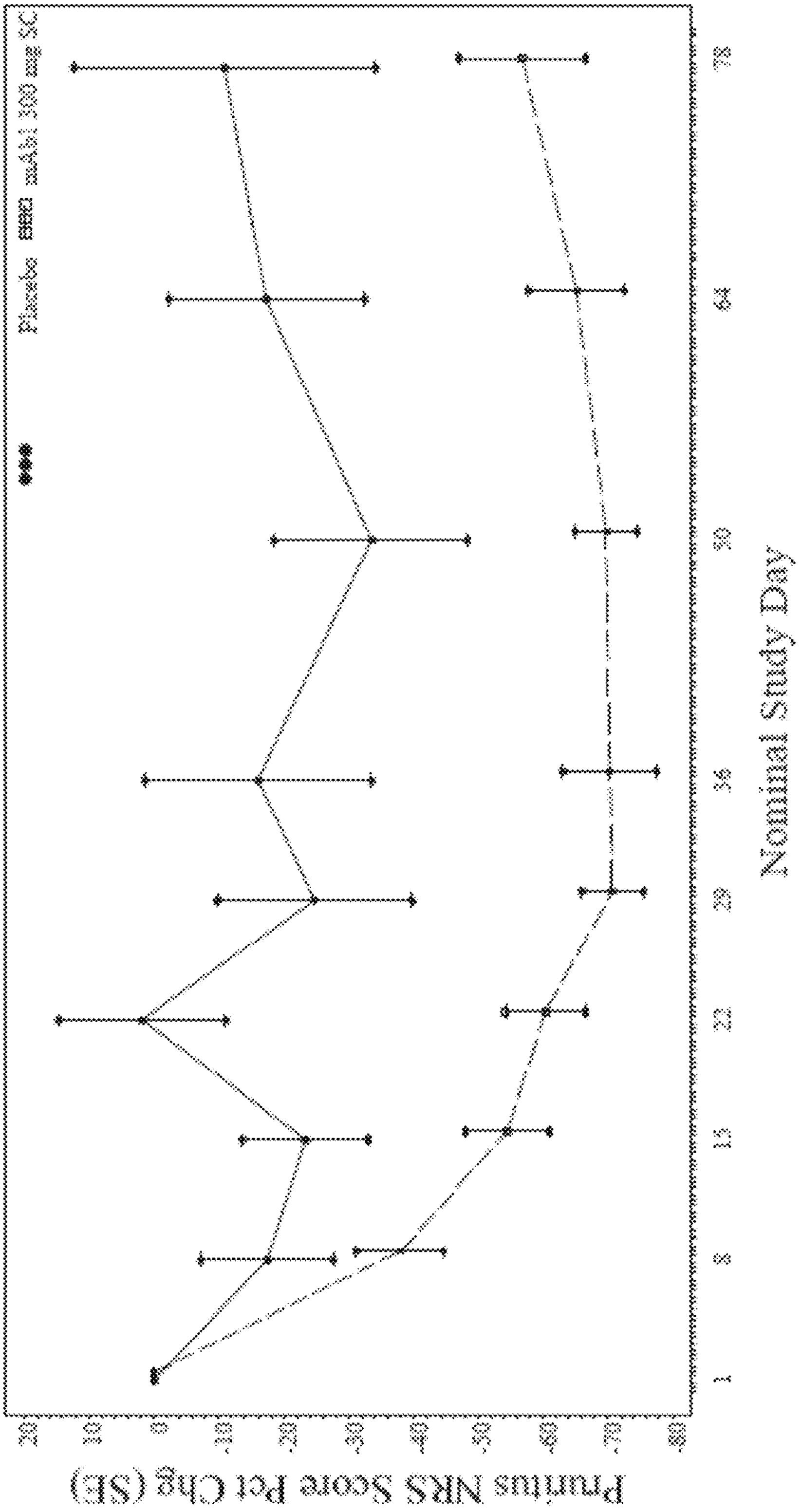
FIG. 46 shows mean pruritus NRS percent change from baseline—censored LOCF, for the study in Example 11.
Figure 47:
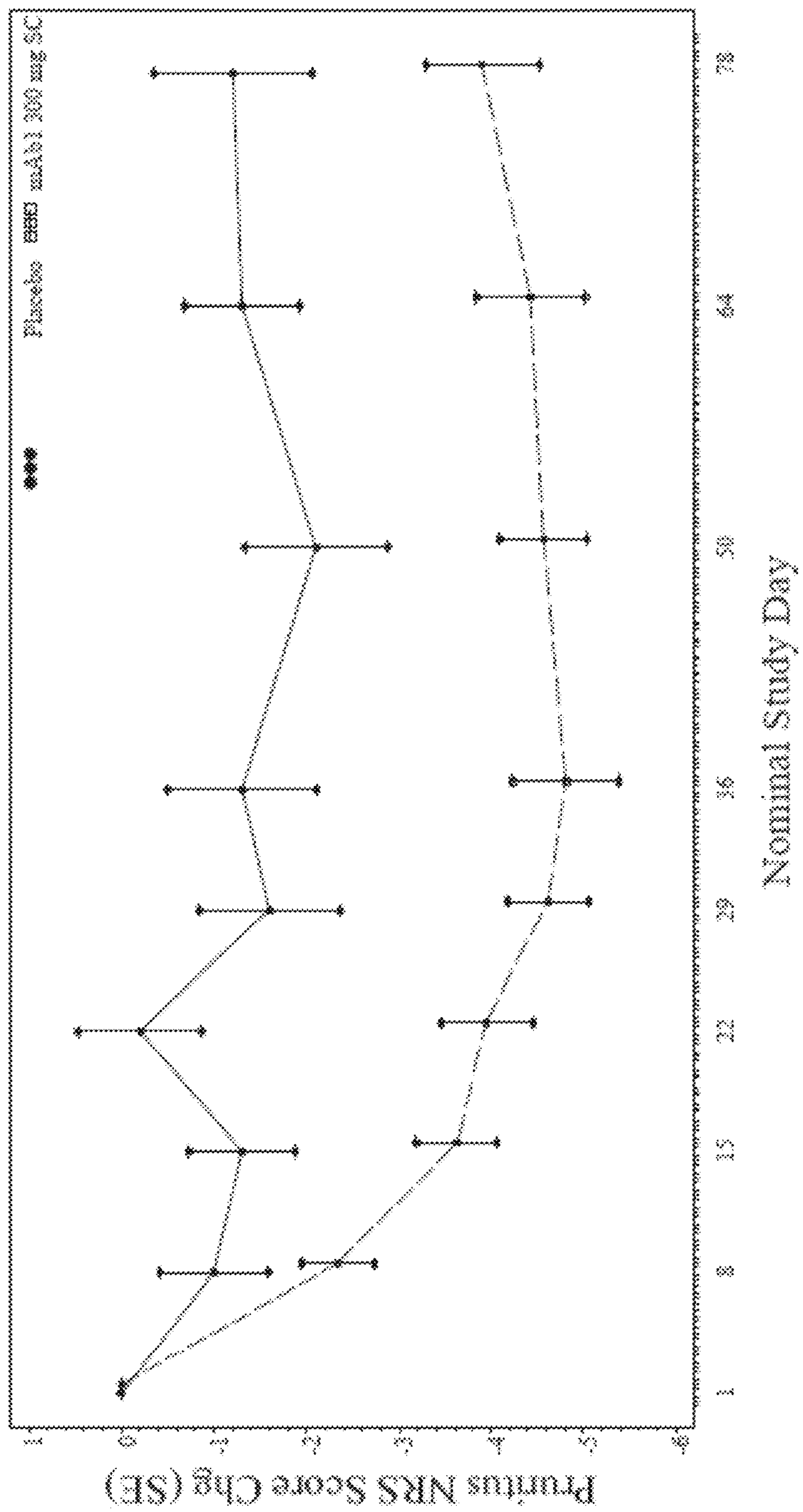
FIG. 47 shows mean pruritus NRS change from baseline—censored LOCF, for the study in Example 11.

For 300 mg mAb1, significant improvement was seen within 2 weeks in % BSA ($p<0.02$), IGA ($p<0.05$), and EASI ($p<0.0001$). Improvements for BSA, IGA and EASI ($p<0.05$ vs. placebo) were maintained for 8 weeks. The proportion of patients with IGA 0 or 1 at week 4 was higher than placebo, but not statistically significant (FIG. 22).

The most common treatment-emergent adverse events (AEs) with mAb1 administration were nasopharyngitis (19.6% vs. 12.5% for placebo) and headache (11.8% vs. 6.3% for placebo).

Example 9: Parallel-Group, Dose-Ranging Clinical Trial of Subcutaneously Administered Anti-IL-4R Antibody (mAb1) in Adult Patients with Moderate-to-Severe Atopic Dermatitis A. Study Design This study was a 32-week, randomized, double-blind, placebo-controlled, parallel group study to assess the dose response profile of weekly doses of mAb1 in adults with moderate-to-severe AD. The primary objective of the study was to assess the efficacy of multiple mAb1 dose regimens, compared to placebo, in adult patients with moderate-to-severe AD. The secondary objectives were: (1) to assess the safety of multiple mAb1 dose regimens, compared to placebo, in adult patients with moderate-to-severe AD; (2) to assess the pharmacokinetics (PK) of multiple mAb1 dose regimens in adult patients with moderate-to-severe AD; and (3) to assess the potential immune response across multiple mAb1 dose regimens, and to compare to placebo, in adult patients with moderate-to-severe AD.

The target population included adults with moderate-to-severe AD which could not be adequately controlled with topical medications or for whom topical treatment is otherwise inadvisable (e.g., side effects or safety risks). Approximately 240 to 288 patients were enrolled. Eligible patients were randomized in a 1:1:1:1:1:1 ratio to receive 1 of 6 weekly treatment regimens (5 active, 1 placebo). Randomization was stratified by disease severity (moderate vs. severe AD) and region (Japan vs. rest of world). The dosing schedule followed is given in Table 26.

TABLE 26

| All loading doses = 2 injections of 2 mL each; All week 1-week 15 doses = 1 injection of 2 mL | | | | |
|---|---|---|---|---|
| | Day 1 (loading dose) | | Subsequent dosing through week 15 | |
| N | 1 injection of each | Total dose | Dose regimen | Cumulative monthly dose |
| 40 | 300 mg<br>300 mg | 600 mg | 300 mg qw | 1200 mg |
| 40 | 300 mg<br>300 mg | 600 mg | 300 mg q2w | 600 mg |
| 40 | 300 mg<br>300 mg | 600 mg | 300 mg q4w | 300 mg |
| 40 | 200 mg<br>200 mg | 400 mg | 200 mg q2w | 400 mg |
| 40 | 200 mg<br>200 mg | 400 mg | 100 mg q4w | 100 mg |
| 40 | Placebo<br>Placebo | 0 mg | PBO qw | 0 mg |

All patients received 2 injections (a loading dose) on day 1, followed by weekly injections. For every 2 weeks (q2w) and every 4 weeks (q4w) dose-regimens, the next dose of study drug was administered at week 2 and week 4, respectively. Patients assigned to q2w and q4w dose-regimens received volume-matched placebo every week when mAb1 was not administered. After providing informed consent, patients were assessed for study eligibility at the screening visit. Patients who met eligibility criteria underwent day 1/baseline assessments, randomization, and then received a weekly injection of study drug from day 1 through week 15. During this time, patients returned for weekly clinic visits with some weeks requiring only a telephone contact. Patients (and/or caregivers) were trained on injecting study drug at visits 2, 3, 4, 5, and 6, and self-injected study drug at later study visits that required only a telephone contact. Patients were closely monitored at the study site for a minimum of 1 hour after each of the first 5 weekly injections. Safety, laboratory, and clinical effect assessments were performed at specified clinic visits. The end of treatment period visit occurred at week 16, 1 week after the last dose of study drug, when the primary endpoint was assessed. Follow-up visits occurred every 2 weeks from week 18 through week 32. The end of study visit occurred at week 32. Rescue treatment for AD (medication and/or phototherapy) was provided to study patients, if necessary, at the discretion of the investigator. Patients who needed rescue treatment were immediately discontinued from study drug, but were asked to continue to follow the schedule of study assessments. Efficacy measurements were obtained (Investigator's Global Assessment [IGA], Eczema Area and Severity Index [EASI], etc.) immediately before administering any rescue treatment. One sample for DNA analysis and multiple samples for RNA analysis were collected from patients who consent to participate in the optional genomic sub-study.

Study Treatment:

mAb1 administered subcutaneously: 300 mg weekly (qw), 300 mg q2w, 300 mg q4w, 200 mg q2w, or 100 mg q4w, from day 1 through week 15 OR once weekly subcutaneous dose of placebo from day 1 through week 15. A basic bland topical emollient was applied twice daily from day −7 through day 8.

Endpoints of the Study:

The primary endpoint of the study was the percent change in EASI score from baseline to week 16. The secondary endpoints included: (1) proportion of patients achieving IGA 0 (clear) or 1 (almost clear) at week 16; (2) proportion of patients achieving IGA score reduction of 2 at week 16; (3) absolute change in EASI scores from baseline to week 16; (4) proportion of patients achieving EASI-50, EASI-75, and EASI-90 (50, 75 and 90% reduction from baseline in EASI score) at week 16; (6) proportion of patients achieving SCORAD-50, SCORAD-75, and SCORAD-90 (50, 75 and 90% reduction from baseline in SCORAD score) at week 16; (7) absolute and percent change from baseline in pruritus scores (NRS and 4-point categorical scale); (8) absolute and percent change from baseline in POEM scores; (9) changes from baseline in GISS components (erythema, infiltration/population, excoriations, and lichenification); 910) changes from baseline in GISS cumulative score; (11) incidence of treatment-emergent adverse events (TEAEs) from baseline through week 32; and (12) pharmacokinetic profile of multiple mAb1 dose regimens.

The other exploratory endpoints included: (1) distribution of disease severity scores (e.g., IGA, EASI, SCORAD) and change from baseline to various time points through week 16; (2) changes in Pruritus NRS, Pruritus categorical scale, SCORAD (pruritus VAS and sleep disturbance VAS), patient global assessment of disease status, patient global assessment of treatment effect, DLQI, POEM, EQ-5D, Itchy QOL, and HADS from baseline to various time points through week 16; (3) absolute and percent change in % BSA, SCORAD score, EASI and Pruritus NRS, from baseline to various time points through week 16; (4) proportion of patients who achieve reduction of IGA score by ≥2 from baseline to various time points through week 16; (5) proportion of patients who achieve reduction of IGA score by ≥3 from baseline to various time points through week 16; (6) changes in efficacy parameters from week 16 to week 32; (7) Incidence and profile (titers over time) of mAb1 ADAs; (8) effect of mAb1 plasma concentration on ADA formation and persistence; (9) effect of ADA on mAb1 plasma concentration; (14) effect of ADA on clinical outcomes (safety and efficacy); (10) effect of PK parameters (Cmax and AUC) on clinical outcomes; and (11) effect of body weight on drug exposure and clinical outcomes.

Rationale for Study Design:

The purpose of this study was to find an optimal dose-regimen, which will be further investigated in confirmatory phase 3 studies. The design of this phase 2b study was informed by results from a previous mAb1 study, which investigated the safety and efficacy of a 300 mg dose of mAb1 administered weekly (qw) for 12 consecutive weeks in patients with moderate-to-severe AD. The selection of phase 2b dose-regimens was also supported by observed and simulated correlations between pharmacokinetic (PK) and pharmacodynamics (PD) parameters (PK/PD models) from earlier clinical trials. Using 300 mg qw (i.e., the dose-regimen studied in phase 2a) as the high anchor of the dose range, the goal was to identify the lowest dose-regimen with maximal or near-maximal efficacy and/or, depending on mAb1's emerging safety profile, find the dose-regimen with the best benefit/risk ratio. Accordingly, 5 mAb1 dose-regimens were selected to reasonably cover the spectrum between a potentially supra-therapeutic dose-regimen (i.e., the high anchor) and a dose-regimen with clearly sub-optimal efficacy (i.e., the low anchor). The protocol also included a placebo arm to allow comparison of each active dose-regimen to a control.

Use of Loading Doses:

Most patients received a loading dose on day 1, consisting of a doubling of the nominal dose that was administered at subsequent visits. This allowed systemic concentrations of mAb1 to reach steady state and the targeted systemic concentration faster, and potentially reducing the time to clinical benefit. Study treatment was administered for 16 weeks so that systemic concentrations of functional mAb1 could stabilize for all dose-regimens investigated. Pharmacokinetic modeling suggested that 'every-4-weeks' (q4w) dose-regimens could result in declining trough concentrations following an initial loading dose. Consequently, the immunogenic potential of these regimens may not be fully expressed within a shorter treatment course. After the last dose of study drug, all patients were followed for 16 additional weeks, which ensured that mAb1 clearance was virtually complete (plasma concentrations below the lower limit of quantification) before the end of study visit.

Rationale for Dose Selection:

The highest mAb1 dose-regimen administered in this study was 300 mg qw. When given as a short (4-week) treatment course, this dose-regimen was safe and appeared to be the most efficacious in earlier phase 1b clinical trials, in which it was investigated alongside lower dose-regimens (150 mg qw and 75 mg qw). Pharmacokinetic modeling suggested that 300 mg qw may be supra-therapeutic in the long run: mAb1 plasma concentrations did not reach steady state by week 4, and were projected to stabilize at levels considerably above those required to saturate the target, i.e., the membrane-bound alpha subunit of the IL-4 receptor. However, this needed to be confirmed by comparing 300 mg qw with lower dose-regimens in the context of a longer study treatment (12 weeks or longer), so that plasma concentrations could reach steady state for all dose-regimens investigated. Although 300 mg qw was administered for 12 weeks in an earlier study (e.g., phase 2a proof-of-concept), this dose-regimen was repeated in phase 2b to confirm phase 2a results and enabled a direct comparison with lower dose-regimens within the same study. Therefore, 300 mg qw was the high anchor of the dose range in the present study.

The low anchor of the dose-regimen range was 100 mg administered q4w. Based on PK/PD modeling, the resulting mAb1 plasma concentrations at steady state were expected to be consistently below target mediated clearance (i.e., at levels low enough such that mAb1 elimination was achieved primarily via its binding to the IL-4 receptor), suggesting that the clinical response associated with this dose-regimen was incomplete. Three other dose-regimens were selected between the high and low anchors. A summary of these dose-regimens and the main rationale for their selection is provided below:

300 mg qw: High anchor. Same dose-regimen studied in phase 2a.

- 300 mg every 2 weeks (q2w): High probability of success based on PK/PD data and models. Could be sufficient to maintain therapeutic drug levels over multiple dosing intervals.
- 300 mg q4w: PK modeling indicated that mAb1 plasma levels climbed rapidly to >60 mg/L after the administration of a loading dose, which was associated with a fast onset of action, q4w dosing could be sufficient to maintain the therapeutic effect over time. Since the 300 mg dose is the highest available, this regimen had the best chance to demonstrate efficacy for q4w administration.
- 200 mg q2w: Some efficacy expected without reaching the maximum therapeutic effect. Useful for dose-response assessment and further PK/PD modeling. Helped evaluate a full spectrum of q2w regimens.
- 100 mg q4w: Low anchor. Likely non-optimally efficacious dose.
- Placebo: Provided a reliable reference for any apparent drug effects.

Inclusion and Exclusion Criteria:

A patient had to meet the following criteria to be eligible for inclusion in the study: (1) Male or female, 18 years or older; (2) Chronic AD, (according to the AAD Consensus Criteria, [Eichenfeld 2004]), that has been present for at least 3 years before the screening visit; (3) EASI score ≥16 at the screening and baseline visits; (4) IGA score ≥3 (on the 0-4 IGA scale) at the screening and baseline visits; (5) 10% body surface area (BSA) of AD involvement at the screening and baseline visits; (6) Patients with documented recent history (within 3 months before the screening visit) of inadequate response to outpatient treatment with topical medications, or for whom topical treatments are otherwise inadvisable (e.g., because of important side effects or safety risks)*; (7) Patients must have applied a stable dose of an additive-free, basic bland emollient twice daily for at least 7 days before the baseline visit; (8) Willing and able to comply with all clinic visits and study-related procedures; (9) Able to understand and complete study-related questionnaires; and (10) Provide signed informed consent. *NOTE: For the purpose of this protocol, inadequate response represented failure to achieve and maintain remission or a low disease activity state (e.g., IGA 0=clear to 2=mild) despite treatment with topical corticosteroids of medium to high potency (±topical calcineurin inhibitors as appropriate), applied daily for at least 28 days or for the maximum duration recommended by the product prescribing information (e.g., 14 days for super-potent topical corticosteroids), whichever is shorter. Important side effects or safety risks are those that outweigh the potential treatment benefits (e.g., hypersensitivity reactions, significant skin atrophy, systemic effects, etc., or imminence thereof), as assessed by the investigator or by patient's treating physician.

A patient who met any of the following criteria was ineligible to participate in this study: (1) Prior treatment with mAb1; (2) Treatment with an investigational drug within 8 weeks or within 5 half-lives (if known), whichever is longer, before the baseline visit; (3) The following treatments within 4 weeks before the baseline visit, or any condition that will likely require such treatment(s) during the first 4 weeks of study treatment: systemic corticosteroids, immunosuppressive/immunomodulating drugs (e.g., cyclosporine, mycophenolate-mofetil, IFN-γ, azathioprine or methotrexate), or phototherapy for AD; (4) Treatment with topical corticosteroids, tacrolimus, and/or pimecrolimus within 1 week before the baseline visit; (5) Treatment with biologics as follows: any cell-depleting agents including but not limited to rituximab: within 6 months before the baseline visit, or until lymphocyte and CD 19+ lymphocyte count returns to normal, whichever is longer, infliximab, adalimumab, golimumab, certolizumab pegol, abatacept, etanercept, anakinra: within 16 weeks before the baseline visit for any indication, or within 5 years for dermatological indications, or other biologics: within 5 half-lives (if known) or 16 weeks, whichever is longer; (6) Treatment of AD with prescription moisturizers classified as medical device (e.g., Atopiclair®, MimyX®, EpiCeram®, CeraVe®, etc.) within 1 week before the baseline visit; (7) Regular use (more than 2 visits per week) of a tanning booth/parlor within 4 weeks before the baseline visit; (8) Planned or anticipated use of any prohibited medications and procedures (including, but not limited to, topical tacrolimus and pimecrolimus; corticosteroids; prescription moisturizers classified as medical devices such as Atopiclair®, MimyX®, EpiCeram®, CeraVe®, etc.; allergen immunotherapy; systemic treatment for AD with an immunosuppressive/immunomodulating substance; treatment with a live (attenuated) vaccine or with an investigational drug (other than mAb1); major elective surgeries) during study treatment; (9) Treatment with a live (attenuated) vaccine within 12 weeks before the baseline visit; (10) Chronic or acute infection requiring treatment with antibiotics, antivirals, antiparasitics, antiprotozoals, or antifungals within 4 weeks before the screening visit, or superficial skin infections within 1 week before the screening visit; (11) Known or suspected immunosuppression, including history of invasive opportunistic infections (e.g., histoplasmosis, listeriosis, coccidioidomycosis, pneumocystosis, aspergillosis) despite infection resolution, or otherwise recurrent infections of abnormal frequency, or prolonged infections suggesting an immune-compromised status, as judged by the investigator; (12) Known history of human immunodeficiency virus (HIV) infection or HIV seropositivity at the screening visit; (13) Positive or indeterminate hepatitis B surface antigen (HBsAg), hepatitis B core antibody (HBcAb), or hepatitis C antibody at the screening visit; (14) Elevated transaminases (ALT and/or AST) more than 3 times the upper limit of normal (>3×ULN) at the screening visit; (15) History of clinical endoparasitosis within 12 months before the baseline visit, other than treated vaginal trichomoniasis; (16) Presence of skin comorbidities that may interfere with study assessments; (17) History of malignancy within 5 years before the baseline visit, except completely treated in situ carcinoma of the cervix, completely excised non-metastatic squamous or basal cell carcinoma of the skin; (18) History of non-malignant lymphoproliferative disorders; (19) High risk of parasite infection, such as residence within or recent travel (within 12 months before the baseline visit) to areas endemic for endoparasitoses, where the circumstances are consistent with parasite exposure (e.g., extended stay, rural or slum areas, lack of running water, consumption of uncooked, undercooked, or otherwise potentially contaminated food, close contact with carriers and vectors, etc.), unless subsequent medical assessments (e.g., stool exam, blood tests, etc.) have ruled out the possibility of parasite infection/infestation; (20) History of alcohol or drug abuse within 2 years before the screening visit; (21) Severe concomitant illness(es) that, in the investigator's judgment, would adversely affect the patient's participation in the study. Examples include, but are not limited to patients with short life expectancy, patients with uncontrolled diabetes (HbA1c≥9%), patients with cardiovascular conditions (e.g., stage III or IV cardiac failure according to the New York Heart Association classification), severe renal conditions (e.g., patients on dialysis) hepato-biliary conditions (e.g., Child-Puig class B or C), neurological conditions (e.g., demyelinating diseases), active major autoimmune diseases (e.g., lupus, inflammatory bowel disease, rheumatoid arthritis, etc.), other severe endocrinological, gastrointestinal, metabolic, pulmonary, or lymphatic diseases. The specific justification for patients excluded under this criterion will be noted in study documents (chart notes, case report forms [CRF], etc.); (22) Any other medical or psychological condition including relevant laboratory abnormalities at screening that, in the opinion of the investigator, suggest a new and/or insufficiently understood disease, may present an unreasonable risk to the study patient as a result of his/her participation in this clinical trial, may make patient's participation unreliable, or may interfere with study assessments. The specific justification for patients excluded under this criterion will be noted in study documents (chart notes, CRF, etc.); (23) Planned major surgical procedure during the patient's participation in this study; (24) Patient is a member of the investigational team or his/her immediate family; (25) Pregnant or breast-feeding women; and (26) Unwilling to use adequate birth control, if of reproductive potential and sexually active. Adequate birth control is defined as agreement to consistently practice an effective and accepted method of contraception throughout the duration of the study and for 16 weeks after last dose of study drug.

B. Safety

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

In addition, laboratory safety variables, vital sign variables, 12-lead electrocardiography (ECG) variables, and physical examination variables were measured throughout the study.

The clinical laboratory data consists of hematology, blood chemistry and urinalysis. Blood samples for hematology testing were collected at every study visit; blood samples for serum chemistry testing and urine samples for urinalysis were collected to measure overall patient health at screening, day 1/baseline (pre-dose), day 15, day 29, day 43, day 57, day 71, day 85, day 99, day 113, day 141, day 169, and day 197 (end-of-study) or early termination if subject is discontinued from the study.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 4, 8, 15, 22, 25, 29, 43, 64, 71, 85, 99, 113, 127, 141, 155, 169, 183, 197 and 211 (end of study) or early termination. Vital signs were taken at 1 and 2 hours post-injection following the study drug dose on days 1, 8, 15, and 22.

12-Lead ECG parameters include: Ventricular HR, PR interval, QRS interval, corrected QT interval (QTcF=QT/[$RR^{0.33}$] and QTcB=QT/[$RR^{0.5}$]) ECG status: normal, abnormal not clinical significant or abnormal clinical significant. A standard 12-lead ECG was performed at screening, day 29, and day 113 (end of treatment) or early termination.

A thorough and complete physical examination was performed at screening, day 29, and day 113 (end of treatment) or early termination.

C. Efficacy Variables

The efficacy variables IGA, BSA, EASI, SCORAD, 5-D Pruritus scale, and Pruritus NRS rating have been described elsewhere herein (see, e.g., Example 7).

The IGA, BSA, EASI and SCORAD scores were assessed at every clinic visit. Patients underwent 5-D pruritus assessment at the following visits: screening, day 1/baseline (pre-dose), day 113 (end of treatment), and day 211 (end of study) or early termination. Patients used the IVRS to record their Pruritus NRS score twice daily through the last study visit.

In addition, other variables such as Global Individual Signs Score (GISS), Pruritus Categorical Scale, Patient Oriented Eczema Measure (POEM), Dermatology Life Quality Index (DLQI), Itchy QOL, EQ-50, HADS, and Patient Global Assessment of Disease Status and Treatment Effect were also assessed.

Baseline for efficacy variable was defined as the last non-missing value on or before the date of randomization. For the patient who had no value on or before his/her randomization date, the last non-missing value on or before the date of first dose injection was used as baseline.

Example 10: Repeat-Dose Clinical Trial of Subcutaneously Administered Anti-IL-4R Antibody (mAb1) in Adult Patients with Moderate-to-Severe Atopic Dermatitis A. Study Design This study was a 28-week randomized, double-blind, placebo-controlled study of the anti-IL-4R mAb, referred herein as "mAb1", administered subcutaneously in patients with moderate-to-severe atopic dermatitis. The treatment period was 12 weeks in duration with the patients followed for a further 16 weeks after end of the treatment.

109 patients were included and randomized in the ratio of 1:1 for the study (54 in placebo and 55 for 300 mg of the antibody). 43 patients (30 in placebo and 13 in 300 mg group) withdrew from the study. Randomization was stratified according to IgE levels (IgE<150 kU/L vs. 150 kU/L at the screening visit) to test the efficacy of mAb1 in patients with extrinsic or intrinsic form of AD. Patients who met eligibility criteria underwent day 1/baseline assessments, randomization, and then received 300 mg of mAb1 or placebo SC. Each weekly dose of study drug was given as one 2-mL injection, or was split into two 1-mL injections. Patients returned for weekly clinic visits and received an injection of study drug on days 8, 15, 22, 29, 36, 43, 50, 57, 64, 71, and 78. Patients were closely monitored at the study site for a minimum of 2 hours after each dose of study drug. The end of the treatment period was day 85. Follow-up visits occurred on days 92, 99, 106, 113, 120, 127, 134, 141, 148, 155, 162, 169, 176, 183, 190, and the end of study visit on day 197.

Inclusion criteria for the study were as follows: (1) Male or female 18 years or older; (2) Chronic AD, diagnosed by the Eichenfield revised criteria of Hannifin and Rajka, that has been present for at least 3 years before the screening visit; (3) EASI score 16 at the screening and baseline visits; (4) IGA score 3 at the screening and baseline visits; (5) 10% BSA of AD involvement at the screening and baseline visits; (6) history of inadequate response to a stable (1 month) regimen of topical corticosteroids or calcineurin inhibitors as treatment for AD within the last 3 months before the screening visit; (7) Patients must have applied a stable dose of an additive-free, basic bland emollient twice-daily for at least 7 days before the baseline visit; and (8) Willingness, commitment, and ability to return for all clinic visits and complete all study-related procedures and willing and able to sign the informed consent form (ICF).

Exclusion criteria for the study were as follows: (1) Prior treatment with mAb1; (2) Presence of any of the following laboratory abnormalities at the screening visit: white blood cell count $<3.5\times10^3/\mu L$; platelet count $<125\times10^3/\mu L$; neutrophil count $<1.75\times10^3/\mu L$; aspartate aminotransferase (AST)/alanine aminotransferase (ALT)>1.5×the ULN; and CPK>2× the ULN; (3) Positive or indeterminate results at the screening visit for hepatitis B surface antigen, hepatitis B core antibody or hepatitis C antibody; (4) Onset of a new exercise routine or major change to a previous exercise routine within 4 weeks prior to screening (visit 1). Subjects had to be willing to maintain a similar level of exercise for the duration of the study and to refrain from unusually strenuous exercise for the duration of the trial; (5) Treatment with an investigational drug within 8 weeks or within 5 half-lives, if known, whichever is longer, before the baseline visit; (6) Treatment with a live (attenuated) vaccine within 12 weeks before the baseline visit; (7) Treatment with allergen immunotherapy within 6 months before the baseline visit; (8) Treatment with leukotriene inhibitors within 4 weeks before the baseline visit; (9) Treatment with systemic corticosteroids within 4 weeks before the baseline visit; (10) Treatment with topical corticosteroids, tacrolimus, and/or pimecrolimus within 1 week before the baseline visit; (11) Systemic treatment for AD with an immunosuppressive/immunomodulating substance, e.g. Cyclosporine, mycophenolate-mofetil, IFN-γ, phototherapy, (narrow band uvB, uvB, uvA1, psoralen+uvA), azathioprine, methotrexate, or biologics, within 4 weeks before the baseline visit; (12) three or more bleach baths during any week within the 4 weeks before the baseline visit; (13) Treatment of AD with a medical device (e.g. Atopiclair®, MimyX®, EpiCeram®, CeraVe®, etc.) within 1 week before the baseline visit; (14) Chronic or acute infection requiring treatment with oral or IV antibiotics, antivirals, anti-parasitics, anti-protozoals, or anti-fungals within 4 weeks before the screening visit, or superficial skin infections within 1 week before the screening visit; (15) Known history of HIV infection; (16) History of hypersensitivity reaction to doxycycline or related compounds; (17) History of clinical parasite infection, other than vaginal trichomoniasis; (18) History of malignancy within 5 years before the baseline visit, with the following exceptions; patients with a history of completely treated carcinoma in situ of cervix, and non-metastatic squamous or basal cell carcinoma of the skin are allowed; (19) Planned surgical procedure during the length of the patient's participation in the study; (20) Use of a tanning booth/parlor within 4 weeks before the screening visit; (21) Significant concomitant illness or history of significant illness such as psychiatric, cardiac, renal, neurological, endocrinological, metabolic or lymphatic disease, or any other illness or condition that would have adversely affected the subject's participation in this study; (22) Pregnant or breast-feeding women; and/or (23) Unwilling to use adequate birth control. Adequate birth control is defined as agreement to consistently practice an effective and accepted method of contraception throughout the duration of the study and for 16 weeks after last dose of study drug. For females, adequate birth control methods are defined as: hormonal contraceptives, intrauterine device (IUD), or double barrier contraception (i.e., condom+diaphragm, condom or diaphragm+spermicidal gel or foam). For males, adequate birth control methods are defined as: double barrier contraception (i.e., condom+diaphragm, condom or diaphragm+spermicidal gel or foam). For females, menopause is defined as 24 months without menses; if in question, a follicle-stimulating hormone of ≥25 U/mL must be documented. Hysterectomy, bilateral oophorectomy, or bilateral tubal ligation must be documented, as applicable.

B. Efficacy Variables

The primary endpoint was the percent change in EASI score from baseline to week 12. The secondary endpoints measured in this study included: (1) proportion of patients who achieved an investigator's global assessment (IGA) score of 0 or 1 at week 12; (2) proportion of patients who achieved 50% overall improvement in EASI score (also called EASI 50) from baseline to week 12; (3) change in EASI score from baseline to week 12; (4) change and percent change in IGA score, body surface area involvement of atopic dermatitis (BSA), eczema area and severity index (EASI), SCORAD, Pruritus NRS and 5-D pruritus scale from baseline to week 12; (5) Incidence of TEAEs from baseline through week 28; (6) change from baseline in eosinophils, TARC, Phadiatop™ results, and total IgE associated with response; (7) change in QoLIAD from baseline to week 12; (8) proportion of patients who achieve reduction of IGA score of ≥2 from baseline to week 12; (9) proportion of patients who achieve reduction of IGA score of ≥3 from baseline to week 12; and (10) PD response of circulating eosinophils, TARC and total IgE.

Baseline for efficacy variable is defined as the last non-missing value on or before the date of randomization. For the patient who has no value on or before his/her randomization date the last non-missing value on or before the date of first dose injection will be used as baseline.

Investigation Procedures

The efficacy variables IGA, BSA, EASI, SCORAD, 5-D Pruritus scale, and Pruritus NRS rating have been described elsewhere herein (see, e.g., Example 7).

The IGA, BSA, EASI and SCORAD scores were assessed at every clinic visit. Patients underwent 5-D pruritus assessment at the following visits: screening, day 1/baseline (pre-dose), and days 15, 29, 43, 57, 71, 85, 99, 113, 127, 141, 155, 169, 183 and 197 (end of study) or early termination. Patients used the IVRS to record their Pruritus NRS score twice daily through the last study visit.

Quality of Life Index for Atopic Dermatitis (QoLIAD):

The QoLIAD is a 25-item, validated questionnaire used in clinical practice and clinical trials to assess the impact of AD disease symptoms and treatment on QoL. The format is a simple yes/no response to 25 items with a scoring system of 0 to 25; a high score is indicative of a poor QoL. The questionnaire was administered at screening and day 1/baseline (pre-dose), and days 29, 57, 85, 99, 113, 127, 141, 155, 169, 183, and 197 (end of study) or early termination.

C. Investigational Treatment mAb1 drug product was supplied as a lyophilized powder in a 5 ml glass vial for SC administration. When delivered SC, the mAb1 drug product was reconstituted with 2.5 ml of sterile water for injection, yielding a solution containing 150 mg/mL of mAb1. The dose level of mAb1 tested was 300 mg for SC administration. mAb1 or placebo was administered as 1 (2 mL) or 2 (1 mL) SC injections in the clinic on day 1/baseline and days 8, 15, 22, 29, 36, 43, 50, 57, 64, 71, and 78. Although it was preferred that each weekly dose of study drug be given as one 2-mL injection, each weekly dose could be split into two 1-mL injections. Subcutaneous injection sites were alternated between the following sites: back of arms, abdomen (except the navel or waist area), and upper thighs. Administration to the extremities was not allowed due to the possibility of different absorption and bioavailability. If administration of multiple injections were required on the same day, each injection was delivered at a different injection site (e.g., 1 injection administered in the right lower quadrant of the abdomen and the other in the left lower quadrant of the abdomen). Subcutaneous injection sites were alternated so that the same sites were not injected for 2 consecutive weeks.

Placebo matching mAb1 was prepared in the same formulation as mAb1, but without addition of antibody.

Patients were monitored at the study site for a minimum of 2 hours after each dose of study drug.

In addition, patients were required to apply stable doses of an additive-free, basic bland emollient twice daily for at least 7 days before the baseline visit and throughout study participation. Patients reported compliance with background treatment during the study using the IVRS or IWRS. The system prompted patients to answer the following question about emollient use: "Did you use a moisturizer approved by the study doctor on the affected areas of your skin?"

D. Safety Assessment

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

In addition, laboratory safety variables, vital sign variables, 12-lead electrocardiography (ECG) variables, and physical examination variables were measured throughout the study.

The clinical laboratory data consists of hematology, blood chemistry and urinalysis. Blood samples for hematology testing were collected at every study visit; blood samples for serum chemistry testing and urine samples for urinalysis were collected to measure overall patient health at screening, day 1/baseline (pre-dose), day 15, day 29, day 43, day 57, day 71, day 85, day 99, day 113, day 141, day 169, and day 197 (end-of study) or early termination if subject is discontinued from the study.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 8, 15, 22, 29, 36, 43, 50, 57, 64, 71, 78, 85, 99, 113, 141, 169 and 197 (end of study) or early termination. Vital signs were taken at 1 and 2 hours post-injection following the study drug dose on days 1, 8, 15, 22, 29, 36, 43, 50, 57, 64, 71 and 78.

12-Lead ECG parameters include: Ventricular HR, PR interval, QRS interval, corrected QT interval ($QTcF=QT/[RR^{0.33}]$ and $QTcB=QT/[RR^{0.5}]$) ECG status: normal, abnormal not clinical significant or abnormal clinical significant. A standard 12-lead ECG was performed at screening, day 141, and day 197 (end of study) or early termination.

Research samples (serum/RNA/plasma) were collected at screening and day1/baseline (pre-dose), and days 8, 15, 22, 29, 57, 85, and 197 (end of study) or early termination, and at unscheduled visits.

A thorough and complete physical examination was performed at screening, day 85, and day 197 (end of study) or early termination.

E. Data Analysis

1. Analyses of Exploratory Efficacy Variables

All categorical variables were analyzed using the Fisher's Exact test with nominal p-value and confidence intervals reported. All continuous variables were analyzed by the ANalysis of COVAriance (ANCOVA) using baseline IgE stratum (<150 kU/L vs. ≥150 kU/L at the screening visit). Unless otherwise specified, assessments of changes from baseline and construction of confidence intervals for continuous measures were based on an ANCOVA model which includes treatment as the main factor and baseline value as covariates. Point estimate and 95% CI of the difference in adjusted mean change from baseline between two treatment groups are provided. Missing values will be imputed by the last observation carried forward (LOCF) approach. In the event that the model assumptions are not warranted, the Rank-based analysis of covariates will be used.

2. Analysis of Safety Data

The safety analysis is based on the reported AEs, clinical laboratory evaluations, vital signs, and 12-lead ECG. Thresholds for Potentially Clinically Significant Values (PCSV) in laboratory variables, vital signs and ECG are defined in SAP. The time interval to detect any event or abnormality is between the infusion of study medication and end of study. Data collected outside this interval are excluded from the calculation of descriptive statistics and identification of abnormalities for laboratory evaluations, vital signs and ECG.

F. Safety: Results mAb1 was generally well-tolerated with a favorable safety profile. The overall adverse event (AE) profile was characteristic of a healthy population. No deaths were reported. There were 8 patients with SAEs, of which 1 was in mAb1 group (facial bones fracture) and 7 were in the placebo group (angina pectoris, cellulitis, eczema herpeticum, skin bacterial infection, renal failure, asthmatic crisis, lung disorder and atopic dermatitis). There were 8 patients with TEAE resulting in discontinuation from study drug, of which 1 was in the mAb1 group and 7 in the placebo group. There were 87 patients with at least one TEAE (n=43 [78.2%] in mAb1 vs. 44 [81.5%] in placebo group). The most frequent TEAEs were nasopharyngitis infections in subjects dosed with mAb1 (n=22 [40%] vs. 10 [18.5%] for placebo). Other TEAEs in the treatment group included eye infections, nervous system disorders, and general disorders and administration site conditions. No other clinically significant laboratory test results (blood chemistry, hematology, or urinalysis) were reported during the study. No trends were seen in mean/median baseline in any laboratory parameter. There were no significant trends in mean or median changes from baseline in temperature or pulse throughout the study. No clinically significant abnormalities were seen on physical examination results, ECGs or vital signs.

Subcutaneous administration of mAb1 to adult patients with moderate-to-severe AD was generally safe and well-tolerated.

G. Efficacy: Results

The baseline and exploratory efficacy results obtained from the study are summarized in FIGS. 23-33 and Tables 27-35. As noted above, patients were treated with 300 mg subcutaneous mAb1 once a week for 12 weeks, or with placebo.

TABLE 27

Summary of Baseline Characteristics-all values represented as Mean (SD)

| | Placebo | mAb1 300 mg | All Subjects Combined |
|---|---|---|---|
| No. Patients | 54 | 55 | 109 |
| Age (years) Mean (SD) | 39.4 (12.29) | 33.7 (10.41) | 36.5 (11.69) |
| Ethnicity n (%) | | | |
| Hispanic or Latino | 1 (1.9%) | 3 (5.5%) | 4 (3.7%) |
| Not Hispanic or Latino | 53 (98.1%) | 52 (94.5%) | 105 (96.3%) |
| Gender n (%) | | | |
| Male | 27 (50.0%) | 31 (56.4%) | 58 (53.2%) |
| Female | 27 (50.0%) | 24 (43.6%) | 51 (46.8%) |
| Height (cm) Mean (SD) | 171.2 (9.89) | 173.4 (9.88) | 172.3 (9.90) |
| Weight (kg) Mean (SD) | 72.41 (17.539) | 78.13 (17.416) | 75.30 (17.632) |
| BMI (kg/m$^2$) Mean (SD) | 24.51 (4.639) | 25.89 (4.837) | 25.20 (4.768) |
| Chronic Atopic Dermatitis Diagnosis Age | 14.4 (18.35) | 6.6 (10.53) | 10.5 (15.37) |
| BSA | 50.8 (24.14) | 46.8 (24.55) | 48.8 (24.32) |
| EASI Score | 30.8 (13.63) | 28.4 (13.57) | 29.6 (13.59) |
| IGA Score | 4.0 (0.69) | 3.9 (0.67) | 3.9 (0.68) |
| NRS Score | 5.8 (1.93) | 6.1 (1.34) | 5.9 (1.66) |
| SCORAD Score | 69.1 (13.38) | 66.7 (13.82) | 67.9 (13.59) |
| Pruritus 5-D Scale | 18.7 (3.50) | 18.4 (3.04) | 18.5 (3.26) |

TABLE 28

Summary of Percentage and Absolute Change in EASI Score from Baseline to Week 12 and Each Visit during Follow-up period-all values represented as Mean (SD)

| | Placebo | 300 mg mAb1 |
|---|---|---|
| No. Patients | 54 | 55 |
| Baseline EASI Score | 30.8 (13.63) | 28.4 (13.57) |
| Day 85 EASI Score | 24.4 (19.01) | 8.5 (12.15) |
| % Change from Baseline to Day 85 | −23.3 (49.26) | −74.0 (26.94) |
| Absolute change from Baseline to Day 85 | −6.4 (14.85) | −19.9 (11.52) |
| Day 99 EASI Score | 24.2 (19.15) | 8.4 (11.86) |
| % Change from Baseline to Day 99 | −23.2 (49.42) | −73.5 (27.21) |
| Absolute change from Baseline to Day 99 | −6.6 (15.20) | −20.0 (12.24) |
| Day 113 EASI Score | 24.1 (18.80) | 9.1 (12.13) |
| % Change from Baseline to Day 113 | −23.4 (47.75) | −71.4 (27.03) |
| Absolute change from Baseline to Day 113 | −6.7 (14.96) | −19.4 (11.42) |
| Day 127 EASI Score | 24.5 (18.91) | 9.2 (12.41) |
| % Change from Baseline to Day 127 | −22.1 (47.11) | −71.2 (27.39) |
| Absolute change from Baseline to Day 127 | −6.3 (14.98) | −19.2 (11.15) |
| Day 141 EASI Score | 23.8 (18.47) | 9.4 (12.18) |
| % Change from Baseline to Day 141 | −23.9 (47.01) | −70.8 (26.91) |
| Absolute change from Baseline to Day 141 | −7.0 (14.77) | −19.0 (10.86) |
| Day 155 EASI Score | 24.0 (18.27) | 9.9 (12.40) |
| % Change from Baseline to Day 155 | −23.0 (46.22) | −68.8 (27.35) |
| Absolute change from Baseline to Day 155 | −6.7 (14.49) | −18.5 (10.74) |
| Day 169 EASI Score | 23.5 (18.22) | 11.0 (12.76) |
| % Change from Baseline to Day 169 | −24.2 (46.66) | −64.4 (29.19) |
| Absolute change from Baseline to Day 169 | −7.3 (14.93) | −17.5 (10.82) |
| Day 183 EASI Score | 23.5 (18.57) | 10.8 (13.00) |
| % Change from Baseline to Day 183 | −24.6 (47.35) | −65.0 (29.21) |
| Absolute change from Baseline to Day 183 | −7.3 (15.12) | −17.6 (10.93) |
| Day 197 EASI Score | 23.4 (18.59) | 11.0 (13.13) |
| % Change from Baseline to Day 197 | −25.0 (48.57) | −64.0 (30.80) |
| Absolute change from Baseline to Day 197 | −7.4 (15.23) | −17.4 (11.88) |

TABLE 29

Summary of Percentage and Absolute Change in IGA Score from Baseline to Week 12 and Each Visit during Follow-up period-all values represented as Mean (SD)

| | Placebo | 300 mg mAb1 |
|---|---|---|
| No. Patients | 54 | 55 |
| Baseline IGA Score | 4.0 (0.69) | 3.9 (0.67) |

TABLE 29-continued

Summary of Percentage and Absolute Change in IGA Score from Baseline to Week 12 and Each Visit during Follow-up period-all values represented as Mean (SD)

| | Placebo | 300 mg mAb1 |
|---|---|---|
| Day 85 IGA Score | 3.4 (1.19) | 2.0 (1.15) |
| % Change from Baseline to Day 85 | −14.7 (27.37) | −49.5 (25.94) |
| Absolute change from Baseline to Day 85 | −0.6 (1.07) | −1.9 (0.98) |
| Day 99 IGA Score | 3.4 (1.16) | 2.1 (1.17) |
| % Change from Baseline to Day 99 | −14.0 (27.03) | −45.8 (26.98) |
| Absolute change from Baseline to Day 99 | −0.6 (1.06) | −1.7 (1.06) |
| Day 113 IGA Score | 3.3 (1.20) | 2.2 (1.08) |
| % Change from Baseline to Day 113 | −15.9 (27.82) | −43.1 (25.53) |
| Absolute change from Baseline to Day 113 | −0.6 (1.12) | −1.7 (1.06) |
| Day 127 IGA Score | 3.4 (1.16) | 2.2 (1.16) |
| % Change from Baseline to Day 127 | −14.5 (26.66) | −44.1 (27.06) |
| Absolute change from Baseline to Day 127 | −0.6 (1.07) | −1.7 (1.07) |
| Day 141 IGA Score | 3.4 (1.15) | 2.2 (1.12) |
| % Change from Baseline to Day 141 | −15.0 (26.52) | −42.8 (26.01) |
| Absolute change from Baseline to Day 141 | −0.6 (1.05) | −1.6 (1.01) |
| Day 155 IGA Score | 3.4 (1.14) | 2.3 (1.08) |
| % Change from Baseline to Day 155 | −14.2 (25.89) | −41.5 (25.20) |
| Absolute change from Baseline to Day 155 | −0.6 (1.02) | −1.6 (1.01) |
| Day 169 IGA Score | 3.3 (1.17) | 2.5 (1.07) |
| % Change from Baseline to Day 169 | −15.9 (26.96) | −36.0 (25.87) |
| Absolute change from Baseline to Day 169 | −0.6 (1.08) | −1.4 (1.03) |
| Day 183 IGA Score | 3.3 (1.18) | 2.4 (1.10) |
| % Change from Baseline to Day 183 | −16.3 (27.33) | −37.2 (26.93) |
| Absolute change from Baseline to Day 183 | −0.7 (1.10) | −1.5 (1.09) |
| Day 197 IGA Score | 3.3 (1.29) | 2.3 (1.09) |
| % Change from Baseline to Day 197 | −16.5 (30.18) | −39.0 (27.42) |
| Absolute change from Baseline to Day 197 | −0.7 (1.20) | −1.5 (1.10) |

TABLE 30

Summary of Absolute Change in BSA Score from Baseline to Week 12 and Each Visit during Follow-up period-all values represented as Mean (SD)

| | Placebo | 300 mg mAb1 |
|---|---|---|
| No. Patients | 54 | 55 |
| Baseline BSA Score | 50.8 (24.13) | 46.8 (24.55) |
| Day 85 BSA Score | 41.8 (30.44) | 19.4 (23.43) |
| Absolute change from Baseline to Day 85 | −9.0 (21.07) | −27.4 (22.81) |
| Day 99 BSA Score | 41.7 (30.85) | 19.9 (22.85) |
| Absolute change from Baseline to Day 99 | −9.2 (21.85) | −26.9 (22.74) |
| Day 113 BSA Score | 41.3 (30.52) | 20.8 (23.16) |
| Absolute change from Baseline to Day 113 | −9.5 (21.34) | −26.0 (21.90) |
| Day 127 BSA Score | 42.1 (30.41) | 21.4 (23.48) |
| Absolute change from Baseline to Day 127 | −8.7 (20.72) | −25.4 (21.29) |
| Day 141 BSA Score | 41.5 (29.85) | 21.3 (22.88) |
| Absolute change from Baseline to Day 141 | −9.4 (20.57) | −25.5 (21.50) |
| Day 155 BSA Score | 41.5 (29.61) | 22.1 (23.05) |
| Absolute change from Baseline to Day 155 | −9.3 (20.26) | −24.6 (21.55) |
| Day 169 BSA Score | 41.2 (29.28) | 24.6 (24.15) |
| Absolute change from Baseline to Day 169 | −9.6 (20.35) | −22.2 (21.50) |
| Day 183 BSA Score | 41.0 (30.28) | 24.1 (24.15) |
| Absolute change from Baseline to Day 183 | −9.9 (21.35) | −22.7 (22.86) |
| Day 197 BSA Score | 40.5 (29.95) | 24.9 (25.70) |
| Absolute change from Baseline to Day 197 | −10.4 (21.40) | −21.9 (24.11) |

TABLE 31

Summary of Absolute Change in SCORAD Score from Baseline to Week 12 and Each Visit during Follow-up period-all values represented as Mean (SD)

| | Placebo | 300 mg mAb1 |
|---|---|---|
| No. Patients | 54 | 55 |
| Baseline SCORAD Score | 69.1 (13.38) | 66.7 (13.82) |
| Day 85 SCORAD Score | 59.3 (23.44) | 31.7 (22.08) |
| Absolute change from Baseline to Day 85 | −9.8 (20.53) | −35.0 (19.43) |
| Day 99 SCORAD Score | 58.8 (23.35) | 32.5 (20.99) |
| Absolute change from Baseline to Day 99 | −10.3 (21.33) | −34.3 (18.94) |

TABLE 31-continued

Summary of Absolute Change in SCORAD Score from Baseline to Week 12 and Each Visit during Follow-up period-all values represented as Mean (SD)

| | Placebo | 300 mg mAb1 |
|---|---|---|
| Day 113 SCORAD Score | 59.1 (22.30) | 34.0 (2051) |
| Absolute change from Baseline to Day 113 | −10.0 (20.89) | −32.7 (18.48) |
| Day 127 SCORAD Score | 59.9 (22.36) | 34.0 (21.25) |
| Absolute change from Baseline to Day 127 | 09.2 (20.59) | −32.7 (18.23) |
| Day 141 SCORAD Score | 59.0 (21.85) | 33.9 (20.51) |
| Absolute change from Baseline to Day 141 | −10.1 (20.12) | −32.8 (17.97) |
| Day 155 SCORAD Score | 59.0 (22.50) | 35.1 (20.16) |
| Absolute change from Baseline to Day 155 | −10.0 (20.17) | −31.6 (17.99) |
| Day 169 SCORAD Score | 58.5 (22.33) | 37.1 (20.82) |
| Absolute change from Baseline to Day 169 | −10.6 (20.90) | −29.6 (19.15) |
| Day 183 SCORAD Score | 58.7 (22.47) | 37.5 (20.89) |
| Absolute change from Baseline to Day 183 | −10.4 (20.86) | −29.2 (19.50) |
| Day 197 SCORAD Score | 57.8 (23.82) | 38.8 (22.04) |
| Absolute change from Baseline to Day 197 | −11.3 (22.05) | −27.9 (21.70) |

TABLE 32

Summary of Absolute Change in 5-D Pruritus Scale from Baseline to Week 12 and Each Week during Follow-up period-all values represented as Mean (SD)

| | Placebo | 300 mg mAb1 |
|---|---|---|
| No. Patients | 54 | 55 |
| Baseline 5-D Pruritus Score | 18.7 (3.50) | 18.4 (3.04) |
| Day 85 5-D Pruritus Score | 16.9 (5.33) | 11.0 (4.22) |
| Absolute change from Baseline to Day 85 | −1.9 (4.28) | −7.4 (4.33) |
| Day 99 5-D Pruritus Score | 16.7 (5.28) | 11.3 (3.96) |
| Absolute change from Baseline to Day 99 | −2.0 (4.63) | −7.0 (4.41) |
| Day 113 5-D Pruritus Score | 16.5 (5.57) | 11.7 (4.05) |
| Absolute change from Baseline to Day 113 | −2.2 (4.91) | −6.7 (4.21) |
| Day 127 5-D Pruritus Score | 16.7 (5.44) | 11.5 (4.07) |
| Absolute change from Baseline to Day 127 | −2.0 (4.72) | −6.9 (4.24) |
| Day 141 5-D Pruritus Score | 16.4 (5.67) | 11.8 (4.19) |

TABLE 32-continued

Summary of Absolute Change in 5-D Pruritus Scale from Baseline to Week 12 and Each Week during Follow-up period-all values represented as Mean (SD)

| | Placebo | 300 mg mAb1 |
|---|---|---|
| Absolute change from Baseline to Day 141 | −2.3 (5.12) | −6.6 (4.56) |
| Day 155 5-D Pruritus Score | 16.6 (5.53) | 12.0 (4.21) |
| Absolute change from Baseline to Day 155 | −2.1 (4.90) | −6.4 (4.49) |
| Day 169 5-D Pruritus Score | 16.8 (5.35) | 12.7 (4.20) |
| Absolute change from Baseline to Day 169 | −1.9 (4.78) | −5.7 (4.58) |
| Day 183 5-D Pruritus Score | 16.6 (5.59) | 12.8 (4.56) |
| Absolute change from Baseline to Day 183 | −2.1 (5.02) | −5.6 (4.90) |
| Day 197 5-D Pruritus Score | 16.6 (5.50) | 13.1 (4.85) |
| Absolute change from Baseline to Day 197 | −2.1 (5.12) | −5.3 (5.06) |

TABLE 33

Summary of Absolute Change in Average NRS Score from Baseline to Week 12 and Each Week during Follow-up period-all values represented as Mean (SD)

| | Placebo | 300 mg mAb1 |
|---|---|---|
| No. Patients | 54 | 55 |
| Baseline NRS Score | 5.8 (1.93) | 6.1 (1.34) |
| Day 85 NRS Score | 4.9 (2.53) | 2.6 (1.67) |
| Absolute change from Baseline to Day 85 | −0.9 (2.07) | −3.5 (2.00) |
| Day 92 NRS Score | 4.8 (2.57) | 2.8 (1.68) |
| Absolute change from Baseline to Day 92 | −1.0 (2.07) | −3.4 (2.12) |
| Day 99 NRS Score | 4.7 (2.54) | 2.7 (1.72) |
| Absolute change from Baseline to Day 99 | −1.0 (2.06) | −3.4 (2.17) |
| Day 106 NRS Score | 4.8 (2.59) | 2.7 (1.63) |
| Absolute change from Baseline to Day 106 | −1.0 (2.15) | −3.4 (2.08) |
| Day 113 NRS Score | 4.9 (2.69) | 2.7 (1.63) |
| Absolute change from Baseline to Day 113 | −0.9 (2.21) | −3.4 (2.00) |
| Day 120 NRS Score | 4.8 (2.61) | 2.7 (1.68) |
| Absolute change from Baseline to Day 120 | −1.0 (2.18) | −3.4 (2.07) |
| Day 127 NRS Score | 4.8 (2.68) | 2.8 (1.79) |
| Absolute change from Baseline to Day 127 | −1.0 (2.24) | −3.3 (2.20) |
| Day 134 NRS Score | 4.7 (2.75) | 2.8 (1.78) |
| Absolute change from Baseline to Day 134 | −1.1 (2.24) | −3.3 (2.18) |
| Day 141 NRS Score | 4.7 (2.73) | 2.9 (1.89) |
| Absolute change from Baseline to Day 141 | −1.1 (2.26) | −3.2 (2.28) |
| Day 148 NRS Score | 4.7 (2.75) | 2.9 (1.89) |
| Absolute change from Baseline to Day 148 | −1.1 (2.28) | −3.2 (2.28) |
| Day 155 NRS Score | 4.7 (2.75) | 2.9 (1.86) |
| Absolute change from Baseline to Day 155 | −1.1 (2.30) | −3.2 (2.19) |
| Day 162 NRS Score | 4.7 (2.75) | 3.0 (1.93) |
| Absolute change from Baseline to Day 162 | −1.1 (2.29) | −3.1 (2.28) |
| Day 169 NRS Score | 4.7 (2.75) | 3.2 (1.99) |
| Absolute change from Baseline to Day 169 | −1.1 (2.28) | −3.0 (2.43) |
| Day 176 NRS Score | 4.7 (2.74) | 3.2 (2.01) |
| Absolute change from Baseline to Day 176 | −1.1 (2.27) | −3.0 (2.49) |
| Day 183 NRS Score | 4.7 (2.75) | 3.1 (1.97) |
| Absolute change from Baseline to Day 183 | −1.1 (2.28) | −3.0 (2.41) |
| Day 190 NRS Score | 4.7 (2.78) | 3.1 (1.91) |
| Absolute change from Baseline to Day 190 | −1.1 (2.31) | −3.1 (2.25) |
| Day 197 NRS Score | 4.7 (2.75) | 3.1 (1.95) |
| Absolute change from Baseline to Day 197 | −1.1 (2.28) | −3.0 (2.28) |

TABLE 34

Summary of Subjects achieving an IGA score of 0 or 1 to Week 12 and each visit during Follow-up period

| Number and proportion of subjects achieving an IGA score of 0 or 1 | Placebo (N = 54) | 300 mg mAb1 (N = 55) |
|---|---|---|
| Week 12, Day 85 | 4 (7.4%) | 22 (40.0%) |
| Week 14, Day 99 | 4 (7.4%) | 22 (40.0%) |
| Week 16, Day 113 | 5 (9.3%) | 18 (32.7%) |
| Week 18, Day 127 | 3 (5.6%) | 20 (36.4%) |
| Week 20, Day 141 | 4 (7.4%) | 17 (30.9%) |

TABLE 34-continued

Summary of Subjects achieving an IGA score of 0 or 1 to Week 12 and each visit during Follow-up period

| Number and proportion of subjects achieving an IGA score of 0 or 1 | Placebo (N = 54) | 300 mg mAb1 (N = 55) |
|---|---|---|
| Week 22, Day 155 | 3 (5.6%) | 17 (30.9%) |
| Week 24, Day 169 | 3 (5.6%) | 13 (23.6%) |
| Week 26, Day 183 | 3 (5.6%) | 15 (27.3%) |
| Week 28, Day 197 | 6 (11.1%) | 16 (29.1%) |

TABLE 35

Summary of Subjects achieving an EASI 50 Week 12 and each visit during Follow-up period

| Number and proportion of subjects achieving an EASI score percent decrease of 50% | Placebo (N = 54) | 300 mg mAb1 (N = 55) |
|---|---|---|
| Week 12, Day 85 | 19 (35.2%) | 47 (85.5%) |
| Week 14, Day 99 | 19 (35.2%) | 46 (83.6%) |
| Week 16, Day 113 | 18 (33.3%) | 46 (83.6%) |
| Week 18, Day 127 | 18 (33.3%) | 45 (81.8%) |
| Week 20, Day 141 | 18 (33.3%) | 46 (83.6%) |
| Week 22, Day 155 | 16 (29.6%) | 43 (78.2%) |
| Week 24, Day 169 | 18 (33.3%) | 40 (72.7%) |
| Week 26, Day 183 | 19 (35.2%) | 41 (74.5%) |
| Week 28, Day 197 | 23 (42.6%) | 40 (72.7%) |

H. Conclusions

Subcutaneous administration of an anti-IL-4R antibody (mAb1) to adult patients with moderate-to-severe atopic dermatitis was generally safe and well tolerated after 12 weekly doses of 300 mg. Administration of mAb1 at 300 mg resulted in significant improvement in IGA, EASI, BSA, SCORAD and NRS pruritus through day 85 in both mean and absolute and percent change, as compared to baseline (see Tables 27-33). The proportion of patients achieving an IGA score of 0 or 1 at Day 85 for the 300 mg group was 40.0%, while the same number for placebo was 7.4% (Table 34). At Day 85, the proportion of patients who achieved an EASI score percent decrease of 50% ("EASI-50") was 85.5% for the 300 mg group, whereas the EASI-50 for placebo-treated patients at Day 85 was 35.2% (Table 35). The percent change in EASI score from baseline to week 12 of mAb1 was statistically significant from placebo group (−74.0% vs. −23.0%, p-value<0.0001). The treatment group was statistically significantly different from placebo group in all of the secondary efficacy endpoints. The following were the p-values for: IGA responder (0 or 1) (<0.0001), EASI responder (<0.0001), EASI absolute change from baseline (<0.0001), absolute change of IGA from baseline (<0.0001), percent change of IGA from baseline (<0.0001), absolute change in BSA (<0.0001), absolute change in SCORAD (<0.0001), absolute change in Pruritus NRS (<0.0001), and absolute change in 5-D pruritus scale from baseline to week 12 (<0.0001) respectively.

Example 11: Clinical Trial to Assess the Safety of mAb1 Administered Concomitantly with Topical Corticosteroids to Patients with Moderate-to-Severe AD A. Study Design This study was a randomized, double-blind, parallel-group, placebo-controlled study to assess the safety and explore the efficacy of repeated subcutaneous doses of mAb1 administered concomitantly with topical corticosteroids (TCS) to treat AD in patients with moderate-to-severe AD. Patients were randomized 2:1 to receive 300 mg mAb1 or placebo once weekly for 4 consecutive weeks via subcutaneous injections (on days 1, 8, 15, and 22). All patients received concomitant open-label, daily treatment for up to 28 days with a potent TCS product (50-100 times as potent as hydrocortisone), such as methylprednisolone aceponate 0.1%, mometasone furoate 0.1%, or betamethasone valerate 0.1%. Other topical medications, such as a lower potency TCS or topical calcineurin inhibitors (TCI), were used to treat AD lesions located on the face, flexural and genital areas.

Starting with the screening visit, patients began applying an additive-free, basic bland emollient twice daily for at least 7 days before the baseline visit and continued its use throughout the study (once daily on treatment days in areas of TCS application). Environmental control measures and non-pharmacologic treatment modalities such as allergen avoidance and bleach baths were allowed at the discretion of the investigator.

Screening occurred between day −21 and −1. Patients received their first drug injection (300 mg mAb1, or placebo) on day 1 and returned to the clinic for additional drug injections on days 8, 15 and 22 (+/−1 day) for a total of 4 weekly doses. Starting on day 1, patients applied the topical medication(s) described above once daily in the evening, and continued the applications to all AD-affected areas (i.e., areas with active AD lesions) until control was achieved for up to 28 days. After control was achieved, TCS application to AD-prone areas without active lesions (i.e., areas from which lesions have cleared) was limited to 2 days every week until study day 28. After day 28, topical treatment of any residual AD lesions continued as needed. Throughout the study, patients continued to apply an additive-free, basic bland emollient, twice daily (once daily on topical treatment days in areas treated with topical medication). Patients returned for clinic visits on days 29, 36, 50, 64 and 78 (end of study).

The inclusion criteria for the study were: (1) male/female patients aged 18 years or older; (2) chronic AD as diagnosed by the Eichenfield revised criteria of Hannifin and Rajka, that had been present for at least 2 years before screening; (3) AD activity as assessed by IGA score 3 and SCORAD>20 at the screening and baseline visits, with one or more active AD lesions for which treatment with potent TCS is indicated; (4) at least 10% BSA affected by AD at the screening and baseline visits; (5) patients must be applying an additive-free, basic bland emollient twice daily for at least 7 days before the baseline visit; (6) willing and able to comply with clinic visits and study-related procedures; and (7) able to read and understand, and willing to sign the consent form.

The exclusion criteria for the study were: (1) prior treatment with mAb1; (2) hypersensitivity to corticosteroids or to any other ingredients contained in the TCS product used during the study; (3) AD lesions located predominantly (50% of the cumulative lesional area) on face, flexural and genital areas; (4) presence of skin comorbidities that may interfere with study assessments; (5) the following treatments within 4 weeks before the baseline visit or any conditions that may require such treatment(s) during the study: systemic corticosteroids, immunosuppressive or immunomodulating drugs, e.g., cyclosporine, mycophenolate-mofetil, IFN-gamma, azathioprine or methotrexate; (6) treatment with biologics as follows: (a) any cell-depleting agents, including but not limited to, rituximab; within 6 months prior to the baseline visit, or until lymphocyte and CD19+ lymphocyte count return to normal, whichever is larger, (b) infliximab, adalimumab, golimumab, certolizumab pegol, abatacept, etanercept, anakinra: within 8 weeks prior to the baseline visit, and 9c) other biologics: within 5 half-lives (if known) or 8 weeks, whichever is longer; (7) any phototherapy for skin disease (such as narrow band UVB, UVB, UVA1, psolaren+UVA within 4 weeks before baseline; (8) regular use (more than 2 visits per week) of a tanning booth/parlor within 4 weeks before the baseline visit; (9) treatment with a live attenuated vaccine within 12 weeks before the baseline visit; (10) treatment with an investigational drug within 8 weeks or within 5 half-lives, whichever is longer, before the baseline visit; (11) chronic or acute infection requiring treatment with oral or IV antibiotics, antivirals, antiparasitics, antiprotozoals, or antifungals within 4 weeks before the screening, or superficial skin infections within 1 week before the screening visit; (12) history of invasive opportunistic infections such as histoplasmosis, listeriosis, coccidioidomycosis, candidiasis, *Pneumocystis jiroveci*, aspergillosis, despite resolution, JC virus (progressive multifocal leukoencephalopathy; (13) known history of HIV infection; (14) positive or indeterminate hepatitis B surface antigen, hepatitis B core antibody, or hepatitis C antibody at the screening visit; (15) presence of any of the following laboratory abnormalities at the screening visit: creatine phosphokinase >2× upper limit normal (ULN); aspartate aminotransferase (AST) and/or alanine aminotransferase (ALT)>2×ULN; neutrophil count <1.75×$10^3$/μl; platelet count <100×$10^3$/μl; (16) onset of a new exercise routine or major change to a previous exercise routine within 2 weeks before randomization, or unwillingness to maintain (without increase) the current level of physical activity throughout the length of participation in the study; (17) history of a hypersensitivity reaction to doxycycline or other tetracyclines; (18) history of a clinical endoparasite infection within 12 months of the baseline visit, other than treated vaginal trichomoniasis; (19) history of malignancy within 5 years before the baseline visit, except completely treated in situ carcinoma of the cervix, completely excised non-metastatic squamous or basal cell carcinoma of the skin; (20) history of non-malignant lymphoproliferative disorders; (21) pregnant or breast-feeding women; (22) men or women of child-bearing potential who are unwilling to practice contraceptive measures; (23) history of alcohol or drug abuse within 2 years of the screening visit; (24) recent travel (within 12 months of randomization) to areas endemic for parasitic infections, such as developing countries in Africa or the tropical/subtropical regions of Asia; (25) prior or current history of significant concomitant illness(es) that would adversely affect the patient's participation in the study, e.g., stage III or IV cardiac failure, severe renal, neurological, endocrinological, GI, hepato-biliary, metabolic, pulmonary or lymphatic disease; and (26) any other conditions that may present an unreasonable risk to the study patient, or may make the patient's participation unreliable, or may interfere with study assessments.

The primary endpoint of the study was the incidence and severity of adverse events. The secondary endpoints were exploratory in nature and included: (1) EAS150 index—Binary response variable of whether or not 50% reduction in EASI is achieved from baseline to day 29, and other post-baseline observation time points; (2) achieving IGA scores of ≤1 (clear or almost clear) at day 29, and at other post-baseline observation time points; (3) time to IGA≤1 and to EAS150; (4) changes in IGA, EASI, and SCORAD scores from baseline to day 29, and to other post-baseline observation time points; and (5) proportion of patients with IGA≤1 at week 4 who remain relapse-free through the end of the observation period.

B. Efficacy Variables

The efficacy variables IGA, BSA, EASI, SCORAD, and Pruritus NRS rating have been described elsewhere herein (see, e.g., Example 7). The IGA, BSA, EASI, pruritus NRS and SCORAD scores were assessed at every clinic visit.

C. Procedures and Assessments

Safety was assessed by evaluating the incidence of adverse events (described elsewhere herein) (AEs) from day 1 to day 78, and by detailed medical history, thorough physical examination, vital signs, electrocardiograms (ECGs), and clinical laboratory testing. Blinded safety data was reviewed on an ongoing basis. Concomitant medications and procedures were collected from screening to day 78 (end of study) or early termination, if applicable. Safety, laboratory, and efficacy assessments were performed at each clinic visit. Blood samples were collected for the determination of systemic trough concentrations of functional mAb1 at every study visit prior to treatment starting at baseline (day 1). Blood samples were collected for the analysis of anti-mAb1 antibody levels at predetermined time points. Research samples and samples for exploratory biomarker analysis were also collected. Efficacy of mAb1 was assessed by the EASI, the IGA, the SCORAD, the Pruritus numerical rating scale (NRS), and % body surface area (BSA) of AD involvement. Blood samples were collected for pharmacokinetic (PK) analyses, and analysis of anti-mAb1 antibody levels at predetermined time points. Research samples and samples for exploratory biomarker analysis were also collected.

D. Statistical Methods

As all statistical analyses described in this section were exploratory in nature, there was no multiplicity adjustment for the type I error. Each test was at the 5% significance level. All categorical variables (EASI-50 and IGA responders at each post-baseline visit, IGA responders at day 29 without later relapse) were analyzed using the Fisher's Exact test with calculated nominal p-value from comparison between mAb1 and placebo groups. The point estimates and confidence intervals of proportions were presented. The graphs of the proportions over time were provided. All continuous variables (change or percent change in IGA, EASI and SCORAD, NRS from baseline to each post-baseline visit) were analyzed by the ANalysis of COVAriance (ANCOVA). Unless otherwise specified, assessments of changes from baseline and construction of confidence intervals for continuous measures were based on an ANCOVA model which included treatment as the main factor and baseline value as covariates. The point estimate and 95% CI of the difference in adjusted mean change from baseline between two treatment groups was provided. The nominal p-value from comparison between mAb1 and placebo groups will be provided. In the event that the model assumptions were not warranted, the Rank-based analysis of covariates was used. Graphs of mean change from baseline over time were provided. Time-to-event variables (time to EASI50 and time to IGA response) were analyzed with a log-rank test to compare mAb1 with placebo group. Kaplan-Meier survival curves across two treatment groups were provided. The following analysis approaches were implemented for this study: (a) Censored LOCF: The efficacy data was set to missing after prohibited medication was used or after the patient was discontinued from the study. Then all missing values were imputed by simple LOCF. (b) Simple Observed Case (OC) approach: Only observed cases were analyzed.

E. Safety

Overall, mAb1 was safe and well tolerated in this study. No deaths were reported. A single serious adverse event (SAE) was recorded for a patient in the placebo group, who experienced loss of consciousness, and who withdrew from the study as a result. No other patients experienced adverse events leading to treatment discontinuation. A total of 19 out of 31 patients enrolled in the study reported at least one treatment emergent adverse event (TEAE)—7 patients (70%) in the placebo group and 12 patients (57%) in the mAb1 group. By system and organ class (SOC), the most frequent TEAE reported for mAb1 treatment group were infections and infestations, 12 patients (57%) vs. 3 patients (30%) for placebo). The most frequent infection was nasopharyngitis—5 patients (24%) in the mAb1 group vs. 2 patients (20%) for placebo. There were no serious or opportunistic infections. Other TEAEs reported in more than a single patient included nonspecific symptoms such as headache—3 patients (14%) in the mAb1 group vs. 1 patient (10%) in the placebo group, somnolence—2 patients (9.5%) in the mab1 group vs. 0% in the placebo group, oropharyngeal pain—3 patients (14%) in the mAb1 group vs. 1 patient (10%) in the placebo group, and cough—2 patients (9.5%) in the mAb1 group vs. 0% in the placebo group. Most AEs were mild to moderate and generally resolved within 2 weeks. A single severe AE was reported in the mAb1 group: bacterial bronchitis, with onset on Day 63 (last dose of study drug on Day 22), which was considered unrelated to the study treatment. There were no adverse events in the mAb1 group suggestive of untoward drug-drug (mAb1-TCS) interactions at the skin level. The analysis of on-treatment potential clinically significant values (PCSV) for safety laboratory tests, vital signs, and ECC showed that the rate of PCSVs was generally balanced between the two study groups, with no systematic distribution or distinct trends, suggesting that PCSV occurrence was incidental and not related to the study treatment.

F. Results

In this study, mAb1 was administered concomitantly with TCS to patients with moderate to severe AD. Consistent with the current standard of care in AD, a controlled TCS regimen was required during the first 4 weeks (i.e., concomitantly with the study treatment), as described elsewhere herein. Table 36 lists the TCS medications used by the patients participating in the study. Patients were to apply TCS to all active lesions, once daily, every day, until lesion clearance, followed by applications to lesion-prone areas (from which lesions had cleared) once daily, two days per week. A potent TCS (Class III) was required to be applied to at least 50% of lesions. For lesions located on face, skin folds, or genital areas (where potent TCS are usually not indicated) lower potency TCS (Class I or II) were allowed. The amount of TCS used each week was measured by weighing the TCS containers at the time they were dispensed to patients and upon their return to the clinic at the next study visit. Tables 37 and 38 summarize the TCS use from day 1 through day 29.

TABLE 36

| TCS medications | Placebo (N = 10) | 300 mg mAb1 (N = 21) | All patients (N = 31) |
|---|---|---|---|
| Subjects with at least one TCS med | 10 (100%) | 21 (100%) | 31 (100%) |
| Corticosteroids, Dermatological Preparations | 10 (100%) | 21 (100%) | 31 (100%) |
| Corticosteroids, Potent (Group III) | 10 (100%) | 21 (100%) | 31 (100%) |
| Mometasone (furoate) | 6 (60%) | 10 (47.6%) | 16 (51.6%) |
| Methylprednisolone (aceponate) | 6 (60%) | 8 (38.1%) | 14 (45.2%) |
| Fluticasone propionate | 0 | 4 (19.0%) | 4 (12.9%) |
| Corticosteroids, Moderately potent (Group II) | 0 | 2 (9.5%) | 2 (6.5%) |
| Hydrocortisone butyrate | 0 | 2 (9.5%) | 2 (6.5%) |
| Corticosteroids, Weak (Group I) | 2 (20.0%) | 1 (4.8%) | 3 (9.7%) |
| Hydrocortisone | 2 (20.0%) | 1 (4.8%) | 3 (9.7%) |

TABLE 39

| Summary of Demographics | Placebo (N = 10) | 300 mg (N = 21) | All Patients (N = 31) |
|---|---|---|---|
| Mean age, years (SD) | 37.8 (16.73) | 36.0 (11.26) | 36.6 (13.01) |
| Race, % | | | |
| Caucasian | 10 (100%) | 20 (95.2%) | 30 (96.8%) |
| Other | 0 | 1 (4.8%) | 1 (3.2%) |
| Ethnicity, % | | | |
| Non-Hispanic | 10 (100%) | 21 (100%) | 31 (100%) |
| Gender, % | | | |
| Male | 5 (50.0%) | 8 (38.1%) | 13 (41.9%) |
| Female | 5 (50.0%) | 132 (61.9%) | 18 (58.1%) |
| Mean BMI, kg/m$^3$ (SD) | 23.92 (3.469) | 25.26 (3.257) | 24.83 (3.330) |

TABLE 40

| Summary of Baseline Characteristics - all values as Mean (SD) | Placebo | mAb1 300 mg | All Subjects Combined |
|---|---|---|---|
| No. Patients | 10 | 21 | 31 |
| Chronic Atopic Dermatitis Diagnosis Age | 5.4 (9.26) | 5.3 (11.12) | 5.4 (10.40) |
| BSA | 38.85 (24.052) | 40.43 (20.912) | 39.92 (21.579) |
| EASI Score | 24.10 (12.695) | 23.12 (12.354) | 23.43 (12.261) |
| IGA Score | 3.35 (0.474) | 3.43 (0.598) | 3.40 (0.554) |
| NRS Score | 5.00 (1.394) | 6.43 (2.002) | 5.97 (1.928) |
| SCORAD Score | 58.20 (13.834) | 66.31 (13.013) | 63.69 (13.607) |

TABLE 37

| TCS used from Day 1 through Day 29 - all values in Mean (SD) | Placebo (N = 10) | 300 mg mAb1 (N = 21) | All patients (N = 31) |
|---|---|---|---|
| Total (g) | 99.4 (152.49) | 48.7 (40.27) | 65.0 (92.94) |
| Visit 3 (week 1) | 26.7 (37.53) | 14.0 (13.13) | 18.1 (23.96) |
| Visit 4 (week 2) | 2.5 (40.03) | 12.7 (9.96) | 16.5 (24.04) |
| Visit 5 (week 3) | 26.6 (37.05) | 11.5 (12.28) | 16.3 (23.75) |
| Visit 6 (week 4) | 26.9 (43.61) | 11.1 (14.71) | 15.6 (26.43) |

TABLE 38

| TCS in Class III used from Day 1 through Day 29 | Placebo (N = 10) | 300 mg mAb1 (N = 21) | All patients (N = 31) |
|---|---|---|---|
| Total (g) | 93.4 (153.51) | 47.2 (39.78) | 62.1 (92.77) |
| Visit 3 (week 1) | 25.2 (37.83) | 13.5 (12.86) | 17.3 (23.89) |
| Visit 4 (week 2) | 23.0 (40.26) | 12.4 (9.76) | 15.8 (23.98) |
| Visit 5 (week 3) | 25.0 (37.34) | 11.0 (12.23) | 15.5 (23.71) |
| Visit 6 (week 4) | 25.2 (44.00) | 11.4 (14.92) | 15.5 (26.78) |

The demographic and disease characteristics were for the most part homogeneous between the two treatment groups (Tables 39 and 40). The mean baseline AD disease severity scores (IGA, EASI, SCORAD, BSA, and pruritus NRS) were reasonably balanced, as well.

The exploratory efficacy results obtained from the study are summarized in FIGS. 34-47 and Tables 41-44. Despite the relatively small sample size and the limited treatment period, the analysis showed statistically significant and clinically relevant effects of mAb1 vs. placebo in key exploratory efficacy endpoints, including EASI-50 responder rate, as well as change and percent change from baseline in EASI, SCORAD, IGA, and pruritus NRS, with some improvements persisting for several weeks after the discontinuation of study treatment. For EASI-50, 100% of patients in the mAb1 plus TCS group met the responder criteria on Day 29, vs. 50% in the placebo plus TCS group (P-value 0.0015). Other endpoints like IGA 0-1 responder rate showed numerical superiority to placebo but did not reach statistical significance (47.6% vs. 30.0% for placebo). Notably, patients treated with mAb1 used on average approximately 50% less TCS, which might have underestimated the mAb1 treatment effect relative to the placebo (TCS alone) comparator group.

TABLE 41

| Summary of Percent and Absolute Change in EASI score from Baseline to Day 29 | Placebo | 300 mg mAb1 |
|---|---|---|
| No. Patients | 10 | 21 |
| Baseline EASI Score Mean (SD) | 24.1 (12.70) | 23.1 (12.35) |
| Day 29 EASI Score Mean (SD) | 14.4 (13.91) | 6.2 (6.68) |
| % Change from Baseline to Day 29 | −52.5 (39.53) | −75.6 (13.29) |
| Absolute change from Baseline to Day 29 | −9.7 (8.42) | −16.9 (8.06) |

TABLE 42

| Summary of Percent and Absolute Change in IGA score from Baseline to Day 29 | | |
|---|---|---|
| | Placebo | 300 mg mAb1 |
| No. Patients | 10 | 21 |
| Baseline IGA Score Mean (SD) | 3.4 (0.47) | 3.4 (0.60) |
| Day 29 IGA Score Mean (SD) | 2.4 (1.43) | 1.6 (0.80) |
| % Change from Baseline to Day 29 | −30.6 (39.00) | −52.5 (21.44) |
| Absolute change from Baseline to Day 29 | −1.0 (1.17) | −1.8 (0.81) |

TABLE 43

| Summary of % and Absolute Change in SCORAD Score from Baseline to Day 29 | | |
|---|---|---|
| | Placebo | 300 mg mAb1 |
| No. Patients | 10 | 21 |
| Baseline SCORAD Score Mean (SD) | 58.2 (13.83) | 66.3 (13.01) |
| Day 29 SCORAD Score Mean (SD) | 37.1 (25.11) | 26.4 (13.53) |
| % Change from Baseline to Day 29 | −40.0 (33.91) | −59.8 (18.35) |
| Absolute change from Baseline to Day 29 | −21.1 (17.99) | −39.9 (15.67) |

TABLE 44

| Summary of % and Absolute Change in Pruritus NRS from Baseline to Day 29 | | |
|---|---|---|
| | Placebo | 300 mg mAb1 |
| No. Patients | 10 | 21 |
| Baseline NRS Score Mean (SD) | 5.0 (1.39) | 6.4 (2.00) |
| Day 29 NRS Score Mean (SD) | 3.4 (1.96) | 1.8 (1.33) |
| % Change from Baseline to Day 29 | −24.7 (47.30) | −70.7 (21.45) |
| Absolute change from Baseline to Day 29 | −1.6 (2.40) | −4.6 (2.01) |

Subcutaneous administration of mAb1 to adult patients with moderate-to-severe AD treated concomitantly with TCS was generally safe and well tolerated. Treatment with mAb1 administered concomitantly with TCS was associated with significantly superior outcomes compared with TCS treatment alone. The proportion of patients achieving an EASI-50 score was numerically much greater that was seen in recent studies in which mAb1 was used as monotherapy (the best EASI-50 so far had been 75%) which suggested that mAb1 and TCS acted additively or synergistically. However, it might also be in part due to the small sample size and slight differences in the patient populations between studies.

The study demonstrated additional efficacy provided by mAb1 in patients with moderate-to-severe AD who received TCS treatment. These results suggested that combination therapy could provide additional clinical benefits to patients with moderate-to-severe AD, compared to either treatment used as monotherapy. The results also suggested the possibility of a TCS sparing effect of mAb1, which could potentially lead to safer long term management of patients with AD.

Example 12: Biomarker Analysis

Biomarker analysis was conducted on samples taken from subjects who participated in clinical trials of mAb1. In particular, IgE and thymus and activation chemokine (TARC) levels were measured in samples from patients at baseline and at different time points following initiation of study treatment(s). The Phadiatop™ test was performed to detect antigen-specific IgE. In addition, molecular profiling was carried out on skin lesions of patients who participated in clinical trials of mAb1.

A. Administration of mAb1 to Healthy Subjects

In a first clinical trial, subjects were administered single intravenous (IV) (1.0, 3.0, 8.0 and 12.0 mg/kg) or subcutaneous (SC) (150 and 300 mg) doses of mAb, or placebo (see Example 2 herein). Samples for biomarker analysis were collected from the antibody- and placebo-treated subjects at days 1 (baseline), 8, 29, and 85 (or early termination). Levels of IgE and TARC were measured in each sample. A p-value of <0.10 was considered statistically significant to allow for small sample size. A mixed-effect repeated measures model was used for mean analyses and non-parametric test for median analyses. The median percent change in IgE and TARC levels from patient samples are summarized in Tables 45 and 46, respectively.

TABLE 45

| Median Percent Change in IgE Level from Baseline Following mAb1 or Placebo Administration | | | | | | | |
|---|---|---|---|---|---|---|---|
| | subcutaneous (SC) | | | intravenous (IV) | | | |
| | | mAb1 | | | mAb1 | | |
| | Placebo | 150 mg | 300 mg | Placebo | 3 mg/kg | 8 mg/kg | 12 mg/kg |
| Baseline | — | — | — | — | — | — | — |
| Day 8 | −1.3 | −4.4 | 0.0 | −1.3 | −3.3 | 1.3 | 0.0 |
| Day 29 | 1.0 | −8.5 | −15.4 | 1.0 | −10.7 | −8.9 | −7.9 |
| Day 85 | 14.7 | −16.5 | −17.2 | 14.7 | −4.8 | −10.7 | −25.6 |

TABLE 46

| Median Percent Change in TARC Level from Baseline Following mAb1 or Placebo Administration | | | | | | | |
|---|---|---|---|---|---|---|---|
| | subcutaneous (SC) | | | intravenous (IV) | | | |
| | | mAb1 | | | mAb1 | | |
| | Placebo | 150 mg | 300 mg | Placebo | 3 mg/kg | 8 mg/kg | 12 mg/kg |
| Baseline | — | — | — | — | — | — | — |
| Day 8 | 7.7 | −16.0 | −34.9 | 7.7 | −28.2 | −20.0 | 3.7 |
| Day 29 | 4.1 | −14.8 | −21.0 | 4.1 | 0.8 | −0.4 | −25.2 |
| Day 85 | −5.7 | −29.9 | −15.1 | −5.7 | −0.5 | −1.6 | −17.0 |

Figure 48A:
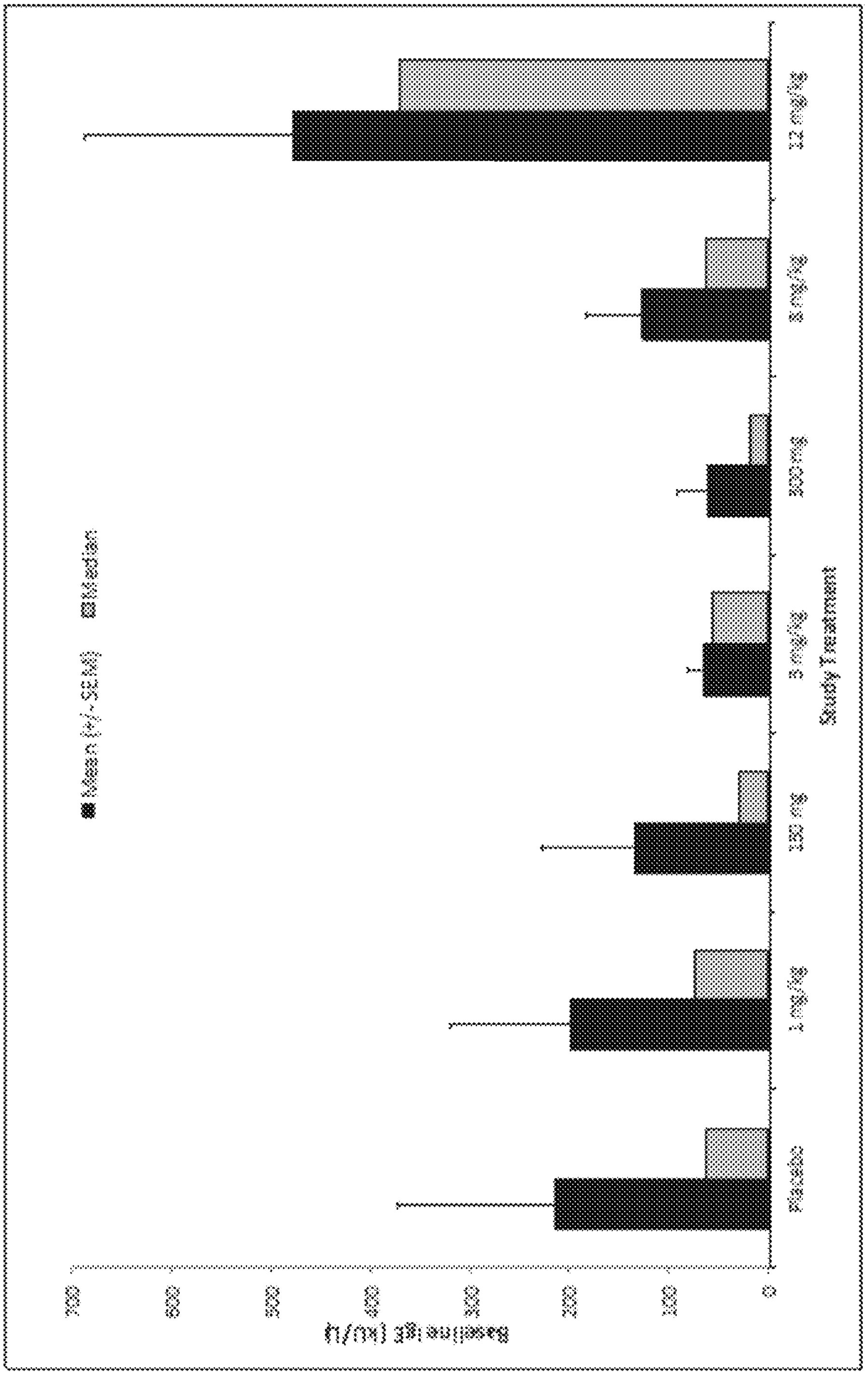
FIG. 48A shows serum IgE levels at baseline.
Figure 48B:
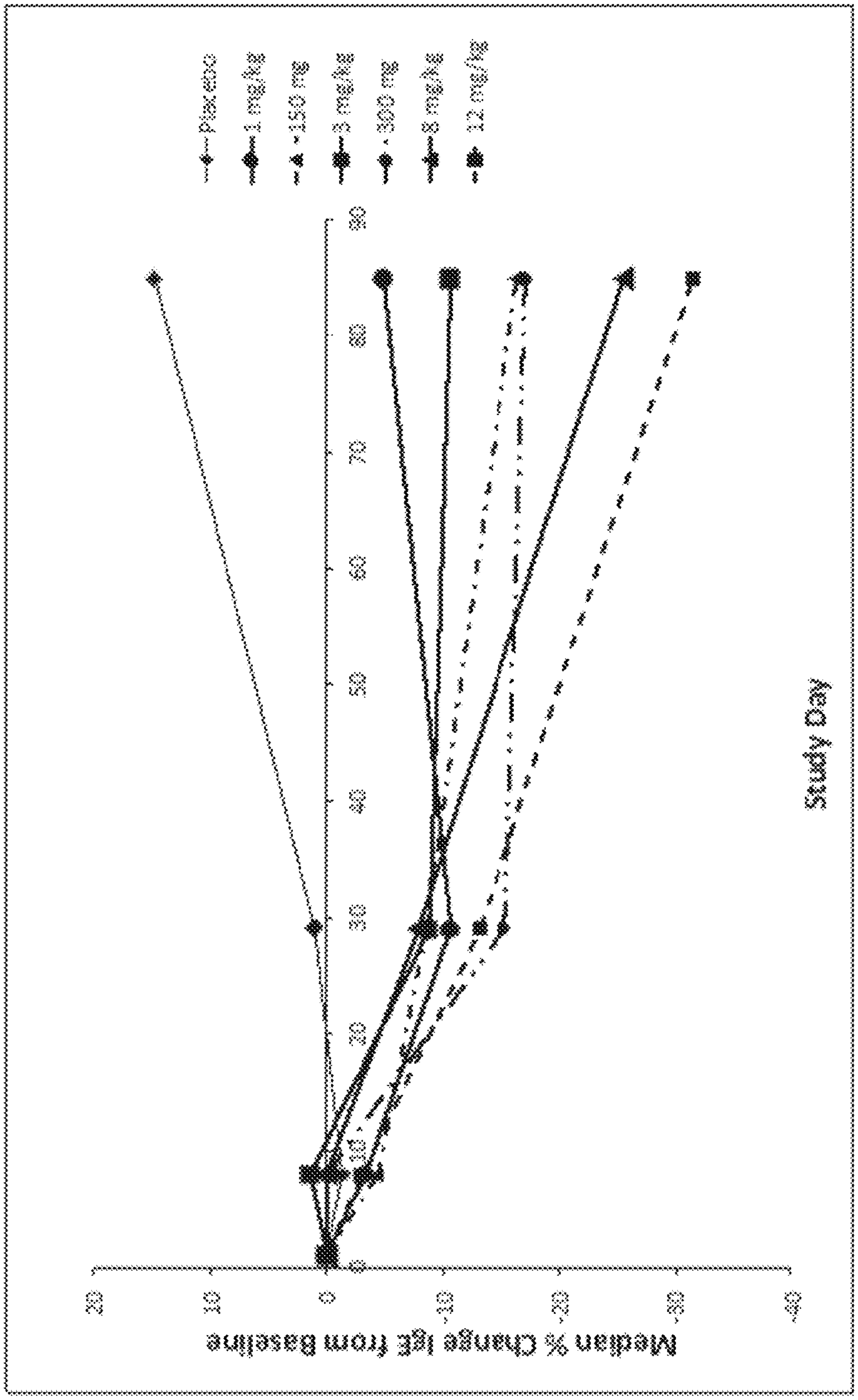
FIG. 48B shows median percentage change in response to various doses of mAb1 or placebo for the study described in Example 12.

Baseline levels of IgE were highly variable as shown in the comparison of mean and median baseline IgE per treatment group (FIG. 48A). The laboratory reference range for the utilized IgE assay is 0-114 kU/L and 15 of the 40 subjects had total IgE levels >114 kU/L at baseline. As shown in Table 43 and FIG. 48B, IgE levels generally declined in proportion to the mAb1 dose and exposure time. By Day 85 after administration, subjects receiving SC-administered mAb1 exhibited a median decrease in IgE level of 16.5% (150 mg) and 17.2% (300 mg). Significant IgE decreases were also observed in patients receiving IV-administered mAb1, with decreases in IgE of 10.7% and 25.6% in the 8 mg/kg and 12 mg/kg groups, respectively. By contrast, IgE levels increased over time in placebo treated subjects.

Figure 49A:
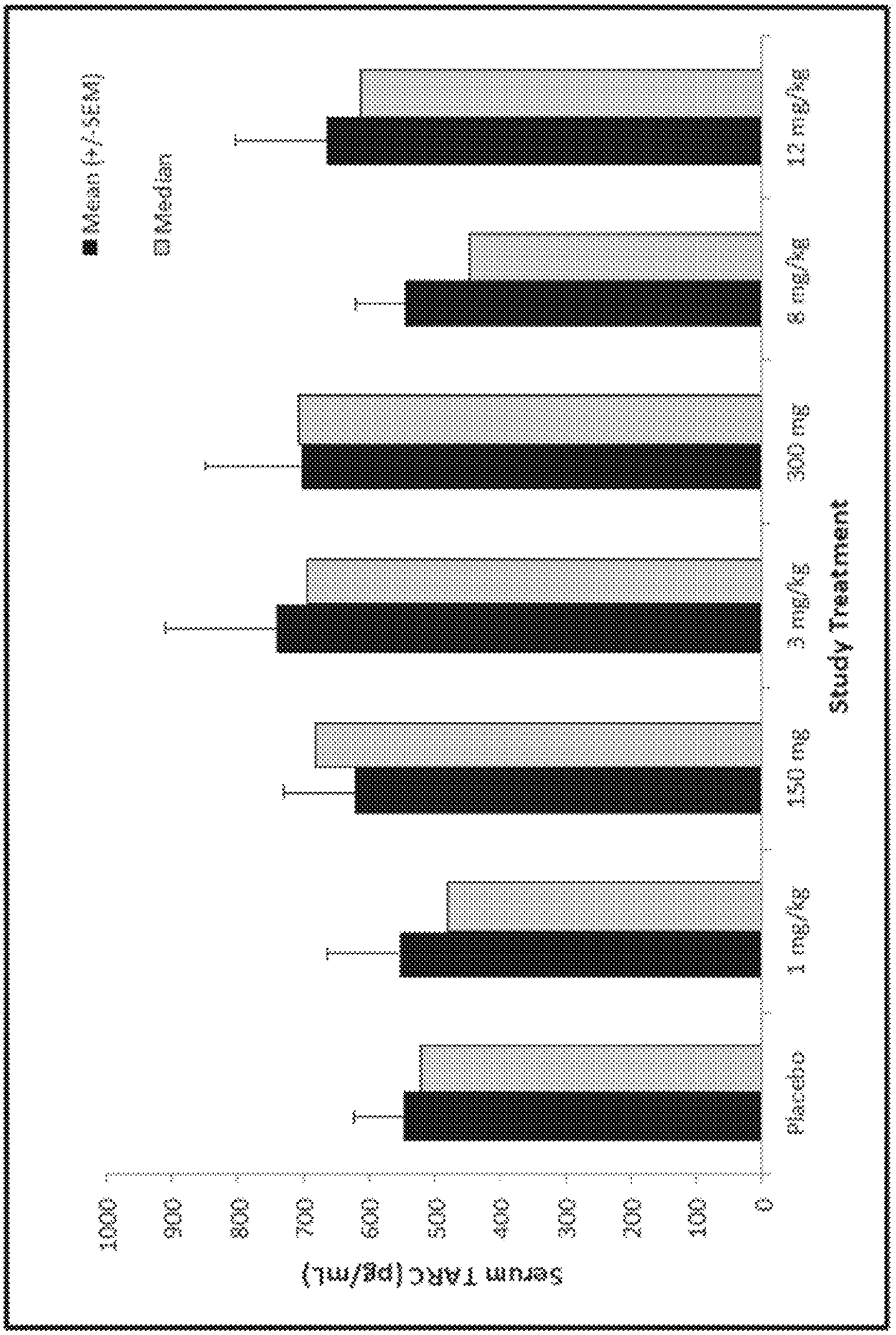
FIG. 49A shows serum TARC levels at baseline.
Figure 49B:
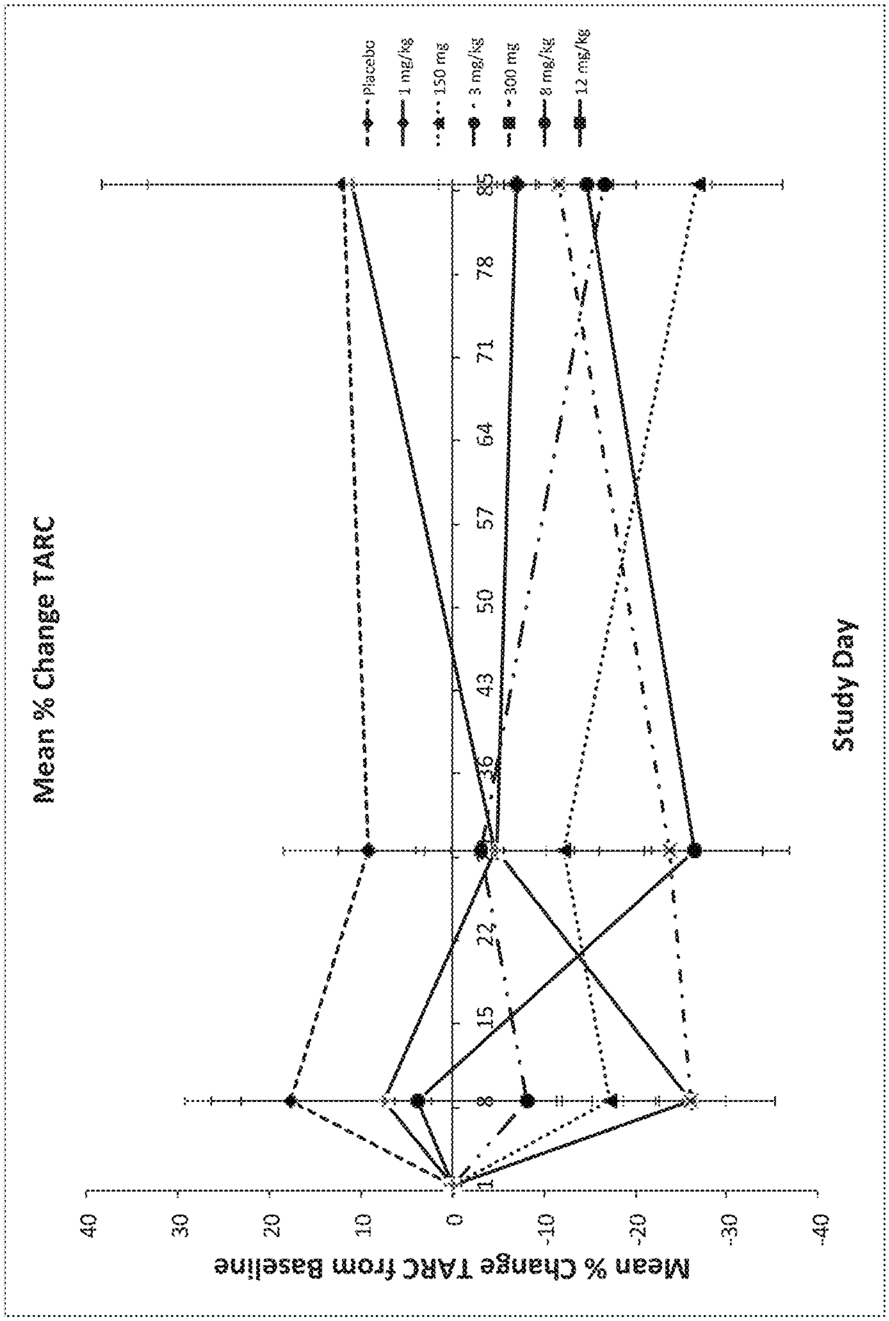
FIG. 49B shows mean percentage change in response to various doses of mAb1 or placebo for the study described in Example 12.
Figure 50:
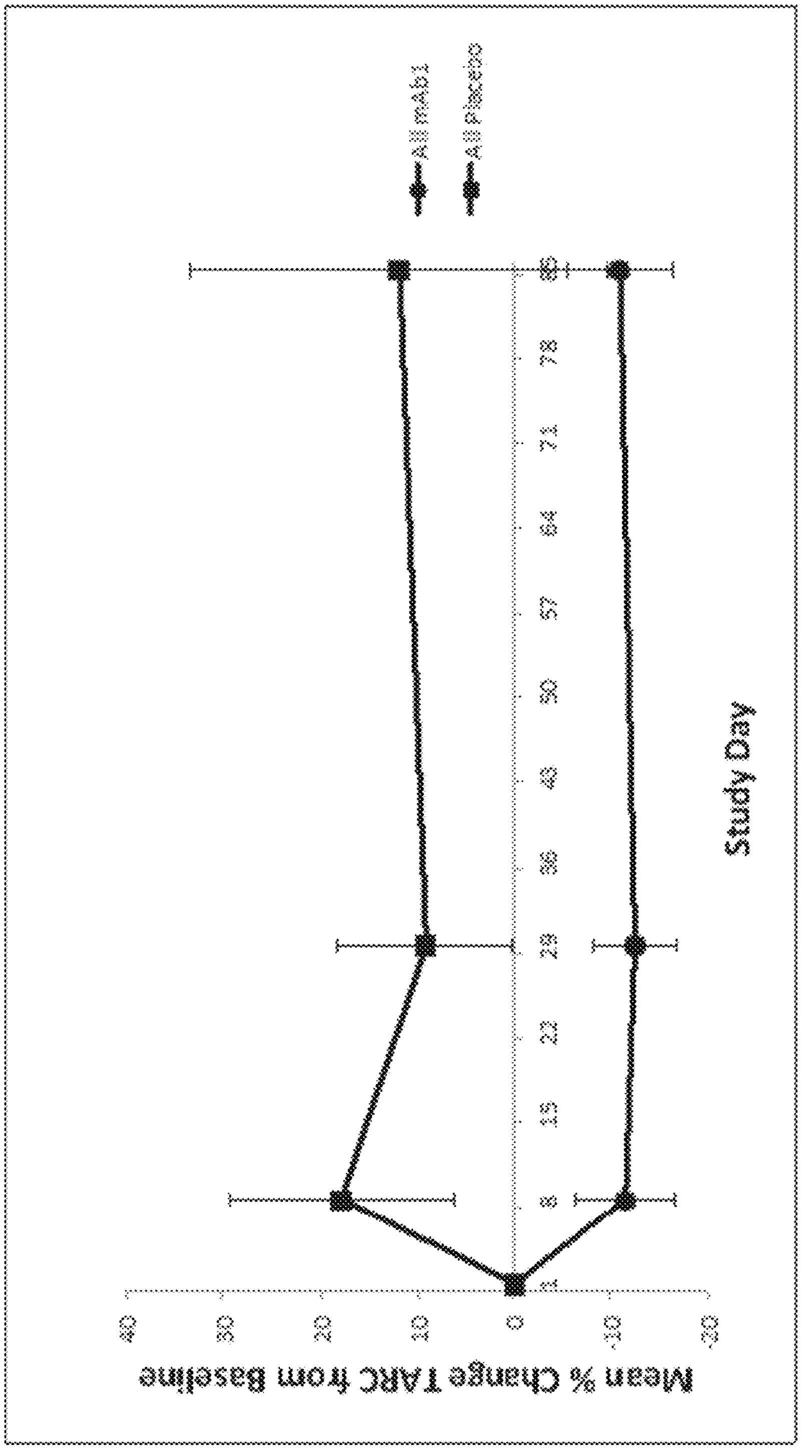
FIG. 50 shows change in TARC levels for pooled mAb1 group compared to placebo for the study in Example 12.

Median serum TARC levels at baseline were generally comparable between the treatment groups (FIG. 49A), and were higher than those reported in the literature. Mean baseline TARC was 616 pg/mL with a range of 134-1327 pg/mL. TARC levels in healthy subjects have been reported in the range of 106-431 ng/L (Hijnen et al 2004, J. Allergy Clin. Immunol. 113: 334-340). Significant reductions in TARC were observed in samples taken from mAb1-treated subjects compared to placebo with both subcutaneous doses (p=0.044 for 150 mg and p=0.047 for 300 mg) (FIG. 49B and Table 44). For example, a single SC dose of 300 mg of mAb1 caused a median decrease in TARC level by almost 35% at day 8 (p=0.052), while TARC level increased by 7.7% in placebo-treated patients. Significant decreases in TARC levels were sustained in mAb1-treated patients at Day 29 through the end of the study (Day 85) in both SC- and IV-administered groups. When data was pooled for all subjects treated with mAb1, the overall difference between mAb1 and placebo for percent change from baseline in TARC was significant (p=0.004) (FIG. 50). Significant differences were also observed at days 8 (p=0.012) and 29 (p=0.022).

B. Administration of mAb1 to Subjects with Atopic Dermatitis

Biomarker levels were also measured in samples from two separate clinical trials involving subjects with atopic dermatitis (AD). In "Study A", AD subjects were administered either mAb1 (75, 150 or 300 mg) or placebo, on days 1, 8, 15 and 22 of the study (i.e., four weekly doses). In "Study B", AD subjects were administered 150 mg or 300 mg of mAb1, or placebo, on days 1, 8, 15 and 22 of the study (i.e., four weekly doses) (see Example 7 herein). All administrations for both studies were subcutaneous (SC). Samples for biomarker analysis were collected from the antibody- and placebo-treated subjects from both studies at days 1 (baseline), 4, 8, 15, 22, 25, 29, 36, 43, 50, 57, 64, 71 and 85 (or early termination). Levels of IgE, TARC, lactate dehydrogenase (LDH), and antigen-specific IgE (Phadiatop) were measured in each sample.

Serum TARC was measured using a validated assay (Human CCL17/TARC Quantikine ELISA kit, R&D Systems; validation and assays performed by Quest Diagnostics). Total serum IgE levels were determined using the ImmunoCAP® Total IgE test (Thermo Scientific FDA cleared test; performed by Quest Diagnostics). Lactate dehydrogenase (LDH) was measured using the Roche Modular test (FDA cleared; performed by Covance Central Laboratories). Phadiatop® (Thermo Scientific FDA cleared test) assays were performed by Viracor-IBT. Two-sample median test was used to compare the biomarker changes from baseline with mAb1 to placebo.

Figure 51A:
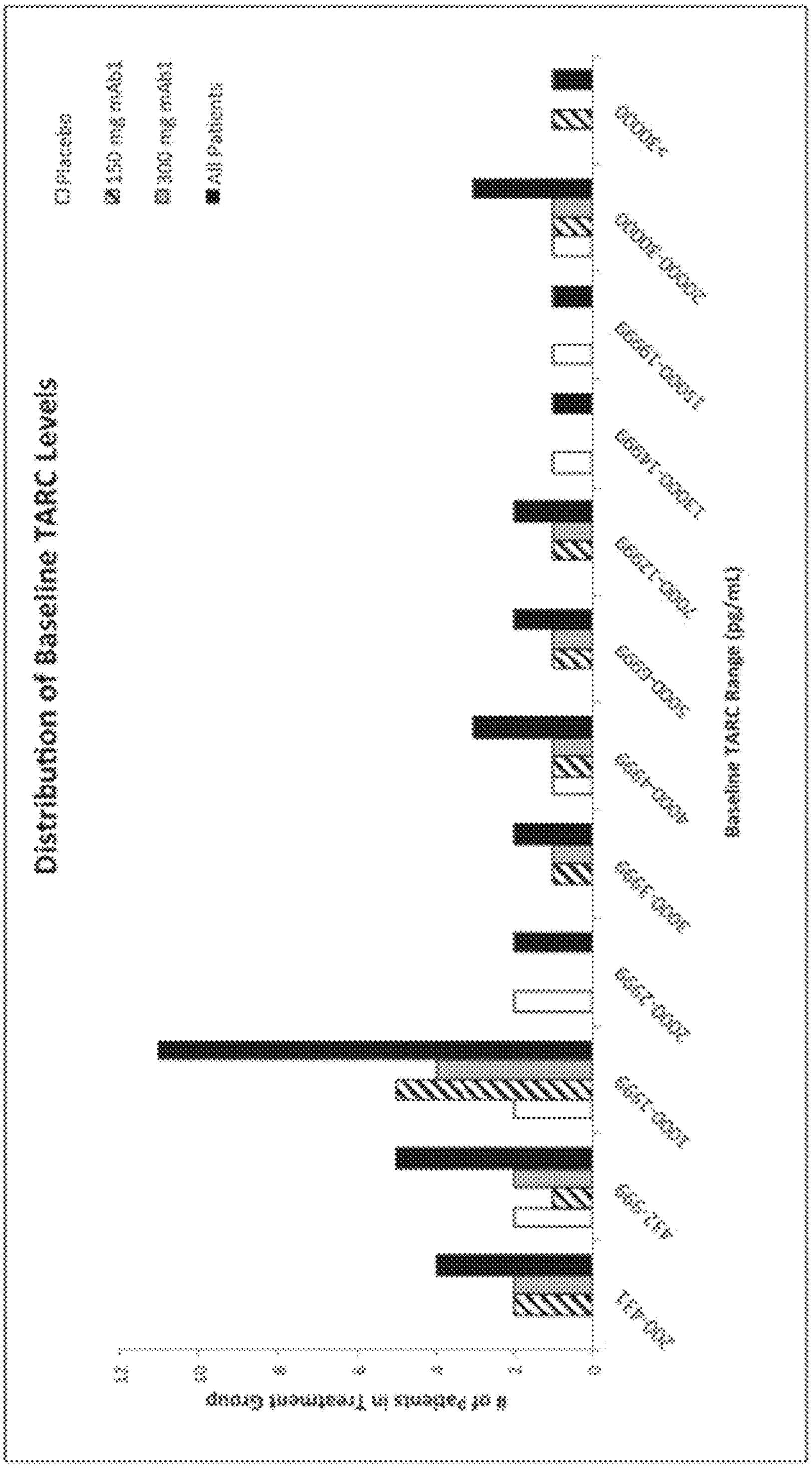
FIG. 51A shows the distribution of baseline levels of TARC in patients in the study in section B of Example 12.
Figure 51B:
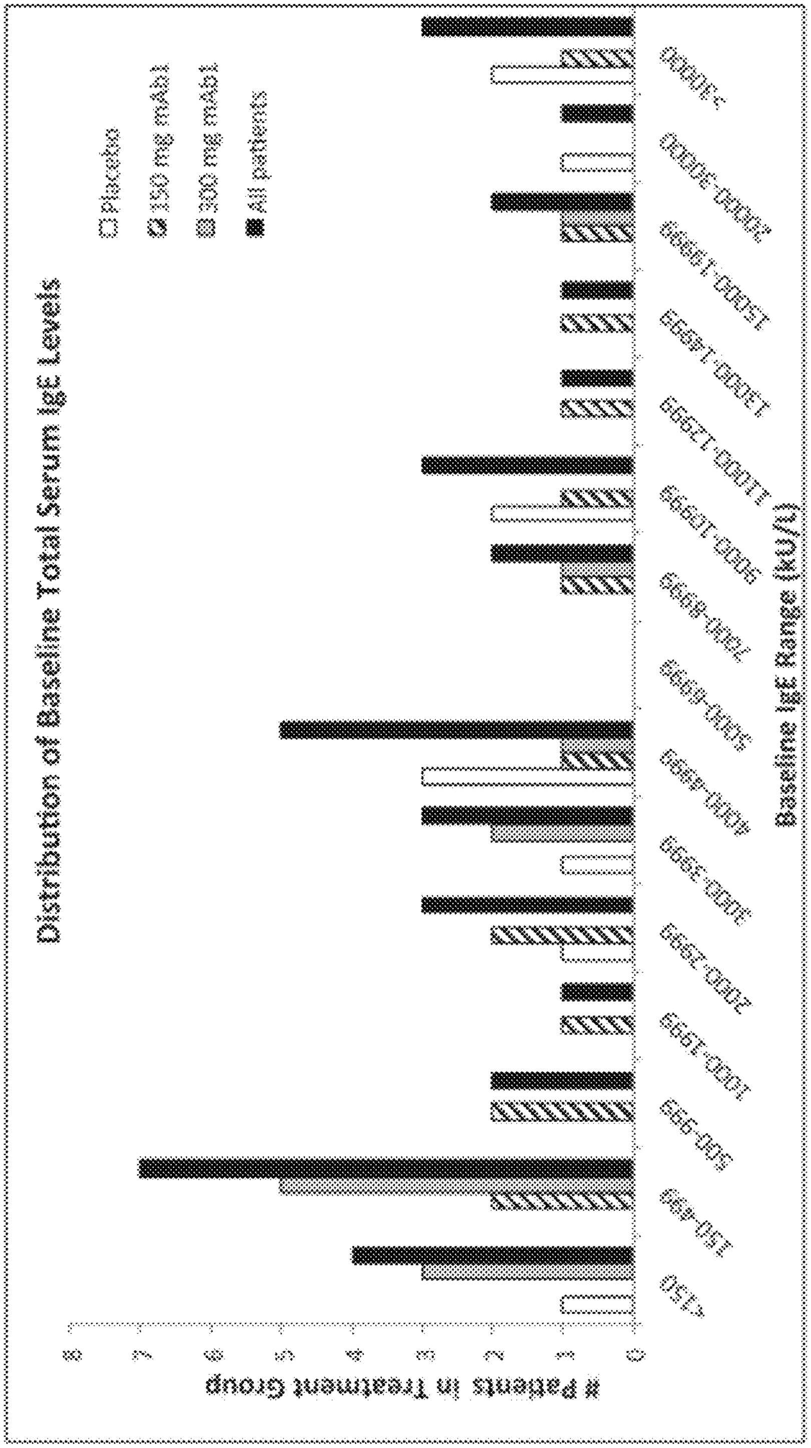
FIG. 51B shows the distribution of baseline levels of total serum IgE in patients in the study in section B of Example 12.

Mean baseline levels of serum TARC, total IgE and LDH for all AD patients enrolled in study 'B' were higher than the reported upper limit of normal (ULN) (Table 47 and FIG. 51).

TABLE 47

| Summary of baseline biomarker characteristics | | | | |
|---|---|---|---|---|
| Biomarker | Mean Baseline (SEM) All patients (n = 37) | Mean Baseline (SEM) Placebo (n = 10) | Mean Baseline (SEM) 150 mg DPL (n = 14) | Mean Baseline (SEM) 300 mg DPL (n = 14) |
| EASI | 28.4 (2.56) | 25.64 (4.34) | 32.55 (4.96) | 25.91 (3.71) |
| TARC (pg/mL) | 6914.9 (2001.3) | 7001 (2669.8) | 9162.2 (4851.7) | 4601.4 (1957.3) |
| IgE (kU/L) | 8038.3 (2052.2) | 15026.5 (4748.6) | 7231.9 (2634.1) | 2931.7 (1383.4) |
| Phadiatop ® | 34/36 patients were + | All + | All + | 2 patients were − |
| LDH (U/L) | 240.4 (13.4) | 296.7 (28.8) | 226.1 (21) | 212.5 (16.1) |
| Eos (10^9 cells/L) | 0.50 (0.06) | 0.65 (0.13) | 0.49 (0.09) | 0.41 (0.11) |
| Eos (%) | 6.37 (0.71) | 8.03 (1.06) | 6.17 (1.18) | 5.29 (1.32) |

Mean baseline eosinophil levels were at the high end of the reference range (Table 47). All but 2 patients with available data tested positive for the Phadiatop test. Both of these patients also had normal total serum IgE levels. Phadiatop results were unavailable for one patient.

Figure 51C:
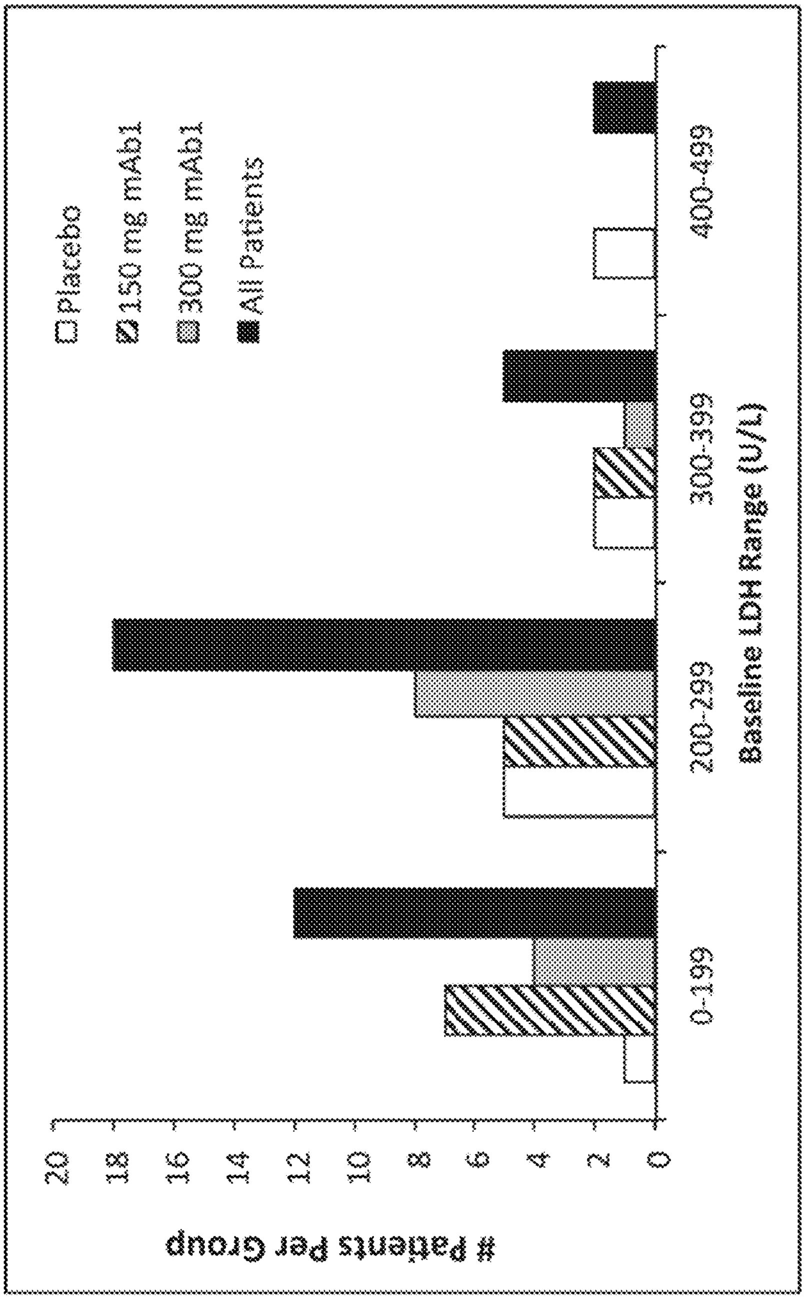
FIG. 51C shows the distribution of baseline levels of lactate dehydrogenase (LDH) in patients in the study in section B of Example 12.

A broad spectrum of baseline TARC and IgE was observed in the enrolled moderate-to-severe AD population. 27/36 of patients had serum TARC levels >1000 pg/mL (~twice the mean levels reported for healthy volunteers (FIG. 51A). 32/36 of patients had IgE levels ≥150 kU/L (a cutoff often cited to distinguish extrinsic and intrinsic AD) (FIG. 51B). 17/37 had LDH levels above 234 U/L (FIG. 51C). No patients had LDH levels below 100 U/L.

Figure 52:
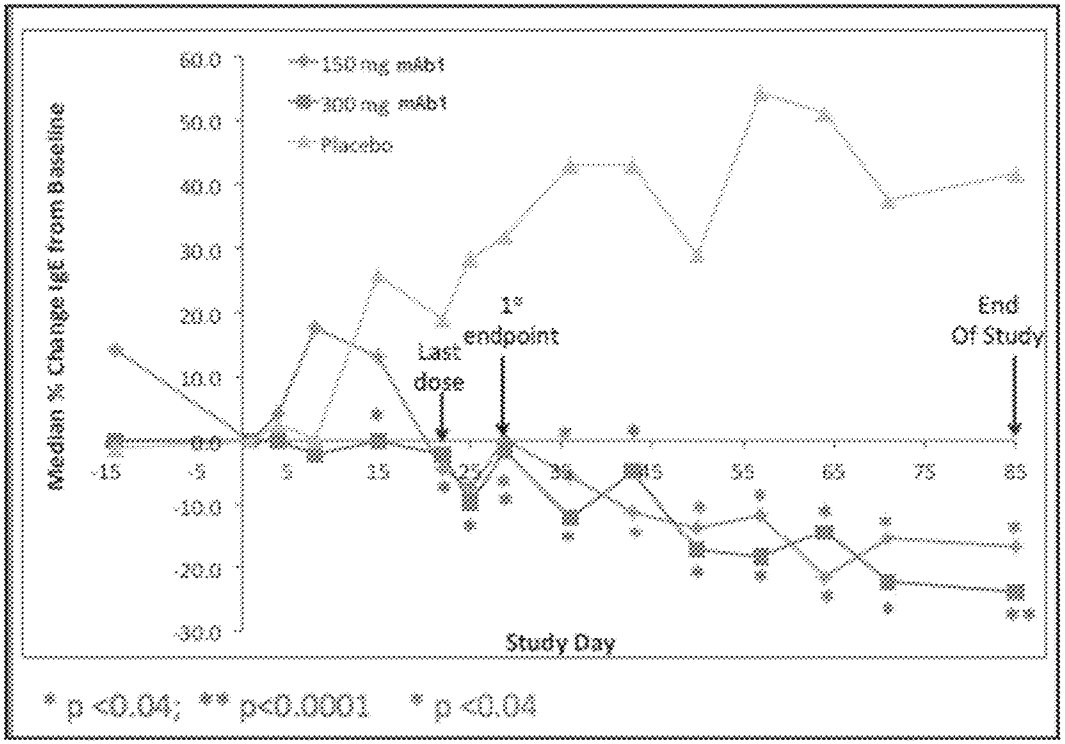
FIG. 52 shows the median percent change in IgE from baseline for the study in section B of Example 12.

Using local linear regression, an overall mAb1 treatment effect (percent change from baseline) on total serum IgE was observed compared to placebo in both dose groups (p<0.0001) (FIG. 52). Total serum IgE levels decreased with mAb1 treatment, while an overall increase was observed at the end of the study in the placebo treated group.

The median percent change in IgE levels from baseline for each group from both studies A and B (combined data) is summarized in Table 48.

TABLE 48

Median Percent Change in IgE Level from Baseline (Study A & B Combined)

| | subcutaneous (SC) | | | |
|---|---|---|---|---|
| | | mAb1 | | |
| | Placebo | 75 mg | 150 mg | 300 mg |
| *Baseline | — | — | — | — |
| Day 4 | 2.7 | TBD | 4.3 | 0.0 |
| *Day 8 | 0.2 | TBD | 17.6 | −2.2 |
| *Day 15 | 25.7 | TBD | 13.2 | 0.0 |
| *Day 22 | 19.0 | TBD | −4.4 | −2.1 |
| Day 25 | 28.4 | TBD | −7.4 | −9.5 |
| Day 29 | 32.0 | TBD | 0.2 | −1.6 |
| Day 36 | 43.0 | TBD | −5.5 | −12.1 |
| Day 43 | 43.0 | TBD | −11.2 | −4.8 |
| Day 50 | 28.9 | TBD | −13.7 | −17.3 |
| Day 57 | 54.2 | TBD | −11.7 | −18.3 |
| Day 64 | 51.2 | TBD | −21.6 | −14.3 |
| Day 71 | 37.5 | TBD | −15.4 | −22.3 |
| Day 85 | 41.7 | TBD | −16.8 | −23.9 |

*Denotes days when drug or placebo was administered

As shown in Table 48 and FIG. 52, a statistically significant decrease in IgE was observed in samples from mAb1-treated subjects compared to placebo. The median percent change IgE at day 85 was −23.9% in patients treated with 300 mg mAb1, compared to a 41.7% increase in the placebo group (p<0.0001). The median percent change from baseline in the 150 mg group compared to placebo was significant at all time-points from days 29-85 (p<0.03). The median percent change from baseline in the 300 mg group compared to placebo was significant at all time-points from days 15-85 (p<0.04).

Figure 53:
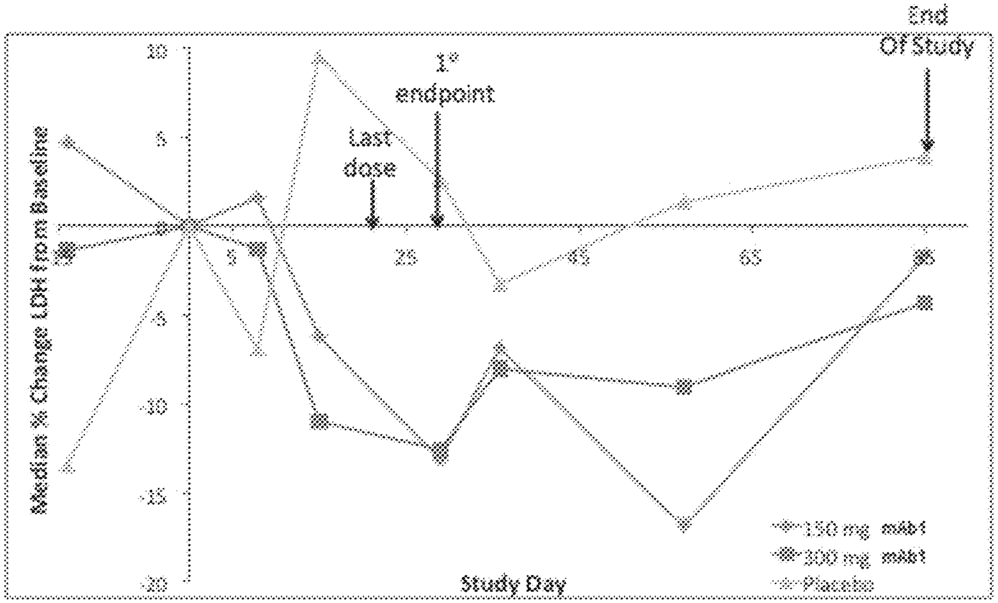
FIG. 53 shows the median percent change in LDH from baseline for the study in section B of Example 12.
Figure 54:
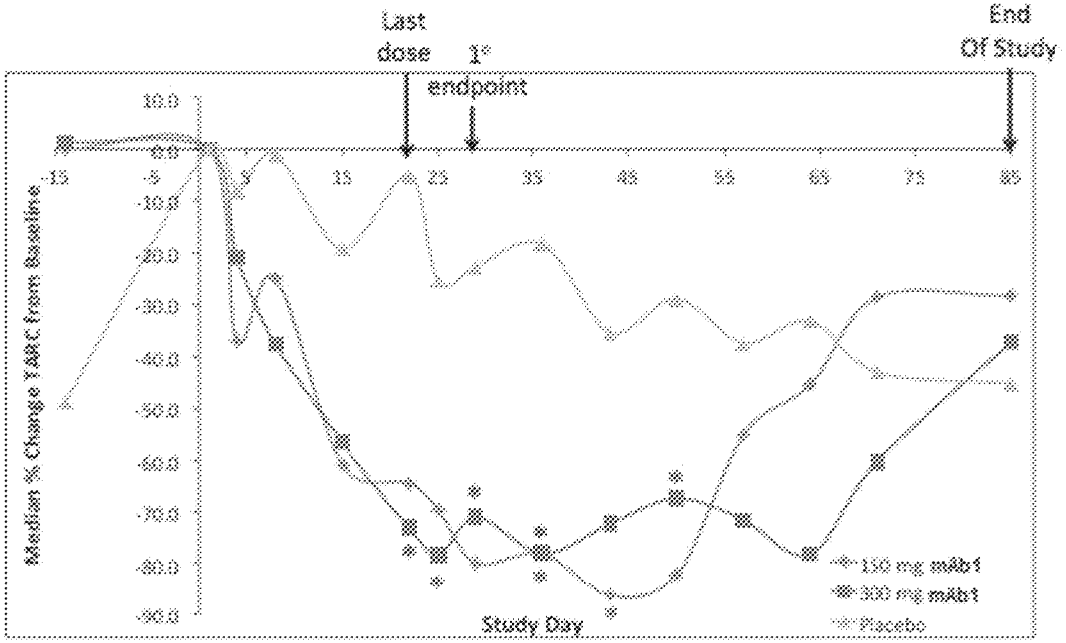
FIG. 54 shows the median percent change in TARC from baseline for the study in section B of Example 12.

Using local linear regression, an overall treatment effect was observed for LDH. There was a statistically significant decrease in LDH in the 300 mg treatment group (p=0.0051) (FIG. 53). Median percent change was not statistically significant at any single time point, however, a temporal trend was observed (p=0.008).

mAb1 treatment rapidly suppressed serum TARC levels in AD patients (FIG. 54). The median percent change in TARC levels from baseline for each group from both studies (combined data) is summarized in Table 49.

TABLE 49

Median Percent Change in TARC Level from Baseline (Study A and B combined)

| | subcutaneous (SC) | | | |
|---|---|---|---|---|
| | | mAb1 | | |
| | Placebo | 75 mg | 150 mg | 300 mg |
| *Baseline | — | — | — | — |
| Day 4 | −7.9 | TBD | −37.0 | −20.8 |
| *Day 8 | −1.1 | TBD | −24.8 | −37.5 |
| *Day 15 | −19.3 | TBD | −61.0 | −56.6 |
| *Day 22 | −5.0 | TBD | −64.4 | −73.1 |
| Day 25 | −25.5 | TBD | −69.5 | −78.5 |
| Day 29 | −22.7 | TBD | −79.9 | −70.9 |
| Day 36 | −18.3 | TBD | −78.1 | −77.9 |
| Day 43 | −35.3 | TBD | −86.3 | −72.3 |
| Day 50 | −28.9 | TBD | −82.2 | −67.4 |
| Day 57 | −37.4 | TBD | −55.2 | −71.4 |
| Day 64 | −33.2 | TBD | −45.5 | −78.1 |
| Day 71 | −43.0 | TBD | −28.6 | −60.3 |
| Day 85 | −45.2 | TBD | −28.3 | −37.3 |

*Denotes days when drug or placebo was administered

A statistically significant reduction in serum TARC was observed in patients treated with 300 mg mAb1 compared to placebo (p<0.0001; local linear regression analysis). Statistically significant suppression was maintained through day 50 in patients treated with 300 mg mAb1, approximately one month after the last dose (administered on study day 21). The 150 mg group achieved comparable magnitude of suppression, but levels were observed to increase sooner than in the 300 mg group. Statistically significant suppression (median percent change TARC from baseline compared to placebo) was observed at days 36 and 43 in the 150 mg group (p<0.03), as well as days 22, 25, 29, 36, and 50 with the 300 mg group (p<0.04).

Intra-patient variability of TARC levels was observed over the course of the study in placebo-treated patients. Data from only 4 placebo-treated patients was available at the end of the study, due to a high dropout rate in that group.

In conclusion, TARC, IgE and LDH, biomarkers associated with Th2 inflammation and/or AD disease activity, were all suppressed by mAb1 treatment in AD patients. mAb1 rapidly decreased serum TARC levels in AD patients, compared to placebo. Duration of suppression appeared to be dose-related and data suggested that the effect might be sustained even after drug discontinuation. Total serum IgE levels significantly declined in mAb1 treated patients. IgE continued to decline (median percent change) in the 300 mg group after the treatment phase, suggesting that maximal IgE suppression had not yet been achieved. A consistent reduction in LDH levels from baseline was observed in patients treated with mAb1. A direct link between LDH and IL-4 and IL-13 is unknown, but its association with disease severity suggested LDH might be a measure of the extent of skin damage in AD patients. The suppression of TARC and IgE demonstrated that mAb1 is a potent inhibitor of Th2 inflammation.

Correlations Among Biomarkers and AD-Associated Parameters

In Study "B" (see Example 7), patients with severe AD were given 150 or 300 mg mAb1 or placebo (PBO) weekly for four weeks. Pruritus was measured using twice-daily pruritus Numeric Rating Scale (NRS; ranging from 0-10) to generate an average weekly NRS score & a bi-weekly 5-D Pruritus Scale assessments. The 5-D scale is a 5 question tool used to assess multiple dimensions of itch: degree, duration, direction, disability, and distribution. Mean baseline NRS & 5-D scores were 5.5 & 19, respectively. The average weekly NRS scores rapidly decreased (mean % change from baseline) by 31.9% at week 2 ($p<0.02$), & 55.2% at week 7 ($p=0.01$) in the 300 mg group vs +1.3% and −17.3% respectively in the PBO group. Rapid reduction in 5-D scores was also observed in patients treated with 300 mg mAb1 (mean % change −28.2% at day 15, $p=0.0009$; −37.1% at day 29, $p=0.0007$; −42.5% at day 43, $p=0.012$; +3.6%, +8.1% & −9.4% respectively in the PBO group). Serum levels of CCL17, a marker of IL4/IL13 activity, also rapidly declined on treatment. Both CCL17 and pruritus were suppressed for several weeks following the end of treatment. Table 50 shows the correlation of pruritus (5D and NRS) with outcomes of dermatitis (EASI) and CCL17.

TABLE 50

| | 5D correlations | | | | NRS correlations | | | |
|---|---|---|---|---|---|---|---|---|
| | EASI | | CCL17 | | EASI | | CCL17 | |
| Time point | Spearman r | P | Spearman r | P | Spearman r | P | Spearman r | P |
| Actual Values | | | | | | | | |
| Baseline | 0.41 | 0.0111 | 0.46 | 0.0044 | 0.35 | 0.0321 | 0.42 | 0.0117 |
| Day 29 | 0.62 | 0.0001 | 0.55 | 0.0024 | 0.64 | <0.0001 | 0.12 | 0.5413 |
| Percent change from baseline | | | | | | | | |
| Day 15 | 0.65 | <0.0001 | 0.46 | 0.0089 | 0.51 | 0.0012 | 0.32 | 0.0795 |
| Day 29 | 0.61 | <0.0001 | 0.48 | 0.0105 | 0.61 | <0.0001 | 0.11 | 0.5640 |

Overall, for all treatment groups, the 5D score significantly correlated with CCL17 ($r=0.46$, $p=0.004$ at baseline; $r=0.55$, $p=0.002$ at day 29) & EASI scores in this study ($r=0.41$, $p=0.011$ at baseline; 0.62, $p<0.0001$ at day 29). The percent change in 5D significantly correlated with the percent change from baseline in EASI ($r=0.65$, $p<0.0001$ for day 15; and $r=0.61$, $p<0.0001$ for day 29) and CCL17 ($r=0.46$, $p=0.0089$ for day 15; and $r=0.48$, $p=0.0105$ for day 29) for the overall treatment groups at Days 15 and 29. Treatment groups were also individually assessed for correlation of Pruritus 5D with EASI and CCL17. At day 15, only the 150 mg group demonstrated strong and significant correlation between the percent change in EASI and percent change in 5D ($r=0.81$, $p=0.0005$). Similarly at day 29, the only significant correlation was for the 150 mg group ($r=0.57$, $p=0.0036$). Although there was a significant overall correlation between percent change in CCL17 and percent change in 5D score at both day 15 and day 29, none of the individual treatment groups showed such a correlation at either day.

Pruritus severity, assessed using the NRS, showed moderate to strong correlations with EASI that were significant. However, NRS values correlated with CCL17 values only at baseline, with no significant correlation for percent change from baseline. The rapid & sustained improvement in pruritus observed in adult AD patients treated with mAb1 suggests IL-4/IL-13 signaling is a key mechanism for AD pruritus. The correlation between pruritus and CCL17 levels highlights the relationship between IL-4/IL-13 mediated inflammation, AD disease activity & pruritus in severe AD.

C. Repeated Administration of mAb1 to Subjects with Moderate-to-Severe Atopic Dermatitis IgE and TARC levels were measured in samples from a clinical trial involving subjects with moderate-to-severe atopic dermatitis (AD). AD subjects were administered 300 mg of mAb1, or placebo, on days 1, 8, 15, 22, 29, 36, 43, 50, 57, 64, 71 and 78 of the study (i.e., 12 weekly doses) (see Example 10 herein). All administrations for both studies were subcutaneous (SC). Serum samples for biomarker analysis were collected from the antibody- and placebo-treated subjects from both studies at days 1 (baseline), 8, 15, 22, 25, 29, 36, 43, 50, 57, 64, 71, 85, 99, 113, 127, 141, 155, 169, 183 and 197 (end of study) or early termination. Levels of IgE, TARC and antigen-specific IgE (Phadiatop™ test) were measured in each sample.

TARC is a chemokine induced by IL-4/IL-13, shown to be strongly associated with disease severity of AD, and may be involved in pathogenesis of the disease. Baseline TARC levels were assessed for potential predictive value for treatment response. Post-treatment samples were evaluated for pharmacodynamics effect of mAb1 on TARC.

Patients with AD often have elevated IgE. Total IgE levels have been found to correlate with AD severity and may be involved in the pathogenesis of the disease. Baseline IgE levels were assessed for potential predictive value for treatment response. Post-treatment samples were evaluated for pharmacodynamics effects of mAb1 on total IgE.

The Phadiatop™ test is an in vitro diagnostic screening tool used to detect antigen-specific IgE for common inhalants. Baseline results of the Phadiatop™ test were assessed for potential predictive value for treatment response. Post-treatment samples were evaluated for pharmacodynamics effects of mAb1 on the Phadiatop™ antigen panel.

Figure 55:
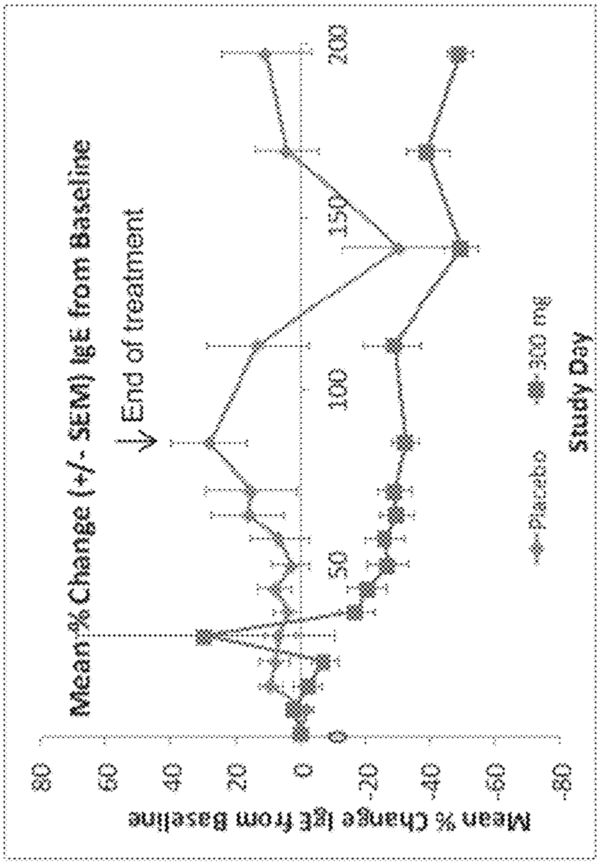
FIG. 55 shows the median percent change in IgE from baseline for the study in section C of Example 12.
Figure 55:
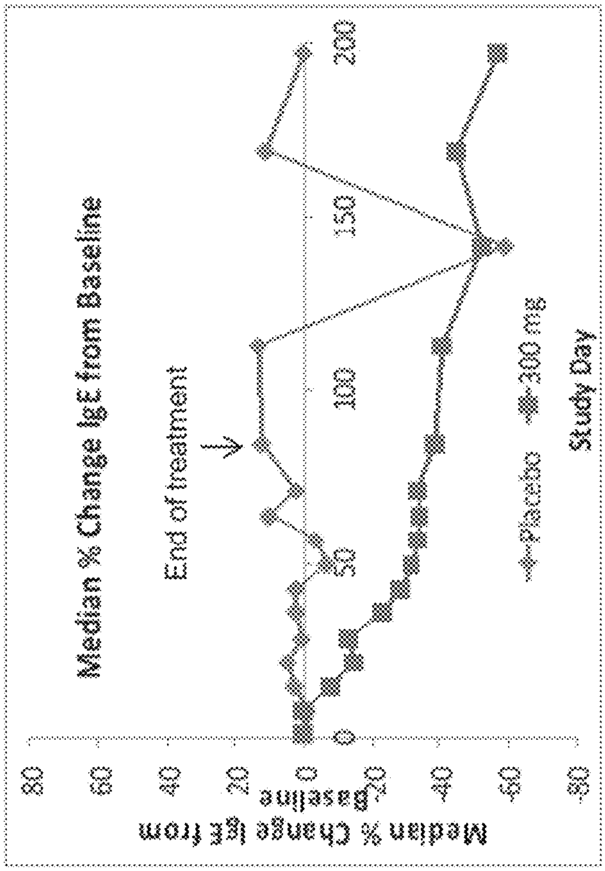
Figure 56:
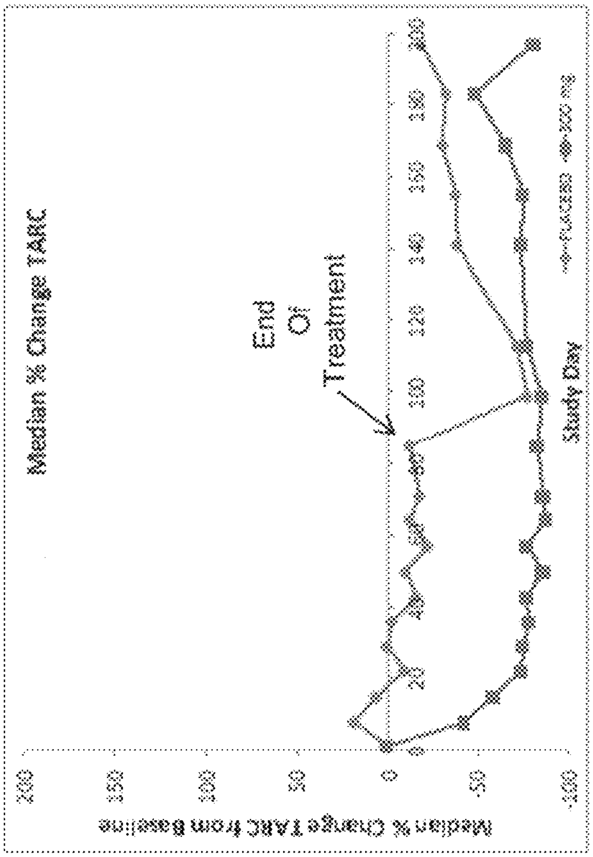
FIG. 56 shows the median percent change in TARC from baseline for the study in section C of Example 12.
Figure 56:
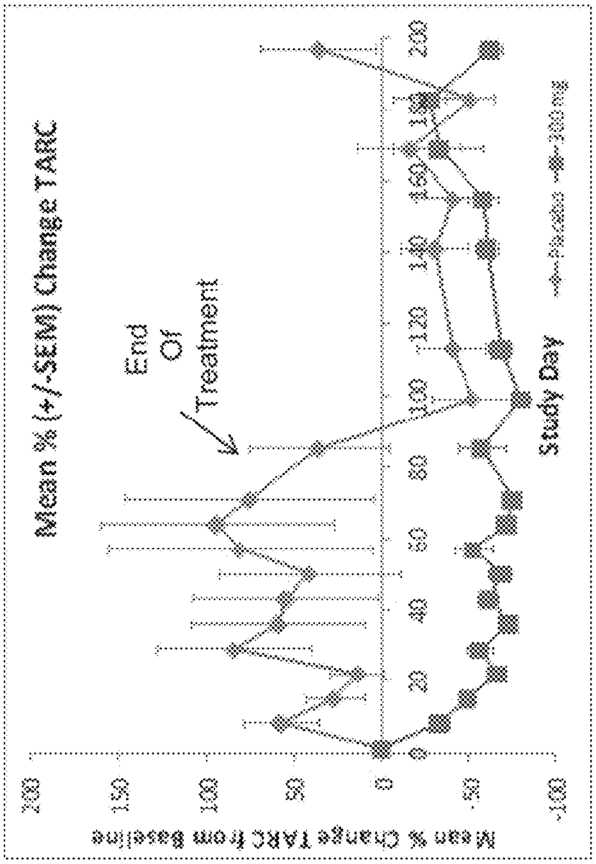

In line with the results obtained from earlier clinical trials (see sections A and B above), the TARC and IgE levels decreased and remained suppressed below baseline through the 16-week post-treatment follow-up period (FIGS. 55-56).

Greater magnitude of IgE suppression was observed with 12 weeks of 300 mg mAb1 treatment during a 16-week follow-up (median −57%) as compared 4 weeks of mAb1. Magnitude of TARC suppression was comparable at the end-of-treatment after 12 weeks (median −83%) and weeks (median −76%) of mAb1 treatment.

D. Concomitant Administration of mAb1 with Topical Corticosteroids in Patients with Moderate-to-Severe Atopic Dermatitis TARC and IgE modulation was studied in a trial evaluating the safety and efficacy of mAb1 in combination with topical corticosteroids (TCS) in adult patients with moderate-to-severe AD. Two treatment groups were compared (weekly dosing for 4 weeks): (300 mg mAb1+TCS), versus (placebo+TCS). TCS were administered from day 1 up to day 28 (patients stopped TCS treatment if lesions cleared) (see Example 11 herein). Patients were evaluated at screening, baseline (day 1), weekly through week 5, then every other week through week 11. TARC levels decreased in both treatment groups, with a trend for greater suppression in the mAb1+TCS group compared to placebo (PBO)+TCS. Differences were statistically significant at days 22, 29 and 50. IgE levels also decreased in both treatment groups. There was no statistically significant difference in IgE suppression between groups.

TABLE 51

Baseline TARC by treatment group

| Treatment group | Placebo + TCS | 300 mg mAb1 + TCS |
|---|---|---|
| n | 9 | 20 |
| Mean (SD; pg/mL) | 2999.2 (4063.88) | 2703.4 (3411.76) |
| Median (pg/mL) | 913 | 1444 |
| Min:max | 325:11966 | 347:14100 |

TARC was measured using the R&D Systems human TARC Quantikine ELISA kit. Table 51 summarizes the baseline TARC levels by treatment group. The mean and median baseline TARC levels for both treatment groups were above the normal range of 106-431 pg/mL (Weihrauch et al 2005; Cancer Res. 65: 13), as well as the observed baseline levels as in Section A above.

TABLE 52

Mean percent change TARC from baseline with standard deviation (SD)

| Treatment group | Study day | n | Mean % change from baseline | SD |
|---|---|---|---|---|
| Placebo + TCS | 8 | 9 | −25.5 | 36.8 |
| | 15 | 9 | −15.6 | 70.5 |
| | 22 | 9 | −5.9 | 48.5 |
| | 29 | 8 | −24.4 | 23.2 |
| | 36 | 8 | −39.7 | 35.7 |
| | 50 | 9 | −33.1 | 47.8 |
| | 64 | 8 | −25.1 | 53.2 |
| | 78 | 9 | −20.8 | 73.0 |
| 300mg mAb1 + TCS | 8 | 20 | −43.8 | 30.9 |
| | 15 | 21 | −49.6 | 38.7 |
| | 22 | 20 | −51.0 | 44.1 |
| | 29 | 21 | −55.2 | 41.3 |
| | 36 | 20 | −57.9 | 42.9 |
| | 50 | 21 | −61.1 | 35.4 |
| | 64 | 21 | −36.8 | 66.8 |
| | 78 | 19 | −35.3 | 47.0 |

TARC levels decreased from baseline in both treatment groups, thus TCS alone may lower serum TARC levels in AD patients. Although the magnitude of median % change TARC from baseline was consistently larger in the mAb1+TCS group compared to placebo+TCS, the difference was only statistically significant at days 22, 29 and 50 (least square mean difference estimated from analysis of covariance) (Table 52).

The mean and median baseline IgE levels are summarized in Table 53.

TABLE 53

Baseline IgE by treatment group

| Treatment group | Placebo + TCS | 300 mg mAb1 + TCS |
|---|---|---|
| n | 9 | 21 |
| Mean (SD; kU/L) | 12016.4 (19659.15) | 4197.8 (5293.78) |
| Median (kU/L) | 4250 | 1728 |
| Min:Max | 119:61600 | 61:19790 |

IgE levels declined in both treatment groups. After day 29, there was a trend for the magnitude of median percent change IgE to be greater in the mAb1+TCS group, there was no statistically significant difference at any time point in the study (LS mean difference estimated from analysis of covariance; Table 54).

TABLE 54 mean percent change from baseline with SD

| Treatment group | Study day | n | Mean % change from baseline | SD |
|---|---|---|---|---|
| Placebo + TCS | 8 | 9 | −1.1 | 8.7 |
| | 15 | 9 | −10.0 | 15.7 |
| | 22 | 9 | −9.5 | 16.7 |
| | 29 | 8 | −9.4 | 23.1 |
| | 36 | 8 | −13.2 | 19.2 |
| | 50 | 9 | −13.0 | 18.3 |
| | 64 | 8 | −20.8 | 15.8 |
| | 78 | 9 | −21.5 | 18.3 |
| 300 mg mAb1 + TCS | 8 | 20 | 0.3 | 16.1 |
| | 15 | 21 | 8.0 | 46.4 |
| | 22 | 20 | 0.7 | 44.0 |
| | 29 | 21 | −7.3 | 40.5 |
| | 36 | 20 | −1.8 | 49.2 |
| | 50 | 21 | −10.0 | 43.7 |
| | 64 | 21 | −22.2 | 44.0 |
| | 78 | 19 | −29.0 | 39.4 |

Approximately 50% of patients achieved at least an EASI50 by day 29 on placebo+TCS and the suppression of TARC and IgE in this group was consistent with the clinical improvement observed. All patients on mAb1+TCS achieved at least an EASI50 by day 29 (see Example 11). Trends were observed for greater suppression of TARC and IgE in the mAb1+TCS compared to placebo+TCS. However, the only statistically significant differences observed were in TARC suppression at days 22, 29 and 50.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating moderate-to-severe atopic dermatitis (AD) in a subject in need thereof, the method comprising:

administering an anti-interleukin-4-receptor (IL-4R) antibody or an antigen-binding fragment thereof to a subject having moderate-to-severe AD, wherein the subject is resistant, non-responsive, or inadequately responsive to treatment with a topical corticosteroid or a topical calcineurin inhibitor, or is a subject for whom topical treatments are inadvisable;

wherein the anti-IL-4R antibody or antigen-binding fragment thereof comprises a heavy chain complementarity determining region (HCDR) 1 comprising the amino acid sequence of SEQ ID NO:148, an HCDR2 comprising the amino acid sequence of SEQ ID NO:150, an HCDR3 comprising the amino acid sequence of SEQ ID NO:152, a light chain complementarity determining region (LCDR)1 comprising the amino acid sequence of SEQ ID NO:156, an LCDR2 comprising the amino acid sequence of LGS, and an LCDR3 comprising the amino acid sequence of SEQ ID NO:160; and wherein the anti-IL-4R antibody or antigen-binding fragment thereof is administered to the subject in a dosing regimen comprising an initial dose followed by one or more secondary doses, wherein the initial dose is 600 mg of the anti-IL-4R antibody or antigen-binding fragment thereof, the secondary dose is 300 mg of the anti-IL-4R antibody or antigen-binding fragment thereof, and each secondary dose is administered 1 to 2 weeks after the immediately preceding dose;

wherein treatment results in an improvement in an AD-associated parameter from baseline to Week 16, wherein the improvement in the AD-associated parameter is:

(i) a decrease from baseline in Eczema Area and Severity Index (EASI) score of at least 50%;

(ii) a decrease from baseline in Investigator's Global Assessment (IGA) score of ≥2; and/or (iii) an improvement in IGA score to an IGA score of 0 or 1.

2. The method of claim 1, wherein the anti-IL-4R antibody or antigen-binding fragment thereof is administered subcutaneously.

3. The method of claim 1, wherein the anti-IL-4R antibody or antigen-binding fragment thereof comprises a heavy chain variable region (HCVR) comprising the amino acid sequence of SEQ ID NO:162 and a light chain variable region (LCVR) comprising the amino acid sequence of SEQ ID NO:164.

4. The method of claim 3, wherein each secondary dose is administered one week after the immediately preceding dose.

5. The method of claim 3, wherein each secondary dose is administered two weeks after the immediately preceding dose.

6. The method of claim 3, wherein treatment results in a decrease from baseline to Week 16 in EASI score of at least 50%.

7. The method of claim 3, wherein treatment results in a decrease from baseline to Week 16 in EASI score of at least 75%.

8. The method of claim 3, wherein treatment results in a decrease from baseline to Week 16 in EASI score of at least 90%.

9. The method of claim 3, wherein treatment results in a decrease from baseline to Week 16 in IGA score of ≥2.

10. The method of claim 3, wherein treatment results in an improvement from baseline to Week 16 in IGA score to an IGA score of 1.

11. The method of claim 3, wherein treatment results in an improvement from baseline to Week 16 in IGA score to an IGA score of 0.

12. The method of claim 3, wherein the anti-IL-4R antibody is a full antibody.

13. The method of claim 12, wherein the full antibody is an IgG antibody.

14. The method of claim 12, wherein the full antibody is an IgG4 antibody.

15. The method of claim 1, wherein the anti-IL-4R antibody or antigen-binding fragment thereof is administered concomitantly with a topical corticosteroid.

16. The method of claim 1, wherein the anti-IL-4R antibody or antigen-binding fragment thereof is contained in a syringe.

17. The method of claim 1, wherein the anti-IL-4R antibody or antigen-binding fragment thereof is contained in a glass vial.

18. The method of claim 1, wherein the anti-IL-4R antibody or antigen-binding fragment thereof is contained in a microinfuser.

19. The method of claim 1, wherein the anti-IL-4R antibody or antigen-binding fragment thereof is contained in a pen delivery device.

20. The method of claim 19, wherein the pen delivery device is pre-filled.

21. The method of claim 1, wherein the anti-IL-4R antibody or antigen-binding fragment thereof is contained in an autoinjector.

22. The method of claim 1, wherein the anti-IL-4R antibody or antigen-binding fragment thereof is human.

23. A method of treating moderate-to-severe atopic dermatitis (AD) in a subject in need thereof, the method comprising:

administering an anti-interleukin-4-receptor (IL-4R) human antibody to a subject having moderate-to-severe AD, wherein the subject is resistant, non-responsive, or inadequately responsive to treatment with a topical corticosteroid or a topical calcineurin inhibitor, or is a subject for whom topical treatments are inadvisable;

wherein the anti-IL-4R human antibody is a full antibody and comprises a heavy chain complementarity determining region (HCDR)1 comprising the amino acid sequence SEQ ID NO:148, an HCDR2 comprising the amino acid sequence SEQ ID NO:150, an HCDR3 comprising the amino acid sequence SEQ ID NO:152, a light chain complementarity determining region (LCDR)1 comprising the amino acid sequence SEQ ID NO:156, an LCDR2 comprising the amino acid sequence LGS, and an LCDR3 comprising the amino acid sequence SEQ ID NO:160; and wherein the anti-IL-4R human antibody is administered to the subject in a dosing regimen comprising an initial dose followed by one or more secondary doses, wherein the initial dose is 600 mg of the anti-IL-4R human antibody, the secondary dose is 300 mg of the anti-IL-4R human antibody, and each secondary dose is administered 1 to 2 weeks after the immediately preceding dose;

wherein treatment results in an improvement in an AD-associated parameter from baseline to Week 16, wherein the improvement in the AD-associated parameter is:

(i) a decrease from baseline in Eczema Area and Severity Index (EASI) score of at least 50%;

(ii) a decrease from baseline in Investigator's Global Assessment (IGA) score of ≥2; and/or (iii) an improvement in IGA score to an IGA score of 0 or 1.

24. The method of claim 23, wherein the anti-IL-4R human antibody comprises a heavy chain variable region (HCVR) comprising the amino acid sequence SEQ ID NO:162 and a light chain variable region (LCVR) comprising the amino acid sequence SEQ ID NO:164.

25. The method of claim 24, wherein the anti-IL-4R human antibody is an IgG antibody.

26. The method of claim 24, wherein the anti-IL-4R human antibody is an IgG4 antibody.

27. The method of claim 26, wherein each secondary dose is administered one week after the immediately preceding dose.

28. The method of claim 26, wherein each secondary dose is administered two weeks after the immediately preceding dose.

29. The method of claim 26, wherein the anti-IL-4R human antibody is administered subcutaneously.

30. The method of claim 26, wherein the anti-IL-4R human antibody is administered concomitantly with a topical corticosteroid.

31. The method of claim 26, wherein the anti-IL-4R human antibody is contained in a syringe.

32. The method of claim 26, wherein the anti-IL-4R human antibody is contained in a glass vial.

33. The method of claim 26, wherein the anti-IL-4R human antibody is contained in a microinfuser.

34. The method of claim 26, wherein the anti-IL-4R human antibody is contained in a pen delivery device.

35. The method of claim 34, wherein the pen delivery device is pre-filled.

36. The method of claim 26, wherein the anti-IL-4R human antibody is contained in an autoinjector.

37. The method of claim 26, wherein treatment results in a decrease from baseline to Week 16 in EASI score of at least 50%.

38. The method of claim 26, wherein treatment results in a decrease from baseline to Week 16 in EASI score of at least 75%.

39. The method of claim 26, wherein treatment results in a decrease from baseline to Week 16 in EASI score of at least 90%.

40. The method of claim 26, wherein treatment results in a decrease from baseline to Week 16 in IGA score of ≥2.

41. The method of claim 26, wherein treatment results in an improvement from baseline to Week 16 in IGA score to an IGA score of 1.

42. The method of claim 26, wherein treatment results in an improvement from baseline to Week 16 in IGA score to an IGA score of 0.

* * * * *

SEQUENCE LISTING

```
Sequence total quantity: 275
SEQ ID NO: 1          moltype = DNA  length = 351
FEATURE               Location/Qualifiers
source                1..351
```

```
                        mol_type = other DNA
                        organism = synthetic construct
SEQUENCE: 1
caggtgcagc tggtggagtc tggggggaggc gtggtccagc ctgggaggtc cctgagactc  60
tcctgtgcag cctctggatt caccttccgc tcttatggca tgcactgggt ccgccaggct  120
ccaggcaagg ggctggagtg ggtggcggtc atatcatatg atggaagtaa taaatattat  180
atagactccg tgaagggccg attcaccatc tccagagaca attccaagaa cacgctgaat  240
ctgcaaatga acagcctgag acttgaggac acggctgtat attactgtgc gaaagagggg  300
aggggggat ttgactactg gggccaggga atcccggtca ccgtctcctc a           351

SEQ ID NO: 2            moltype = AA  length = 117
FEATURE                 Location/Qualifiers
source                  1..117
                        mol_type = protein
                        organism = synthetic construct
SEQUENCE: 2
QVQLVESGGG VVQPGRSLRL SCAASGFTFR SYGMHWVRQA PGKGLEWVAV ISYDGSNKYY  60
IDSVKGRFTI SRDNSKNTLN LQMNSLRLED TAVYYCAKEG RGGFDYWGQG IPVTVSS     117

SEQ ID NO: 3            moltype = DNA  length = 24
FEATURE                 Location/Qualifiers
source                  1..24
                        mol_type = other DNA
                        organism = synthetic construct
SEQUENCE: 3
ggattcacct tccgctctta tggc                                         24

SEQ ID NO: 4            moltype = AA  length = 8
FEATURE                 Location/Qualifiers
source                  1..8
                        mol_type = protein
                        organism = synthetic construct
SEQUENCE: 4
GFTFRSYG                                                           8

SEQ ID NO: 5            moltype = DNA  length = 24
FEATURE                 Location/Qualifiers
source                  1..24
                        mol_type = other DNA
                        organism = synthetic construct
SEQUENCE: 5
atatcatatg atggaagtaa taaa                                         24

SEQ ID NO: 6            moltype = AA  length = 8
FEATURE                 Location/Qualifiers
source                  1..8
                        mol_type = protein
                        organism = synthetic construct
SEQUENCE: 6
ISYDGSNK                                                           8

SEQ ID NO: 7            moltype = DNA  length = 30
FEATURE                 Location/Qualifiers
source                  1..30
                        mol_type = other DNA
                        organism = synthetic construct
SEQUENCE: 7
gcgaaagagg ggaggggggg atttgactac                                   30

SEQ ID NO: 8            moltype = AA  length = 10
FEATURE                 Location/Qualifiers
source                  1..10
                        mol_type = protein
                        organism = synthetic construct
SEQUENCE: 8
AKEGRGGFDY                                                         10

SEQ ID NO: 9            moltype = DNA  length = 324
FEATURE                 Location/Qualifiers
source                  1..324
                        mol_type = other DNA
                        organism = synthetic construct
SEQUENCE: 9
gacatccaga tgacccagtc tccatcctca ctgtctgcat ctgtaggaga cagagtcacc  60
atcacttgtc gggcgagtca ggtcataaac aattatttag cctggtttca gcagaaacca  120
gggaaagtcc ctaagtccct gatccatgct gcatccagtt tacaaagtgg ggtcccatca  180
aagttcagcg gcagtggatc tgggacagat ttcactctca ccatcagcag cctgcagcct  240
gaagattttg caacttatta ctgccaacag tataatagtc acccgtggac gttcggccaa  300
gggaccaagg tggaaatcaa acga                                         324
```

```
SEQ ID NO: 10          moltype = AA  length = 108
FEATURE                Location/Qualifiers
source                 1..108
                       mol_type = protein
                       organism = synthetic construct
SEQUENCE: 10
DIQMTQSPSS LSASVGDRVT ITCRASQVIN NYLAWFQQKP GKVPKSLIHA ASSLQSGVPS  60
KFSGSGSGTD FTLTISSLQP EDFATYYCQQ YNSHPWTFGQ GTKVEIKR               108

SEQ ID NO: 11          moltype = DNA  length = 18
FEATURE                Location/Qualifiers
source                 1..18
                       mol_type = other DNA
                       organism = synthetic construct
SEQUENCE: 11
caggtcataa acaattat                                                18

SEQ ID NO: 12          moltype = AA  length = 6
FEATURE                Location/Qualifiers
source                 1..6
                       mol_type = protein
                       organism = synthetic construct
SEQUENCE: 12
QVINNY                                                             6

SEQ ID NO: 13          moltype =   length =
SEQUENCE: 13
000

SEQ ID NO: 14          moltype =   length =
SEQUENCE: 14
000

SEQ ID NO: 15          moltype = DNA  length = 27
FEATURE                Location/Qualifiers
source                 1..27
                       mol_type = other DNA
                       organism = synthetic construct
SEQUENCE: 15
caacagtata atagtcaccc gtggacg                                      27

SEQ ID NO: 16          moltype = AA  length = 9
FEATURE                Location/Qualifiers
source                 1..9
                       mol_type = protein
                       organism = synthetic construct
SEQUENCE: 16
QQYNSHPWT                                                          9

SEQ ID NO: 17          moltype = DNA  length = 351
FEATURE                Location/Qualifiers
source                 1..351
                       mol_type = other DNA
                       organism = synthetic construct
SEQUENCE: 17
caggtgcagc tggtggagtc tgggggaggc gtggtccagc ctgggaggtc cctgagactc  60
tcctgtgcag cctctggatt caccttccgc tcttatggca tgcactgggt ccgccaggct  120
ccaggcaagg ggctggagtg ggtggcggtc atatcatatg atggaagtaa taaatattat  180
atagactccg tgaagggccg attcaccatc tccagagaca attccaagaa cacgctgaat  240
ctgcaaatga acagcctgag acttgaggac acggctgtat attactgtgc gaaagagggg  300
agggggggat ttgactactg gggccaggga accctggtca ccgtctcctc a           351

SEQ ID NO: 18          moltype = AA  length = 117
FEATURE                Location/Qualifiers
source                 1..117
                       mol_type = protein
                       organism = synthetic construct
SEQUENCE: 18
QVQLVESGGG VVQPGRSLRL SCAASGFTFR SYGMHWVRQA PGKGLEWVAV ISYDGSNKYY  60
IDSVKGRFTI SRDNSKNTLN LQMNSLRLED TAVYYCAKEG RGGFDYWGQG TLVTVSS     117

SEQ ID NO: 19          moltype = DNA  length = 321
FEATURE                Location/Qualifiers
source                 1..321
                       mol_type = other DNA
                       organism = synthetic construct
SEQUENCE: 19
gacatccaga tgacccagtc tccatcctca ctgtctgcat ctgtaggaga cagagtcacc  60
```

```
atcacttgtc gggcgagtca ggtcataaac aattatttag cctggtttca gcagaaacca  120
gggaaagtcc ctaagtccct gatccatgct gcatccagtt tacaaagtgg ggtcccatca  180
aagttcagcg gcagtggatc tgggacagat ttcactctca ccatcagcag cctgcagcct  240
gaagattttg caacttatta ctgccaacag tataatagtc acccgtggac gttcggccaa  300
gggaccaagg tggaaatcaa a                                            321

SEQ ID NO: 20          moltype = AA  length = 107
FEATURE                Location/Qualifiers
source                 1..107
                       mol_type = protein
                       organism = synthetic construct
SEQUENCE: 20
DIQMTQSPSS LSASVGDRVT ITCRASQVIN NYLAWFQQKP GKVPKSLIHA ASSLQSGVPS  60
KFSGSGSGTD FTLTISSLQP EDFATYYCQQ YNSHPWTFGQ GTKVEIK                107

SEQ ID NO: 21          moltype = DNA  length = 351
FEATURE                Location/Qualifiers
source                 1..351
                       mol_type = other DNA
                       organism = synthetic construct
SEQUENCE: 21
caggtgcagc tggtggagtc tgggggaggc gtggtccagc ctgggaggtc cctgagactc  60
tcctgtgcag cctctggatt caccttccgc tcttatggca tgcactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag agctgaggac acggctgtgt attactgtgc gaaagagggg  300
aggggggggat ttgactactg gggccaggga accctggtca ccgtctcctc a          351

SEQ ID NO: 22          moltype = AA  length = 117
FEATURE                Location/Qualifiers
source                 1..117
                       mol_type = protein
                       organism = synthetic construct
SEQUENCE: 22
QVQLVESGGG VVQPGRSLRL SCAASGFTFR SYGMHWVRQA PGKGLEWVAV ISYDGSNKYY  60
ADSVKGRFTI SRDNSKNTLY LQMNSLRAED TAVYYCAKEG RGGFDYWGQG TLVTVSS     117

SEQ ID NO: 23          moltype = DNA  length = 322
FEATURE                Location/Qualifiers
source                 1..322
                       mol_type = other DNA
                       organism = synthetic construct
SEQUENCE: 23
gacatccaga tgacccagtc tccatcctca ctgtctgcat ctgtaggaga cagagtcacc  60
atcacttgtc gggcgagtca ggtcataaac aattatttag cctggtttca gcagaaacca  120
gggaaagccc ctaagtccct gatctatgct gcatccagtt tgcaaagtgg ggtcccatca  180
aggttcagcg gcagtggatc tgggacagat ttcactctca ccatcagcag cctgcagcct  240
gaagattttg caacttatta ctgccaacag tataatagtc acccgtggac gttcggccaa  300
gggaccaagg tggaaatcaa ac                                           322

SEQ ID NO: 24          moltype = AA  length = 107
FEATURE                Location/Qualifiers
source                 1..107
                       mol_type = protein
                       organism = synthetic construct
SEQUENCE: 24
DIQMTQSPSS LSASVGDRVT ITCRASQVIN NYLAWFQQKP GKAPKSLIYA ASSLQSGVPS  60
RFSGSGSGTD FTLTISSLQP EDFATYYCQQ YNSHPWTFGQ GTKVEIK                107

SEQ ID NO: 25          moltype = DNA  length = 351
FEATURE                Location/Qualifiers
source                 1..351
                       mol_type = other DNA
                       organism = synthetic construct
SEQUENCE: 25
caggtgcagc tggtggagtc tgggggaggc gtggtccagc ctgggaggtc cctgagactc  60
tcctgtgcag cctctggatt caccttcaga agctatggca tacactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacactgtat  240
ctgcaaatga acagcctgat aactgaggac acggctgtgt attattgtgt gaaagagggg  300
agggggggggt ttgactactg gggccaggga accacggtca ccgtctcctc a          351

SEQ ID NO: 26          moltype = AA  length = 117
FEATURE                Location/Qualifiers
source                 1..117
                       mol_type = protein
                       organism = synthetic construct
SEQUENCE: 26
QVQLVESGGG VVQPGRSLRL SCAASGFTFR SYGIHWVRQA PGKGLEWVAV ISYDGSNKYY  60
```

```
ADSVKGRFTI SRDNSKNTLY LQMNSLITED TAVYYCVKEG RGGFDYWGQG TTVTVSS     117

SEQ ID NO: 27          moltype = DNA  length = 24
FEATURE                Location/Qualifiers
source                 1..24
                       mol_type = other DNA
                       organism = synthetic construct
SEQUENCE: 27
ggattcacct tcagaagcta tggc                                         24

SEQ ID NO: 28          moltype = AA  length = 8
FEATURE                Location/Qualifiers
source                 1..8
                       mol_type = protein
                       organism = synthetic construct
SEQUENCE: 28
GFTFRSYG                                                           8

SEQ ID NO: 29          moltype = DNA  length = 24
FEATURE                Location/Qualifiers
source                 1..24
                       mol_type = other DNA
                       organism = synthetic construct
SEQUENCE: 29
atatcatatg atggaagtaa taaa                                         24

SEQ ID NO: 30          moltype = AA  length = 8
FEATURE                Location/Qualifiers
source                 1..8
                       mol_type = protein
                       organism = synthetic construct
SEQUENCE: 30
ISYDGSNK                                                           8

SEQ ID NO: 31          moltype = DNA  length = 30
FEATURE                Location/Qualifiers
source                 1..30
                       mol_type = other DNA
                       organism = synthetic construct
SEQUENCE: 31
gtgaaagagg ggaggggggg gtttgactac                                   30

SEQ ID NO: 32          moltype = AA  length = 10
FEATURE                Location/Qualifiers
source                 1..10
                       mol_type = protein
                       organism = synthetic construct
SEQUENCE: 32
VKEGRGGFDY                                                         10

SEQ ID NO: 33          moltype = DNA  length = 324
FEATURE                Location/Qualifiers
source                 1..324
                       mol_type = other DNA
                       organism = synthetic construct
SEQUENCE: 33
gacatccaga tgacccagtc tccatcctca ctgtctgcat ctgtaggaga cagagtcacc  60
atcacttgtc gggcgagtca ggtcattaat aattatttag cctggtttca gcagaaacca  120
gggaaagtcc ctaagtccct gatccatgct gcatccagtt tgcaaagagg ggtcccatca  180
aagttcagcg gcagtggatc tgggacagat ttcactctca ccatcaacag cctgcagcct  240
gaagattttg caacttatta ctgccaacaa tataatagtt acccgtggac gttcggccaa  300
gggaccaagg tggaaatcaa acga                                         324

SEQ ID NO: 34          moltype = AA  length = 108
FEATURE                Location/Qualifiers
source                 1..108
                       mol_type = protein
                       organism = synthetic construct
SEQUENCE: 34
DIQMTQSPSS LSASVGDRVT ITCRASQVIN NYLAWFQQKP GKVPKSLIHA ASSLQRGVPS  60
KFSGSGSGTD FTLTINSLQP EDFATYYCQQ YNSYPWTFGQ GTKVEIKR               108

SEQ ID NO: 35          moltype = DNA  length = 18
FEATURE                Location/Qualifiers
source                 1..18
                       mol_type = other DNA
                       organism = synthetic construct
SEQUENCE: 35
caggtcatta ataattat                                                18
```

```
SEQ ID NO: 36          moltype = AA  length = 6
FEATURE                Location/Qualifiers
source                 1..6
                       mol_type = protein
                       organism = synthetic construct
SEQUENCE: 36
QVINNY                                                                      6

SEQ ID NO: 37          moltype =   length =
SEQUENCE: 37
000

SEQ ID NO: 38          moltype =   length =
SEQUENCE: 38
000

SEQ ID NO: 39          moltype = DNA  length = 27
FEATURE                Location/Qualifiers
source                 1..27
                       mol_type = other DNA
                       organism = synthetic construct
SEQUENCE: 39
caacaatata atagttaccc gtggacg                                               27

SEQ ID NO: 40          moltype = AA  length = 9
FEATURE                Location/Qualifiers
source                 1..9
                       mol_type = protein
                       organism = synthetic construct
SEQUENCE: 40
QQYNSYPWT                                                                   9

SEQ ID NO: 41          moltype = DNA  length = 351
FEATURE                Location/Qualifiers
source                 1..351
                       mol_type = other DNA
                       organism = synthetic construct
SEQUENCE: 41
caggtgcagc tggtggagtc tgggggaggc gtggtccagc ctgggaggtc cctgagactc  60
tcctgtgcag cctctggatt caccttcaga agctatggca tacactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacactgtat  240
ctgcaaatga acagcctgat aactgaggac acggctgtgt attattgtgt gaaagagggg  300
aggggggggt ttgactactg gggccaggga accctggtca ccgtctcctc a            351

SEQ ID NO: 42          moltype = AA  length = 117
FEATURE                Location/Qualifiers
source                 1..117
                       mol_type = protein
                       organism = synthetic construct
SEQUENCE: 42
QVQLVESGGG VVQPGRSLRL SCAASGFTFR SYGIHWVRQA PGKGLEWVAV ISYDGSNKYY  60
ADSVKGRFTI SRDNSKNTLY LQMNSLITED TAVYYCVKEG RGGFDYWGQG TLVTVSS     117

SEQ ID NO: 43          moltype = DNA  length = 321
FEATURE                Location/Qualifiers
source                 1..321
                       mol_type = other DNA
                       organism = synthetic construct
SEQUENCE: 43
gacatccaga tgacccagtc tccatcctca ctgtctgcat ctgtaggaga cagagtcacc  60
atcacttgtc gggcgagtca ggtcattaat aattatttag cctggtttca gcagaaacca  120
gggaaagtcc ctaagtccct gatccatgct gcatccagtt tgcaaagagg ggtcccatca  180
aagttcagcg gcagtggatc tgggacagat ttcactctca ccatcaacag cctgcagcct  240
gaagattttg caacttatta ctgccaacaa tataatagtt acccgtggac gttcggccaa  300
gggaccaagg tggaaatcaa a                                               321

SEQ ID NO: 44          moltype = AA  length = 107
FEATURE                Location/Qualifiers
source                 1..107
                       mol_type = protein
                       organism = synthetic construct
SEQUENCE: 44
DIQMTQSPSS LSASVGDRVT ITCRASQVIN NYLAWFQQKP GKVPKSLIHA ASSLQRGVPS  60
KFSGSGSGTD FTLTINSLQP EDFATYYCQQ YNSYPWTFGQ GTKVEIK                107

SEQ ID NO: 45          moltype = DNA  length = 351
FEATURE                Location/Qualifiers
```

```
source                 1..351
                       mol_type = other DNA
                       organism = synthetic construct
SEQUENCE: 45
caggtgcagc tggtggagtc tgggggaggc gtggtccagc ctgggaggtc cctgagactc  60
tcctgtgcag cctctggatt caccttcaga agctatggca tgcactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag agctgaggac acggctgtgt attactgtgt gaaagagggg  300
agggggggt ttgactactg gggccaggga accctggtca ccgtctcctc a          351

SEQ ID NO: 46          moltype = AA  length = 117
FEATURE                Location/Qualifiers
source                 1..117
                       mol_type = protein
                       organism = synthetic construct
SEQUENCE: 46
QVQLVESGGG VVQPGRSLRL SCAASGFTFR SYGMHWVRQA PGKGLEWVAV ISYDGSNKYY  60
ADSVKGRFTI SRDNSKNTLY LQMNSLRAED TAVYYCVKEG RGGFDYWGQG TLVTVSS     117

SEQ ID NO: 47          moltype = DNA  length = 322
FEATURE                Location/Qualifiers
source                 1..322
                       mol_type = other DNA
                       organism = synthetic construct
SEQUENCE: 47
gacatccaga tgacccagtc tccatcctca ctgtctgcat ctgtaggaga cagagtcacc  60
atcacttgtc gggcgagtca ggtcattaat aattatttag cctggtttca gcagaaacca  120
gggaaagccc ctaagtccct gatctatgct gcatccagtt tgcaaagtgg ggtcccatca  180
aggttcagcg gcagtggatc tgggacagat ttcactctca ccatcagcag cctgcagcct  240
gaagattttg caacttatta ctgccaacaa tataatagtt acccgtggac gttcggccaa  300
gggaccaagg tggaaatcaa ac                                          322

SEQ ID NO: 48          moltype = AA  length = 107
FEATURE                Location/Qualifiers
source                 1..107
                       mol_type = protein
                       organism = synthetic construct
SEQUENCE: 48
DIQMTQSPSS LSASVGDRVT ITCRASQVIN NYLAWFQQKP GKAPKSLIYA ASSLQSGVPS  60
RFSGSGSGTD FTLTISSLQP EDFATYYCQQ YNSYPWTFGQ GTKVEIK               107

SEQ ID NO: 49          moltype = DNA  length = 375
FEATURE                Location/Qualifiers
source                 1..375
                       mol_type = other DNA
                       organism = synthetic construct
SEQUENCE: 49
caggtgcagc tggtggagtc tgggggaggc ttggaacagc cggggggggtc cttgagactc  60
tcctgtgcag gctctggatt cacgtttaga gactatgcca tgacctgggt ccgccaggct  120
ccagggaagg ggctggagtg ggtcgcatcg attagtggtt ccggtggtaa cacatacttc  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggtccacg  360
gtcaccgtct cctca                                                  375

SEQ ID NO: 50          moltype = AA  length = 125
FEATURE                Location/Qualifiers
source                 1..125
                       mol_type = protein
                       organism = synthetic construct
SEQUENCE: 50
QVQLVESGGG LEQPGGSLRL SCAGSGFTFR DYAMTWVRQA PGKGLEWVAS ISGSGGNTYF  60
ADSVKGRFTI SRDNSKNTLY LQMNSLRAED TAVYYCAKDR LSITIRPRYY GLDVWGQGST  120
VTVSS                                                             125

SEQ ID NO: 51          moltype = DNA  length = 24
FEATURE                Location/Qualifiers
source                 1..24
                       mol_type = other DNA
                       organism = synthetic construct
SEQUENCE: 51
ggattcacgt ttagagacta tgcc                                        24

SEQ ID NO: 52          moltype = AA  length = 8
FEATURE                Location/Qualifiers
source                 1..8
                       mol_type = protein
                       organism = synthetic construct
```

```
SEQUENCE: 52
GFTFRDYA                                                    8

SEQ ID NO: 53           moltype = DNA  length = 24
FEATURE                 Location/Qualifiers
source                  1..24
                        mol_type = other DNA
                        organism = synthetic construct
SEQUENCE: 53
attagtggtt ccggtggtaa caca                                  24

SEQ ID NO: 54           moltype = AA  length = 8
FEATURE                 Location/Qualifiers
source                  1..8
                        mol_type = protein
                        organism = synthetic construct
SEQUENCE: 54
ISGSGGNT                                                    8

SEQ ID NO: 55           moltype = DNA  length = 54
FEATURE                 Location/Qualifiers
source                  1..54
                        mol_type = other DNA
                        organism = synthetic construct
SEQUENCE: 55
gcgaaagatc gactctctat aacaattcgc ccacgctatt atggtttgga cgtc  54

SEQ ID NO: 56           moltype = AA  length = 18
FEATURE                 Location/Qualifiers
source                  1..18
                        mol_type = protein
                        organism = synthetic construct
SEQUENCE: 56
AKDRLSITIR PRYYGLDV                                         18

SEQ ID NO: 57           moltype = DNA  length = 324
FEATURE                 Location/Qualifiers
source                  1..324
                        mol_type = other DNA
                        organism = synthetic construct
SEQUENCE: 57
gacatccaga tgacccagtc tccatcctca ctgtctgcat ctgttggaga cagagtcacc  60
atcacttgtc gggcgagtca ggccattaac aatcatttag cctggtttca gcagaaacca  120
gggaaagccc ctaagtccct gatctttgct gtatccagtt tgcaaagtgg ggtcccatca  180
aagttcagcg gcagtggatc tgggacagac ttcactctca ccatcagcag cctgcagcct  240
gaagattttg caacttatta ctgccaacag tataatagtt acccgtggac gttcggccaa  300
gggaccaagg tggaaatcaa acga                                  324

SEQ ID NO: 58           moltype = AA  length = 108
FEATURE                 Location/Qualifiers
source                  1..108
                        mol_type = protein
                        organism = synthetic construct
SEQUENCE: 58
DIQMTQSPSS LSASVGDRVT ITCRASQAIN NHLAWFQQKP GKAPKSLIFA VSSLQSGVPS  60
KFSGSGSGTD FTLTISSLQP EDFATYYCQQ YNSYPWTFGQ GTKVEIKR          108

SEQ ID NO: 59           moltype = DNA  length = 18
FEATURE                 Location/Qualifiers
source                  1..18
                        mol_type = other DNA
                        organism = synthetic construct
SEQUENCE: 59
caggccatta acaatcat                                         18

SEQ ID NO: 60           moltype = AA  length = 6
FEATURE                 Location/Qualifiers
source                  1..6
                        mol_type = protein
                        organism = synthetic construct
SEQUENCE: 60
QAINNH                                                      6

SEQ ID NO: 61           moltype =   length =
SEQUENCE: 61
000

SEQ ID NO: 62           moltype =   length =
SEQUENCE: 62
```

```
000

SEQ ID NO: 63          moltype = DNA  length = 27
FEATURE                Location/Qualifiers
source                 1..27
                       mol_type = other DNA
                       organism = synthetic construct
SEQUENCE: 63
caacagtata atagttaccc gtggacg                                      27

SEQ ID NO: 64          moltype = AA  length = 9
FEATURE                Location/Qualifiers
source                 1..9
                       mol_type = protein
                       organism = synthetic construct
SEQUENCE: 64
QQYNSYPWT                                                          9

SEQ ID NO: 65          moltype = DNA  length = 372
FEATURE                Location/Qualifiers
source                 1..372
                       mol_type = other DNA
                       organism = synthetic construct
SEQUENCE: 65
gaggtgcagc tggtggagtc tgggggaggc ttggaacagc cggggggggtc cttgagactc  60
tcctgtgcag gctctggatt cacgtttaga gactatgcca tgacctgggt ccgccaggct  120
ccagggaagg ggctggagtg ggtcgcatcg attagtggtt ccggtggtaa cacatacttc  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cc                                                      372

SEQ ID NO: 66          moltype = AA  length = 124
FEATURE                Location/Qualifiers
source                 1..124
                       mol_type = protein
                       organism = synthetic construct
SEQUENCE: 66
EVQLVESGGG LEQPGGSLRL SCAGSGFTFR DYAMTWVRQA PGKGLEWVAS ISGSGGNTYF  60
ADSVKGRFTI SRDNSKNTLY LQMNSLRAED TAVYYCAKDR LSITIRPRYY GLDVWGQGTT  120
VTVS                                                               124

SEQ ID NO: 67          moltype = DNA  length = 321
FEATURE                Location/Qualifiers
source                 1..321
                       mol_type = other DNA
                       organism = synthetic construct
SEQUENCE: 67
gacatccaga tgacccagtc tccatcctca ctgtctgcat ctgttggaga cagagtcacc  60
atcacttgtc gggcgagtca ggccattaac aatcatttag cctggtttca gcagaaacca  120
gggaaagccc ctaagtccct gatctttgct gtatccagtt tgcaaagtgg ggtcccatca  180
aagttcagcg gcagtggatc tgggacagac ttcactctca ccatcagcag cctgcagcct  240
gaagattttg caacttatta ctgccaacag tataatagtt acccgtggac gttcggccaa  300
gggaccaagg tggaaatcaa a                                            321

SEQ ID NO: 68          moltype = AA  length = 107
FEATURE                Location/Qualifiers
source                 1..107
                       mol_type = protein
                       organism = synthetic construct
SEQUENCE: 68
DIQMTQSPSS LSASVGDRVT ITCRASQAIN NHLAWFQQKP GKAPKSLIFA VSSLQSGVPS  60
KFSGSGSGTD FTLTISSLQP EDFATYYCQQ YNSYPWTFGQ GTKVEIK                107

SEQ ID NO: 69          moltype = DNA  length = 373
FEATURE                Location/Qualifiers
source                 1..373
                       mol_type = other DNA
                       organism = synthetic construct
SEQUENCE: 69
gaggtgcagc tggtggagtc tgggggaggc ttggtacagc ctggggggtc cctgagactc  60
tcctgtgcag cctctggatt cacgtttaga gactatgcca tgagctgggt ccgccaggct  120
ccagggaagg ggctggagtg ggtctcagct attagtggtt ccggtggtaa cacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cct                                                     373

SEQ ID NO: 70          moltype = AA  length = 124
```

-continued

```
FEATURE                 Location/Qualifiers
source                  1..124
                        mol_type = protein
                        organism = synthetic construct
SEQUENCE: 70
EVQLVESGGG LVQPGGSLRL SCAASGFTFR DYAMSWVRQA PGKGLEWVSA ISGSGGNTYY  60
ADSVKGRFTI SRDNSKNTLY LQMNSLRAED TAVYYCAKDR LSITIRPRYY GLDVWGQGTT  120
VTVS                                                               124

SEQ ID NO: 71           moltype = DNA  length = 322
FEATURE                 Location/Qualifiers
source                  1..322
                        mol_type = other DNA
                        organism = synthetic construct
SEQUENCE: 71
gacatccaga tgacccagtc tccatcctca ctgtctgcat ctgtaggaga cagagtcacc  60
atcacttgtc gggcgagtca ggccattaac aatcatttag cctggtttca gcagaaacca  120
gggaaagccc ctaagtccct gatctatgct gtatccagtt tgcaaagtgg ggtcccatca  180
aggttcagcg gcagtggatc tgggacagat ttcactctca ccatcagcag cctgcagcct  240
gaagattttg caacttatta ctgccaacag tataatagtt acccgtggac gttcggccaa  300
gggaccaagg tggaaatcaa ac                                           322

SEQ ID NO: 72           moltype = AA  length = 107
FEATURE                 Location/Qualifiers
source                  1..107
                        mol_type = protein
                        organism = synthetic construct
SEQUENCE: 72
DIQMTQSPSS LSASVGDRVT ITCRASQAIN NHLAWFQQKP GKAPKSLIYA VSSLQSGVPS  60
RFSGSGSGTD FTLTISSLQP EDFATYYCQQ YNSYPWTFGQ GTKVEIK                107

SEQ ID NO: 73           moltype = DNA  length = 375
FEATURE                 Location/Qualifiers
source                  1..375
                        mol_type = other DNA
                        organism = synthetic construct
SEQUENCE: 73
caggtgcagc tggtggagtc tgggggaggc ttggaacagc cggggggggtc cttgagactc  60
tcctgtgcag gctctggatt cacgtttaga gactatgcca tgacctgggt ccgccaggct  120
ccagggaagg ggctggagtg ggtcgcatcg attagtggtt ccggtggtaa cacatacttc  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggtccacg  360
gtcaccgtct cctca                                                   375

SEQ ID NO: 74           moltype = AA  length = 125
FEATURE                 Location/Qualifiers
source                  1..125
                        mol_type = protein
                        organism = synthetic construct
SEQUENCE: 74
QVQLVESGGG LEQPGGSLRL SCAGSGFTFR DYAMTWVRQA PGKGLEWVAS ISGSGGNTYF  60
ADSVKGRFTI SRDNSKNTLY LQMNSLRAED TAVYYCAKDR LSITIRPRYY GLDVWGQGST  120
VTVSS                                                              125

SEQ ID NO: 75           moltype = DNA  length = 24
FEATURE                 Location/Qualifiers
source                  1..24
                        mol_type = other DNA
                        organism = synthetic construct
SEQUENCE: 75
ggattcacgt ttagagacta tgcc                                         24

SEQ ID NO: 76           moltype = AA  length = 8
FEATURE                 Location/Qualifiers
source                  1..8
                        mol_type = protein
                        organism = synthetic construct
SEQUENCE: 76
GFTFRDYA                                                           8

SEQ ID NO: 77           moltype = DNA  length = 24
FEATURE                 Location/Qualifiers
source                  1..24
                        mol_type = other DNA
                        organism = synthetic construct
SEQUENCE: 77
attagtggtt ccggtggtaa caca                                         24
```

```
SEQ ID NO: 78          moltype = AA  length = 8
FEATURE                Location/Qualifiers
source                 1..8
                       mol_type = protein
                       organism = synthetic construct
SEQUENCE: 78
ISGSGGNT                                                           8

SEQ ID NO: 79          moltype = DNA  length = 54
FEATURE                Location/Qualifiers
source                 1..54
                       mol_type = other DNA
                       organism = synthetic construct
SEQUENCE: 79
gcgaaagatc gactctctat aacaattcgc ccacgctatt atggtttgga cgtc        54

SEQ ID NO: 80          moltype = AA  length = 18
FEATURE                Location/Qualifiers
source                 1..18
                       mol_type = protein
                       organism = synthetic construct
SEQUENCE: 80
AKDRLSITIR PRYYGLDV                                                18

SEQ ID NO: 81          moltype = DNA  length = 339
FEATURE                Location/Qualifiers
source                 1..339
                       mol_type = other DNA
                       organism = synthetic construct
SEQUENCE: 81
gaaatagtgt tgacgcagtc tccactctcc ctgcccgtca cccctggaga gccggcctcc  60
atctcctgca ggtctagtca gagcctcctg tatagtattg gatacaacta tttggattgg  120
tacctgcaga agtcagggca gtctccacag ctccttatct atttgggttc taatcgggcc  180
tccggggtcc ctgacaggtt cagtggcagt ggatcaggca cagattttac actgaaaatc  240
agcagagtgg aggctgagga tgttgggttt tattactgca tgcaagctct acaaactccg  300
tacacttttg gcccggggac caagctggag atcaaacga                         339

SEQ ID NO: 82          moltype = AA  length = 113
FEATURE                Location/Qualifiers
source                 1..113
                       mol_type = protein
                       organism = synthetic construct
SEQUENCE: 82
EIVLTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGPGTKLE IKR         113

SEQ ID NO: 83          moltype = DNA  length = 33
FEATURE                Location/Qualifiers
source                 1..33
                       mol_type = other DNA
                       organism = synthetic construct
SEQUENCE: 83
cagagcctcc tgtatagtat tggatacaac tat                               33

SEQ ID NO: 84          moltype = AA  length = 11
FEATURE                Location/Qualifiers
source                 1..11
                       mol_type = protein
                       organism = synthetic construct
SEQUENCE: 84
QSLLYSIGYN Y                                                       11

SEQ ID NO: 85          moltype =   length =
SEQUENCE: 85
000

SEQ ID NO: 86          moltype =   length =
SEQUENCE: 86
000

SEQ ID NO: 87          moltype = DNA  length = 27
FEATURE                Location/Qualifiers
source                 1..27
                       mol_type = other DNA
                       organism = synthetic construct
SEQUENCE: 87
atgcaagctc tacaaactcc gtacact                                      27

SEQ ID NO: 88          moltype = AA  length = 9
```

```
FEATURE                Location/Qualifiers
source                 1..9
                       mol_type = protein
                       organism = synthetic construct
SEQUENCE: 88
MQALQTPYT                                                         9

SEQ ID NO: 89          moltype = DNA  length = 372
FEATURE                Location/Qualifiers
source                 1..372
                       mol_type = other DNA
                       organism = synthetic construct
SEQUENCE: 89
gaggtgcagc tggtggagtc tggggggaggc ttggaacagc cggggggggtc cttgagactc  60
tcctgtgcag gctctggatt cacgtttaga gactatgcca tgacctgggt ccgccaggct  120
ccagggaagg ggctggagtg ggtcgcatcg attagtggtt ccggtggtaa cacatacttc  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cc                                                     372

SEQ ID NO: 90          moltype = AA  length = 124
FEATURE                Location/Qualifiers
source                 1..124
                       mol_type = protein
                       organism = synthetic construct
SEQUENCE: 90
EVQLVESGGG LEQPGGSLRL SCAGSGFTFR DYAMTWVRQA PGKGLEWVAS ISGSGGNTYF  60
ADSVKGRFTI SRDNSKNTLY LQMNSLRAED TAVYYCAKDR LSITIRPRYY GLDVWGQGTT  120
VTVS                                                              124

SEQ ID NO: 91          moltype = DNA  length = 336
FEATURE                Location/Qualifiers
source                 1..336
                       mol_type = other DNA
                       organism = synthetic construct
SEQUENCE: 91
gatattgtga tgactcagtc tccactctcc ctgcccgtca cccctggaga gccggcctcc  60
atctcctgca ggtctagtca gagcctcctg tatagtattg gatacaacta tttggattgg  120
tacctgcaga agtcagggca gtctccacag ctccttatct atttgggttc taatcgggcc  180
tccggggtcc ctgacaggtt cagtggcagt ggatcaggca cagattttac actgaaaatc  240
agcagagtgg aggctgagga tgttgggttt tattactgca tgcaagctct acaaactccg  300
tacacttttg gcccggggac caagctggag atcaaa                           336

SEQ ID NO: 92          moltype = AA  length = 112
FEATURE                Location/Qualifiers
source                 1..112
                       mol_type = protein
                       organism = synthetic construct
SEQUENCE: 92
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGPGTKLE IK          112

SEQ ID NO: 93          moltype = DNA  length = 373
FEATURE                Location/Qualifiers
source                 1..373
                       mol_type = other DNA
                       organism = synthetic construct
SEQUENCE: 93
gaggtgcagc tggtggagtc tggggggaggc ttggtacagc ctggggggtc cctgagactc  60
tcctgtgcag cctctggatt cacgtttaga gactatgcca tgagctgggt ccgccaggct  120
ccagggaagg ggctggagtg ggtctcagct attagtggtt ccggtggtaa cacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cct                                                    373

SEQ ID NO: 94          moltype = AA  length = 124
FEATURE                Location/Qualifiers
source                 1..124
                       mol_type = protein
                       organism = synthetic construct
SEQUENCE: 94
EVQLVESGGG LVQPGGSLRL SCAASGFTFR DYAMSWVRQA PGKGLEWVSA ISGSGGNTYY  60
ADSVKGRFTI SRDNSKNTLY LQMNSLRAED TAVYYCAKDR LSITIRPRYY GLDVWGQGTT  120
VTVS                                                              124

SEQ ID NO: 95          moltype = DNA  length = 337
FEATURE                Location/Qualifiers
```

```
source                  1..337
                        mol_type = other DNA
                        organism = synthetic construct
SEQUENCE: 95
gatattgtga tgactcagtc tccactctcc ctgcccgtca cccctggaga gccggcctcc  60
atctcctgca ggtctagtca gagcctcctg tatagtattg gatacaacta tttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctct acaaactccg  300
tacacttttg gccaggggac caagctggag atcaaac                            337

SEQ ID NO: 96           moltype = AA  length = 112
FEATURE                 Location/Qualifiers
source                  1..112
                        mol_type = protein
                        organism = synthetic construct
SEQUENCE: 96
DIVMTQSPLS LPVTPGEPAS ISCRSSQSLL YSIGYNYLDW YLQKPGQSPQ LLIYLGSNRA  60
SGVPDRFSGS GSGTDFTLKI SRVEAEDVGV YYCMQALQTP YTFGQGTKLE IK           112

SEQ ID NO: 97           moltype = DNA  length = 375
FEATURE                 Location/Qualifiers
source                  1..375
                        mol_type = other DNA
                        organism = synthetic construct
SEQUENCE: 97
caggtgcagc tggtggagtc tgagggactc ttggaacagc ctggggggtc cctgagactc  60
tcctgtgcag cctctggatt caactttaga gactttgcca tgacctgggt ccgccaggct  120
ccagggaagg ggctggagtg ggtctcatct attagtggta gtggtagtaa tacatactac  180
gcagactccg tgaagggccg gttcaccatc tccagagaca attccaacca cacgctgtat  240
ctgcgaatga acagcctgag agccgaagac acggccgtgt attactgtgc gaaagatcga  300
ctctctataa caattcgccc acgctattac ggtctggacg tctggggcca agggtccacg  360
gtcaccgtct cctca                                                    375

SEQ ID NO: 98           moltype = AA  length = 125
FEATURE                 Location/Qualifiers
source                  1..125
                        mol_type = protein
                        organism = synthetic construct
SEQUENCE: 98
QVQLVESEGL LEQPGGSLRL SCAASGFNFR DFAMTWVRQA PGKGLEWVSS ISGSGSNTYY  60
ADSVKGRFTI SRDNSNHTLY LRMNSLRAED TAVYYCAKDR LSITIRPRYY GLDVWGQGST  120
VTVSS                                                               125

SEQ ID NO: 99           moltype = DNA  length = 24
FEATURE                 Location/Qualifiers
source                  1..24
                        mol_type = other DNA
                        organism = synthetic construct
SEQUENCE: 99
ggattcaact ttagagactt tgcc                                          24

SEQ ID NO: 100          moltype = AA  length = 8
FEATURE                 Location/Qualifiers
source                  1..8
                        mol_type = protein
                        organism = synthetic construct
SEQUENCE: 100
GFNFRDFA                                                            8

SEQ ID NO: 101          moltype = DNA  length = 24
FEATURE                 Location/Qualifiers
source                  1..24
                        mol_type = other DNA
                        organism = synthetic construct
SEQUENCE: 101
attagtggta gtggtagtaa taca                                          24

SEQ ID NO: 102          moltype = AA  length = 8
FEATURE                 Location/Qualifiers
source                  1..8
                        mol_type = protein
                        organism = synthetic construct
SEQUENCE: 102
ISGSGSNT                                                            8

SEQ ID NO: 103          moltype = DNA  length = 54
FEATURE                 Location/Qualifiers
source                  1..54
```

```
                        mol_type = other DNA
                        organism = synthetic construct
SEQUENCE: 103
gcgaaagatc gactctctat aacaattcgc ccacgctatt acggtctgga cgtc       54

SEQ ID NO: 104          moltype = AA  length = 18
FEATURE                 Location/Qualifiers
source                  1..18
                        mol_type = protein
                        organism = synthetic construct
SEQUENCE: 104
AKDRLSITIR PRYYGLDV                                               18

SEQ ID NO: 105          moltype = DNA  length = 324
FEATURE                 Location/Qualifiers
source                  1..324
                        mol_type = other DNA
                        organism = synthetic construct
SEQUENCE: 105
gacatccaga tgacccagtc tccatcctcc ctgtctgcat ctgtaggaga cagagtcacc  60
atcacttgcc gggcgagtca ggacattagc aattattttg cctggtatca gcagaagcca  120
gggaaagttc ctaagctcct gatctttgct gcatccactt tgcatccagg ggtcccatct  180
cggttcagtg gcagtggatc tgggacagat ttcactctca ccattcgcag cctgcagcct  240
gaagatgttg caacttatta ctgtcaaaaa tatgacagtg ccccgtacac ttttggccag  300
gggaccaagg tggaaatcaa acga                                        324

SEQ ID NO: 106          moltype = AA  length = 108
FEATURE                 Location/Qualifiers
source                  1..108
                        mol_type = protein
                        organism = synthetic construct
SEQUENCE: 106
DIQMTQSPSS LSASVGDRVT ITCRASQDIS NYFAWYQQKP GKVPKLLIFA ASTLHPGVPS  60
RFSGSGSGTD FTLTIRSLQP EDVATYYCQK YDSAPYTFGQ GTKVEIKR                108

SEQ ID NO: 107          moltype = DNA  length = 18
FEATURE                 Location/Qualifiers
source                  1..18
                        mol_type = other DNA
                        organism = synthetic construct
SEQUENCE: 107
caggacatta gcaattat                                               18

SEQ ID NO: 108          moltype = AA  length = 6
FEATURE                 Location/Qualifiers
source                  1..6
                        mol_type = protein
                        organism = synthetic construct
SEQUENCE: 108
QDISNY                                                            6

SEQ ID NO: 109          moltype =   length =
SEQUENCE: 109
000

SEQ ID NO: 110          moltype =   length =
SEQUENCE: 110
000

SEQ ID NO: 111          moltype = DNA  length = 27
FEATURE                 Location/Qualifiers
source                  1..27
                        mol_type = other DNA
                        organism = synthetic construct
SEQUENCE: 111
caaaaatatg acagtgcccc gtacact                                     27

SEQ ID NO: 112          moltype = AA  length = 9
FEATURE                 Location/Qualifiers
source                  1..9
                        mol_type = protein
                        organism = synthetic construct
SEQUENCE: 112
QKYDSAPYT                                                         9

SEQ ID NO: 113          moltype = DNA  length = 372
FEATURE                 Location/Qualifiers
source                  1..372
                        mol_type = other DNA
```

```
                         organism = synthetic construct
SEQUENCE: 113
gaggtgcagc tggtggagtc tgagggactc ttggaacagc ctggggggtc cctgagactc  60
tcctgtgcag cctctggatt caactttaga gactttgcca tgacctgggt ccgccaggct  120
ccagggaagg ggctggagtg ggtctcatct attagtggta gtggtagtaa tacatactac  180
gcagactccg tgaagggccg gttcaccatc tccagagaca attccaacca cacgctgtat  240
ctgcgaatga acagcctgag agccgaagac acggccgtgt attactgtgc gaaagatcga  300
ctctctataa caattcgccc acgctattac ggtctggacg tctggggcca agggaccacg  360
gtcaccgtct cc                                                       372

SEQ ID NO: 114           moltype = AA  length = 124
FEATURE                  Location/Qualifiers
source                   1..124
                         mol_type = protein
                         organism = synthetic construct
SEQUENCE: 114
EVQLVESEGL LEQPGGSLRL SCAASGFNFR DFAMTWVRQA PGKGLEWVSS ISGSGSNTYY  60
ADSVKGRFTI SRDNSNHTLY LRMNSLRAED TAVYYCAKDR LSITIRPRYY GLDVWGQGTT  120
VTVS                                                                124

SEQ ID NO: 115           moltype = DNA  length = 321
FEATURE                  Location/Qualifiers
source                   1..321
                         mol_type = other DNA
                         organism = synthetic construct
SEQUENCE: 115
gacatccaga tgacccagtc tccatcctcc ctgtctgcat ctgtaggaga cagagtcacc  60
atcacttgcc gggcgagtca ggacattagc aattattttg cctggtatca gcagaagcca  120
gggaaagttc ctaagctcct gatctttgct gcatccactt tgcatccagg ggtcccatct  180
cggttcagtg gcagtggatc tgggacagat ttcactctca ccattcgcag cctgcagcct  240
gaagatgttg caacttatta ctgtcaaaaa tatgacagtg ccccgtacac ttttggccag  300
gggaccaagc tggagatcaa a                                             321

SEQ ID NO: 116           moltype = AA  length = 107
FEATURE                  Location/Qualifiers
source                   1..107
                         mol_type = protein
                         organism = synthetic construct
SEQUENCE: 116
DIQMTQSPSS LSASVGDRVT ITCRASQDIS NYFAWYQQKP GKVPKLLIFA ASTLHPGVPS  60
RFSGSGSGTD FTLTIRSLQP EDVATYYCQK YDSAPYTFGQ GTKLEIK                 107

SEQ ID NO: 117           moltype = DNA  length = 373
FEATURE                  Location/Qualifiers
source                   1..373
                         mol_type = other DNA
                         organism = synthetic construct
SEQUENCE: 117
gaggtgcagc tggtggagtc tgggggaggc ttggtacagc ctggggggtc cctgagactc  60
tcctgtgcag cctctggatt caactttaga gactttgcca tgagctgggt ccgccaggct  120
ccagggaagg ggctggagtg ggtctcagct attagtggta gtggtagtaa tacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattac ggtctggacg tctggggcca agggaccacg  360
gtcaccgtct cct                                                      373

SEQ ID NO: 118           moltype = AA  length = 124
FEATURE                  Location/Qualifiers
source                   1..124
                         mol_type = protein
                         organism = synthetic construct
SEQUENCE: 118
EVQLVESGGG LVQPGGSLRL SCAASGFNFR DFAMSWVRQA PGKGLEWVSA ISGSGSNTYY  60
ADSVKGRFTI SRDNSKNTLY LQMNSLRAED TAVYYCAKDR LSITIRPRYY GLDVWGQGTT  120
VTVS                                                                124

SEQ ID NO: 119           moltype = DNA  length = 322
FEATURE                  Location/Qualifiers
source                   1..322
                         mol_type = other DNA
                         organism = synthetic construct
SEQUENCE: 119
gacatccaga tgacccagtc tccatcctcc ctgtctgcat ctgtaggaga cagagtcacc  60
atcacttgcc gggcgagtca ggacattagc aattatttag cctggtatca gcagaaacca  120
gggaaagttc ctaagctcct gatctatgct gcatccactt tgcaatcagg ggtcccatct  180
cggttcagtg gcagtggatc tgggacagat ttcactctca ccatcagcag cctgcagcct  240
gaagatgttg caacttatta ctgtcaaaaa tatgacagtg ccccgtacac ttttggccag  300
gggaccaagc tggagatcaa ac                                            322
```

```
SEQ ID NO: 120         moltype = AA  length = 107
FEATURE                Location/Qualifiers
source                 1..107
                       mol_type = protein
                       organism = synthetic construct
SEQUENCE: 120
DIQMTQSPSS LSASVGDRVT ITCRASQDIS NYLAWYQQKP GKVPKLLIYA ASTLQSGVPS  60
RFSGSGSGTD FTLTISSLQP EDVATYYCQK YDSAPYTFGQ GTKLEIK                107

SEQ ID NO: 121         moltype = DNA  length = 357
FEATURE                Location/Qualifiers
source                 1..357
                       mol_type = other DNA
                       organism = synthetic construct
SEQUENCE: 121
caggtgcagc tggtggagtc tgggggaggc ttggtacagc ctggggggtc cctgagactc  60
tcctgtgtag cttctggatt cacccttaac aactttgtca tgaactgggt ccgccaggtt  120
ccagggaagg gactggagtg ggtctctttt attagtgcta gtggtggtag tatatactac  180
gcagactccg tgaagggccg gttcaccatc tccagagaca cttccaagaa cacattatat  240
ctgcaaatga acagcctgag agccgacgac acggccgtct attactgtgc gaaatccccg  300
tataactgga accccttga ctattggggc cagggaacca cggtcaccgt ctcctca     357

SEQ ID NO: 122         moltype = AA  length = 119
FEATURE                Location/Qualifiers
source                 1..119
                       mol_type = protein
                       organism = synthetic construct
SEQUENCE: 122
QVQLVESGGG LVQPGGSLRL SCVASGFTLN NFVMNWVRQV PGKGLEWVSF ISASGGSIYY  60
ADSVKGRFTI SRDTSKNTLY LQMNSLRADD TAVYYCAKSP YNWNPFDYWG QGTTVTVSS   119

SEQ ID NO: 123         moltype = DNA  length = 24
FEATURE                Location/Qualifiers
source                 1..24
                       mol_type = other DNA
                       organism = synthetic construct
SEQUENCE: 123
ggattcaccc ttaacaactt tgtc                                         24

SEQ ID NO: 124         moltype = AA  length = 8
FEATURE                Location/Qualifiers
source                 1..8
                       mol_type = protein
                       organism = synthetic construct
SEQUENCE: 124
GFTLNNFV                                                           8

SEQ ID NO: 125         moltype = DNA  length = 24
FEATURE                Location/Qualifiers
source                 1..24
                       mol_type = other DNA
                       organism = synthetic construct
SEQUENCE: 125
attagtgcta gtggtggtag tata                                         24

SEQ ID NO: 126         moltype = AA  length = 8
FEATURE                Location/Qualifiers
source                 1..8
                       mol_type = protein
                       organism = synthetic construct
SEQUENCE: 126
ISASGGSI                                                           8

SEQ ID NO: 127         moltype = DNA  length = 36
FEATURE                Location/Qualifiers
source                 1..36
                       mol_type = other DNA
                       organism = synthetic construct
SEQUENCE: 127
gcgaaatccc cgtataactg gaaccccttt gactat                            36

SEQ ID NO: 128         moltype = AA  length = 12
FEATURE                Location/Qualifiers
source                 1..12
                       mol_type = protein
                       organism = synthetic construct
SEQUENCE: 128
AKSPYNWNPF DY                                                      12
```

```
SEQ ID NO: 129          moltype = DNA  length = 327
FEATURE                 Location/Qualifiers
source                  1..327
                        mol_type = other DNA
                        organism = synthetic construct
SEQUENCE: 129
gacatccagt tgacccagtc tccagccacc ctgtctgtgt ctccagggga acgagccacc  60
ctctcctgca gggccagtct gagtgttagc agcaaattag cctggtacca gcagacacct  120
ggccaggctc ccagactcct catctatagt gcctccaccc gggccactgg tatcccagtc  180
aggttcagtg gcagtgggtc tgggacagag ttcactctca ccatcagcag cctgcagtct  240
gaagattttg cggtttatta ctgtcagcag tataatcatt ggcctccgta cacttttggc  300
caggggacca aggtggagat caaacga                                       327

SEQ ID NO: 130          moltype = AA  length = 109
FEATURE                 Location/Qualifiers
source                  1..109
                        mol_type = protein
                        organism = synthetic construct
SEQUENCE: 130
DIQLTQSPAT LSVSPGERAT LSCRASLSVS SKLAWYQQTP GQAPRLLIYS ASTRATGIPV  60
RFSGSGSGTE FTLTISSLQS EDFAVYYCQQ YNHWPPYTFG QGTKVEIKR              109

SEQ ID NO: 131          moltype = DNA  length = 18
FEATURE                 Location/Qualifiers
source                  1..18
                        mol_type = other DNA
                        organism = synthetic construct
SEQUENCE: 131
ctgagtgtta gcagcaaa                                                 18

SEQ ID NO: 132          moltype = AA  length = 6
FEATURE                 Location/Qualifiers
source                  1..6
                        mol_type = protein
                        organism = synthetic construct
SEQUENCE: 132
LSVSSK                                                              6

SEQ ID NO: 133          moltype =   length =
SEQUENCE: 133
000

SEQ ID NO: 134          moltype =   length =
SEQUENCE: 134
000

SEQ ID NO: 135          moltype = DNA  length = 30
FEATURE                 Location/Qualifiers
source                  1..30
                        mol_type = other DNA
                        organism = synthetic construct
SEQUENCE: 135
cagcagtata atcattggcc tccgtacact                                    30

SEQ ID NO: 136          moltype = AA  length = 10
FEATURE                 Location/Qualifiers
source                  1..10
                        mol_type = protein
                        organism = synthetic construct
SEQUENCE: 136
QQYNHWPPYT                                                          10

SEQ ID NO: 137          moltype = DNA  length = 357
FEATURE                 Location/Qualifiers
source                  1..357
                        mol_type = other DNA
                        organism = synthetic construct
SEQUENCE: 137
gaggtgcagc tggtggagtc tgggggaggc ttggtacagc ctggggggtc cctgagactc  60
tcctgtgtag cttctggatt cacccttaac aactttgtca tgaactgggt ccgccaggtt  120
ccagggaagg gactggagtg ggtctctttt attagtgcta gtggtggtag tatatactac  180
gcagactccg tgaagggccg gttcaccatc tccagagaca cttccaagaa cacattatat  240
ctgcaaatga acagcctgag agccgacgac acggccgtct attactgtgc gaaatccccg  300
tataactgga accccttga ctattggggc cagggaaccc tggtcaccgt ctcctca     357

SEQ ID NO: 138          moltype = AA  length = 119
FEATURE                 Location/Qualifiers
source                  1..119
                        mol_type = protein
```

```
                        organism = synthetic construct
SEQUENCE: 138
EVQLVESGGG LVQPGGSLRL SCVASGFTLN NFVMNWVRQV PGKGLEWVSF ISASGGSIYY  60
ADSVKGRFTI SRDTSKNTLY LQMNSLRADD TAVYYCAKSP YNWNPFDYWG QGTLVTVSS   119

SEQ ID NO: 139          moltype = DNA  length = 324
FEATURE                 Location/Qualifiers
source                  1..324
                        mol_type = other DNA
                        organism = synthetic construct
SEQUENCE: 139
gaaatagtga tgacgcagtc tccagccacc ctgtctgtgt ctccagggga acgagccacc  60
ctctcctgca gggccagtct gagtgttagc agcaaattag cctggtacca gcagacacct  120
ggccaggctc ccagactcct catctatagt gcctccaccc gggccactgg tatcccagtc  180
aggttcagtg gcagtgggtc tgggacagag ttcactctca ccatcagcag cctgcagtct  240
gaagattttg cggtttatta ctgtcagcag tataatcatt ggcctccgta cacttttggc  300
caggggacca agctggagat caaa                                         324

SEQ ID NO: 140          moltype = AA  length = 108
FEATURE                 Location/Qualifiers
source                  1..108
                        mol_type = protein
                        organism = synthetic construct
SEQUENCE: 140
EIVMTQSPAT LSVSPGERAT LSCRASLSVS SKLAWYQQTP GQAPRLLIYS ASTRATGIPV  60
RFSGSGSGTE FTLTISSLQS EDFAVYYCQQ YNHWPPYTFG QGTKLEIK               108

SEQ ID NO: 141          moltype = DNA  length = 357
FEATURE                 Location/Qualifiers
source                  1..357
                        mol_type = other DNA
                        organism = synthetic construct
SEQUENCE: 141
gaggtgcagc tggtggagtc tggggggaggc ttggtacagc ctggggggtc cctgagactc  60
tcctgtgcag cctctggatt caccottaac aactttgtca tgagctgggt ccgccaggct  120
ccagggaagg ggctggagtg ggtctcagct attagtgcta gtggtggtag tatatactac  180
gcagactccg tgaagggccg gttcaccatc tccagagaca attccaagaa cacgctgtat  240
ctgcaaatga acagcctgag agccgaggac acggccgtat attactgtgc gaaatccccg  300
tataactgga accccttga ctattggggc cagggaaccc tggtcaccgt ctcctca     357

SEQ ID NO: 142          moltype = AA  length = 119
FEATURE                 Location/Qualifiers
source                  1..119
                        mol_type = protein
                        organism = synthetic construct
SEQUENCE: 142
EVQLVESGGG LVQPGGSLRL SCAASGFTLN NFVMSWVRQA PGKGLEWVSA ISASGGSIYY  60
ADSVKGRFTI SRDNSKNTLY LQMNSLRAED TAVYYCAKSP YNWNPFDYWG QGTLVTVSS   119

SEQ ID NO: 143          moltype = DNA  length = 325
FEATURE                 Location/Qualifiers
source                  1..325
                        mol_type = other DNA
                        organism = synthetic construct
SEQUENCE: 143
gaaatagtga tgacgcagtc tccagccacc ctgtctgtgt ctccagggga aagagccacc  60
ctctcctgca gggccagtct gagtgttagc agcaaattag cctggtacca gcagaaacct  120
ggccaggctc ccaggctcct catctatagt gcctccacca gggccactgg tatcccagcc  180
aggttcagtg gcagtgggtc tgggacagag ttcactctca ccatcagcag cctgcagtct  240
gaagattttg cagtttatta ctgtcagcag tataatcatt ggcctccgta cacttttggc  300
caggggacca agctggagat caaac                                        325

SEQ ID NO: 144          moltype = AA  length = 108
FEATURE                 Location/Qualifiers
source                  1..108
                        mol_type = protein
                        organism = synthetic construct
SEQUENCE: 144
EIVMTQSPAT LSVSPGERAT LSCRASLSVS SKLAWYQQKP GQAPRLLIYS ASTRATGIPA  60
RFSGSGSGTE FTLTISSLQS EDFAVYYCQQ YNHWPPYTFG QGTKLEIK               108

SEQ ID NO: 145          moltype = DNA  length = 375
FEATURE                 Location/Qualifiers
source                  1..375
                        mol_type = other DNA
                        organism = synthetic construct
SEQUENCE: 145
caggtgcagc tggtggagtc tgggggaggc ttggaacagc cggggggggtc cctgagactc  60
tcctgtgcag gctctggatt cacctttaga gactatgcca tgacctgggt ccgccaggct  120
```

```
ccagggaagg gactggagtg ggtctcatct attagtggtt ccggtggtaa cacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggtccacg  360
gtcaccgtct cctca                                                   375

SEQ ID NO: 146         moltype = AA  length = 125
FEATURE                Location/Qualifiers
source                 1..125
                       mol_type = protein
                       organism = synthetic construct
SEQUENCE: 146
QVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGST  120
VTVSS                                                              125

SEQ ID NO: 147         moltype = DNA  length = 24
FEATURE                Location/Qualifiers
source                 1..24
                       mol_type = other DNA
                       organism = synthetic construct
SEQUENCE: 147
ggattcacct ttagagacta tgcc                                         24

SEQ ID NO: 148         moltype = AA  length = 8
FEATURE                Location/Qualifiers
source                 1..8
                       mol_type = protein
                       organism = synthetic construct
SEQUENCE: 148
GFTFRDYA                                                           8

SEQ ID NO: 149         moltype = DNA  length = 24
FEATURE                Location/Qualifiers
source                 1..24
                       mol_type = other DNA
                       organism = synthetic construct
SEQUENCE: 149
attagtggtt ccggtggtaa caca                                         24

SEQ ID NO: 150         moltype = AA  length = 8
FEATURE                Location/Qualifiers
source                 1..8
                       mol_type = protein
                       organism = synthetic construct
SEQUENCE: 150
ISGSGGNT                                                           8

SEQ ID NO: 151         moltype = DNA  length = 54
FEATURE                Location/Qualifiers
source                 1..54
                       mol_type = other DNA
                       organism = synthetic construct
SEQUENCE: 151
gcgaaagatc gactctctat aacaattcgc ccacgctatt atggtttgga cgtc        54

SEQ ID NO: 152         moltype = AA  length = 18
FEATURE                Location/Qualifiers
source                 1..18
                       mol_type = protein
                       organism = synthetic construct
SEQUENCE: 152
AKDRLSITIR PRYYGLDV                                                18

SEQ ID NO: 153         moltype = DNA  length = 339
FEATURE                Location/Qualifiers
source                 1..339
                       mol_type = other DNA
                       organism = synthetic construct
SEQUENCE: 153
gacatcgtgt tgacccagtc tccactctcc ctgcccgtca cccctggaga gccggcctcc  60
atctcctgca ggtctagtca gagcctcctg tatagtattg gatacaacta tttggattgg  120
tacctgcaga agtcagggca gtctccacag ctccttatct atttgggttc taatcgggcc  180
tccggggtcc ctgacaggtt cagtggcagt ggatcaggca cagattttac actgaaaatc  240
agcagagtgg aggctgagga tgttgggttt tattactgca tgcaagctct acaaactccg  300
tacacttttg gccaggggac caagctggag atcaaacga                         339

SEQ ID NO: 154         moltype = AA  length = 113
FEATURE                Location/Qualifiers
```

```
source                  1..113
                        mol_type = protein
                        organism = synthetic construct
SEQUENCE: 154
DIVLTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IKR        113

SEQ ID NO: 155          moltype = DNA  length = 33
FEATURE                 Location/Qualifiers
source                  1..33
                        mol_type = other DNA
                        organism = synthetic construct
SEQUENCE: 155
cagagcctcc tgtatagtat tggatacaac tat                              33

SEQ ID NO: 156          moltype = AA  length = 11
FEATURE                 Location/Qualifiers
source                  1..11
                        mol_type = protein
                        organism = synthetic construct
SEQUENCE: 156
QSLLYSIGYN Y                                                      11

SEQ ID NO: 157          moltype =   length =
SEQUENCE: 157
000

SEQ ID NO: 158          moltype =   length =
SEQUENCE: 158
000

SEQ ID NO: 159          moltype = DNA  length = 27
FEATURE                 Location/Qualifiers
source                  1..27
                        mol_type = other DNA
                        organism = synthetic construct
SEQUENCE: 159
atgcaagctc tacaaactcc gtacact                                     27

SEQ ID NO: 160          moltype = AA  length = 9
FEATURE                 Location/Qualifiers
source                  1..9
                        mol_type = protein
                        organism = synthetic construct
SEQUENCE: 160
MQALQTPYT                                                         9

SEQ ID NO: 161          moltype = DNA  length = 372
FEATURE                 Location/Qualifiers
source                  1..372
                        mol_type = other DNA
                        organism = synthetic construct
SEQUENCE: 161
gaggtgcagc tggtggagtc tggggggaggc ttggaacagc cggggggggtc cctgagactc  60
tcctgtgcag gctctggatt cacctttaga gactatgcca tgacctgggt ccgccaggct  120
ccagggaagg gactggagtg ggtctcatct attagtggtt ccggtggtaa cacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cc                                                     372

SEQ ID NO: 162          moltype = AA  length = 124
FEATURE                 Location/Qualifiers
source                  1..124
                        mol_type = protein
                        organism = synthetic construct
SEQUENCE: 162
EVQLVESGGG LEQPGGSLRL SCAGSGFTFR DYAMTWVRQA PGKGLEWVSS ISGSGGNTYY  60
ADSVKGRFTI SRDNSKNTLY LQMNSLRAED TAVYYCAKDR LSITIRPRYY GLDVWGQGTT  120
VTVS                                                              124

SEQ ID NO: 163          moltype = DNA  length = 336
FEATURE                 Location/Qualifiers
source                  1..336
                        mol_type = other DNA
                        organism = synthetic construct
SEQUENCE: 163
gacatcgtga tgacccagtc tccactctcc ctgcccgtca cccctggaga gccggcctcc  60
atctcctgca ggtctagtca gagcctcctg tatagtattg gatacaacta tttggattgg  120
```

```
tacctgcaga agtcagggca gtctccacag ctccttatct atttgggttc taatcgggcc  180
tccggggtcc ctgacaggtt cagtggcagt ggatcaggca cagattttac actgaaaatc  240
agcagagtgg aggctgagga tgttgggttt tattactgca tgcaagctct acaaactccg  300
tacacttttg gccaggggac caagctggag atcaaa                            336

SEQ ID NO: 164         moltype = AA  length = 112
FEATURE                Location/Qualifiers
source                 1..112
                       mol_type = protein
                       organism = synthetic construct
SEQUENCE: 164
DIVMTQSPLS LPVTPGEPAS ISCRSSQSLL YSIGYNYLDW YLQKSGQSPQ LLIYLGSNRA  60
SGVPDRFSGS GSGTDFTLKI SRVEAEDVGF YYCMQALQTP YTFGQGTKLE IK          112

SEQ ID NO: 165         moltype = DNA  length = 373
FEATURE                Location/Qualifiers
source                 1..373
                       mol_type = other DNA
                       organism = synthetic construct
SEQUENCE: 165
gaggtgcagc tggtggagtc tggggggaggc ttggtacagc ctggggggtc cctgagactc  60
tcctgtgcag cctctggatt cacctttaga gactatgcca tgagctgggt ccgccaggct  120
ccagggaagg ggctggagtg ggtctcagct attagtggtt ccggtggtaa cacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctctataa caattcgccc acgctattat ggtttggacg tctggggcca agggaccacg  360
gtcaccgtct cct                                                     373

SEQ ID NO: 166         moltype = AA  length = 124
FEATURE                Location/Qualifiers
source                 1..124
                       mol_type = protein
                       organism = synthetic construct
SEQUENCE: 166
EVQLVESGGG LVQPGGSLRL SCAASGFTFR DYAMSWVRQA PGKGLEWVSA ISGSGGNTYY  60
ADSVKGRFTI SRDNSKNTLY LQMNSLRAED TAVYYCAKDR LSITIRPRYY GLDVWGQGTT  120
VTVS                                                               124

SEQ ID NO: 167         moltype = DNA  length = 337
FEATURE                Location/Qualifiers
source                 1..337
                       mol_type = other DNA
                       organism = synthetic construct
SEQUENCE: 167
gatattgtga tgactcagtc tccactctcc ctgcccgtca cccctggaga gccggcctcc  60
atctcctgca ggtctagtca gagcctcctg tatagtattg gatacaacta tttggattgg  120
tacctgcaga agccagggca gtctccacag ctcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctct acaaactccg  300
tacacttttg gccaggggac caagctggag atcaaac                           337

SEQ ID NO: 168         moltype = AA  length = 112
FEATURE                Location/Qualifiers
source                 1..112
                       mol_type = protein
                       organism = synthetic construct
SEQUENCE: 168
DIVMTQSPLS LPVTPGEPAS ISCRSSQSLL YSIGYNYLDW YLQKPGQSPQ LLIYLGSNRA  60
SGVPDRFSGS GSGTDFTLKI SRVEAEDVGV YYCMQALQTP YTFGQGTKLE IK          112

SEQ ID NO: 169         moltype = DNA  length = 375
FEATURE                Location/Qualifiers
source                 1..375
                       mol_type = other DNA
                       organism = synthetic construct
SEQUENCE: 169
caggtgcagc tggtggagtc tggggggagtc ttggagcagc ctggggggtc cctgagactc  60
tcctgtacag cctctggatt cacctttaga gactatgcca tgacctgggt ccgccaggct  120
ccagggaagg ggctggagtg ggtctcatct attagtggta gtggtggtaa tacatactac  180
gcagactccg tgaggggccg gttcaccatc tccagagaca actccaacca cacgctgtat  240
ctgcaaatga acagcctgag agccgaagac acggccgtat attactgtgc gaaagatcga  300
ctctccataa caattcgccc acgctattac ggtttggacg tctggggcca agggtccacg  360
gtcaccgtct cctca                                                   375

SEQ ID NO: 170         moltype = AA  length = 125
FEATURE                Location/Qualifiers
source                 1..125
                       mol_type = protein
                       organism = synthetic construct
```

```
SEQUENCE: 170
QVQLVESGGV LEQPGGSLRL SCTASGFTFR DYAMTWVRQA PGKGLEWVSS ISGSGGNTYY  60
ADSVRGRFTI SRDNSNHTLY LQMNSLRAED TAVYYCAKDR LSITIRPRYY GLDVWGQGST  120
VTVSS                                                             125

SEQ ID NO: 171          moltype = DNA  length = 24
FEATURE                 Location/Qualifiers
source                  1..24
                        mol_type = other DNA
                        organism = synthetic construct
SEQUENCE: 171
ggattcacct ttagagacta tgcc                                        24

SEQ ID NO: 172          moltype = AA  length = 8
FEATURE                 Location/Qualifiers
source                  1..8
                        mol_type = protein
                        organism = synthetic construct
SEQUENCE: 172
GFTFRDYA                                                          8

SEQ ID NO: 173          moltype = DNA  length = 24
FEATURE                 Location/Qualifiers
source                  1..24
                        mol_type = other DNA
                        organism = synthetic construct
SEQUENCE: 173
attagtggta gtggtggtaa taca                                        24

SEQ ID NO: 174          moltype = AA  length = 8
FEATURE                 Location/Qualifiers
source                  1..8
                        mol_type = protein
                        organism = synthetic construct
SEQUENCE: 174
ISGSGGNT                                                          8

SEQ ID NO: 175          moltype = DNA  length = 54
FEATURE                 Location/Qualifiers
source                  1..54
                        mol_type = other DNA
                        organism = synthetic construct
SEQUENCE: 175
gcgaaagatc gactctccat aacaattcgc ccacgctatt acggtttgga cgtc       54

SEQ ID NO: 176          moltype = AA  length = 18
FEATURE                 Location/Qualifiers
source                  1..18
                        mol_type = protein
                        organism = synthetic construct
SEQUENCE: 176
AKDRLSITIR PRYYGLDV                                               18

SEQ ID NO: 177          moltype = DNA  length = 324
FEATURE                 Location/Qualifiers
source                  1..324
                        mol_type = other DNA
                        organism = synthetic construct
SEQUENCE: 177
gatattgtga tgacccagtc tccatcctcc ctgtctgcat ctgtaggaga cagagtcacc  60
attacttgcc gggcgagtca ggacattagc aattattttg cctggtatca gcagaagcca  120
gggaaagttc ctaaactcct gatctttgct gcatccactt tgcatccagg ggtcccatct  180
cggttcagtg gcagtggatc tgggacagat ttcactctca ccattagtag cctgcagcct  240
gaagatgttg caacttatta ctgtcaaaag tataacagtg ccccgtacac ttttggccag  300
gggaccaagg tggaaatcaa acga                                        324

SEQ ID NO: 178          moltype = AA  length = 108
FEATURE                 Location/Qualifiers
source                  1..108
                        mol_type = protein
                        organism = synthetic construct
SEQUENCE: 178
DIVMTQSPSS LSASVGDRVT ITCRASQDIS NYFAWYQQKP GKVPKLLIFA ASTLHPGVPS  60
RFSGSGSGTD FTLTISSLQP EDVATYYCQK YNSAPYTFGQ GTKVEIKR              108

SEQ ID NO: 179          moltype = DNA  length = 18
FEATURE                 Location/Qualifiers
source                  1..18
                        mol_type = other DNA
```

```
                      organism = synthetic construct
SEQUENCE: 179
caggacatta gcaattat                                            18

SEQ ID NO: 180        moltype = AA  length = 6
FEATURE               Location/Qualifiers
source                1..6
                      mol_type = protein
                      organism = synthetic construct
SEQUENCE: 180
QDISNY                                                         6

SEQ ID NO: 181        moltype =   length =
SEQUENCE: 181
000

SEQ ID NO: 182        moltype =   length =
SEQUENCE: 182
000

SEQ ID NO: 183        moltype = DNA  length = 27
FEATURE               Location/Qualifiers
source                1..27
                      mol_type = other DNA
                      organism = synthetic construct
SEQUENCE: 183
caaaagtata acagtgcccc gtacact                                  27

SEQ ID NO: 184        moltype = AA  length = 9
FEATURE               Location/Qualifiers
source                1..9
                      mol_type = protein
                      organism = synthetic construct
SEQUENCE: 184
QKYNSAPYT                                                      9

SEQ ID NO: 185        moltype = DNA  length = 372
FEATURE               Location/Qualifiers
source                1..372
                      mol_type = other DNA
                      organism = synthetic construct
SEQUENCE: 185
gaggtgcagc tggtggagtc tgggggagtc ttggagcagc ctggggggtc cctgagactc  60
tcctgtacag cctctggatt cacctttaga gactatgcca tgacctgggt ccgccaggct  120
ccagggaagg ggctggagtg ggtctcatct attagtggta gtggtggtaa tacatactac  180
gcagactccg tgaggggccg gttcaccatc tccagagaca actccaacca cacgctgtat  240
ctgcaaatga acagcctgag agccgaagac acggccgtat attactgtgc gaaagatcga  300
ctctccataa caattcgccc acgctattac ggtttggacg tctggggcca agggaccacg  360
gtcaccgtct cc                                                  372

SEQ ID NO: 186        moltype = AA  length = 124
FEATURE               Location/Qualifiers
source                1..124
                      mol_type = protein
                      organism = synthetic construct
SEQUENCE: 186
EVQLVESGGV LEQPGGSLRL SCTASGFTFR DYAMTWVRQA PGKGLEWVSS ISGSGGNTYY  60
ADSVRGRFTI SRDNSNHTLY LQMNSLRAED TAVYYCAKDR LSITIRPRYY GLDVWGQGTT  120
VTVS                                                           124

SEQ ID NO: 187        moltype = DNA  length = 321
FEATURE               Location/Qualifiers
source                1..321
                      mol_type = other DNA
                      organism = synthetic construct
SEQUENCE: 187
gacatccaga tgacccagtc tccatcctcc ctgtctgcat ctgtaggaga cagagtcacc  60
attacttgcc gggcgagtca ggacattagc aattattttg cctggtatca gcagaagcca  120
gggaaagttc ctaaactcct gatctttgct gcatccactt tgcatccagg ggtcccatct  180
cggttcagtg gcagtggatc tgggacagat ttcactctca ccattagtag cctgcagcct  240
gaagatgttg caacttatta ctgtcaaaag tataacagtg ccccgtacac ttttggccag  300
gggaccaagc tggagatcaa a                                        321

SEQ ID NO: 188        moltype = AA  length = 107
FEATURE               Location/Qualifiers
source                1..107
                      mol_type = protein
                      organism = synthetic construct
SEQUENCE: 188
```

```
DIQMTQSPSS LSASVGDRVT ITCRASQDIS NYFAWYQQKP GKVPKLLIFA ASTLHPGVPS  60
RFSGSGSGTD FTLTISSLQP EDVATYYCQK YNSAPYTFGQ GTKLEIK                107

SEQ ID NO: 189         moltype = DNA  length = 373
FEATURE                Location/Qualifiers
source                 1..373
                       mol_type = other DNA
                       organism = synthetic construct
SEQUENCE: 189
gaggtgcagc tggtggagtc tgggggaggc ttggtacagc ctggggggtc cctgagactc  60
tcctgtgcag cctctggatt cacctttaga gactatgcca tgagctgggt ccgccaggct  120
ccagggaagg ggctggagtg ggtctcagct attagtggta gtggtggtaa tacatactac  180
gcagactccg tgaagggccg gttcaccatc tccagagaca attccaagaa cacgctgtat  240
ctgcaaatga acagcctgag agccgaggac acggccgtat attactgtgc gaaagatcga  300
ctctccataa caattcgccc acgctattac ggtttggacg tctggggcca agggaccacg  360
gtcaccgtct cct                                                     373

SEQ ID NO: 190         moltype = AA  length = 124
FEATURE                Location/Qualifiers
source                 1..124
                       mol_type = protein
                       organism = synthetic construct
SEQUENCE: 190
EVQLVESGGG LVQPGGSLRL SCAASGFTFR DYAMSWVRQA PGKGLEWVSA ISGSGGNTYY  60
ADSVKGRFTI SRDNSKNTLY LQMNSLRAED TAVYYCAKDR LSITIRPRYY GLDVWGQGTT  120
VTVS                                                               124

SEQ ID NO: 191         moltype = DNA  length = 322
FEATURE                Location/Qualifiers
source                 1..322
                       mol_type = other DNA
                       organism = synthetic construct
SEQUENCE: 191
gacatccaga tgacccagtc tccatcctcc ctgtctgcat ctgtaggaga cagagtcacc  60
atcacttgcc gggcgagtca ggacattagc aattatttag cctggtatca gcagaaacca  120
gggaaagttc ctaagctcct gatctatgct gcatccactt tgcaatcagg ggtcccatct  180
cggttcagtg gcagtggatc tgggacagat ttcactctca ccatcagcag cctgcagcct  240
gaagatgttg caacttatta ctgtcaaaag tataacagtg ccccgtacac ttttggccag  300
gggaccaagc tggagatcaa ac                                           322

SEQ ID NO: 192         moltype = AA  length = 107
FEATURE                Location/Qualifiers
source                 1..107
                       mol_type = protein
                       organism = synthetic construct
SEQUENCE: 192
DIQMTQSPSS LSASVGDRVT ITCRASQDIS NYLAWYQQKP GKVPKLLIYA ASTLQSGVPS  60
RFSGSGSGTD FTLTISSLQP EDVATYYCQK YNSAPYTFGQ GTKLEIK                107

SEQ ID NO: 193         moltype = DNA  length = 355
FEATURE                Location/Qualifiers
source                 1..355
                       mol_type = other DNA
                       organism = synthetic construct
SEQUENCE: 193
gaagtgcacc tggtggaatc tgggggaggc ttggtacagc ctggcaggtc cctgagactc  60
tcctgtgagg cctctggatt cacctttgat gattatgcca tgcactgggt ccggcaagct  120
ccggggaagg gcctggaatg ggtctcaggt cttagtcgga caagtgtcag tataggctat  180
gcggactctg tgaagggccg attcaccatc tccagagaca acgccaagaa ctccctttat  240
ttggaaatga acagtctgag acctgaggac acggccttat attactgtgc aaaatggggg  300
acccgggggt attttgacta ctggggccag ggaaccctgg tcaccgtctc ctcag       355

SEQ ID NO: 194         moltype = AA  length = 118
FEATURE                Location/Qualifiers
source                 1..118
                       mol_type = protein
                       organism = synthetic construct
SEQUENCE: 194
EVHLVESGGG LVQPGRSLRL SCEASGFTFD DYAMHWVRQA PGKGLEWVSG LSRTSVSIGY  60
ADSVKGRFTI SRDNAKNSLY LEMNSLRPED TALYYCAKWG TRGYFDYWGQ GTLVTVSS    118

SEQ ID NO: 195         moltype = DNA  length = 24
FEATURE                Location/Qualifiers
source                 1..24
                       mol_type = other DNA
                       organism = synthetic construct
SEQUENCE: 195
ggattcacct ttgatgatta tgcc                                         24
```

```
SEQ ID NO: 196         moltype = AA  length = 8
FEATURE                Location/Qualifiers
source                 1..8
                       mol_type = protein
                       organism = synthetic construct
SEQUENCE: 196
GFTFDDYA                                                       8

SEQ ID NO: 197         moltype = DNA  length = 24
FEATURE                Location/Qualifiers
source                 1..24
                       mol_type = other DNA
                       organism = synthetic construct
SEQUENCE: 197
cttagtcgga caagtgtcag tata                                     24

SEQ ID NO: 198         moltype = AA  length = 8
FEATURE                Location/Qualifiers
source                 1..8
                       mol_type = protein
                       organism = synthetic construct
SEQUENCE: 198
LSRTSVSI                                                       8

SEQ ID NO: 199         moltype = DNA  length = 33
FEATURE                Location/Qualifiers
source                 1..33
                       mol_type = other DNA
                       organism = synthetic construct
SEQUENCE: 199
gcaaaatggg ggacccgggg gtattttgac tac                           33

SEQ ID NO: 200         moltype = AA  length = 11
FEATURE                Location/Qualifiers
source                 1..11
                       mol_type = protein
                       organism = synthetic construct
SEQUENCE: 200
AKWGTRGYFD Y                                                   11

SEQ ID NO: 201         moltype = DNA  length = 322
FEATURE                Location/Qualifiers
source                 1..322
                       mol_type = other DNA
                       organism = synthetic construct
SEQUENCE: 201
gacatccaga tgacccagtc tccatcttcc gtgtctgcat ctgtgggaga cagagtcacc  60
atcacttgtc gggcgagtca ggatattagt atttggttag cctggtatca gcagagtcca  120
gggaaagccc ctaaactcct gatcaatgtt gcatcccgtt tgcaaagtgg ggtcccatca  180
aggttcagcg gcagtggatc tgggacagat ttcactctca ccatcaacag tctgcagcct  240
gaagattttg taacttacta ttgtcaacag gctaacagtt tcccgatcac cttcggccaa  300
gggacacgac tggcgaccaa ac                                       322

SEQ ID NO: 202         moltype = AA  length = 107
FEATURE                Location/Qualifiers
source                 1..107
                       mol_type = protein
                       organism = synthetic construct
SEQUENCE: 202
DIQMTQSPSS VSASVGDRVT ITCRASQDIS IWLAWYQQSP GKAPKLLINV ASRLQSGVPS  60
RFSGSGSGTD FTLTINSLQP EDFVTYYCQQ ANSFPITFGQ GTRLATK            107

SEQ ID NO: 203         moltype = DNA  length = 18
FEATURE                Location/Qualifiers
source                 1..18
                       mol_type = other DNA
                       organism = synthetic construct
SEQUENCE: 203
caggatatta gtatttgg                                            18

SEQ ID NO: 204         moltype = AA  length = 6
FEATURE                Location/Qualifiers
source                 1..6
                       mol_type = protein
                       organism = synthetic construct
SEQUENCE: 204
QDISIW                                                         6

SEQ ID NO: 205         moltype =   length =
```

```
SEQUENCE: 205
000

SEQ ID NO: 206         moltype =   length =
SEQUENCE: 206
000

SEQ ID NO: 207         moltype = DNA  length = 27
FEATURE                Location/Qualifiers
source                 1..27
                       mol_type = other DNA
                       organism = synthetic construct
SEQUENCE: 207
caacaggcta acagtttccc gatcacc                                     27

SEQ ID NO: 208         moltype = AA  length = 9
FEATURE                Location/Qualifiers
source                 1..9
                       mol_type = protein
                       organism = synthetic construct
SEQUENCE: 208
QQANSFPIT                                                         9

SEQ ID NO: 209         moltype = DNA  length = 355
FEATURE                Location/Qualifiers
source                 1..355
                       mol_type = other DNA
                       organism = synthetic construct
SEQUENCE: 209
gaggtgcagc tggtggagtc tgggggaggc ttggtacagc ctggcaggtc cctgagactc  60
tcctgtgagg cctctggatt cacctttgat gattatgcca tgcactgggt ccggcaagct  120
ccggggaagg gcctggaatg ggtctcaggt cttagtcgga caagtgtcag tataggctat  180
gcggactctg tgaagggccg attcaccatc tccagagaca acgccaagaa ctccctttat  240
ttggaaatga acagtctgag acctgaggac acggccttat attactgtgc aaaatggggg  300
acccgggggt attttgacta ctggggccag ggaaccctgg tcaccgtctc ctcag       355

SEQ ID NO: 210         moltype = AA  length = 118
FEATURE                Location/Qualifiers
source                 1..118
                       mol_type = protein
                       organism = synthetic construct
SEQUENCE: 210
EVQLVESGGG LVQPGRSLRL SCEASGFTFD DYAMHWVRQA PGKGLEWVSG LSRTSVSIGY  60
ADSVKGRFTI SRDNAKNSLY LEMNSLRPED TALYYCAKWG TRGYFDYWGQ GTLVTVSS    118

SEQ ID NO: 211         moltype = DNA  length = 322
FEATURE                Location/Qualifiers
source                 1..322
                       mol_type = other DNA
                       organism = synthetic construct
SEQUENCE: 211
gacatccaga tgacccagtc tccatcttcc gtgtctgcat ctgtgggaga cagagtcacc  60
atcacttgtc gggcgagtca ggatattagt atttggttag cctggtatca gcagagtcca  120
gggaaagccc ctaaactcct gatcaatgtt gcatcccgtt tgcaaagtgg ggtcccatca  180
aggttcagcg gcagtggatc tgggacagat ttcactctca ccatcaacag tctgcagcct  240
gaagattttg taacttacta ttgtcaacag gctaacagtt tcccgatcac cttcggccaa  300
gggacacgac tggagattaa ac                                          322

SEQ ID NO: 212         moltype = AA  length = 107
FEATURE                Location/Qualifiers
source                 1..107
                       mol_type = protein
                       organism = synthetic construct
SEQUENCE: 212
DIQMTQSPSS VSASVGDRVT ITCRASQDIS IWLAWYQQSP GKAPKLLINV ASRLQSGVPS  60
RFSGSGSGTD FTLTINSLQP EDFVTYYCQQ ANSFPITFGQ GTRLEIK                107

SEQ ID NO: 213         moltype = DNA  length = 355
FEATURE                Location/Qualifiers
source                 1..355
                       mol_type = other DNA
                       organism = synthetic construct
SEQUENCE: 213
gaagtgcagc tggtggagtc tgggggaggc ttggtacagc ctggcaggtc cctgagactc  60
tcctgtgcag cctctggatt cacctttgat gattatgcca tgcactgggt ccggcaagct  120
ccagggaagg gcctggagtg ggtctcaggt cttagtcgga caagtgtcag tataggctat  180
gcggactctg tgaagggccg attcaccatc tccagagaca acgccaagaa ctccctgtat  240
ctgcaaatga acagtctgag agctgaggac acggccttgt attactgtgc aaaatggggg  300
acccgggggt attttgacta ctggggccaa ggaaccctgg tcaccgtctc ctcag       355
```

```
SEQ ID NO: 214          moltype = AA  length = 118
FEATURE                Location/Qualifiers
source                 1..118
                       mol_type = protein
                       organism = synthetic construct
SEQUENCE: 214
EVQLVESGGG LVQPGRSLRL SCAASGFTFD DYAMHWVRQA PGKGLEWVSG LSRTSVSIGY  60
ADSVKGRFTI SRDNAKNSLY LQMNSLRAED TALYYCAKWG TRGYFDYWGQ GTLVTVSS    118

SEQ ID NO: 215          moltype = DNA  length = 322
FEATURE                Location/Qualifiers
source                 1..322
                       mol_type = other DNA
                       organism = synthetic construct
SEQUENCE: 215
gacatccaga tgacccagtc tccatcttcc gtgtctgcat ctgtaggaga cagagtcacc  60
atcacttgtc gggcgagtca ggatattagt atttggttag cctggtatca gcagaaacca  120
gggaaagccc ctaagctcct gatctatgtt gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tcccgatcac cttcggccaa  300
gggacacgac tggagattaa ac                                          322

SEQ ID NO: 216          moltype = AA  length = 107
FEATURE                Location/Qualifiers
source                 1..107
                       mol_type = protein
                       organism = synthetic construct
SEQUENCE: 216
DIQMTQSPSS VSASVGDRVT ITCRASQDIS IWLAWYQQKP GKAPKLLIYV ASSLQSGVPS  60
RFSGSGSGTD FTLTISSLQP EDFATYYCQQ ANSFPITFGQ GTRLEIK               107

SEQ ID NO: 217          moltype = DNA  length = 363
FEATURE                Location/Qualifiers
source                 1..363
                       mol_type = other DNA
                       organism = synthetic construct
SEQUENCE: 217
gaggtgcagc tgttggagtc tggggggaggc ttgctacagc cgggggggtc cctgagactc  60
tcctgtgcag cctctggaat cacctttagc acctatgcca tgagctgggt ccgtcaggct  120
ccagggaggg ggctggagtg ggtctcagct attagtggta gtggtgatag cacatcctac  180
gcagactccg tgaagggccg gttcaccagc tccagagaca attccaagaa cacgctgtat  240
ctgcaaatga acagcctgag agccgaggac acggccgtat attactgtgc gaaagtcata  300
gcagctcgtc ctcactggaa cttcgatctc tggggccgtg gcaccctggt cactgtctcc  360
tca                                                               363

SEQ ID NO: 218          moltype = AA  length = 121
FEATURE                Location/Qualifiers
source                 1..121
                       mol_type = protein
                       organism = synthetic construct
SEQUENCE: 218
EVQLLESGGG LLQPGGSLRL SCAASGITFS TYAMSWVRQA PGRGLEWVSA ISGSGDSTSY  60
ADSVKGRFTS SRDNSKNTLY LQMNSLRAED TAVYYCAKVI AARPHWNFDL WGRGTLVTVS  120
S                                                                 121

SEQ ID NO: 219          moltype = DNA  length = 24
FEATURE                Location/Qualifiers
source                 1..24
                       mol_type = other DNA
                       organism = synthetic construct
SEQUENCE: 219
ggaatcacct ttagcaccta tgcc                                        24

SEQ ID NO: 220          moltype = AA  length = 8
FEATURE                Location/Qualifiers
source                 1..8
                       mol_type = protein
                       organism = synthetic construct
SEQUENCE: 220
GITFSTYA                                                          8

SEQ ID NO: 221          moltype = DNA  length = 24
FEATURE                Location/Qualifiers
source                 1..24
                       mol_type = other DNA
                       organism = synthetic construct
SEQUENCE: 221
attagtggta gtggtgatag caca                                        24
```

```
SEQ ID NO: 222         moltype = AA  length = 8
FEATURE                Location/Qualifiers
source                 1..8
                       mol_type = protein
                       organism = synthetic construct
SEQUENCE: 222
ISGSGDST                                                           8

SEQ ID NO: 223         moltype = DNA  length = 42
FEATURE                Location/Qualifiers
source                 1..42
                       mol_type = other DNA
                       organism = synthetic construct
SEQUENCE: 223
gcgaaagtca tagcagctcg tcctcactgg aacttcgatc tc                     42

SEQ ID NO: 224         moltype = AA  length = 14
FEATURE                Location/Qualifiers
source                 1..14
                       mol_type = protein
                       organism = synthetic construct
SEQUENCE: 224
AKVIAARPHW NFDL                                                    14

SEQ ID NO: 225         moltype = DNA  length = 324
FEATURE                Location/Qualifiers
source                 1..324
                       mol_type = other DNA
                       organism = synthetic construct
SEQUENCE: 225
gaaattgtgt tgacacagtc tccagccacc ctgtctttgt ctccagggga aagagccacc  60
ctctcctgca gggccagtca gagtgttagt agatatttag cctggtatca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg gagtttatta ctgtcagcag cgtagtgact ggccgctcac tttcggcgga  300
gggaccaagg tggagatcaa acgg                                         324

SEQ ID NO: 226         moltype = AA  length = 107
FEATURE                Location/Qualifiers
source                 1..107
                       mol_type = protein
                       organism = synthetic construct
SEQUENCE: 226
EIVLTQSPAT LSLSPGERAT LSCRASQSVS RYLAWYQQKP GQAPRLLIYD ASNRATGIPA  60
RFSGSGSGTD FTLTISSLEP EDFGVYYCQQ RSDWPLTFGG GTKVEIK                107

SEQ ID NO: 227         moltype = DNA  length = 18
FEATURE                Location/Qualifiers
source                 1..18
                       mol_type = other DNA
                       organism = synthetic construct
SEQUENCE: 227
cagagtgtta gtagatat                                                18

SEQ ID NO: 228         moltype = AA  length = 6
FEATURE                Location/Qualifiers
source                 1..6
                       mol_type = protein
                       organism = synthetic construct
SEQUENCE: 228
QSVSRY                                                             6

SEQ ID NO: 229         moltype =   length =
SEQUENCE: 229
000

SEQ ID NO: 230         moltype =   length =
SEQUENCE: 230
000

SEQ ID NO: 231         moltype = DNA  length = 27
FEATURE                Location/Qualifiers
source                 1..27
                       mol_type = other DNA
                       organism = synthetic construct
SEQUENCE: 231
cagcagcgta gtgactggcc gctcact                                      27
```

```
SEQ ID NO: 232          moltype = AA  length = 9
FEATURE                 Location/Qualifiers
source                  1..9
                        mol_type = protein
                        organism = synthetic construct
SEQUENCE: 232
QQRSDWPLT                                                         9

SEQ ID NO: 233          moltype = DNA  length = 363
FEATURE                 Location/Qualifiers
source                  1..363
                        mol_type = other DNA
                        organism = synthetic construct
SEQUENCE: 233
gaggtgcagc tgttggagtc tgggggaggc ttgctacagc cggggggtc cctgagactc  60
tcctgtgcag cctctggaat cacctttagc acctatgcca tgagctgggt ccgtcaggct  120
ccagggaggg ggctggagtg ggtctcagct attagtggta gtggtgatag cacatcctac  180
gcagactccg tgaagggccg gttcaccagc tccagagaca attccaagaa cacgctgtat  240
ctgcaaatga acagcctgag agccgaggac acggccgtat attactgtgc gaaagtcata  300
gcagctcgtc ctcactggaa cttcgatctc tggggccgtg gcaccctggt cactgtctcc  360
tca                                                               363

SEQ ID NO: 234          moltype = AA  length = 121
FEATURE                 Location/Qualifiers
source                  1..121
                        mol_type = protein
                        organism = synthetic construct
SEQUENCE: 234
EVQLLESGGG LLQPGGSLRL SCAASGITFS TYAMSWVRQA PGRGLEWVSA ISGSGDSTSY  60
ADSVKGRFTS SRDNSKNTLY LQMNSLRAED TAVYYCAKVI AARPHWNFDL WGRGTLVTVS  120
S                                                                 121

SEQ ID NO: 235          moltype = DNA  length = 324
FEATURE                 Location/Qualifiers
source                  1..324
                        mol_type = other DNA
                        organism = synthetic construct
SEQUENCE: 235
gaaattgtgt tgacacagtc tccagccacc ctgtctttgt ctccagggga aagagccacc  60
ctctcctgca gggccagtca gagtgttagt agatatttag cctggtatca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg gagtttatta ctgtcagcag cgtagtgact ggccgctcac tttcggcgga  300
gggaccaagg tggagatcaa acgg                                        324

SEQ ID NO: 236          moltype = AA  length = 107
FEATURE                 Location/Qualifiers
source                  1..107
                        mol_type = protein
                        organism = synthetic construct
SEQUENCE: 236
EIVLTQSPAT LSLSPGERAT LSCRASQSVS RYLAWYQQKP GQAPRLLIYD ASNRATGIPA  60
RFSGSGSGTD FTLTISSLEP EDFGVYYCQQ RSDWPLTFGG GTKVEIK               107

SEQ ID NO: 237          moltype = DNA  length = 363
FEATURE                 Location/Qualifiers
source                  1..363
                        mol_type = other DNA
                        organism = synthetic construct
SEQUENCE: 237
gaggtgcagc tgttggagtc tgggggaggc ttggtacagc cggggggtc cctgagactc  60
tcctgtgcag cctctggaat cacctttagc acctatgcca tgagctgggt ccgtcaggct  120
ccagggaagg ggctggagtg ggtctcagct attagtggta gtggtgatag cacatactac  180
gcagactccg tgaagggccg gttcaccatc tccagagaca attccaagaa cacgctgtat  240
ctgcaaatga acagcctgag agccgaggac acggccgtat attactgtgc gaaagtcata  300
gcagctcgtc ctcactggaa cttcgatctc tggggccgtg gcaccctggt cactgtctcc  360
tca                                                               363

SEQ ID NO: 238          moltype = AA  length = 121
FEATURE                 Location/Qualifiers
source                  1..121
                        mol_type = protein
                        organism = synthetic construct
SEQUENCE: 238
EVQLLESGGG LVQPGGSLRL SCAASGITFS TYAMSWVRQA PGKGLEWVSA ISGSGDSTYY  60
ADSVKGRFTI SRDNSKNTLY LQMNSLRAED TAVYYCAKVI AARPHWNFDL WGRGTLVTVS  120
S                                                                 121

SEQ ID NO: 239          moltype = DNA  length = 324
```

```
FEATURE                Location/Qualifiers
source                 1..324
                       mol_type = other DNA
                       organism = synthetic construct
SEQUENCE: 239
gaaattgtgt tgacacagtc tccagccacc ctgtctttgt ctccagggga aagagccacc  60
ctctcctgca gggccagtca gagtgttagt agatatttag cctggtatca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcagcag cgtagtgact ggccgctcac tttcggcgga  300
gggaccaagg tggagatcaa acgg                                        324

SEQ ID NO: 240         moltype = AA  length = 108
FEATURE                Location/Qualifiers
source                 1..108
                       mol_type = protein
                       organism = synthetic construct
SEQUENCE: 240
EIVLTQSPAT LSLSPGERAT LSCRASQSVS RYLAWYQQKP GQAPRLLIYD ASNRATGIPA  60
RFSGSGSGTD FTLTISSLEP EDFAVYYCQQ RSDWPLTFGG GTKVEIKR              108

SEQ ID NO: 241         moltype = DNA  length = 366
FEATURE                Location/Qualifiers
source                 1..366
                       mol_type = other DNA
                       organism = synthetic construct
SEQUENCE: 241
caggtgcagc tggtggagtc tgggggaggc gtggtccagc ctgggaggtc cctgagactc  60
acctgtgcag cctctggatt caccttcagt agtaatggca tgcactgggt ccgccaggct  120
ccaggcaagg ggctggagtg ggtggcaatt atatcatatg atggaaataa tcaatactat  180
gcagactccg tgaagggccg attcaccatc tccagagaca attccaagca cacgctgtat  240
ctggaaatga acagcctgag agctgaggac acggctgtgt attactgtac aaaagccatc  300
tctataagtg gaacttacaa ctggttcgat tcctggggcc agggaaccct ggtcaccgtc  360
tcctca                                                            366

SEQ ID NO: 242         moltype = AA  length = 122
FEATURE                Location/Qualifiers
source                 1..122
                       mol_type = protein
                       organism = synthetic construct
SEQUENCE: 242
QVQLVESGGG VVQPGRSLRL TCAASGFTFS SNGMHWVRQA PGKGLEWVAI ISYDGNNQYY  60
ADSVKGRFTI SRDNSKHTLY LEMNSLRAED TAVYYCTKAI SISGTYNWFD SWGQGTLVTV  120
SS                                                                122

SEQ ID NO: 243         moltype = DNA  length = 24
FEATURE                Location/Qualifiers
source                 1..24
                       mol_type = other DNA
                       organism = synthetic construct
SEQUENCE: 243
ggattcacct tcagtagtaa tggc                                        24

SEQ ID NO: 244         moltype = AA  length = 8
FEATURE                Location/Qualifiers
source                 1..8
                       mol_type = protein
                       organism = synthetic construct
SEQUENCE: 244
GFTFSSNG                                                          8

SEQ ID NO: 245         moltype = DNA  length = 24
FEATURE                Location/Qualifiers
source                 1..24
                       mol_type = other DNA
                       organism = synthetic construct
SEQUENCE: 245
atatcatatg atggaaataa tcaa                                        24

SEQ ID NO: 246         moltype = AA  length = 8
FEATURE                Location/Qualifiers
source                 1..8
                       mol_type = protein
                       organism = synthetic construct
SEQUENCE: 246
ISYDGNNQ                                                          8

SEQ ID NO: 247         moltype = DNA  length = 45
FEATURE                Location/Qualifiers
```

```
source                1..45
                      mol_type = other DNA
                      organism = synthetic construct
SEQUENCE: 247
acaaaagcca tctctataag tggaacttac aactggttcg attcc                  45

SEQ ID NO: 248        moltype = AA  length = 15
FEATURE               Location/Qualifiers
source                1..15
                      mol_type = protein
                      organism = synthetic construct
SEQUENCE: 248
TKAISISGTY NWFDS                                                   15

SEQ ID NO: 249        moltype = DNA  length = 324
FEATURE               Location/Qualifiers
source                1..324
                      mol_type = other DNA
                      organism = synthetic construct
SEQUENCE: 249
gaaattgtat tgacacagtc tccagccatc ctgtctttgt ctccagggga aagagccacc  60
ctctcctgca gggccagtca gagtgttagc aggtacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcaacag cgtagcaact ggccgctcac tttcggcgga  300
gggaccaagg tggagatcaa acgg                                         324

SEQ ID NO: 250        moltype = AA  length = 107
FEATURE               Location/Qualifiers
source                1..107
                      mol_type = protein
                      organism = synthetic construct
SEQUENCE: 250
EIVLTQSPAI LSLSPGERAT LSCRASQSVS RYLAWYQQKP GQAPRLLIYD ASNRATGIPA  60
RFSGSGSGTD FTLTISSLEP EDFAVYYCQQ RSNWPLTFGG GTKVEIK                107

SEQ ID NO: 251        moltype = DNA  length = 18
FEATURE               Location/Qualifiers
source                1..18
                      mol_type = other DNA
                      organism = synthetic construct
SEQUENCE: 251
cagagtgtta gcaggtac                                                18

SEQ ID NO: 252        moltype = AA  length = 6
FEATURE               Location/Qualifiers
source                1..6
                      mol_type = protein
                      organism = synthetic construct
SEQUENCE: 252
QSVSRY                                                             6

SEQ ID NO: 253        moltype =   length =
SEQUENCE: 253
000

SEQ ID NO: 254        moltype =   length =
SEQUENCE: 254
000

SEQ ID NO: 255        moltype = DNA  length = 27
FEATURE               Location/Qualifiers
source                1..27
                      mol_type = other DNA
                      organism = synthetic construct
SEQUENCE: 255
caacagcgta gcaactggcc gctcact                                      27

SEQ ID NO: 256        moltype = AA  length = 9
FEATURE               Location/Qualifiers
source                1..9
                      mol_type = protein
                      organism = synthetic construct
SEQUENCE: 256
QQRSNWPLT                                                          9

SEQ ID NO: 257        moltype = DNA  length = 366
FEATURE               Location/Qualifiers
source                1..366
```

```
                        mol_type = other DNA
                        organism = synthetic construct
SEQUENCE: 257
caggtgcagc tggtggagtc tgggggaggc gtggtccagc ctgggaggtc cctgagactc  60
acctgtgcag cctctggatt caccttcagt agtaatggca tgcactgggt ccgccaggct  120
ccaggcaagg ggctggagtg ggtggcaatt atatcatatg atggaaataa tcaatactat  180
gcagactccg tgaagggccg attcaccatc tccagagaca attccaagca cacgctgtat  240
ctggaaatga acagcctgag agctgaggac acggctgtgt attactgtac aaaagccatc  300
tctataagtg gaacttacaa ctggttcgat tcctggggcc agggaaccct ggtcaccgtc  360
tcctca                                                             366

SEQ ID NO: 258          moltype = AA  length = 122
FEATURE                 Location/Qualifiers
source                  1..122
                        mol_type = protein
                        organism = synthetic construct
SEQUENCE: 258
QVQLVESGGG VVQPGRSLRL TCAASGFTFS SNGMHWVRQA PGKGLEWVAI ISYDGNNQYY  60
ADSVKGRFTI SRDNSKHTLY LEMNSLRAED TAVYYCTKAI SISGTYNWFD SWGQGTLVTV  120
SS                                                                 122

SEQ ID NO: 259          moltype = DNA  length = 324
FEATURE                 Location/Qualifiers
source                  1..324
                        mol_type = other DNA
                        organism = synthetic construct
SEQUENCE: 259
gaaattgtat tgacacagtc tccagccatc ctgtctttgt ctccagggga aagagccacc  60
ctctcctgca gggccagtca gagtgttagc aggtacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcaacag cgtagcaact ggccgctcac tttcggcgga  300
gggaccaagg tggagatcaa acgg                                         324

SEQ ID NO: 260          moltype = AA  length = 107
FEATURE                 Location/Qualifiers
source                  1..107
                        mol_type = protein
                        organism = synthetic construct
SEQUENCE: 260
EIVLTQSPAI LSLSPGERAT LSCRASQSVS RYLAWYQQKP GQAPRLLIYD ASNRATGIPA  60
RFSGSGSGTD FTLTISSLEP EDFAVYYCQQ RSNWPLTFGG GTKVEIK                107

SEQ ID NO: 261          moltype = DNA  length = 366
FEATURE                 Location/Qualifiers
source                  1..366
                        mol_type = other DNA
                        organism = synthetic construct
SEQUENCE: 261
caggtgcagc tggtggagtc tgggggaggc gtggtccagc ctgggaggtc cctgagactc  60
tcctgtgcag cctctggatt caccttcagt agtaatggca tgcactgggt ccgccaggct  120
ccaggcaagg ggctggagtg ggtggcagtt atatcatatg atggaaataa tcaatactat  180
gcagactccg tgaagggccg attcaccatc tccagagaca attccaagaa cacgctgtat  240
ctgcaaatga acagcctgag agctgaggac acggctgtgt attactgtac aaaagccatc  300
tctataagtg gaacttacaa ctggttcgat tcctggggcc agggaaccct ggtcaccgtc  360
tcctca                                                             366

SEQ ID NO: 262          moltype = AA  length = 122
FEATURE                 Location/Qualifiers
source                  1..122
                        mol_type = protein
                        organism = synthetic construct
SEQUENCE: 262
QVQLVESGGG VVQPGRSLRL SCAASGFTFS SNGMHWVRQA PGKGLEWVAV ISYDGNNQYY  60
ADSVKGRFTI SRDNSKNTLY LQMNSLRAED TAVYYCTKAI SISGTYNWFD SWGQGTLVTV  120
SS                                                                 122

SEQ ID NO: 263          moltype = DNA  length = 324
FEATURE                 Location/Qualifiers
source                  1..324
                        mol_type = other DNA
                        organism = synthetic construct
SEQUENCE: 263
gaaattgtat tgacacagtc tccagccacc ctgtctttgt ctccagggga aagagccacc  60
ctctcctgca gggccagtca gagtgttagc aggtacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcaacag cgtagcaact ggccgctcac tttcggcgga  300
gggaccaagg tggagatcaa acgg                                         324
```

```
SEQ ID NO: 264          moltype = AA  length = 108
FEATURE                Location/Qualifiers
source                 1..108
                       mol_type = protein
                       organism = synthetic construct
SEQUENCE: 264
EIVLTQSPAT LSLSPGERAT LSCRASQSVS RYLAWYQQKP GQAPRLLIYD ASNRATGIPA  60
RFSGSGSGTD FTLTISSLEP EDFAVYYCQQ RSNWPLTFGG GTKVEIKR               108

SEQ ID NO: 265         moltype =   length =
SEQUENCE: 265
000

SEQ ID NO: 266         moltype =   length =
SEQUENCE: 266
000

SEQ ID NO: 267         moltype =   length =
SEQUENCE: 267
000

SEQ ID NO: 268         moltype =   length =
SEQUENCE: 268
000

SEQ ID NO: 269         moltype =   length =
SEQUENCE: 269
000

SEQ ID NO: 270         moltype =   length =
SEQUENCE: 270
000

SEQ ID NO: 271         moltype = AA  length = 330
FEATURE                Location/Qualifiers
source                 1..330
                       mol_type = protein
                       organism = synthetic construct
SEQUENCE: 271
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 272         moltype = AA  length = 327
FEATURE                Location/Qualifiers
source                 1..327
                       mol_type = protein
                       organism = synthetic construct
SEQUENCE: 272
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 273         moltype = AA  length = 327
FEATURE                Location/Qualifiers
source                 1..327
                       mol_type = protein
                       organism = synthetic construct
SEQUENCE: 273
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 274         moltype = AA  length = 207
FEATURE                Location/Qualifiers
source                 1..207
                       mol_type = protein
                       organism = Homo sapiens
SEQUENCE: 274
```

-continued

```
MKVLQEPTCV SDYMSISTCE WKMNGPTNCS TELRLLYQLV FLLSEAHTCI PENNGGAGCV  60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQH                                     207

SEQ ID NO: 275          moltype = AA  length = 231
FEATURE                 Location/Qualifiers
source                  1..231
                        mol_type = protein
                        organism = Macaca fascicularis
SEQUENCE: 275
MGWLCSGLLF PVSCLVLLQV ASSGSMKVLQ EPTCVSDYMS ISTCEWKMGG PTNCSAELRL  60
LYQLVFQSSE THTCVPENNG GVGCVCHLLM DDVVSMDNYT LDLWAGQQLL WKGSFKPSEH  120
VKPRAPGNLT VHTNVSDTVL LTWSNPYPPD NYLYNDLTYA VNIWSENDPA YSRIHNVTYL  180
KPTLRIPAST LKSGISYRAR VRAWAQHYNT TWSEWSPSTK WYNSYREPFE Q           231
```